United States Patent [19]
De Waal Malefyt et al.

[11] Patent Number: 5,837,293
[45] Date of Patent: Nov. 17, 1998

[54] USE OF INTERLEUKIN-10 ANALOGS FOR ANTAGONISTS TO TREAT ENDOTOXIN- OR SUPERANTIGEN-INDUCED TOXICITY

[75] Inventors: Rene De Waal Malefyt, Sunnyvale; Maureen Howard, Los Altos Hills; Di-Hwei Hsu, Sunnyvale, all of Calif.; Hiroshi Ishida, Kyoto, Japan; Anne O'Garra, Palo Alto, Calif.; Hergen Spits, Badhoevedorp, Netherlands; Albert Zlotnik, Palo Alto, Calif.

[73] Assignee: Schering Corporation, Kenilworth, N.J.

[21] Appl. No.: 481,560

[22] Filed: Jun. 7, 1995

Related U.S. Application Data

[60] Division of Ser. No. 410,654, Mar. 24, 1995, which is a continuation-in-part of Ser. No. 229,854, Apr. 19, 1994, abandoned, which is a continuation-in-part of Ser. No. 926,853, Aug. 6, 1992, abandoned, which is a continuation-in-part of Ser. No. 742,129, Aug. 6, 1991, abandoned.

[51] Int. Cl.$^6$ ........................... A61K 38/19; A61K 38/20
[52] U.S. Cl. ........................ 424/852; 424/85.1; 514/886; 514/921
[58] Field of Search .................................. 424/85.1, 85.2

[56] References Cited

FOREIGN PATENT DOCUMENTS

| 9100349 | 1/1991 | WIPO . |
|---|---|---|
| WO 91/00349 | 1/1991 | WIPO . |
| WO 91/09127 | 6/1991 | WIPO . |

OTHER PUBLICATIONS

Ikijina et al, *Infect Dis* 158(5) 1988 pp. 1017–1025.
Fiorentino et al *J. Exp Med* 170, 1987, p. 2081–2095.
Girardin et al, *NEJM* 319(7) 1988, pp. 397–400.
Ramilo et al *J. Exp Med*, 172, 1990, pp. 497–501.
Howard et al, *Immunol Today* vol. 13(6) 1992, pp. 198–200.
Howard et al J *Clin. Immunol* 12(4) 1992 pp. 239–247.
Hsu, et al., "Differential Effects of IL–4 and IL–10 on Il–2–Induced IFN–γ Synthesis and Lymhokine–Activated Killer Activity," *International Immunology*, vol. 4, No. 5, pp. 563–569, Jan. 27, 1992.
de Waal Malefyt, "Interleukin 10 (IL–120) Inhibits Cytokine Synthesis by Human Monocytes: An Autoregulatory Role of IL–10 Produced by Monocytes," *J. Exp. Med.*, vol. 174, pp. 1209–1220, Nov., 1991.
Fiorentino, et al., "IL–10 Inhibits Cytokine Production by Activated Macrophages," *The Journal of Immunology*, vol. 147, No. 11, pp. 3815–3822, Dec. 1, 1991.
Scuderi, et al., "Raised Serum Levels of Tumour Necrosis Factor in Parasitic Infections," *The Lancet*, pp. 1364–1365, Dec. 13, 1986.
Westphal, O., "Bacterial Endotoxins," *Int. Archs Allergy appl. Immun.*, vol. 49, pp. 1–43, 1975.
Kevin J. Tracey, et al., "Shock and Tissue Injury Induced by Recombinant Human Cachectin," *Science*, vol. 234, pp. 470–474, May 13, 1986.
Beutler, et al., "Cachectin and Tumour Necrosis Factor as Two Sides of the same Biological Coin," *Nature*, vol. 320, pp. 584–588, Apr. 17, 1986.
Tracey, et. al., "Anti–cachectin/TNF Monoclonal Antibodies Prevent Septic Shock During Lethal Bacteraemia," *Nature*, vol. 330, pp. 662–664, Dec. 17, 1987.
Waage, et al., "Association Between Tumour Necrosis Factor in Serum and Fatal Outcome in Patients with Meningococcal Disease," *The Lancet*, pp. 355–357, Feb. 14, 1987.
Girardin, et al., "Tumor Necrosis Factor and Interleukin–1 in the Serum of Children with Severe Infectious Purpura," *Children with Severe Infectious Purpura*, vol. 319, No. 7, pp. 397–400, Aug. 18, 1988.
Kern, et al., "Elevated Tumor Necrosis Factor Alpha and Interleukin–6 Serum Levels as Markers for Complicated *Plasmodium falciparum* Malaria," *The American Journal of Medicine*, vol. 87, pp. 139–143, Aug., 1989.
McIntosh, et al., "In Vivo Induction of IL–6 by Administration of Exogenous Cytokines and Dectection of De Novo Serum Levels of IL–6 in Tumor–Bearing Mice," *The Journal of Immunology*, vol. 143, pp. 162–167, Jul. 1, 1989.
Kishimoto, Tadamitsu, "The Biology of Interleukin–6," *The Journal of The American Society of Hematology,* vol. 74, No. 1, pp. 1–10, Jul., 1989.
Starnes, Jr., et al., "Anti–6 Monoclonal Antibodies Protect Against Lethal *Escherichia coli*, Infection and Lethal Tumor Necrosis Factor–α Challenge in Mice," *The Journal of Immunology*, vol. 145, No. 12, pp. 4185–4191, Dec. 15, 1990.
"Principles and Practice of Infectious Diseases," Second Edition, *A Wiley Medical Publication*, pp. 468–471.
Fiorentino, et al., "Two Types of Mouse T Helper Cell IV., Th2 Clones Secrete a Factor that Inhibits Cytokine Production by Th1 Clones," *J. Exp. Med.*, vol. 170, pp. 2081–2095, Dec., 1989.
Moore et al., "Homology of Cytokine Synthesis Inhibitory Factor (IL–10) to the Epstein–Barr Virus Gene BCRFI," *Science*, vol. 248, pp. 1230–1234, Apr. 23, 1990.
Vieira et al., "Isolation and Expression of Human Cytokine Synthesis Inhibitory Factor cDNA Clones: Homology to Epstein–Barr Virus Open Reading Frame BCRFI," *Proc. Natl. Acad. Sci. USA, Immunology*, vol. 88, pp. 1172–1176, Feb., 1991.
Young, et al., "One Signal Requirement for Interferon–γ Production by Human Large Granular Lymphocytes," *The Journal of Immunology*, vol. 139, pp. 724–727, Aug. 1, 1987.

(List continued on next page.)

*Primary Examiner*—Garnette D. Draper
*Attorney, Agent, or Firm*—Cynthia L. Foulke; Norman C. Dulak; Edwin P. Ching

[57] ABSTRACT

A method is provided for reducing an inflammatory response in a mammal comprising administering to a mammal at risk of developing or afflicted with an inflammatory response characterized by substantially elevated levels of IL-1α, IL-1β, IL-6, IL-8 and TNFα, an amount of IL-10 effective to substantially lower the levels of such cytokines.

18 Claims, 59 Drawing Sheets

OTHER PUBLICATIONS

Kawakami, et al., "IL–4 Regulates IL–2 Induction of Lymphokine–Activity Killer Activity from Human Lymphocytes," *The Journal of Immunology*, vol. 142, No. 10, pp. 3452–3461, May 15, 1989.

de Waal Malefyt, et al., "Interleukin 10 (IL–10) and Viral IL–10 Strongly Reduce Antigen–specific Human T Cell Proliferation by Diminishing the Antigen–presenting Capacity of Monocytes via Downregulation of Class II Major Histocompatibility Complex Expression," *J. Exp. Med.*, vol. 174, pp. 915–924, Oct., 1991.

te Velde, et al., "Interleukin–4 (IL–4) Inhibits Secretion of Il–1β, Tumor Necrosis Factor–α and IL–6 by Human Monocytes," *Blood*, vol. 76, No. 7, pp. 1392–1397, Oct. 1, 1990.

Aarden, et al., "Production of Hybridoma Growth Factor by Human Monocytes," *Eur. J. Immunol.*, vol. 17, pp. 1411–1416, Jul. 11, 1987.

Lonnemann, et al., Differences in the Synthesis and Kinetics of Release of Interleukin 1α, Interleukin 1β and Tumor Necrosis Factor from Human Mononuclear Cells, *Eur. J. Immunol.*, vol. 19, pp. 1531–1536, Apr. 1, 1989.

Fiorentino, et al., "IL–10 Acts on the Antigen–Presenting Cell to Inhibit Cytokine Production by Th1 Cells," *The Journal of Immunology*, vol. 146, No. 10, pp. 3444–3451, May 15, 1991.

Kappler, et al., "Vβ–Specific Stimulation of Human T Cells by Staphylococcal Toxins," *Science*, vol. 244, pp. 811–813, May 19, 1989.

Simpson, Elizabeth, "Positive and Negative Selection of the T Cell Repertoire: Role of MHC and Other Ligands," *Intern. Rev. Immunol.*, vol. 8, pp. 269–277, 1992.

Marrack et al., "The Toxicity of Staphylococcal Enterotoxin B in Mice is Mediated by T Cells," *J. Exp. Med.*, vol. 171, pp. 455–464, Feb., 1990.

Miethke, et al., "T Cell–mediated Lethal Shock Triggered in Mice by the Superantigen Staphylococcal Enterotoxin B: Critical Role of Tumor Necrosis Factor," *J. Exp. Med.*, vol. 175, pp. 91–98, Jan., 1992.

Beutler, et al., "Passive Immunization Against Cachectin/Tumor Necrosis Factor Protects Mice from Lethal Effect of Endotoxin," *Science*, vol. 229, pp. 869–871, Jul. 16, 1985.

Alexander, et al., "A Recombinant Human Receptor Antagonist to Interleukin 1 Improves Survival after Lethal Endotoxemia in Mice," *The Journal of Experimental Medicine*, vol. 173, pp. 1029–1032, Apr., 1991.

Ishida, et al., "Continuous Anti–Interleukin 10 Antibody Administration Depletes Mice of Ly–1 B Cells but Not Conventional B Cells," *The Journal of Experimental Medicine*, vol. 175, pp. 1213–1220, May, 1992.

Herzenberg, et al., "The LY–1 B Cell Lineage," *Immunological Reviews*, No. 93, pp. 81–102.

Hayakawa, et al., "Normal, Autoimmune, and Malignant CD5+ B Cells: The LY–1 B Lineage?" *Ann. Rev. Immunol.*, vol. 6, pp. 197–218, 1988.

Jacob, et al., "Tumour Necrosis Factor–α in Murine Autoimmune 'Lupus' Nephritis," *Nature*, vol. 331, pp. 356–358, Jan., 1988.

Gordon, et al., "Chronic Therapy with Recombinant Tumor Necrosis Factor–α in Autoimmune NZB/NZW $F_1$ Mice," *Clinical Immunology and Immunopathology*, vol. 52, pp. 421–434, 1989.

Theofilopoulos, et al., "Murine Models of Systemic Lupus Erythematosus," *Advances in Immunology*, vol. 37, pp. 269–390, 1985.

René de Waal Malefyt et al., "Interleukin–10," *Current Opinion in Immunology*, vol. 4, No. 3, pp. 314–320, Jun. 1992.

Maureen Howard et al., "Biological properties of interleukin–10," *Immunology Today*, vol. 13, No. 6, pp. 198–200, Jun. 1992.

Maureen Howard et al., "Biological Properties of Interleukin–10," *Journal of Clinical Immunology*, vol. 12, No. 4, pp. 239–247, Jul. 1992.

Ian A. MacNeil et al., "IL–10, a Novel Growth Cofactor for Mature and Immature T Cells," *Journal of Immunology*, vol. 145, No. 12, pp. 4167–4173, Dec. 1990.

Tim R. Mosmann, et al., "Isolation of Monoclonal Antibodies Specific For IL–4, IL–5, IL–6, and a New Th2–Specific Cytokine (IL–10), Cytokine Synthesis Inhibitory Factor, By Using A Solid Phase Radioimmunoadsorbent Assay," *The Journal of Immunology*,145(9):2938–2945, Nov. 1, 1990.

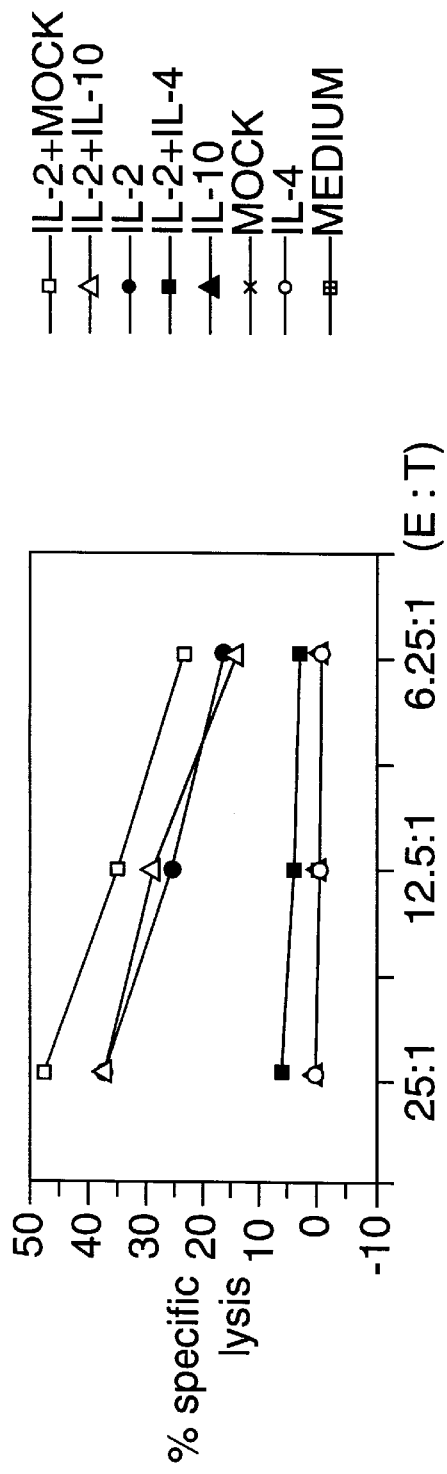
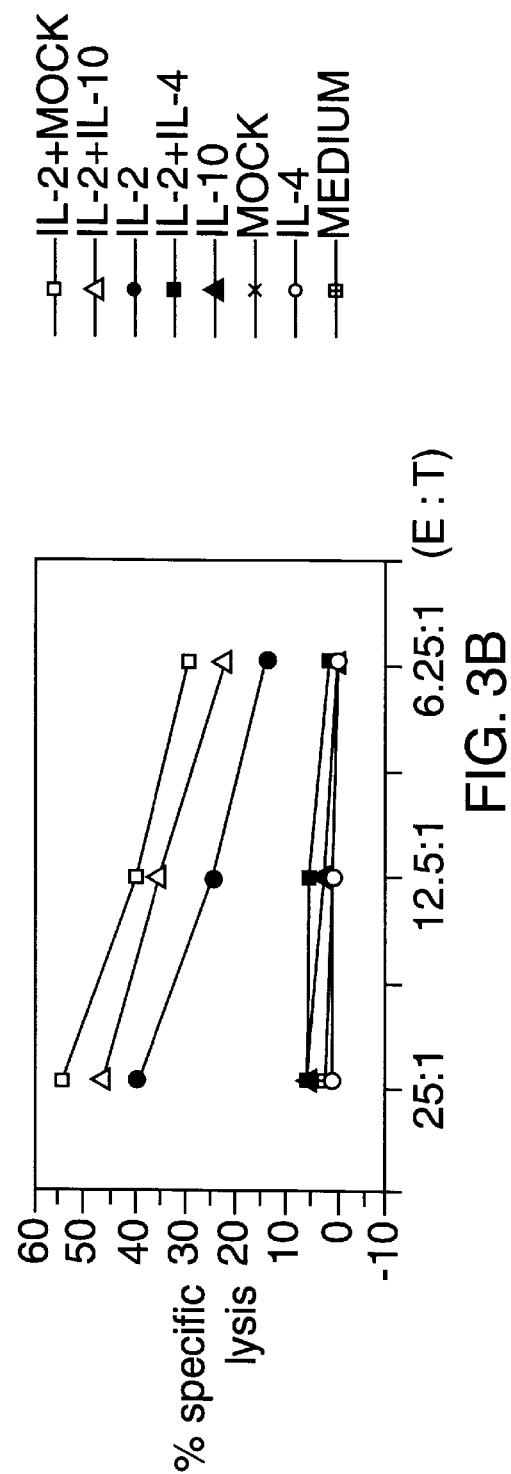

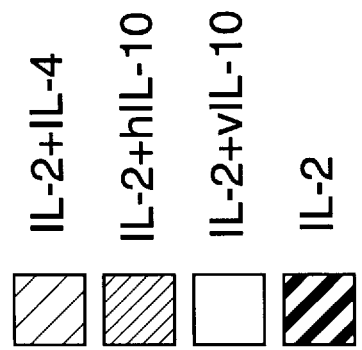
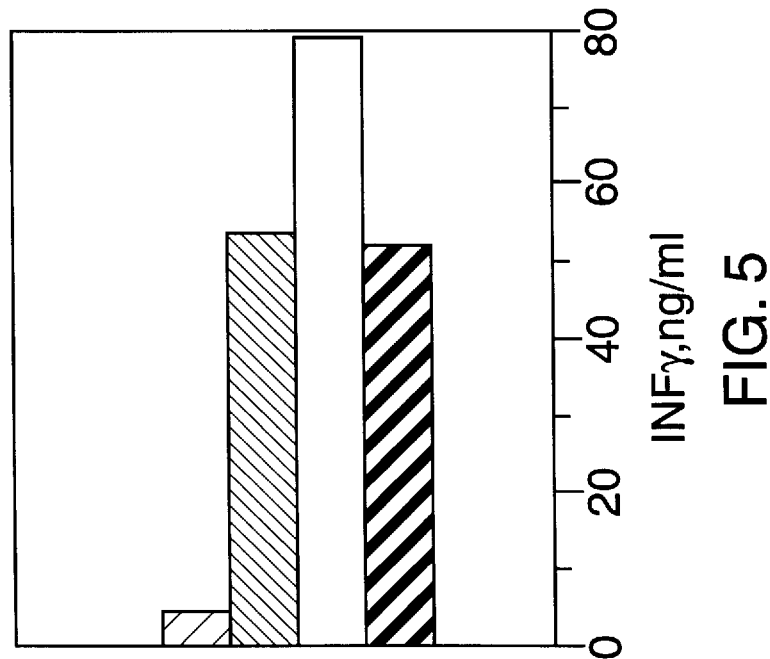
FIG. 5

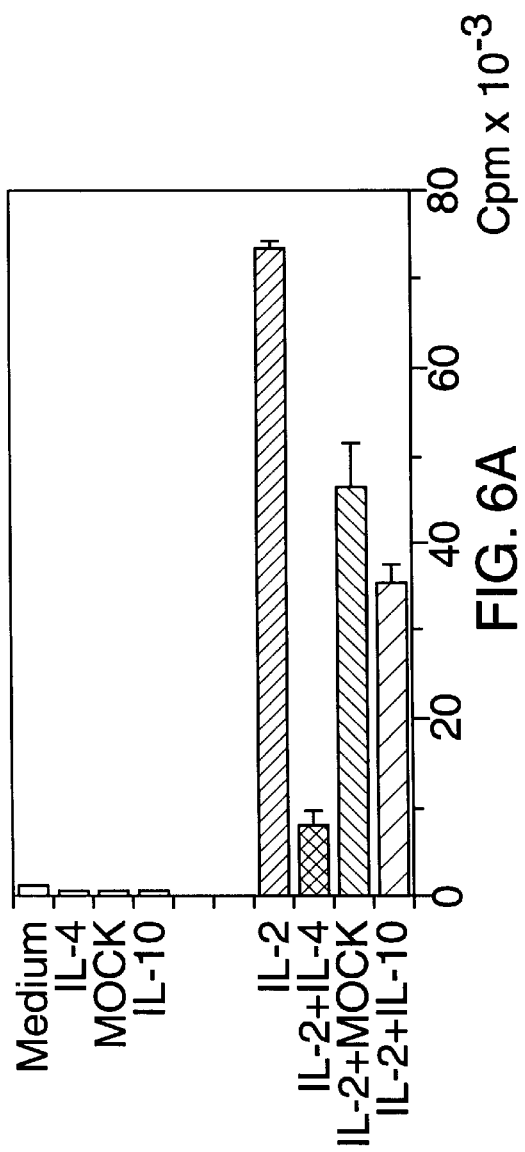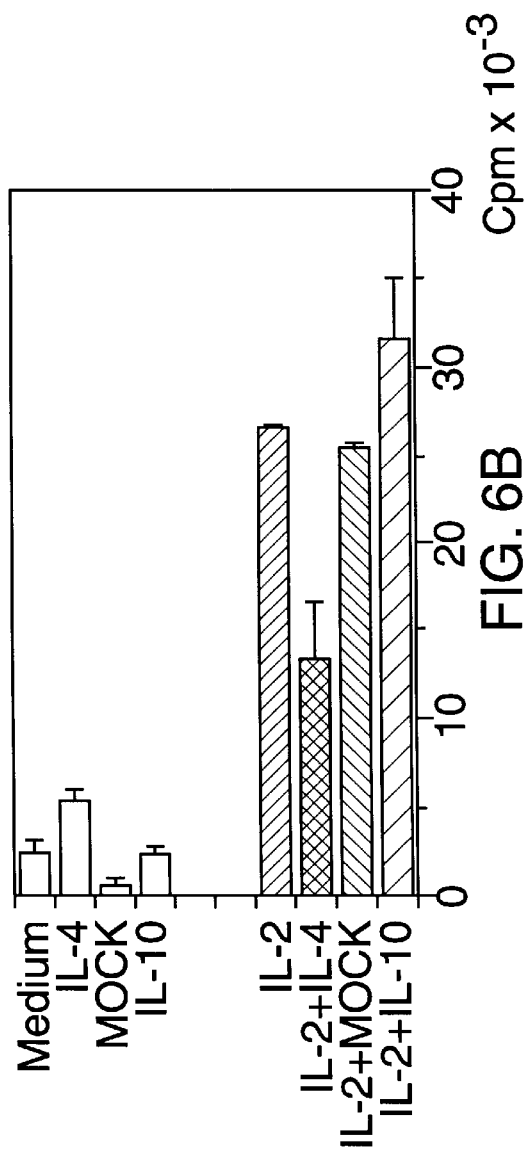

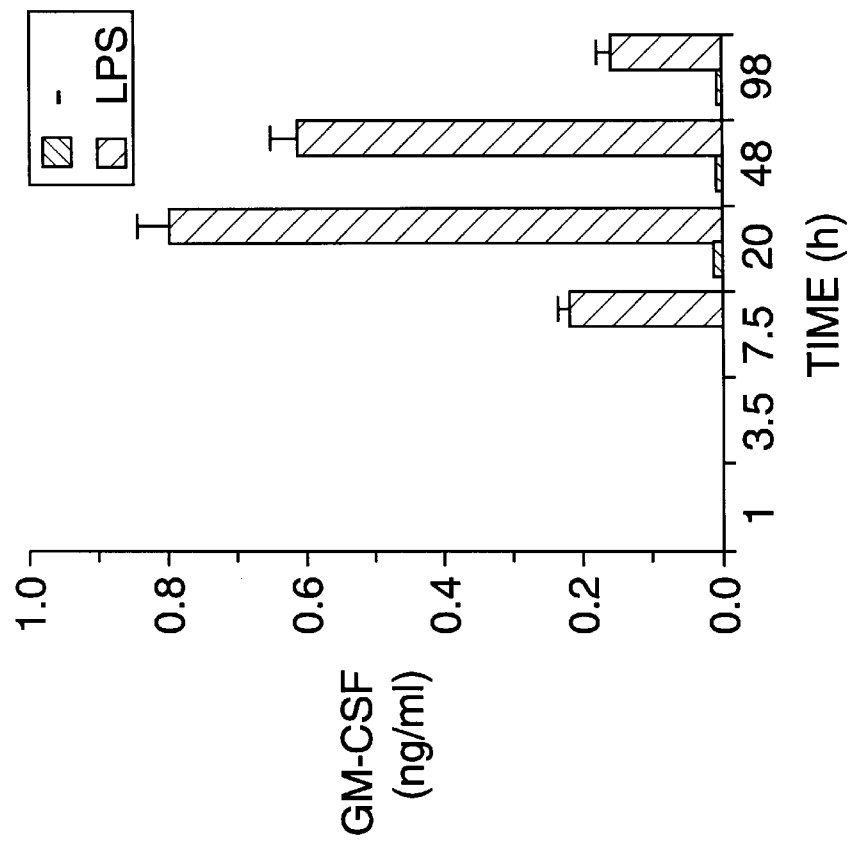
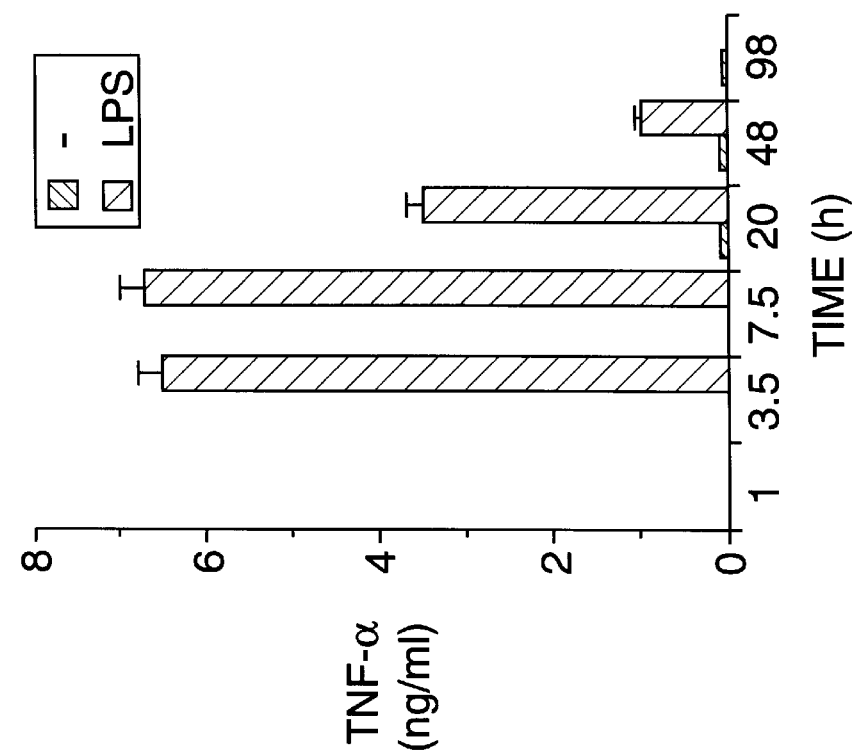
FIG. 9D
FIG. 9C

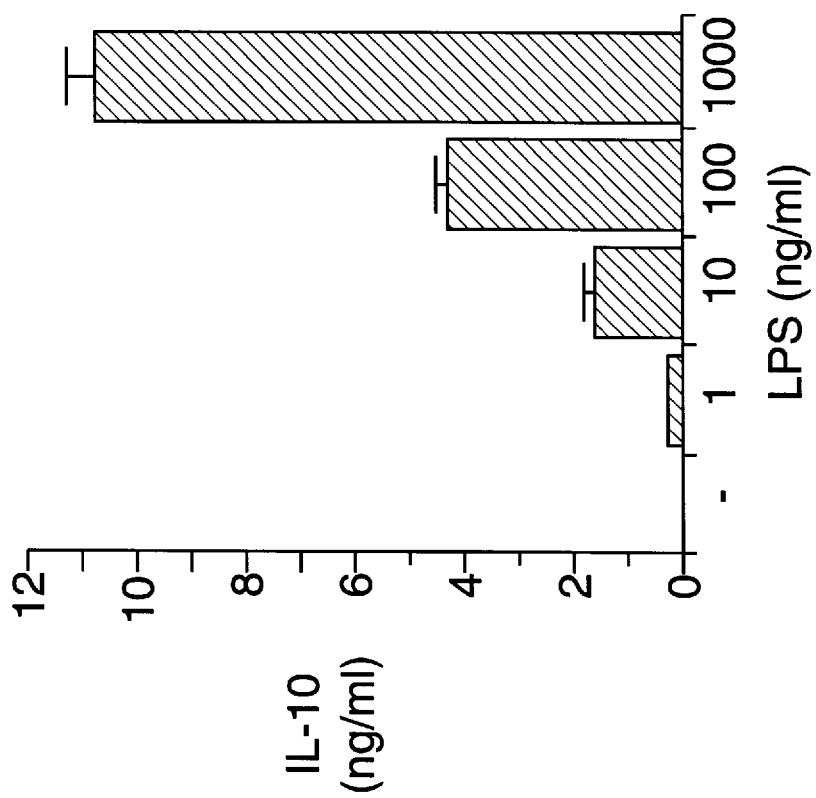

|  | LPS | LPS+IL-10 |
|---|---|---|
| IL-6 | 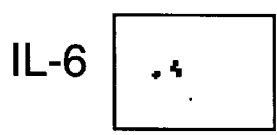 | |
| IL-8 | 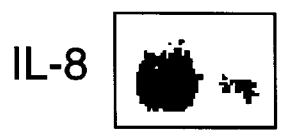 | |
| IL-10 | 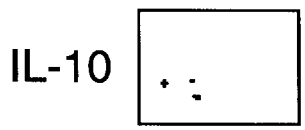 | |
| TGF-β | 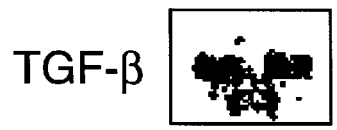 | |
| β-ACTIN |  | |
FIG. 14

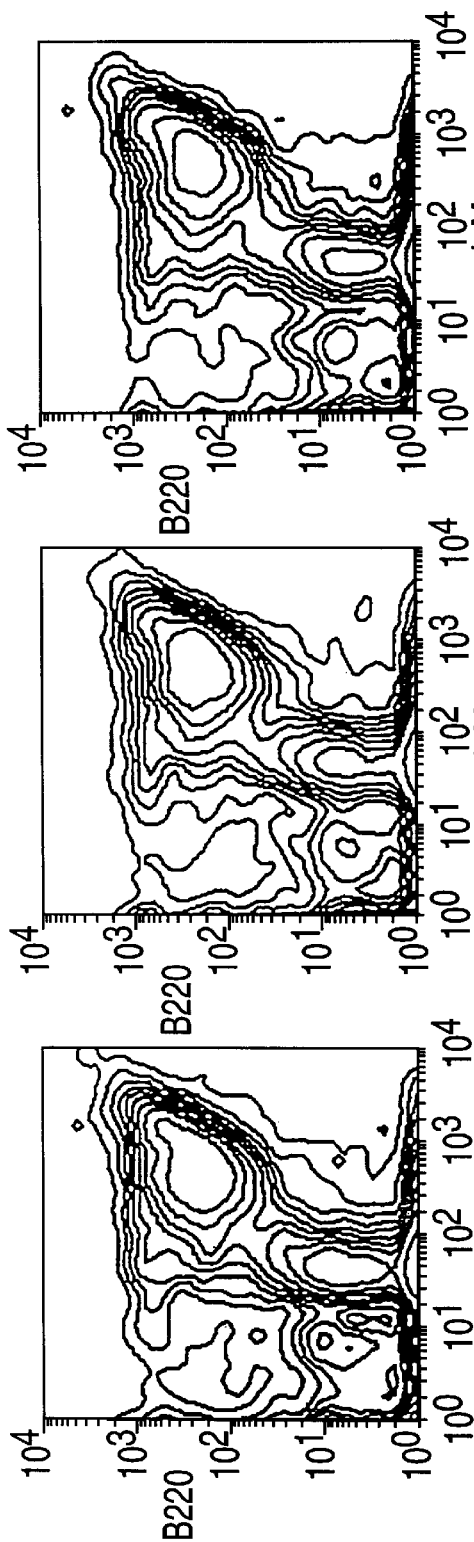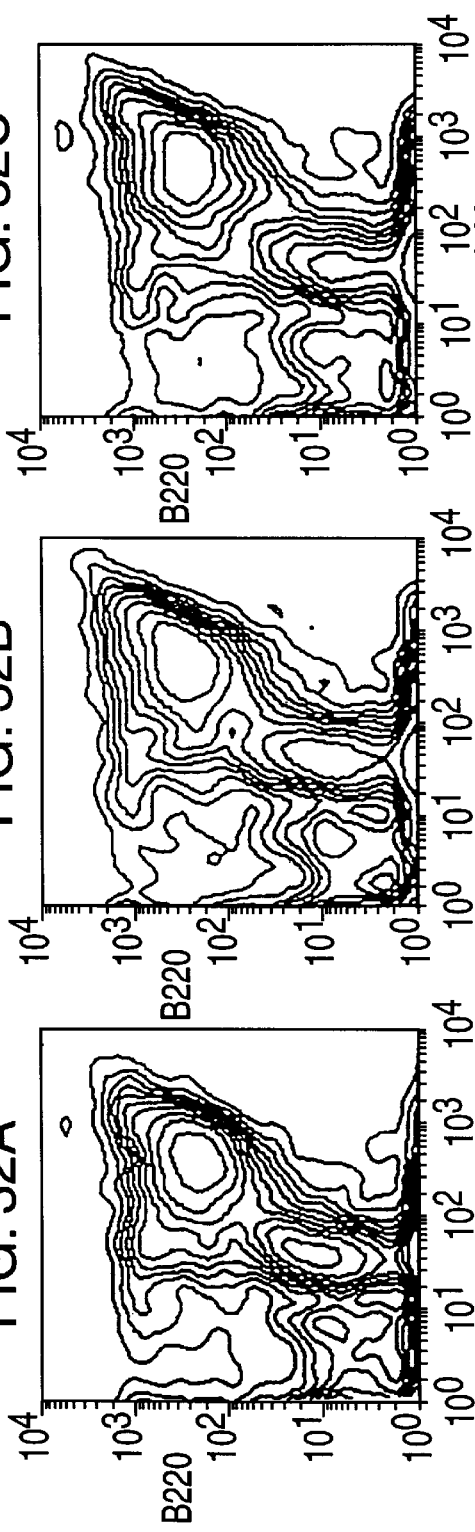

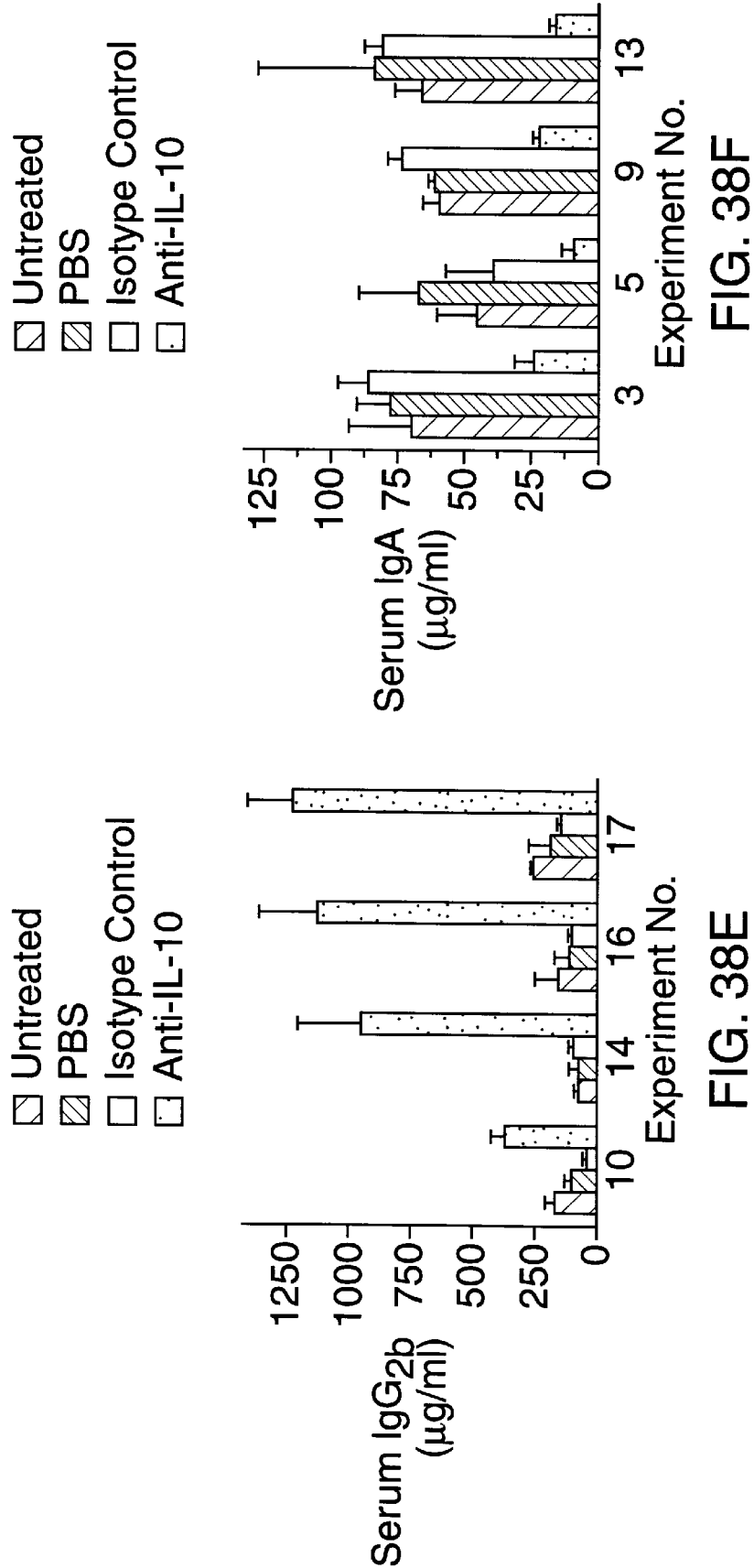

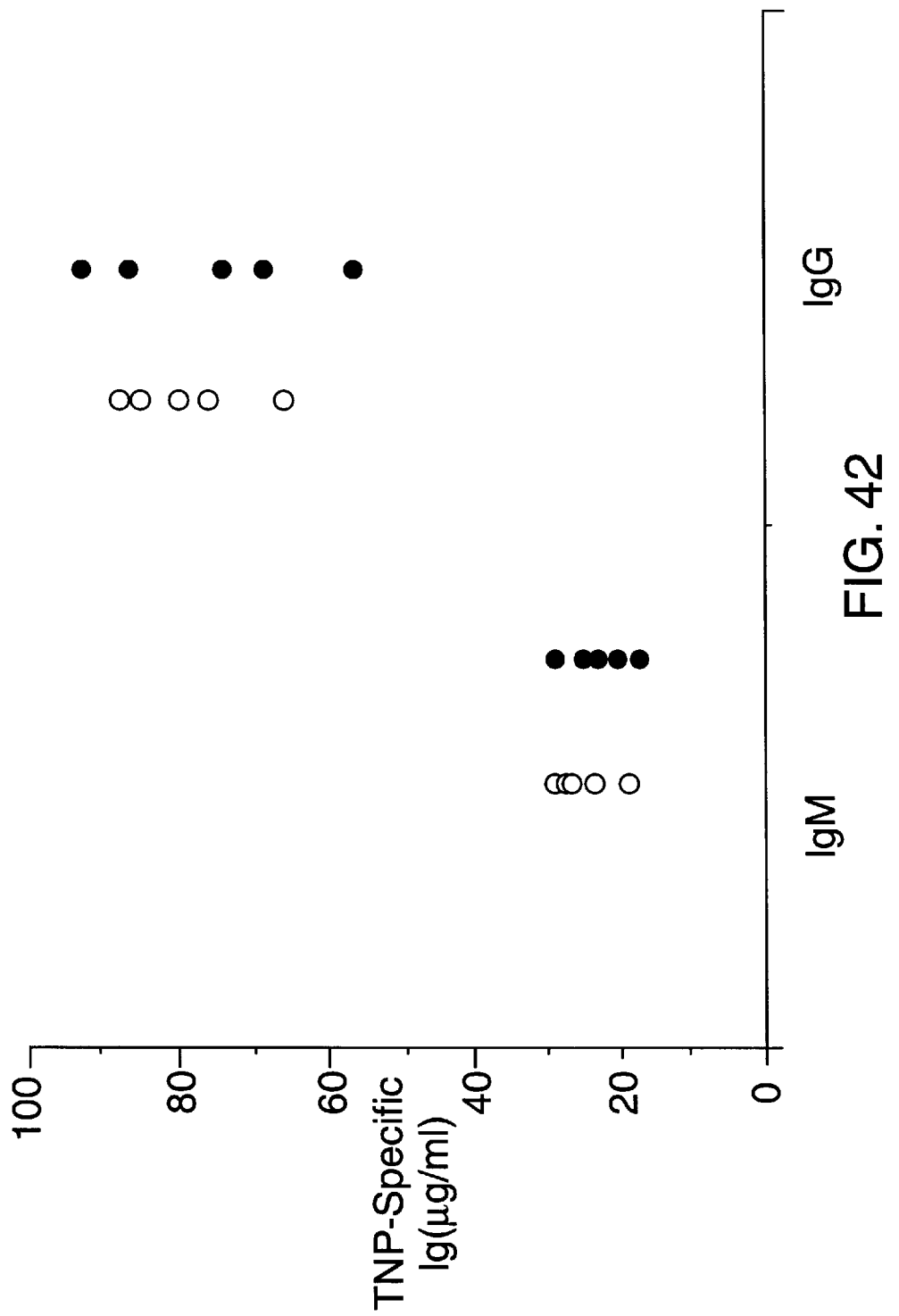

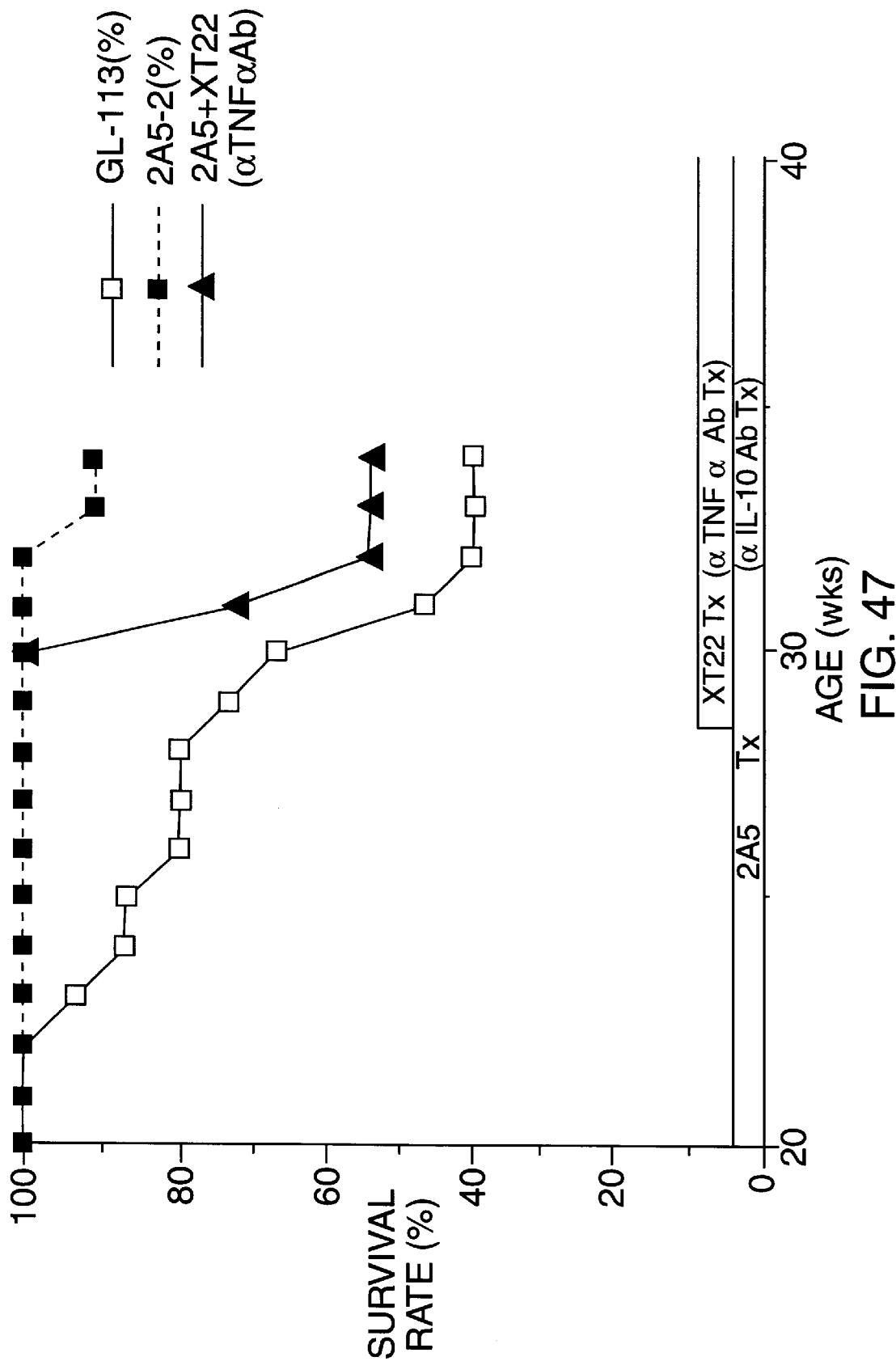

USE OF INTERLEUKIN-10 ANALOGS FOR ANTAGONISTS TO TREAT ENDOTOXIN- OR SUPERANTIGEN-INDUCED TOXICITY

This is a divisional of U.S. Ser. No. 08/410,654, filed Mar. 24, 1995, which is a continuation-in-part of U.S. Ser. No. 08/229,854 filed Apr. 19, 1994, now abandoned, which is a continuation-in-part of U.S. Ser. No. 07/926,853 filed Aug. 6, 1992, now abandoned, which is a continuation-in-part of U.S. Ser. No. 07/742,129 filed Aug. 6, 1991, now abandoned.

FIELD OF THE INVENTION

The present invention relates to a method of modulating immune responses, including treating septic- or toxic-shock-like symptoms, e.g., endotoxin or superantigen-induced toxicity, and autoimmune conditions by administering an effective amount of interleukin-10 (IL-10), or an analog or antagonist thereof.

BACKGROUND

Severe infections can result in profound physiological and metabolic alterations. Symptoms may vary, but include fever, hypotension, metabolic acidosis, tissue necrosis, widespread organ dysfunction, and, if not correctly treated, ultimately death. See, e.g., Berkow (ed) *The Merck Manual*, Rahway, N.J.; Weatherall et al. (eds) *Oxford Textbook of Medicine*, Oxford University Press, New York; Braunwald et al. (eds) *Harrison's Textbook of Internal Medicine*, McGraw-Hill, New York; or Wyngaarden et al. (eds) *Cecil's Textbook of Medicine*, Saunders Co., Philadelphia. Septic shock and toxic shock conditions are characteristic of different infection responses, and often display some or all of these symptoms.

Septic shock is a model of endotoxin-induced responses. Septic shock is caused by the presentation of an endotoxin, typically a lipopolysaccaride (LPS) component from gram-negative bacteria cell walls, to the immune system. Toxic shock is a model for superantigen-induced responses and is caused by release of a protein component from gram-positive bacteria cell membranes, e.g., staphylococcal enterotoxin B (SEB). Although both responses are initally caused by a microbial infection, the immune system responds differently to the microbial product causing their respective response.

In the shock response induced by endotoxin, e.g., LPS, a host-derived protein, tumor necrosis factor (TNF), has recently been demonstrated to induce many of the deleterious effects of gram negative septicemia. Passive immunization with antisera to TNF can prevent many of the lethal effects of gram negative bacteremia or endotoxemia. See, e.g., Tracey et al. (1986) *Science*, 234:470–474; Beutler et al. (1986) *Nature* 320:584–588; and Tracey et al. (1987) *Nature* 330:662–664. High serum levels of TNF have also been observed in several other infectious diseases, including meningococcal meningitis, malaria, and leishmaniasis. Many patients with high circulating levels of TNF have increased organ dysfunction along with higher mortality. See, e.g., Waage et al. (1987) *Lancet* 355–357; Girardin et al. (1988) *New Engl. J. Med.*, 319:397–400; Scuderi et al. (1988) *Lancet* 1364–1365; and Kern et al. (1989) *Am. J. Med.*, 87:139–143.

It has been reported that administration of TNF either to animals or to human subjects resulted in detectable interleukin-6 (IL-6) serum levels 2–6 hours later. McIntosh et al. (1989) *J. Immunol.* 143:162–167; Jablons et al, J. Immunol., Vol. 142, pg. 1542 (1989); and Brouckaert et al, J. Exp. Med., Vol. 169, pg. 2257 (1989). IL-6, also known as B cell stimulating factor-2, interferon-$\beta_2$, or hepatocyte stimulating factor, has been identified as a T cell-derived glycoprotein that causes B cell maturation. See, e.g., Kishimoto, *Blood* 74:1–10. More recently, IL-6 has been demonstrated to possess pleiotropic biological activities, including induction of acute phase proteins in hepatocytes and actions on hematopoietic progenitor cell and T cells. See, e.g., Geiger et al, *Eur. J. Immunol.*, Vol. 18, pg. 717 (1988); Marinjovic et al,. *J. Immunol.*, Vol. 1.42, pg. 808 (1989); Morrone et al, *J. Biol. Chem.*, Vol. 263, pg. 12554 (1988); and Perlmutter et al, J. Clin. Invest., Vol. 84, pg. 138 (1989). Starnes et al. *J . Immunol*, Vol. 145, pgs. 4185–4191 (1990), have shown that an antibody antagonist to IL-6 prolongs survival in mouse models of septic shock.

Staphylococcal enterotoxin B (SEB) is a superantigen, and can induce a toxic shock reaction. These reactions result from the activation of a substantial subset of T cells, leading to severe T cell-mediated systemic immune reactions. This response is characteristic of T cell mediated responses, for which IL-10, or its analogs or antagonists, will be useful to treat therapeutically. Mechanistically, the superantigens appear to interact directly with the V$\beta$ element of the T cell receptor and activate T cells with relatively little MHC II class specificity. See Herman et al. (1991) in *An. Rev. Immunol.* 9:745–772, Presently, septic conditions, such as septicemia, bacteremia, and the like, are typically treated with antimicrobial compounds. Septicemia is common in hospital settings, where bacterial infection often occurs from catheter insertions or surgical procedures. However, when such conditions are associated with shock there are no effective adjunctive measures in the therapy for ameliorating the shock syndrome that is caused, in part, by cytokines induced in response to the infection. See, e.g., Young (1985) pgs. 468–470, in Mandell et al., (eds) Principles and Practice of Infectious Diseases (2nd Ed.) John Wiley & Sons, New York. In particular, treatment with antibiotics leads to microbial death and release of bacterial products which cause the shock response.

Bacterial sepsis and related septic shock are frequently lethal conditions caused by infections which result from certain types of surgery, abdominal trauma, and immune suppression from cancer or transplantation therapy, or other medical conditions. In the United States, over 700,000 patients suffer septic-shock causing bacterial infections each year. Of these, some 160,000 develop septic shock symptoms, and some 50,000 die as a result of such. Toxic shock strikes fewer persons each year, but the seriousness of the response is typically far more life threatening.

In view of the serious consequences of these severe immunological responses to infection, effective techniques for treating microbially-induced shock, prophylactically or therapeutically, are desperately needed. The present invention provides compositions and methods of treating these and other severe immunological reactions.

SUMMARY OF THE INVENTION

The present invention provides methods of treating various microbially induced shock symptoms by administering an effective amount of interleukin-10, or analogs or antagonists thereof. The invention also includes pharmaceutical compositions comprising these interleukin-10 related compounds. Preferably, the interleukin-10 of the invention is selected from the group consisting of the mature polypeptides of the open reading frames defined by the following amino acid sequences:

| Met | His | Ser | Ser | Ala | Leu | Leu | Cys | Cys | Leu | Val | Leu | Leu | Thr | Gly |
|---|---|---|---|---|---|---|---|---|---|---|---|---|---|---|
| Val | Arg | Ala | Ser | Pro | Gly | Gln | Gly | Thr | Gln | Ser | Glu | Asn | Ser | Cys |
| Thr | His | Phe | Pro | Gly | Asn | Leu | Pro | Asn | Met | Leu | Arg | Asp | Leu | Arg |
| Asp | Ala | Phe | Ser | Arg | Val | Lys | Thr | Phe | Phe | Gln | Met | Lys | Asp | Gln |
| Leu | Asp | Asn | Leu | Leu | Leu | Lys | Glu | Ser | Leu | Leu | Glu | Asp | Phe | Lys |
| Gly | Tyr | Leu | Gly | Cys | Gln | Ala | Leu | Ser | Glu | Met | Ile | Gln | Phe | Tyr |
| Leu | Glu | Glu | Val | Met | Pro | Gln | Ala | Glu | Asn | Gln | Asp | Pro | Asp | Ile |
| Lys | Ala | His | Val | Asn | Ser | Leu | Gly | Glu | Asn | Leu | Lys | Thr | Leu | Arg |
| Leu | Arg | Leu | Arg | Arg | Cys | His | Arg | Phe | Leu | Pro | Cys | Glu | Asn | Lys |
| Ser | Lys | Ala | Val | Glu | Gln | Val | Lys | Asn | Ala | Phe | Asn | Lys | Leu | Gln |
| Glu | Lys | Gly | Ile | Tyr | Lys | Ala | Met | Ser | Glu | Phe | Asp | Ile | Phe | Ile |
| Asn | Tyr | Ile | Glu | Ala | Tyr | Met | Thr | Met | Lys | Ile | Arg | Asn | (SEQ ID NO: 1) | |
| and | | | | | | | | | | | | | | |
| Met | Glu | Arg | Arg | Leu | Val | Val | Thr | Leu | Gln | Cys | Leu | Val | Leu | Leu |
| Tyr | Leu | Ala | Pro | Glu | Cys | Gly | Gly | Thr | Asp | Gln | Cys | Asp | Asn | Phe |
| Pro | Gln | Met | Leu | Arg | Asp | Leu | Arg | Asp | Ala | Phe | Ser | Arg | Val | Lys |
| Thr | Phe | Phe | Gln | Thr | Lys | Asp | Glu | Val | Asp | Asn | Leu | Leu | Leu | Lys |
| Glu | Ser | Leu | Leu | Glu | Asp | Phe | Lys | Gly | Tyr | Leu | Gly | Cys | Gln | Ala |
| Leu | Ser | Glu | Met | Ile | Gln | Phe | Tyr | Leu | Glu | Glu | Val | Met | Pro | Gln |
| Ala | Glu | Asn | Gln | Asp | Pro | Glu | Ala | Lys | Asp | His | Val | Asn | Ser | Leu |
| Gly | Glu | Asn | Leu | Lys | Thr | Leu | Arg | Leu | Arg | Leu | Arg | Arg | Cys | His |
| Arg | Phe | Leu | Pro | Cys | Glu | Asn | Lys | Ser | Lys | Ala | Val | Glu | Gln | Ile |
| Lys | Asn | Ala | Phe | Asn | Lys | Leu | Gln | Glu | Lys | Gly | Ile | Tyr | Lys | Ala |
| Met | Ser | Glu | Phe | Asp | Ile | Phe | Ile | Asn | Tyr | Ile | Glu | Ala | Tyr | Met |
| Thr | Ile | Lys | Ala | Arg, | (SEQ ID NO: 2) | | | | | | | | | | wherein the standard three letter abbreviation is used to indicate L-amino acids, starting from the N-terminus. These two forms of IL-10 are sometimes referred to as human IL-10 (or human cytokine synthesis inhibitory factor) and viral IL-10 (or BCRF1), respectively. See, Moore et al. (1990) *Science* 248:1230–1234; Vieira et al. (1991) *Proc. Natl. Acad. Sci.* 88:1172–1176; Fiorentino et al. (1989) *J. Exp. Med.* 170:2081–2095; and Hsu et al. (1990) *Science* 250:830–832. Mutants of the natural protein sequence, e.g., allelic variants and muteins, including deletion and insertion variants, are alternative compositions whose uses are provided herein.

More preferably, the mature IL-10 used in the method of the invention is selected from the group consisting of:

event which leads to toxic shock-like syndromes. Conversely, Il-10 antagonists will enhance these same immune responses, and such enhancement is, in fact, desirable in other clinical settings, e.g., in certain tumor and autoimmune models.

BRIEF DESCRIPTION OF THE FIGURES

FIG. 3 is a graphical representation of the effects of IL-4, hIL-10, and vIL-10 on IL-2-induced LAK activity in PBMC.

| Ser | Pro | Gly | Gln | Gly | Thr | Gln | Ser | Glu | Asn | Ser | Cys | Thr | His | Phe |
|---|---|---|---|---|---|---|---|---|---|---|---|---|---|---|
| Pro | Gly | Asn | Leu | Pro | Asn | Met | Leu | Arg | Asp | Leu | Arg | Asp | Ala | Phe |
| Ser | Arg | Val | Lys | Thr | Phe | Phe | Gln | Met | Lys | Asp | Gln | Leu | Asp | Asn |
| Leu | Leu | Leu | Lys | Glu | Ser | Leu | Leu | Glu | Asp | Phe | Lys | Gly | Tyr | Leu |
| Gly | Cys | Gln | Ala | Leu | Ser | Glu | Met | Ile | Gln | Phe | Tyr | Leu | Glu | Glu |
| Val | Met | Pro | Gln | Ala | Glu | Asn | Gln | Asp | Pro | Asp | Ile | Lys | Ala | His |
| Val | Asn | Ser | Leu | Gly | Glu | Asn | Leu | Lys | Thr | Leu | Arg | Leu | Arg | Leu |
| Arg | Arg | Gys | His | Arg | Phe | Leu | Pro | Gys | Glu | Asn | Lys | Ser | Lys | Ala |
| Val | Glu | Gln | Val | Lys | Asn | Ala | Phe | Asn | Lys | Leu | Gln | Glu | Lys | Gly |
| Ile | Tyr | Lys | Ala | Met | Ser | Glu | Phe | Asp | Ile | Phe | Ile | Asn | Tyr | Ile |
| Glu | Ala | Tyr | Met | Thr | Met | Lys | Ile | Arg | Asn | (SEQ ID NO: 3) | | | | |
| and | | | | | | | | | | | | | | |
| Thr | Asp | Gln | Cys | Asp | Asn | Phe | Pro | Gln | Met | Leu | Arg | Asp | Leu | Arg |
| Asp | Ala | Phe | Ser | Arg | Val | Lys | Thr | Phe | Phe | Gln | Phr | Lys | Asp | Glu |
| Val | Asp | Asn | Leu | Leu | Leu | Lys | Glu | Ser | Leu | Leu | Glu | Asp | Phe | Lys |
| Gly | Tyr | Leu | Gly | Cys | Gln | Ala | Leu | Ser | Glu | Met | Ile | Gln | Phe | Tyr |
| Leu | Glu | Glu | Val | Met | Pro | Gln | Ala | Glu | Asn | Gln | Asp | Pro | Glu | Ala |
| Lys | Asp | His | Val | Asn | Ser | Leu | Gly | Glu | Asn | Leu | Lys | Thr | Leu | Arg |
| Leu | Arg | Leu | Arg | Arg | Cys | His | Arg | Phe | Leu | Pro | Cys | Glu | Asn | Lys |
| Ser | Lys | Ala | Val | Glu | Gln | Ile | Lys | Asn | Ala | Phe | Asn | Lys | Leu | Gln |
| Glu | Lys | Gly | Ile | Tyr | Lys | Ala | Met | Ser | Glu | Phe | Asp | Ile | Phe | Ile |
| Asn | Tyr | Ile | Glu | Ala | Tyr | Met | Thr | Ile | Lys | Ala | Arg. | (SEQ ID NO: 4) | | |

The present invention is based, in part, on the discovery that IL-10 inhibits both the synthesis of several cytokines that mediate undesirable inflammatory reactions (e.g. septic shock), and the activation of T cells by superantigens, an FIG. 5 is a graphical representation of the effects of IL-4, hIL-10, and vIL-10 on IL-2-induced IFNγ synthesis in purified NK cells.

FIG. 6 is a graphical representation of the effects of IL-4 and hIL-10 on IL-2-induced proliferation of purified NK cells (FIG. 6A) and PBMC (FIG. 6B).

Figure 7A:
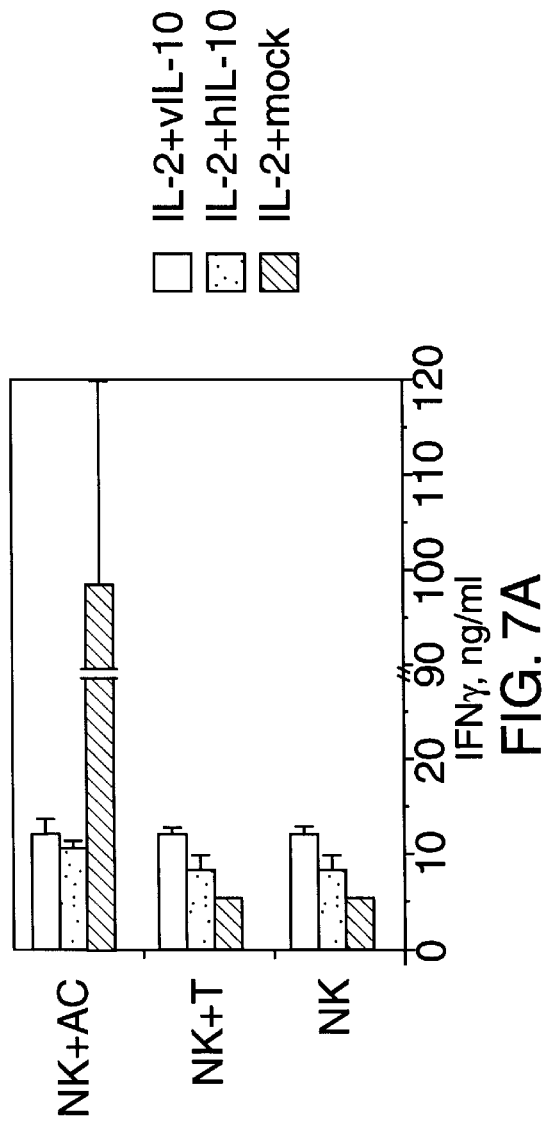
Figure 7B:
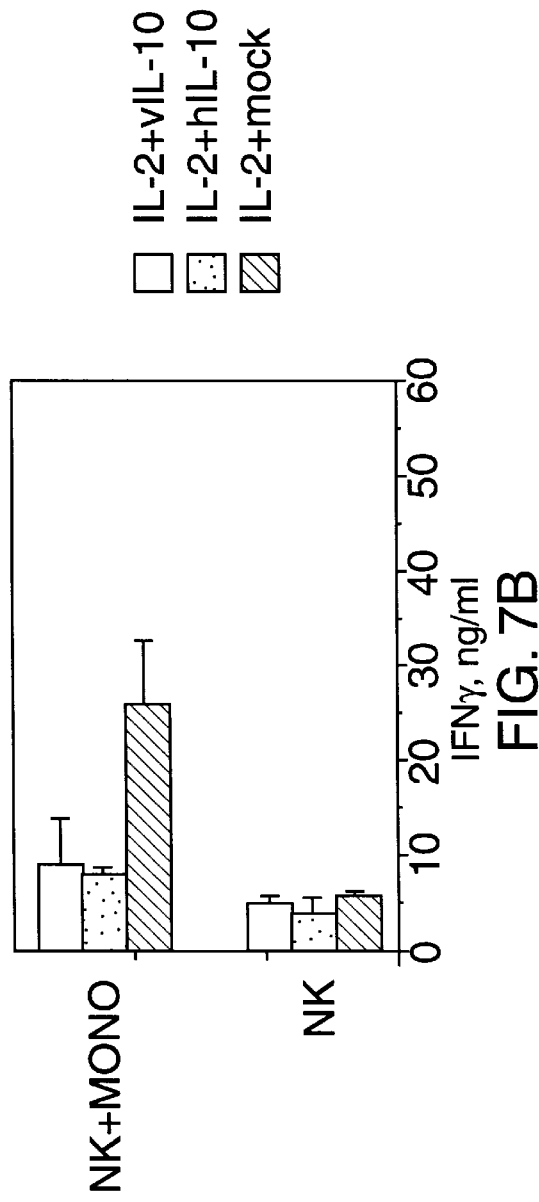

FIG. 7 is a graphical representation of the effects of added adherent cells and T cells (FIG. 7A) and monocytes (FIG. 7B) on IL-10-mediated inhibition of IL-2-induced IFNγ synthesis in purified NK cells.

Figure 8:
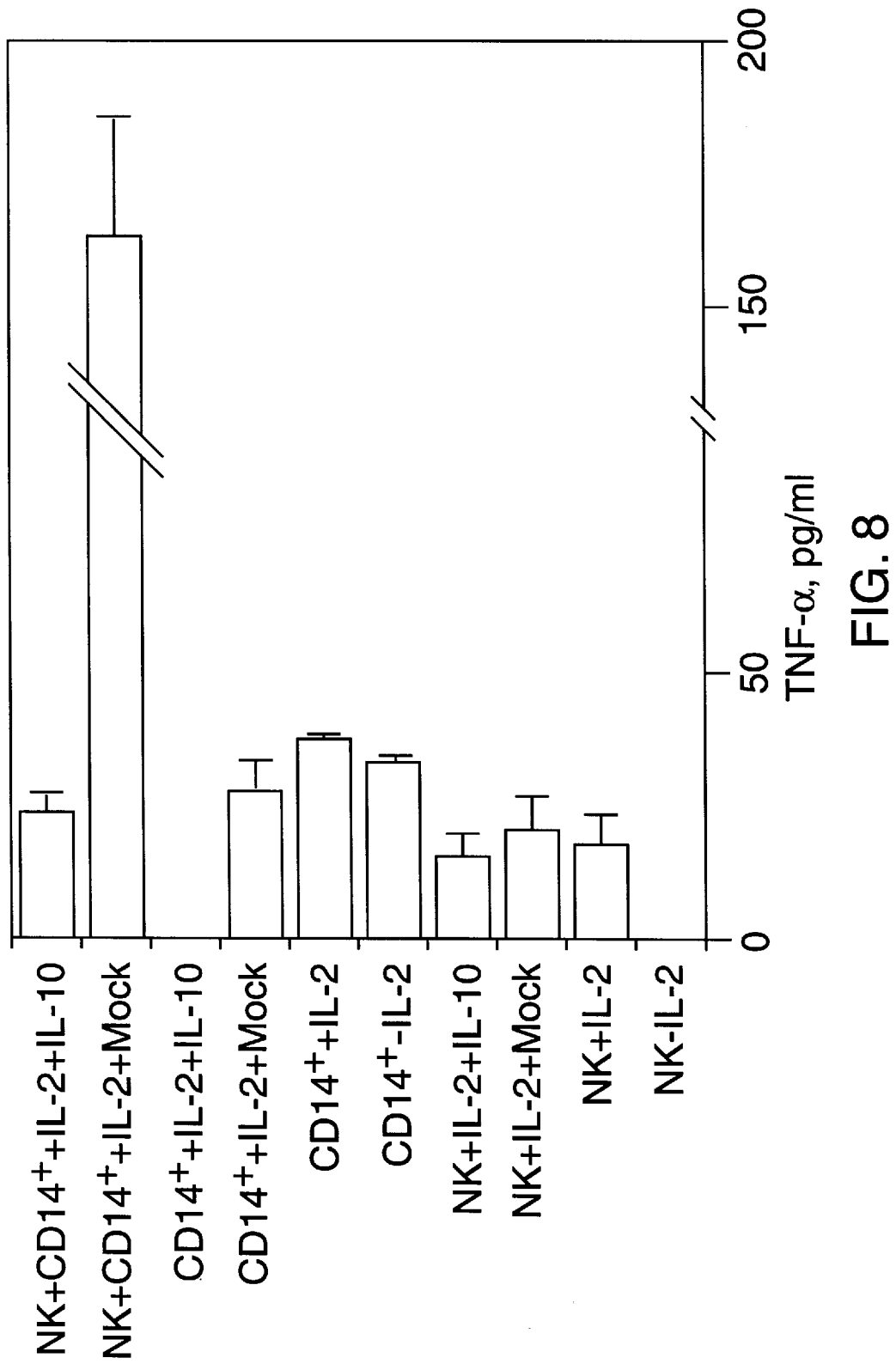

FIG. 8 is a graphical representation of the effects of IL-10 on IL-2-induced TNFα synthesis in NK cells, CD14+ cells, and in a mixture of the two.

Figure 9B:
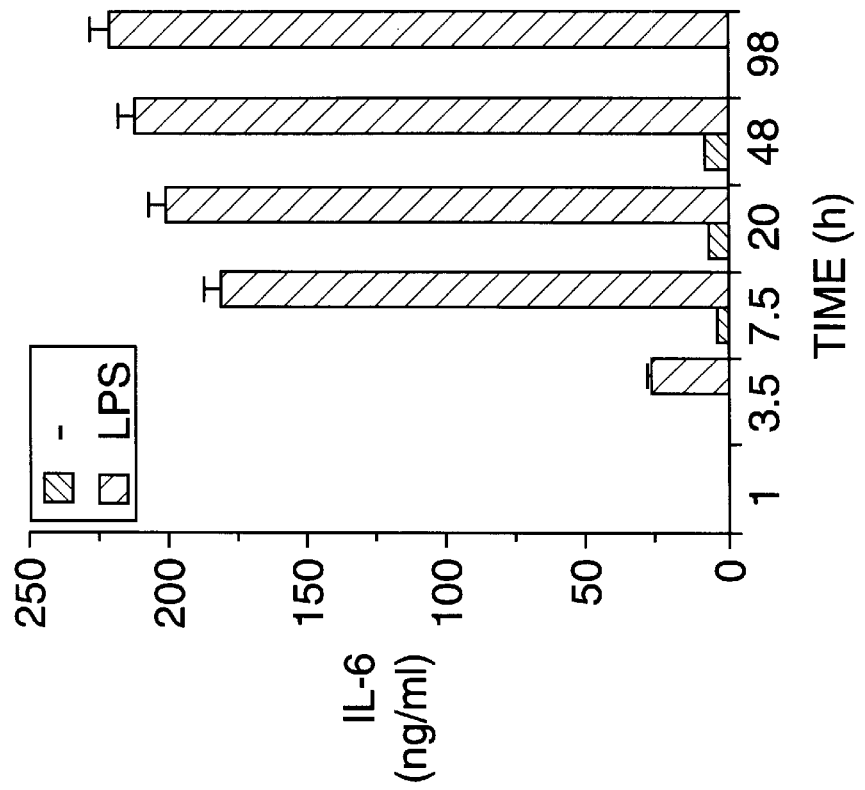
Figure 9A:
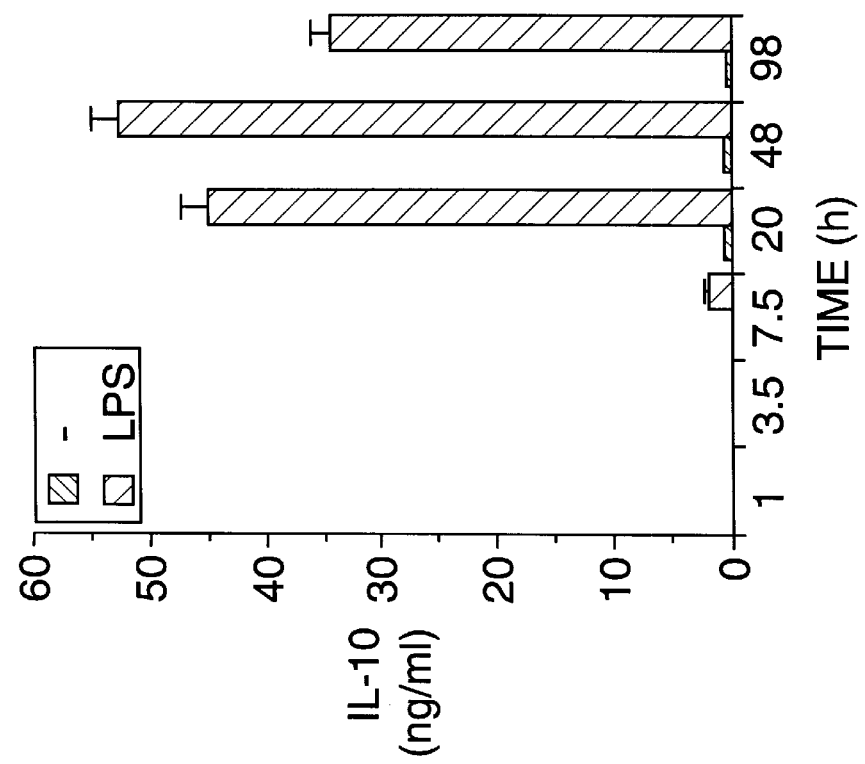
Figure 11A:
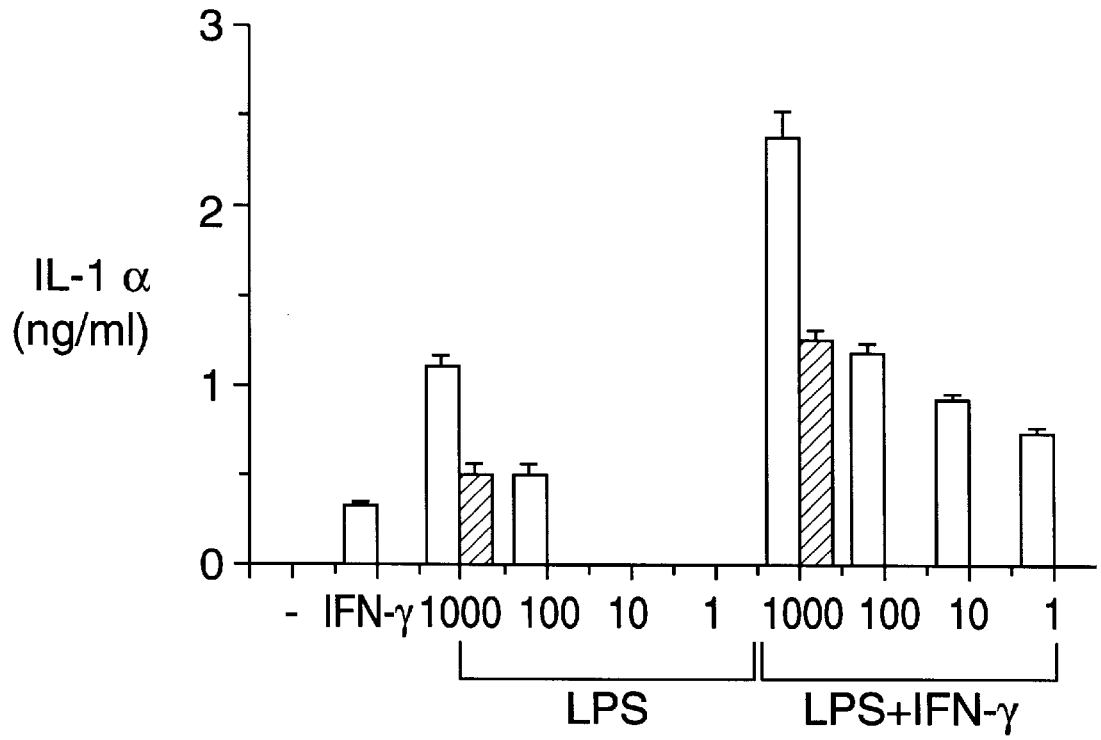
Figure 11B:
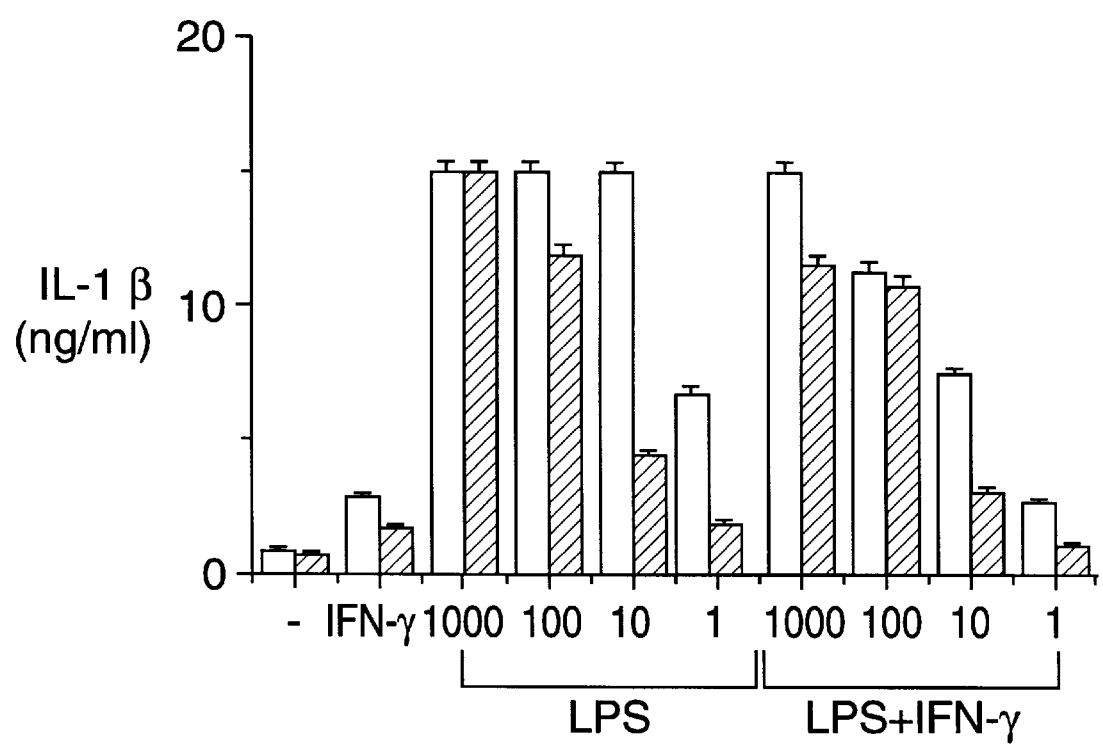
Figure 11C:
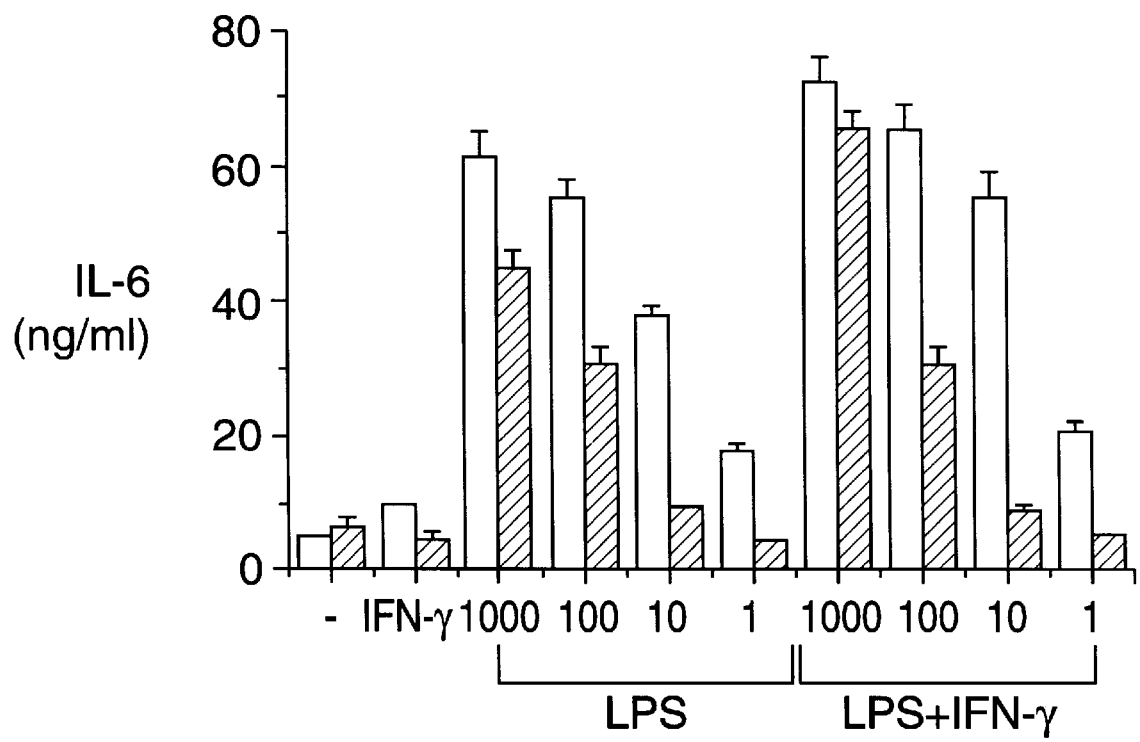
Figure 11D:
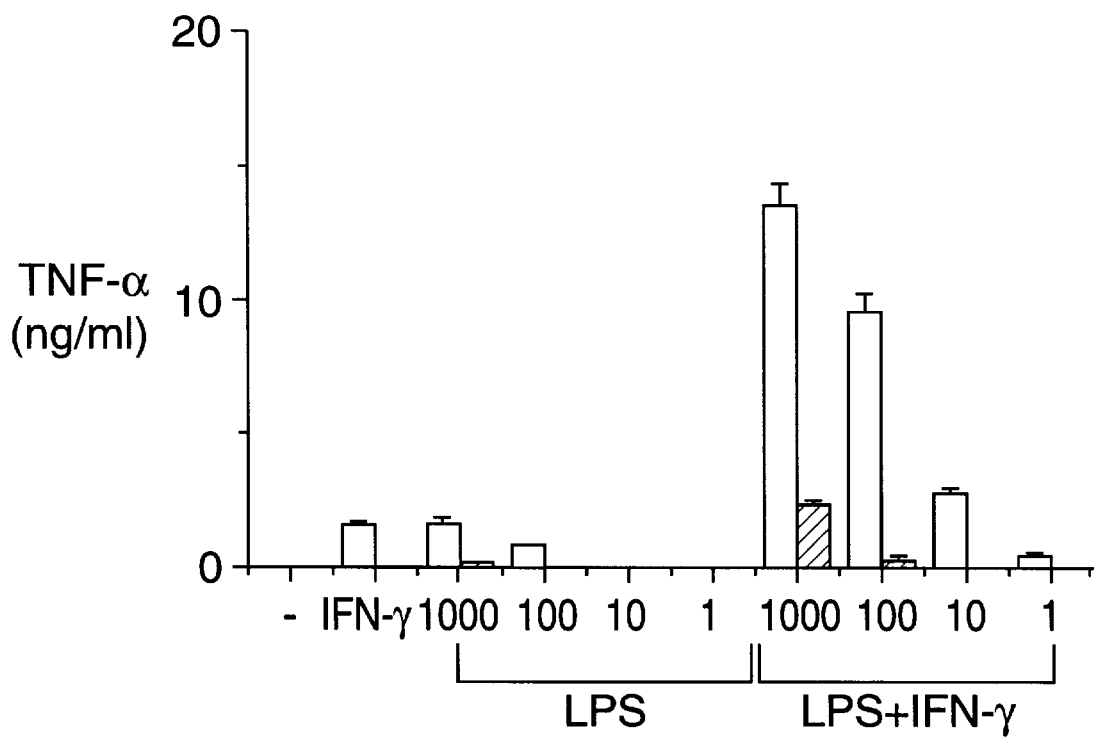
Figure 11E:
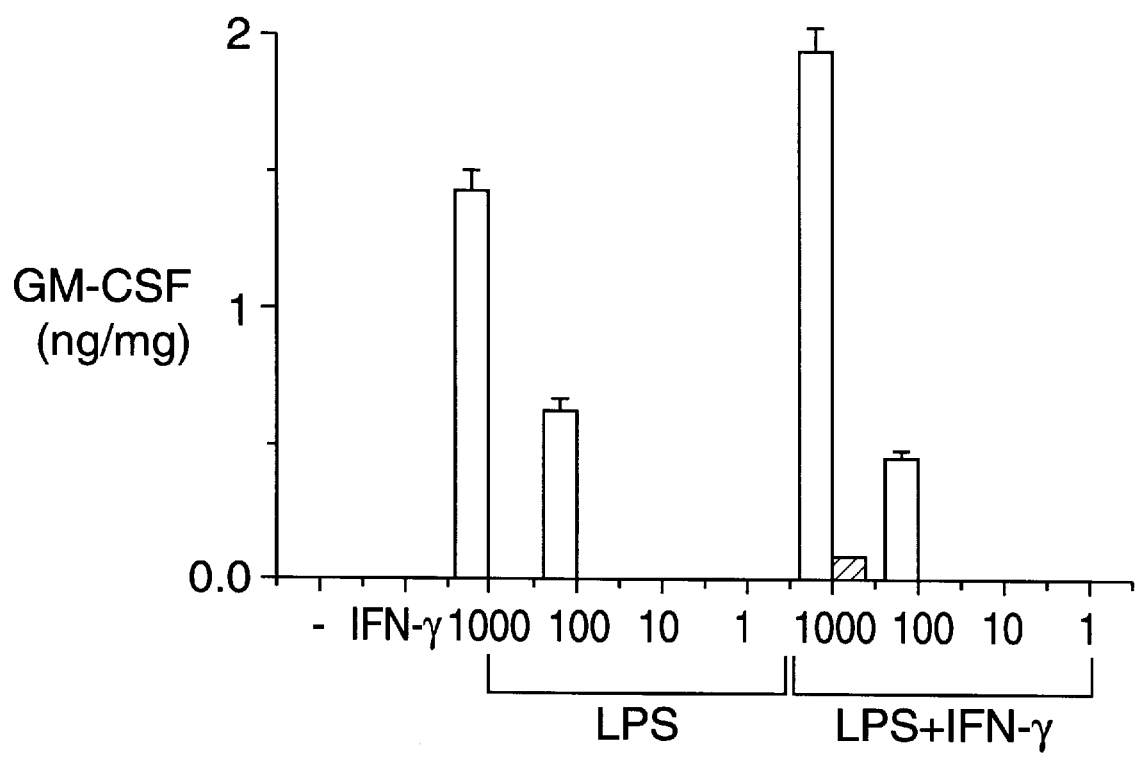

FIG. 9 is a graphical representation of the kinetics of IL-10 (FIG. 9A), IL-6 (FIG. 9B), TNFα (FIG. 9C), and GM-CSF (FIG. 9D) production by human monocytes which had been activated by LPS.

FIG. 10 is a graphical representation of the production of IL-10 by human monocytes in response to increasing concentrations of LPS.

FIG. 11 is a graphical representation of the effect of IL-10 on the production of IL-1α (FIG. 11A), IL-1β (FIG. 11B), IL-6 (FIG. 11C), TNFα (FIG. 11D), and GM-CSF (FIG. 11E) by monocytes activated by IFNγ, LPS, or LPS and IFNγ.

Figure 12A:
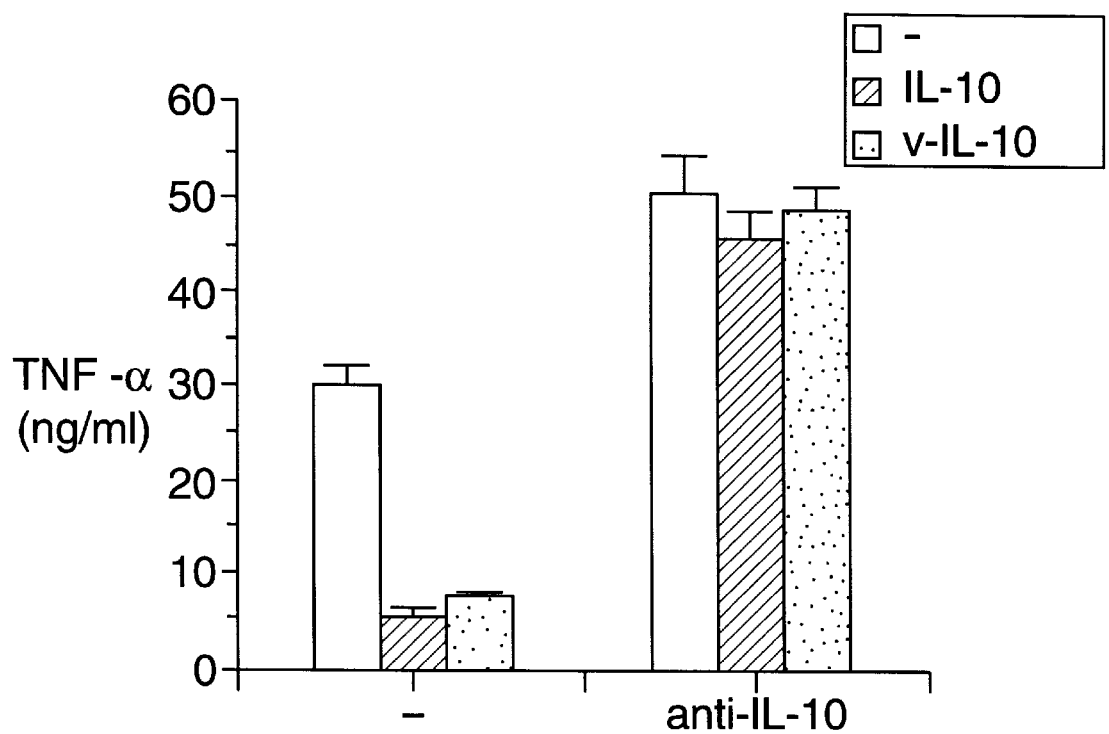
Figure 12B:
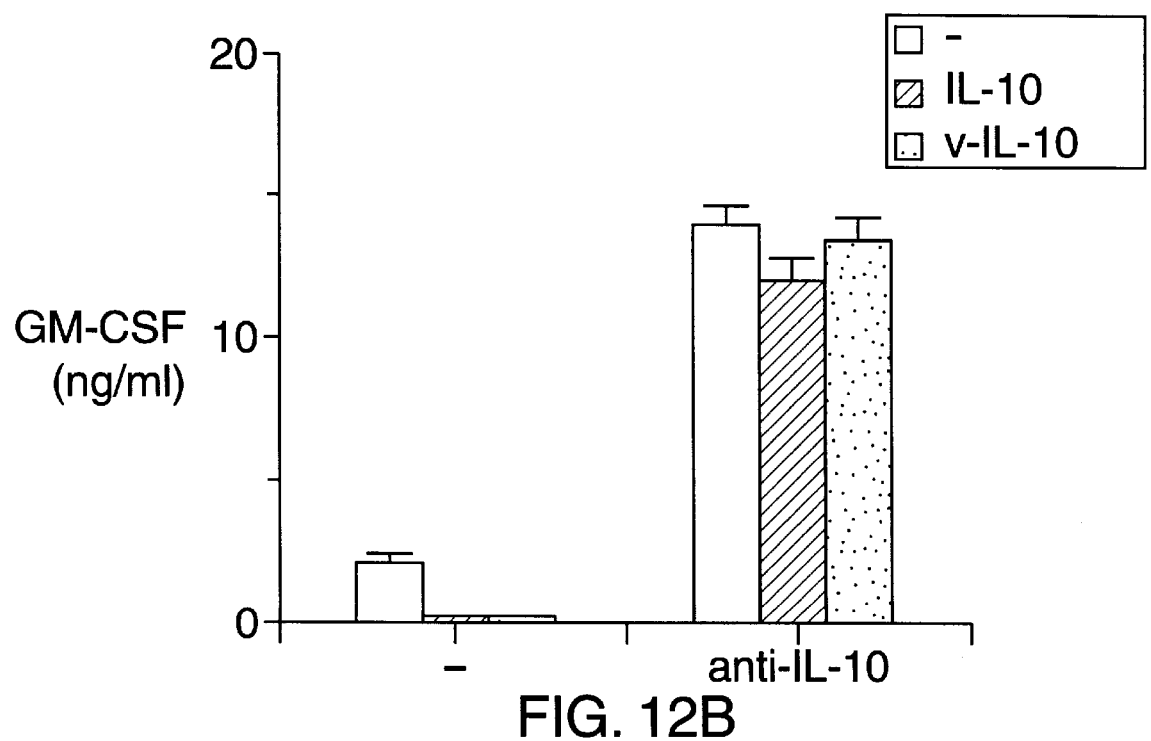

FIG. 12 is a graphical representation of the effect of human or viral IL-10 on the production of TNFα (FIG. 12A) and GM-CSF (FIG. 12B) by LPS-activated monocytes.

Figure 13:
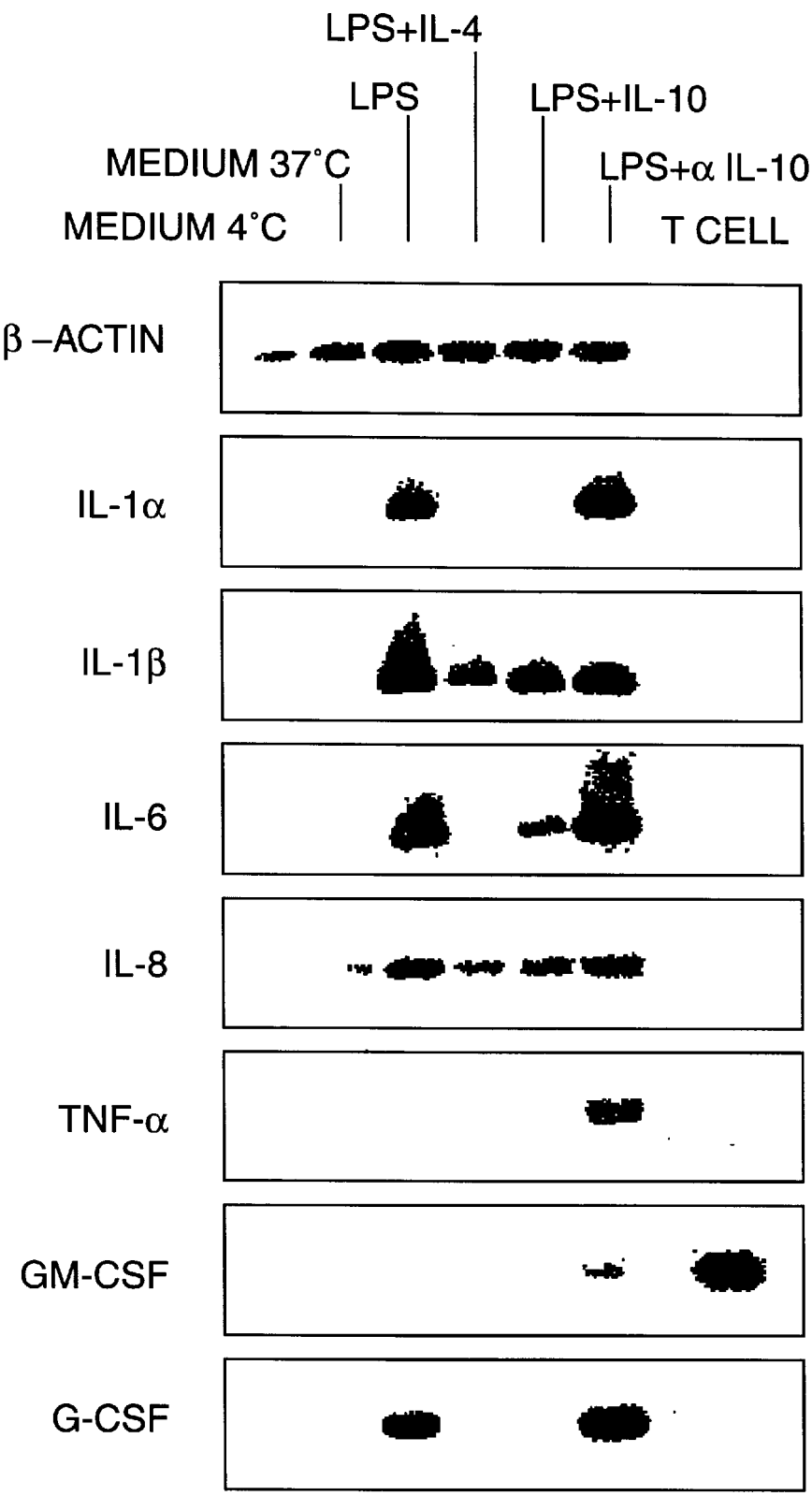

FIG. 13 is a graphical representation of the effect of exogenous IL-10, endogenously produced IL-10, and IL-4 on the expression of various cytokine-specific mRNA levels by human monocytes activated by LPS.

FIG. 14 is a graphical representation of the effects of IL-10 on the expression of various cytokine-specific mRNA levels by human monocytes activated by LPS.

Figure 15:
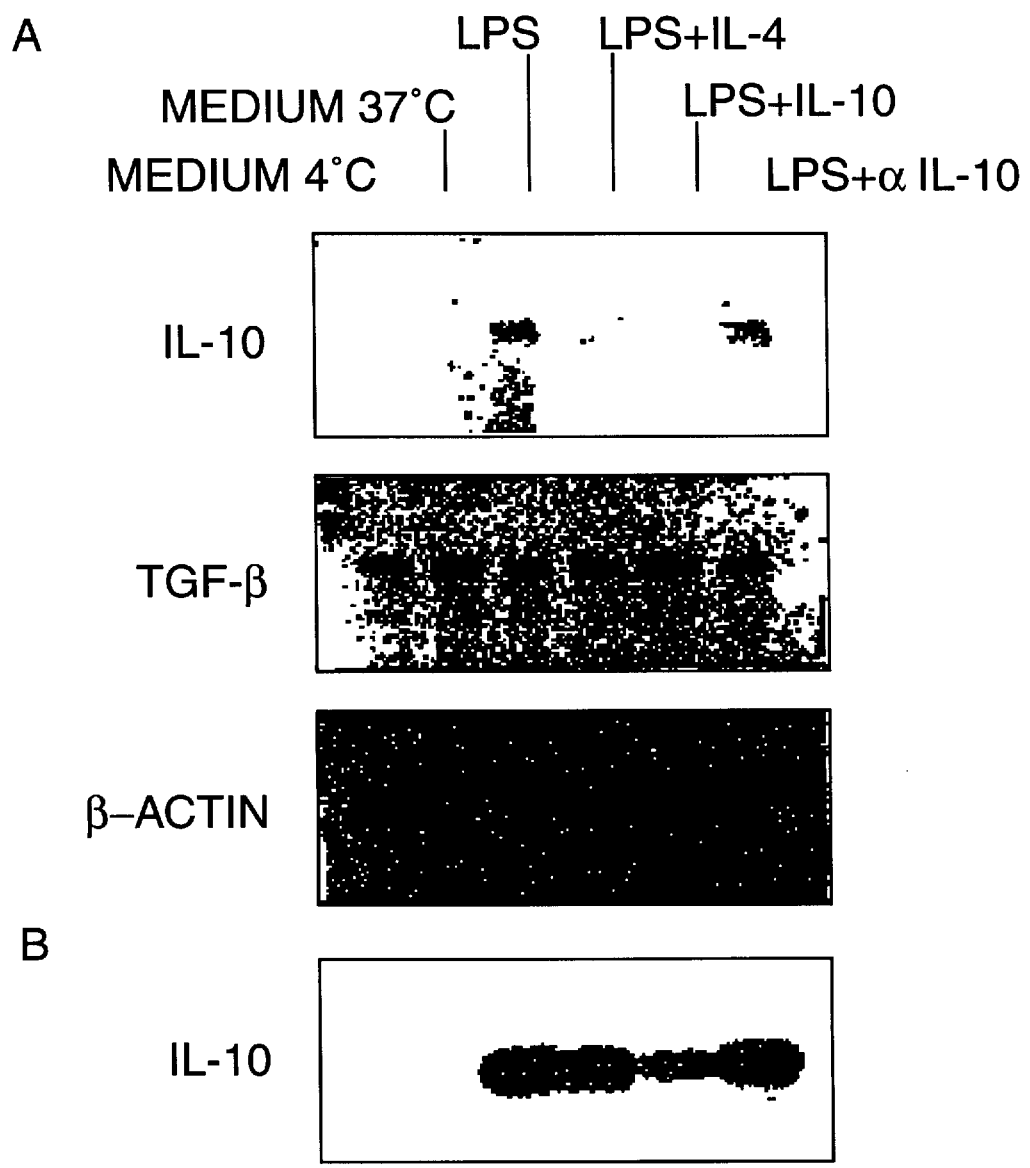
Figure 16A:
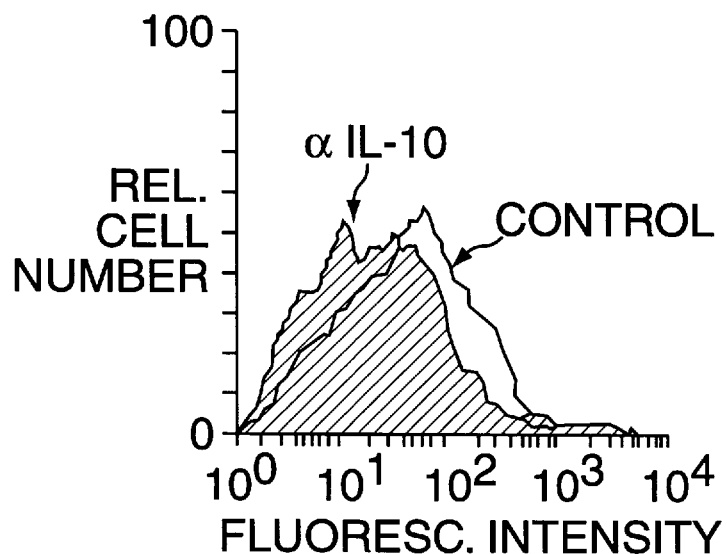
Figure 16B:
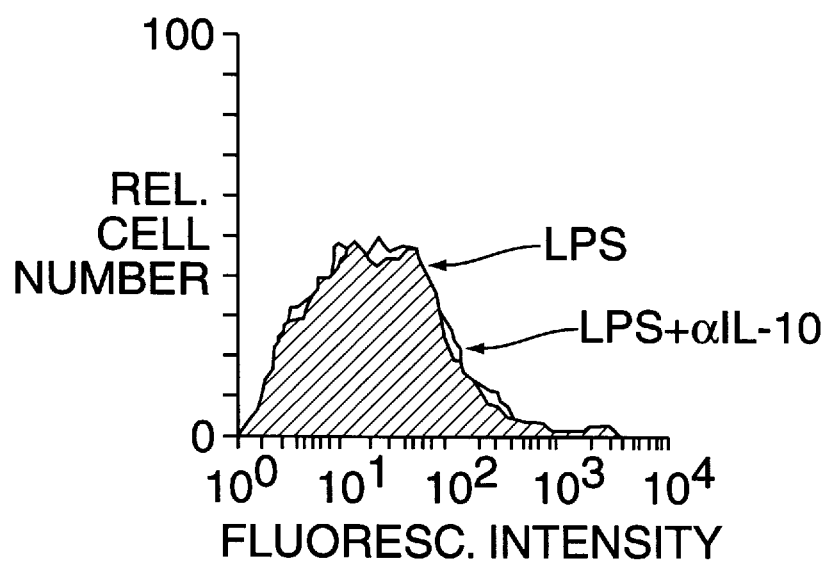
Figure 16C:
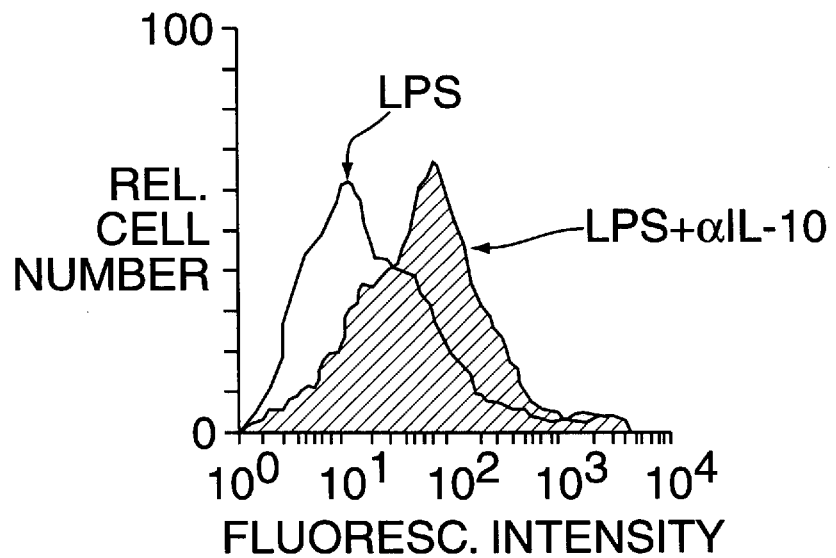
Figure 16D:
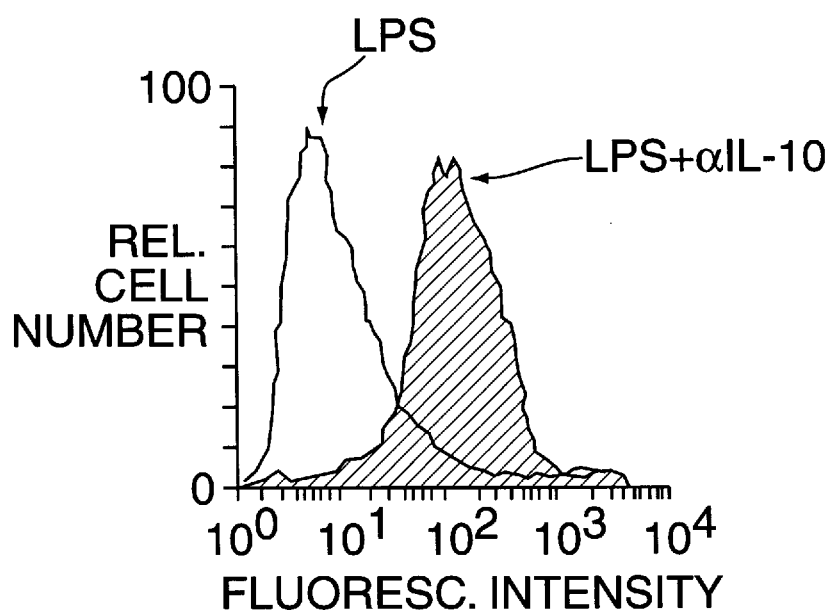

FIG. 15 is a graphical representation of the effects of exogenous IL-10, endogenously produced IL-10, and IL-4 on the expression of IL-10, TGFβ and β-actin specific mRNA levels by human monocytes activated by LPS.

FIG. 16 is a graphical representation of the effects of endogenously produced IL-10, in the presence or absence of a neutralizing anti-IL-10 monoclonal antibody (αIL-10) on class II MHC expression by human monocytes which had been activated with LPS. The data in FIGS. 16A–D were produced in the presence of 0, 0.1, 10, and 1000 ng/ml LPS, respectively.

Figure 17A:
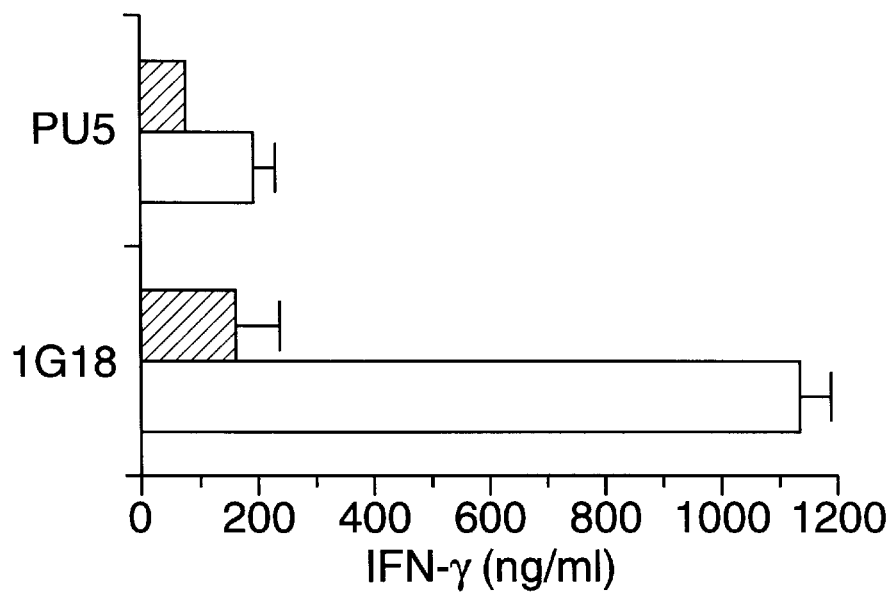
Figure 17B:
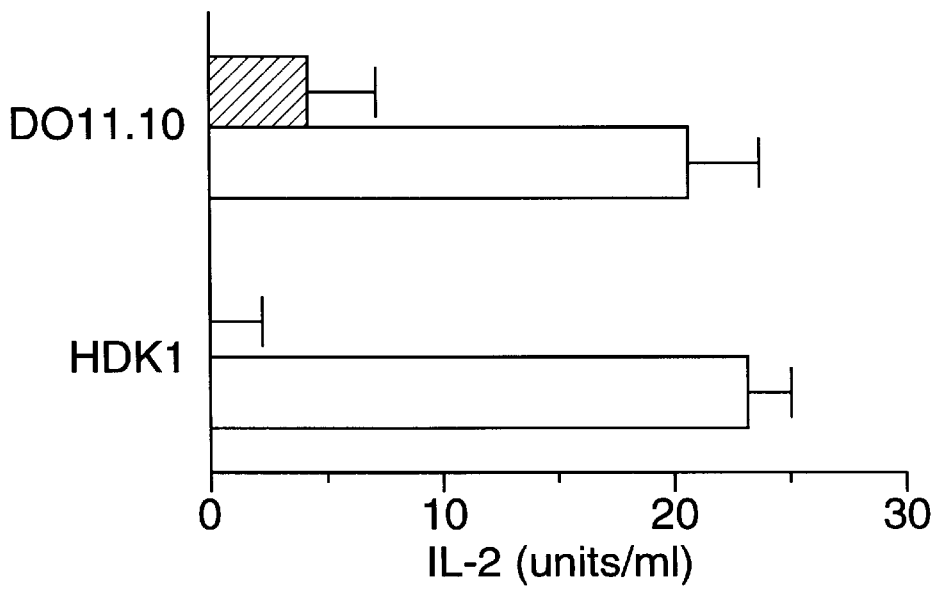

FIG. 17 is a graphical representation of effect of IL-10 on the APC function of macrophage cell lines. FIG. 17A shows the effect of IL-10 on the production of IFNγ by Th1 cells when the IFN-γ activated 1G18.LA and PU5.1 macrophage cell lines are used as APC. FIG. 17B shows the effect of IL-10 on antigen-specific IL-2 production, in the presence of antigens and activated 1G18.LA macrophages, by HDK.1 Th1 cells or by DO11.10 T cell hybridoma cells. The presence of IL-10 is indicated by ◨, the absence by (■).

Figure 18A:
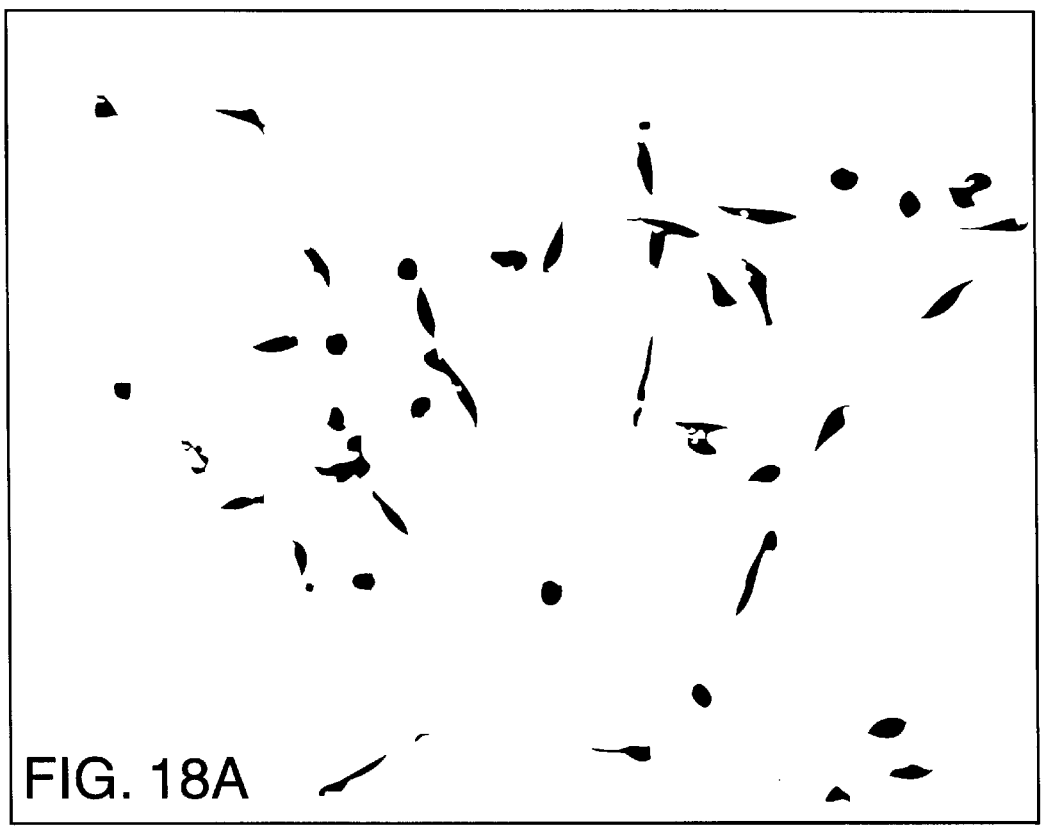
Figure 18B:
Figure 19A:
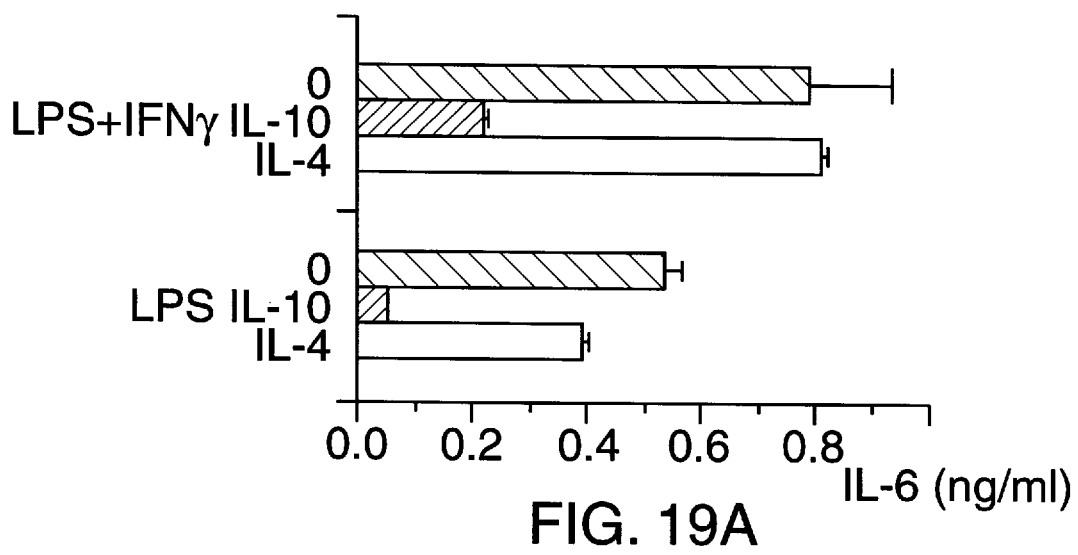
Figure 19B:
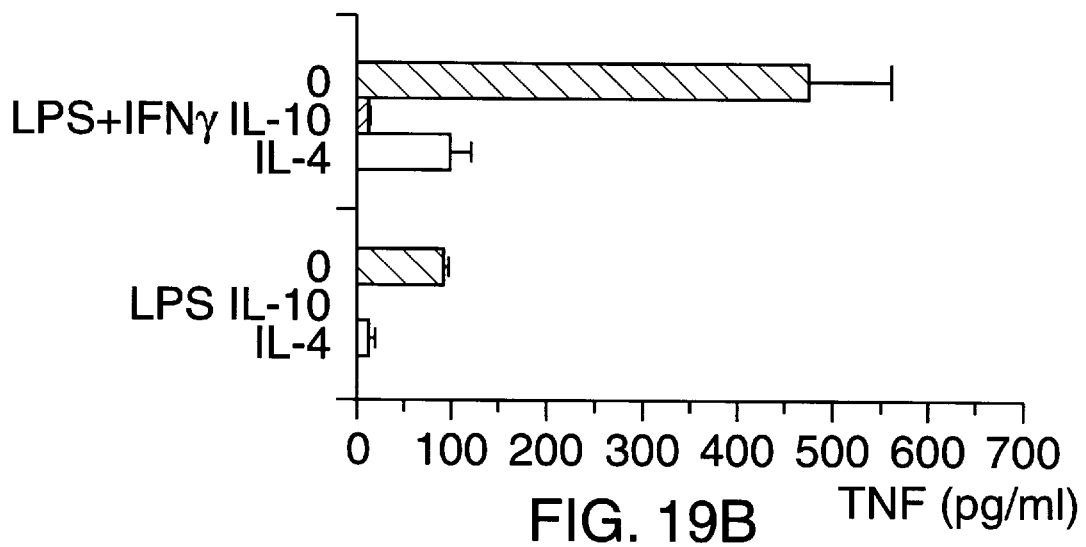
Figure 19C:
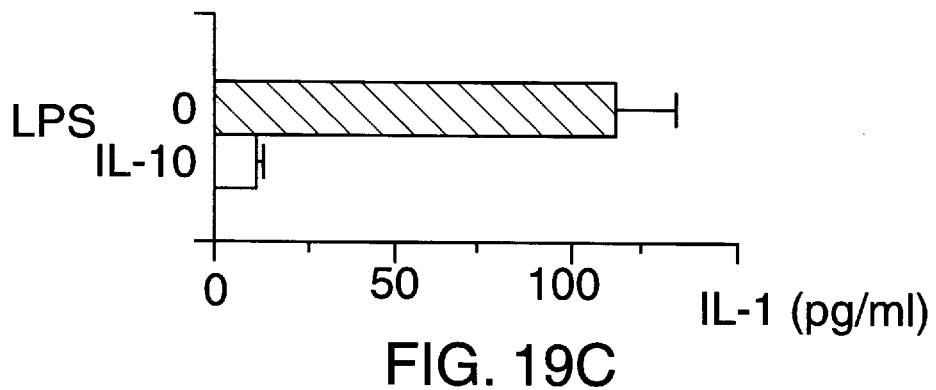
Figure 19D:
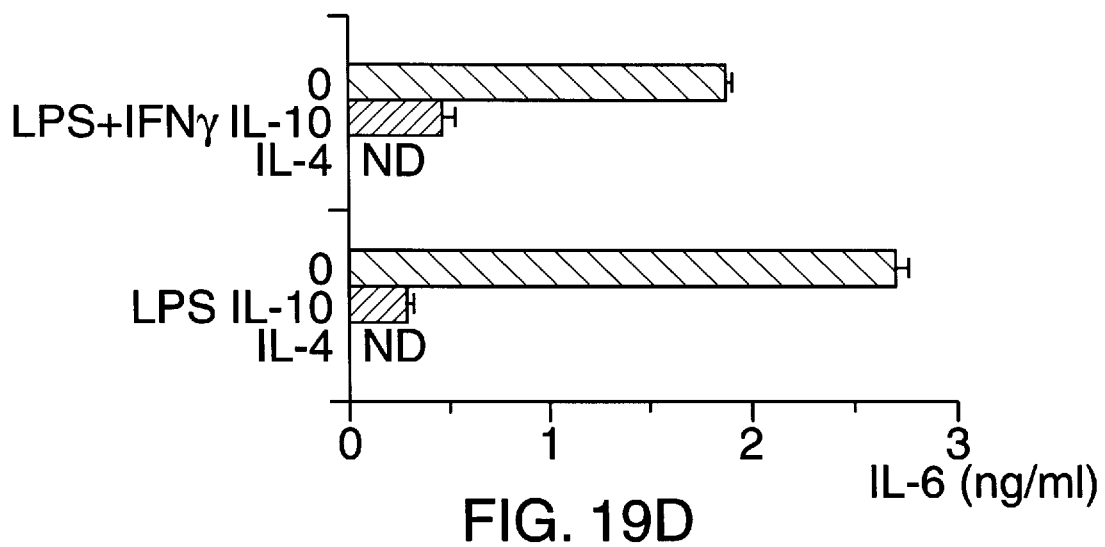
Figure 19E:
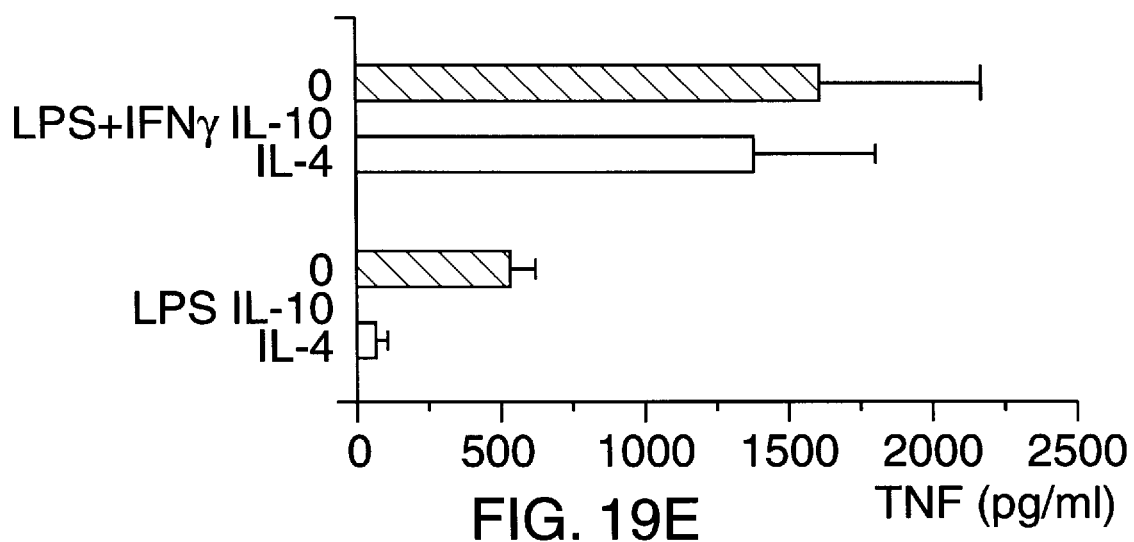
Figure 19F:
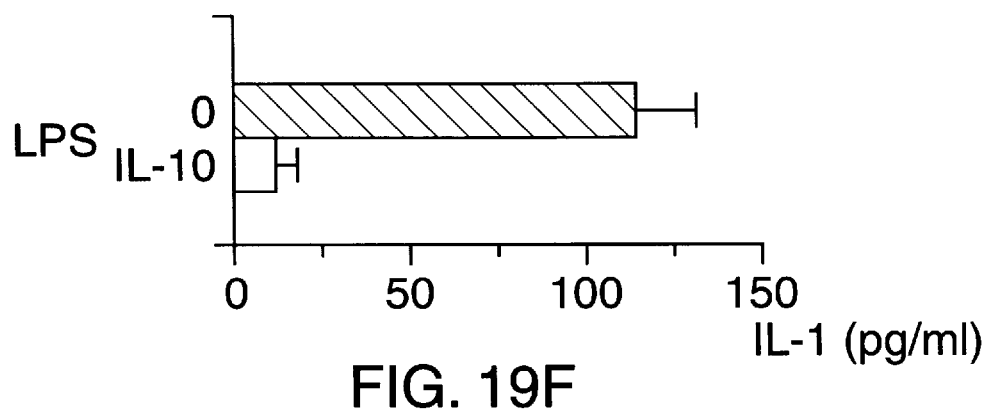

FIG. 18 illustrates the morphology of purified peritoneal macrophages (Mac-1+, bright, B220−) in the presence of IFNγ, both without (FIG. 18A) and with (FIG. 18B) IL-10.

FIG. 19 is a graphical representation of effects of IL-4 and IL-10 on LPS-induced production of IL-1, TNF-α and IL-6 by the 1G18.LA (FIGS. 19A–C) and PU5.1 (FIGS. 19D–F) macrophage cell lines.

Figure 20:

FIG. 20 shows a gel blot analysis of the effects of IL-4 and IL-10 on LPS-induced production of TNF-α and actin by the 1G18.LA macrophage cell line.

Figure 21A:
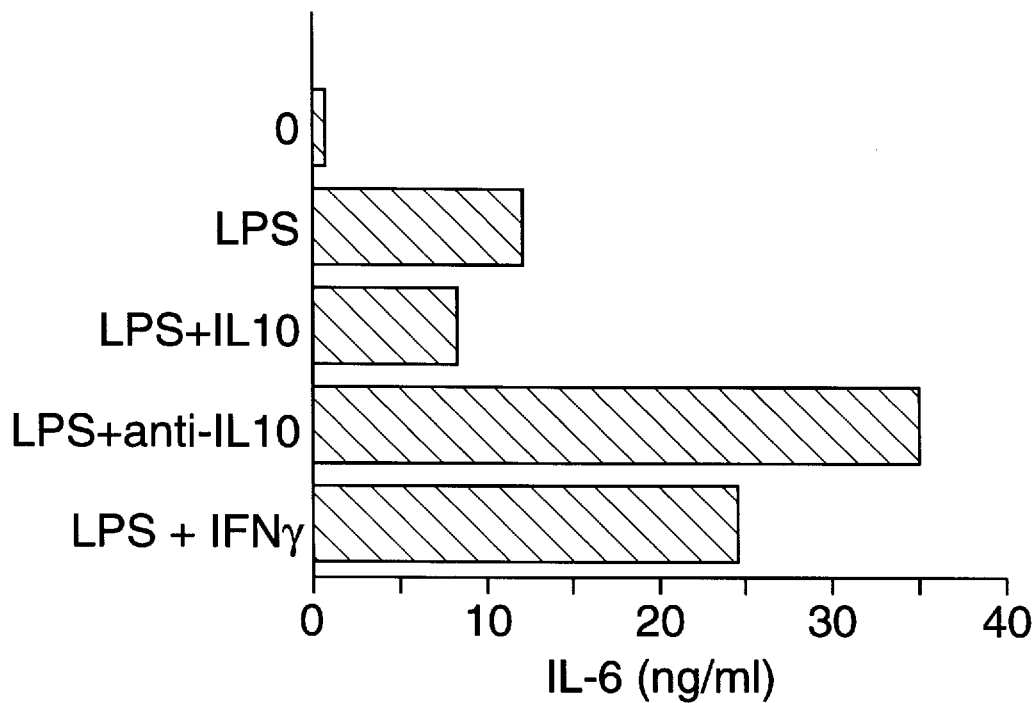
Figure 21B:
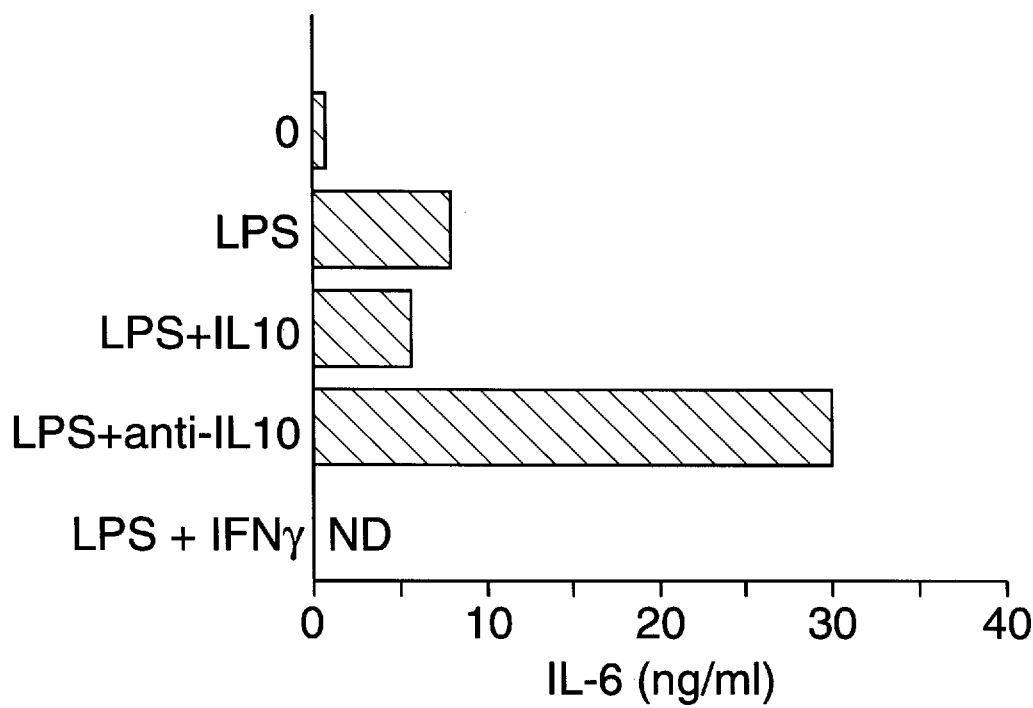

FIG. 21 is a graphical representation of IL-6 production by peritoneal macrophages (Mac-1+,bright, B220−) from BALB/c (FIG. 21A) or CBA/J mice (FIG. 21B) incubated alone or with LPS in the presence or absence of IL-10, anti-IL-10, or IFNγ.

Figure 22A:
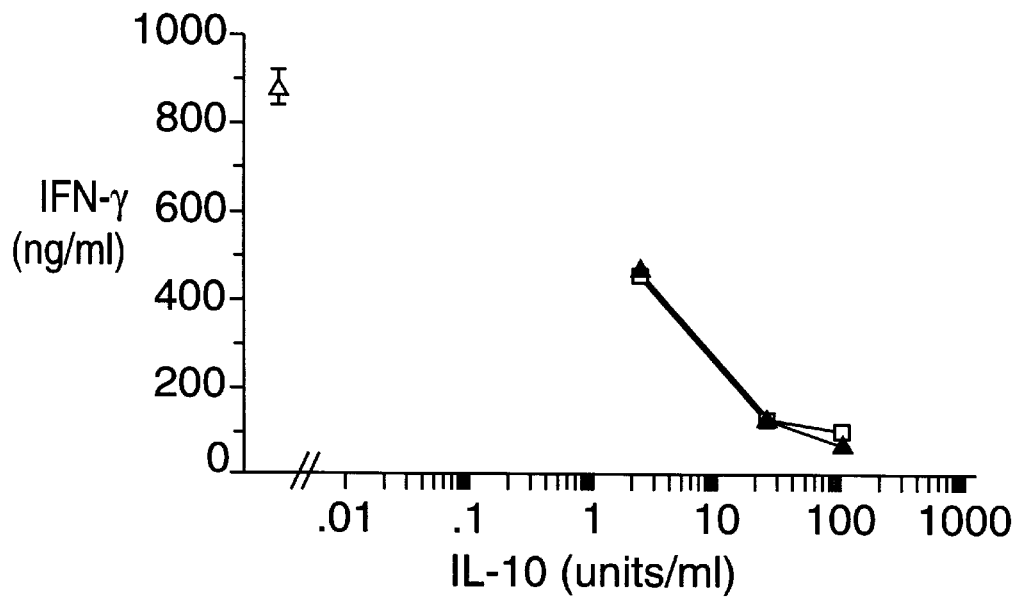
Figure 22B:
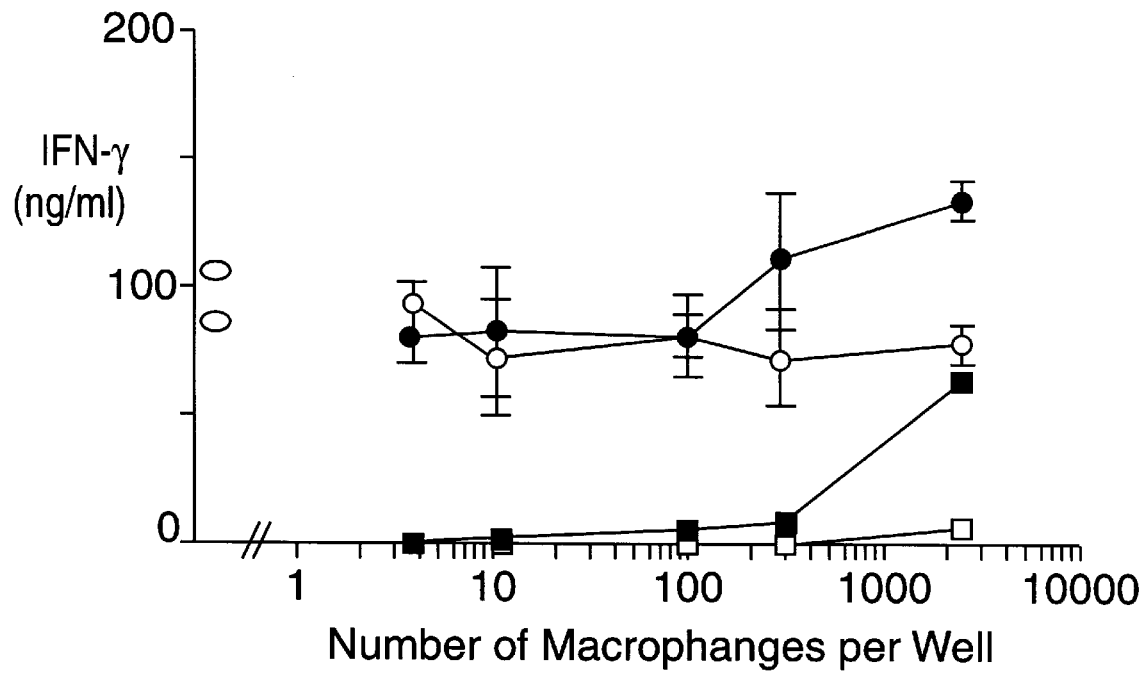
Figure 23A:
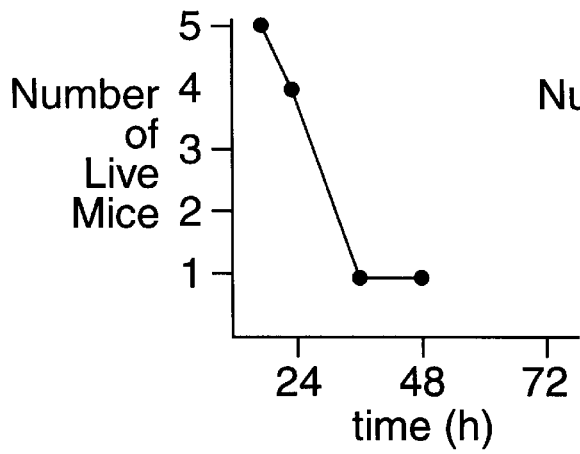
Figure 23B:
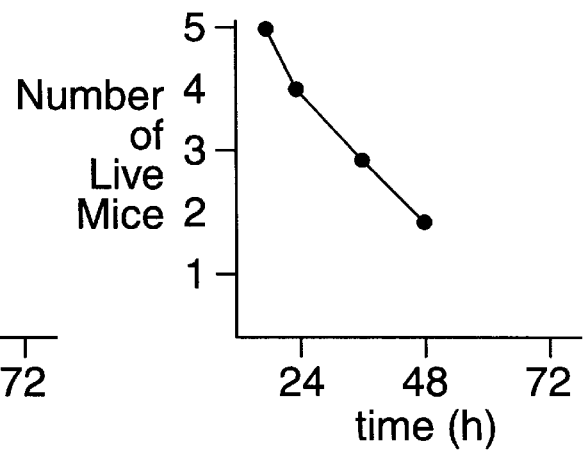
Figure 23C:
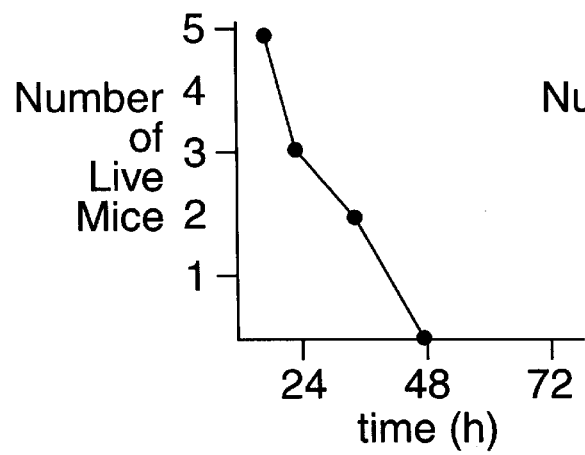
Figure 23D:
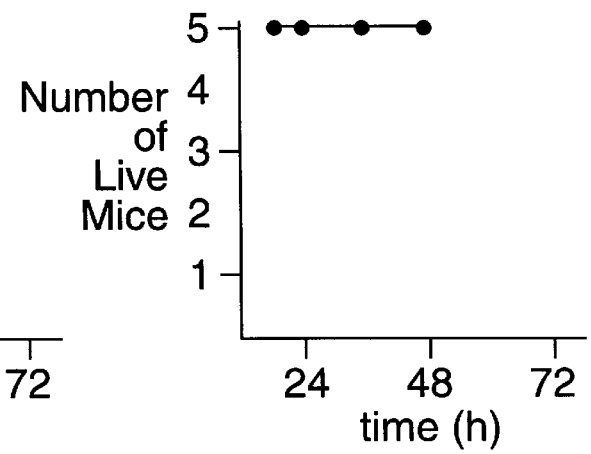
Figure 23E:
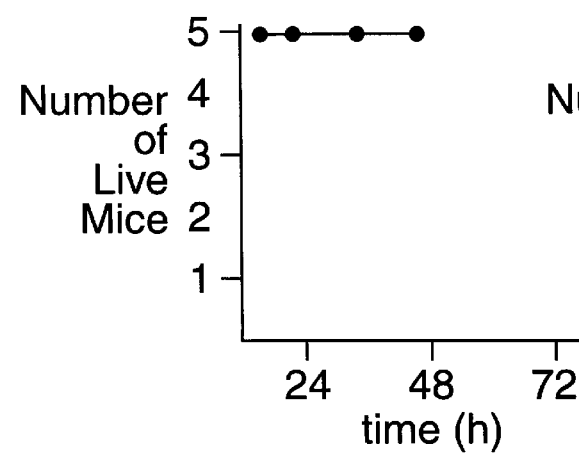
Figure 23F:
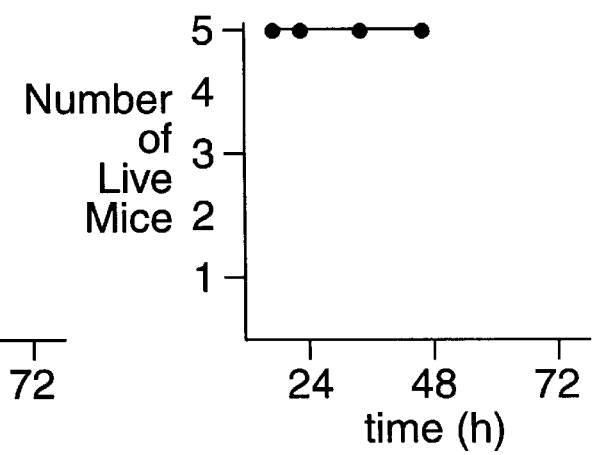

FIG. 22 is a graphical representation of the results of a mechanistic study (see Example 20) of the effects of IL-10 on IFNγ production by macrophages. The data of FIG. 22A were obtained using the 1G18.LA macrophage cell line which had been activated with IFNγ and then incubated with HDK-1 Th1 cells and an antigen, either alone (Δ) or in the presence of varying amounts of IL-10 with (□) or without (▲) supernatants from cultured macrophage cells. The supernatants were obtained from the same macrophage cell line after similar stimulation by IFNγ and Th1 cells followed by concentration and depletion of the supernatants of IFNγ and IL-2. FIG. 22B shows IFNγ production by HDK-1 Th1 cells incubated with an antigen and with graded doses of purified splenic macrophages, in the absence (■) or presence of IL-10 (□); or with a mixture of graded doses of purified macrophages and B cells in the absence (●) or presence of IL-10 (○) (200 units/ml); or with B cells alone in the absence (▨) or presence of IL-10 (○).

FIG. 23 shows protection by IL-10 of BALB/C mice against SEB-induced toxicity. The results obtained using 20 μg SEB+30 mg d-Gal (FIG. 23A), 10 μg IL-10+20 μg SEB+30 mg d-Gal (FIG. 23B), 10 μg SEB+30 mg d-Gal (FIG. 23C), 10 μg IL-10+10 μg SEB+30 mg d-Gal (FIG. 23D), 30 mg d-Gal (FIG. 23E), and 10 μg IL-10 (FIG. 23F).

Figure 24:
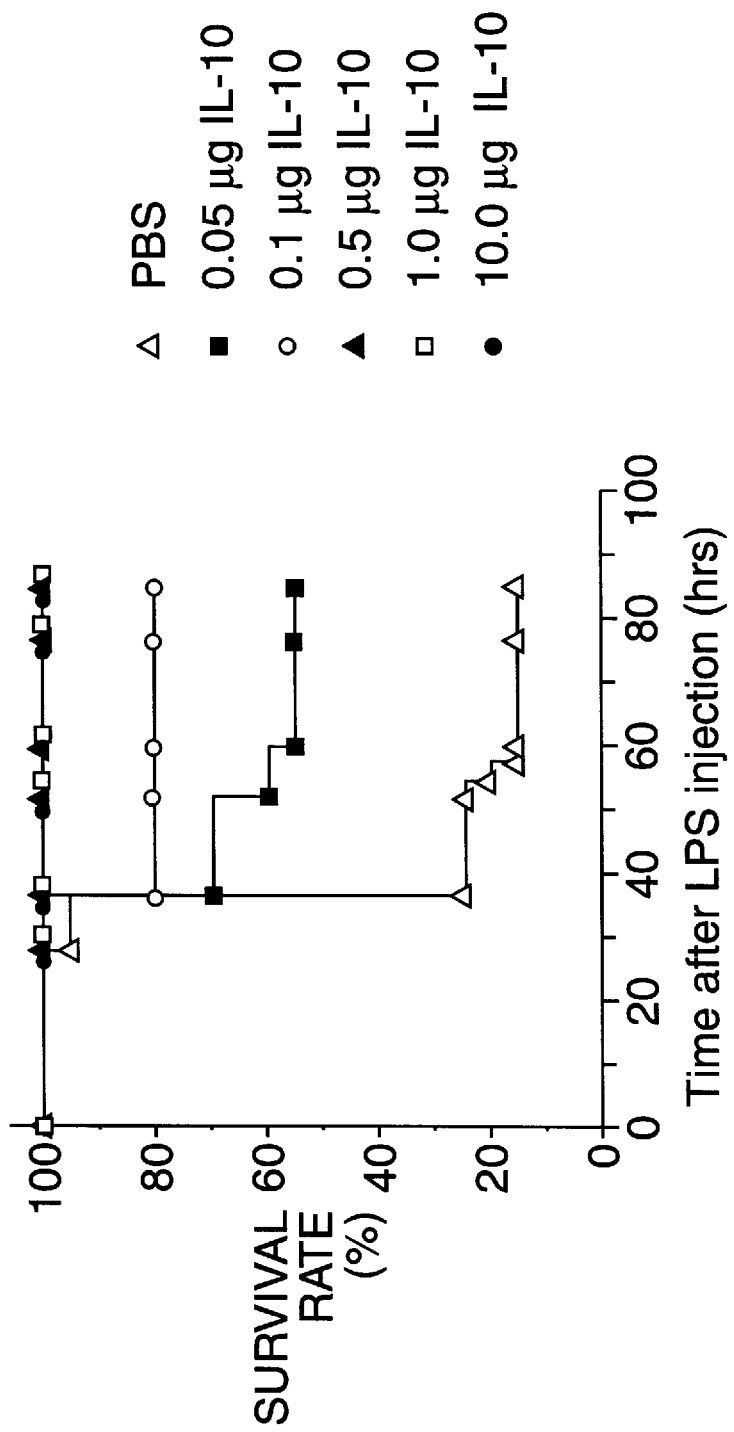

FIG. 24 shows survival of BALB/c mice following i.p. administration of 350 μg of LPS, either alone with varying doses of purified recombinant murine IL-10.

Figures 25A, 25B:
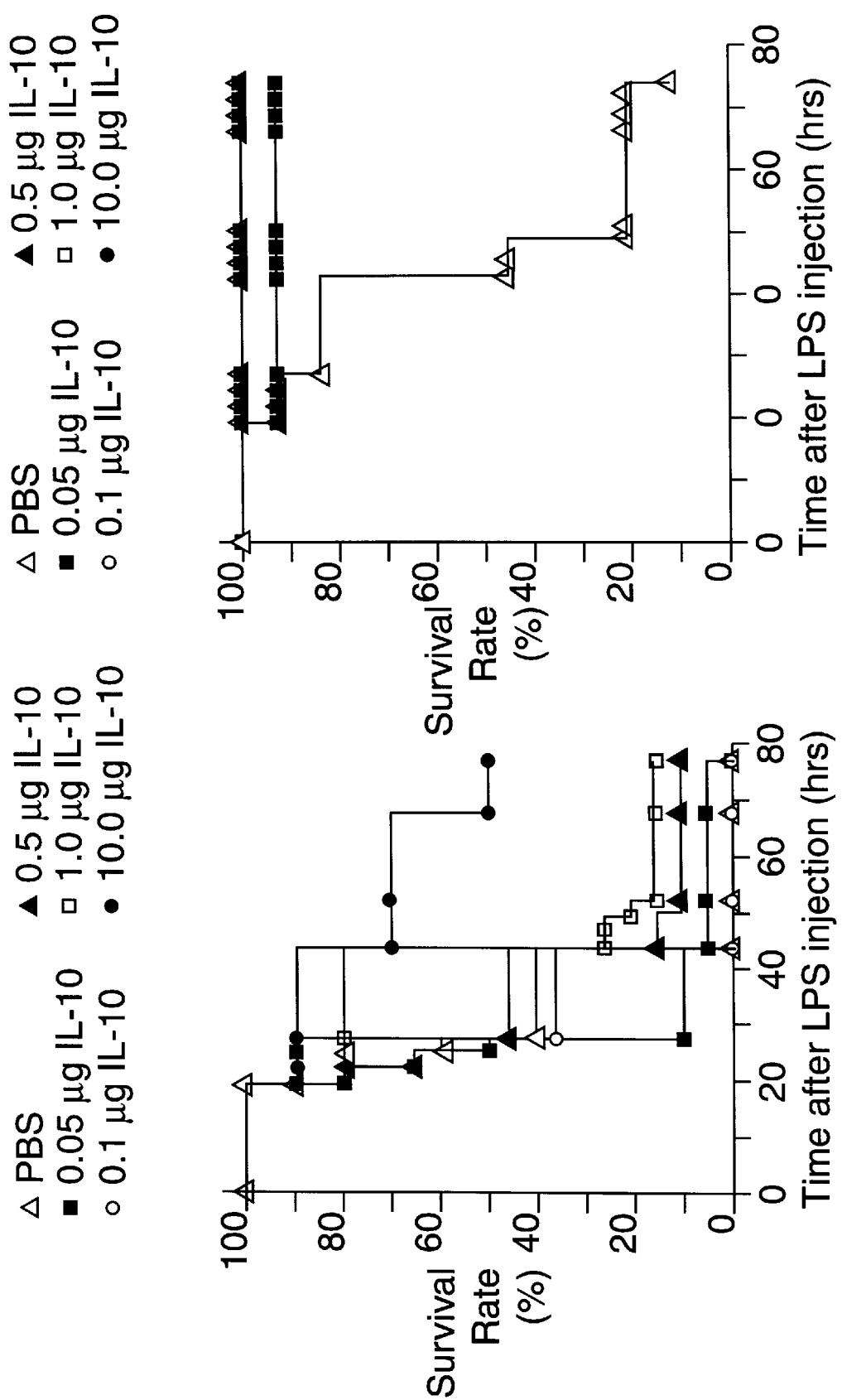

FIG. 25 shows survival of BALB/c mice which were administered a neutralizing anti-IL-10 antibody (FIG. 25A) or a control antibody (FIG. 25B), and then one hour later treated with 350 μg of LPS, either alone with varying doses of murine IL-10.

Figure 26:
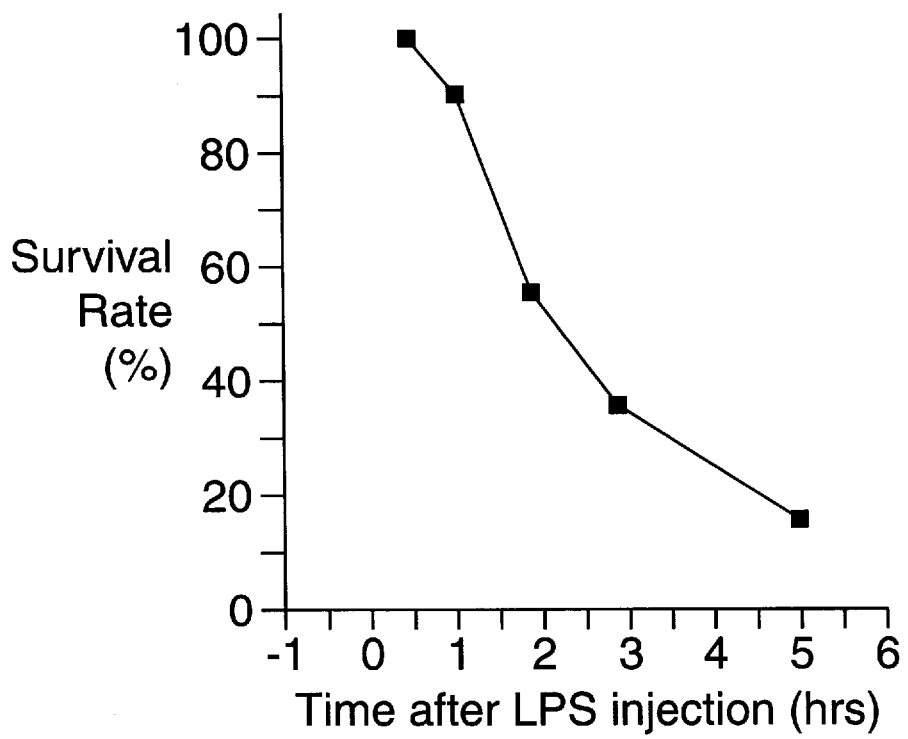
Figure 27A:
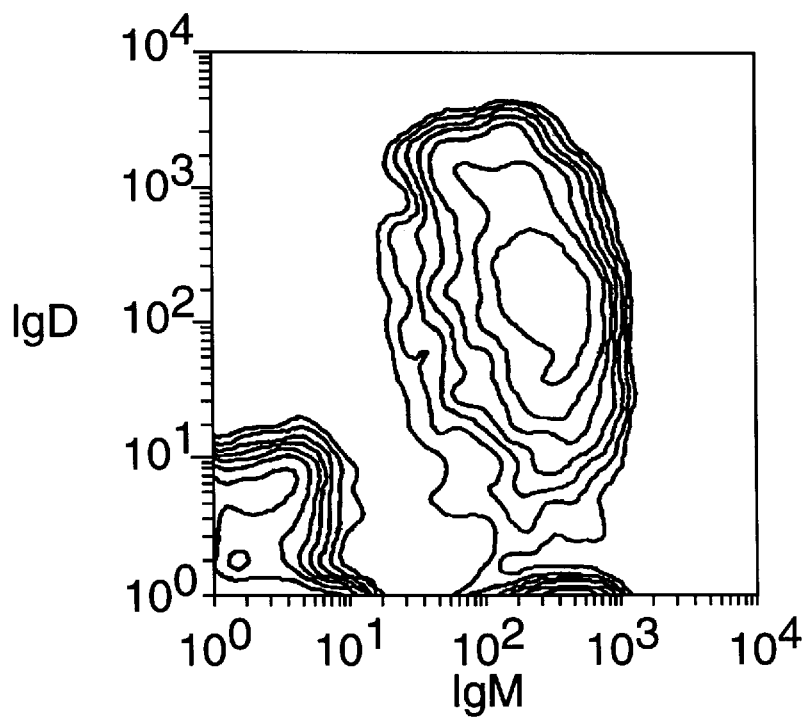
Figure 27B:
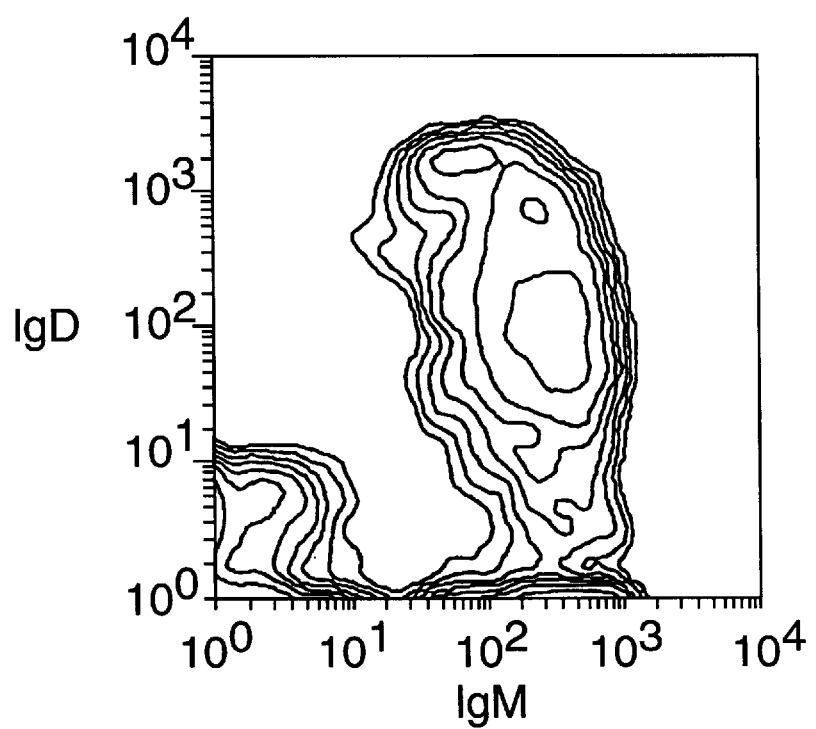
Figure 27C:
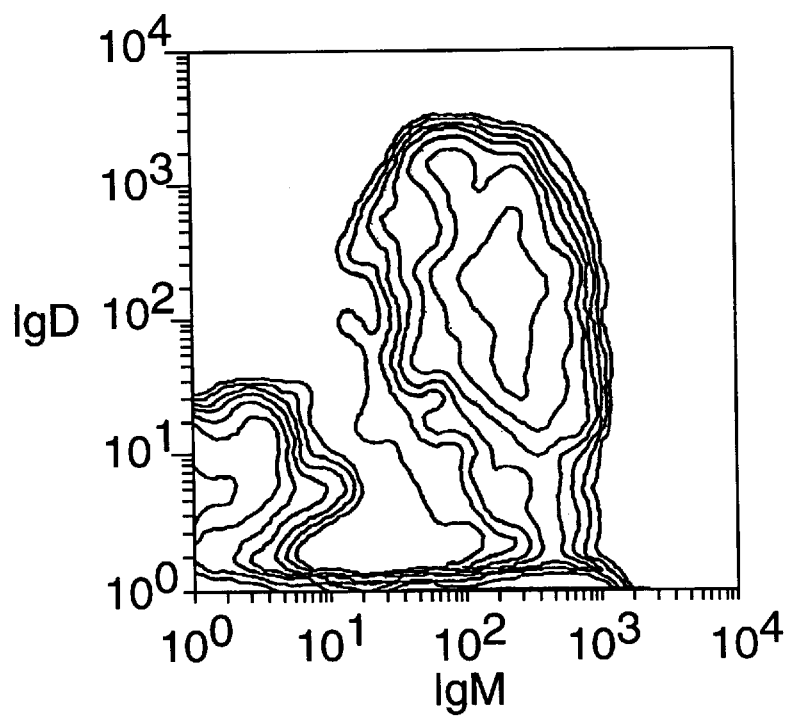
Figure 27D:
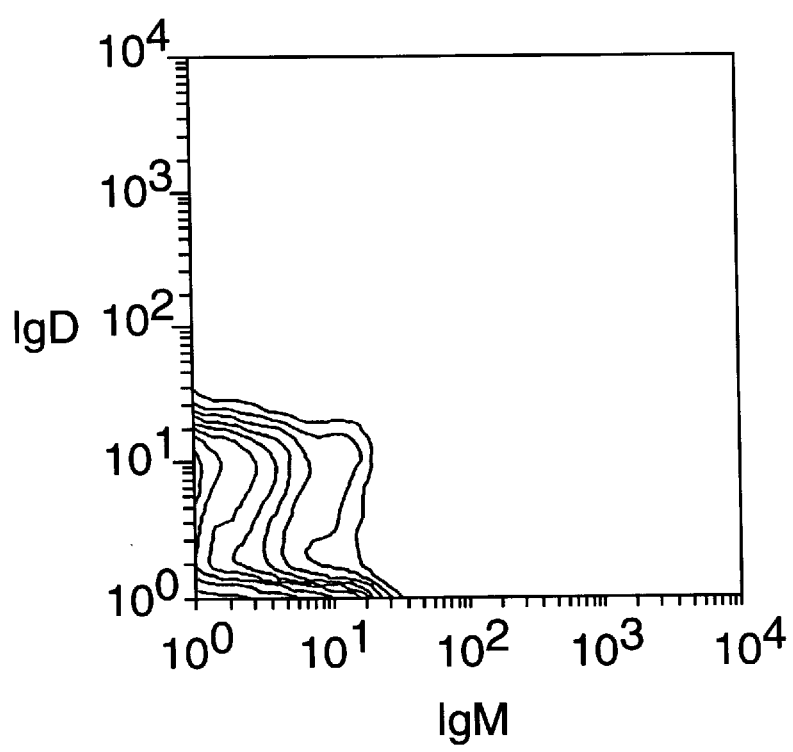

FIG. 26 shows survival of BALB/c mice following i.p. administration of 350 μg of LPS at time 0, and 1.0 μg of recombinant IL-10 i.p. at varying times thereafter. Control mice receiving the LPS but no IL-10 all died.

FIG. 27 shows an immunofluorescence analysis of surface IgM and IgD expression by total live peritoneal wash cells obtained from BALB/c mice. The mice were untreated (FIG. 27A) or injected from birth until week 8 with PBS (FIG. 27B), a control antibody (FIG. 27C), or an anti-IL-10 antibody (FIG. 27D).

Figure 28:
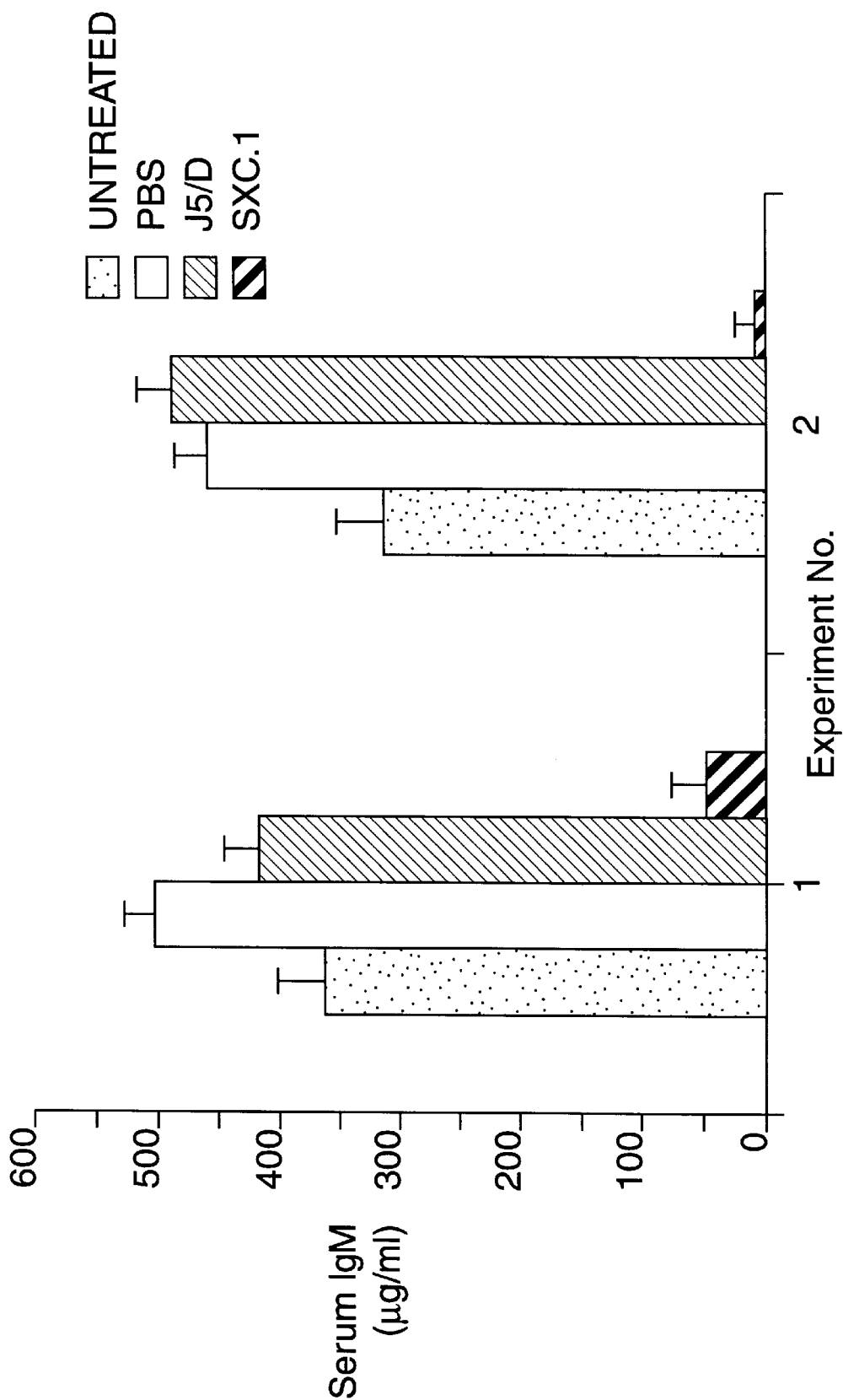

FIG. 28 is a graphical representation of the effects on serum IgM levels in BALB/c mice treated for 8 weeks with phosphate buffered saline (PBS), a control antibody (J5/D) and a neutralizing anti-IL-10 antibody SXC.1.

Figure 29A:
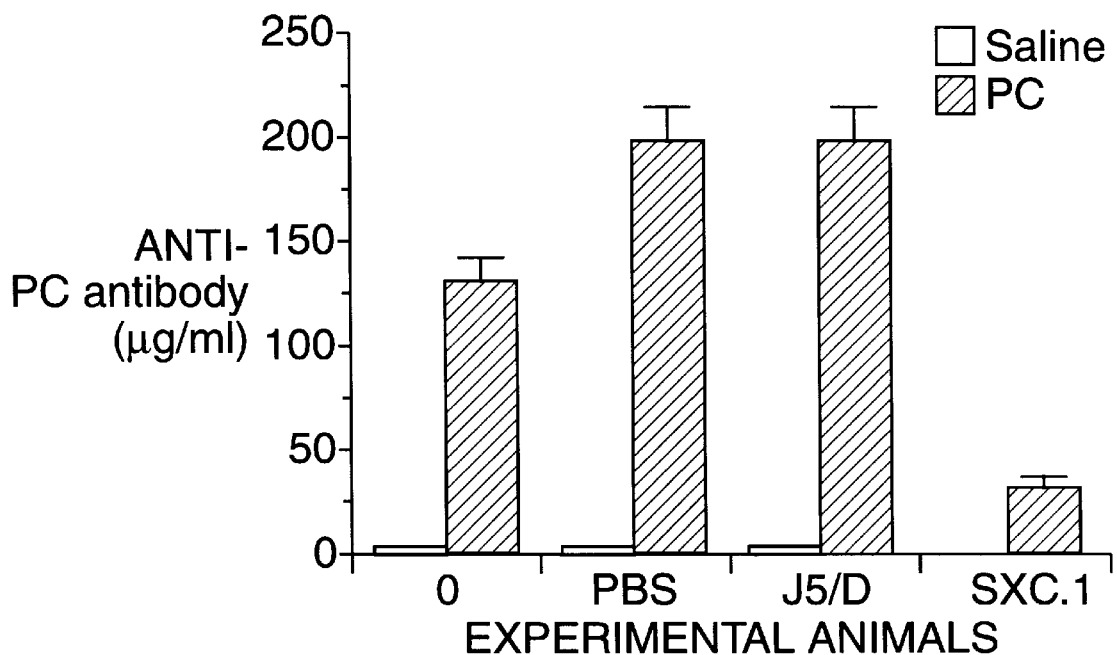
Figure 29B:
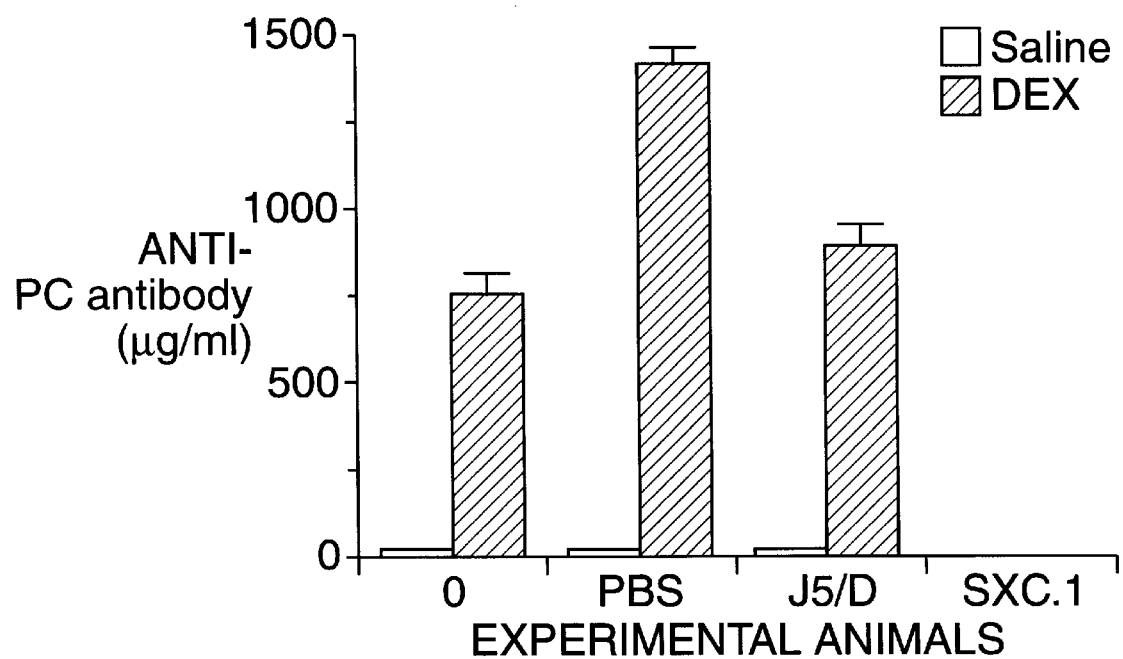
Figure 30A:
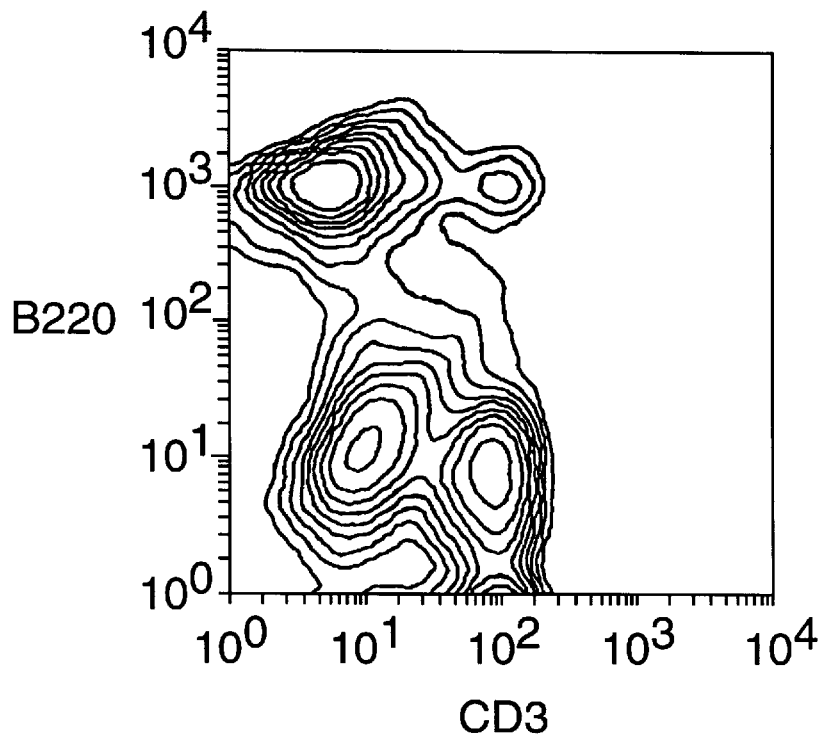
Figure 30B:
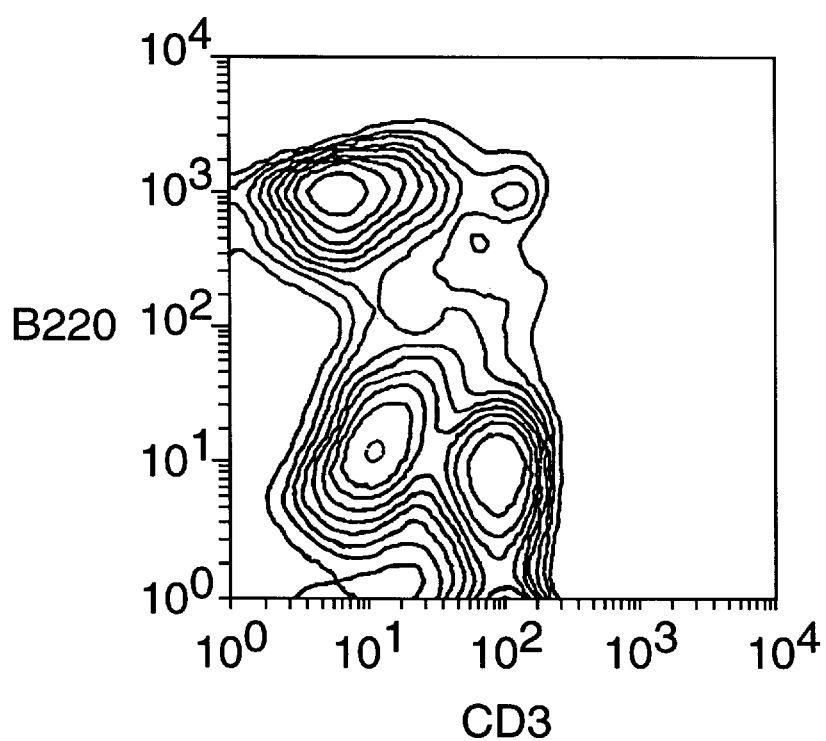
Figure 30C:
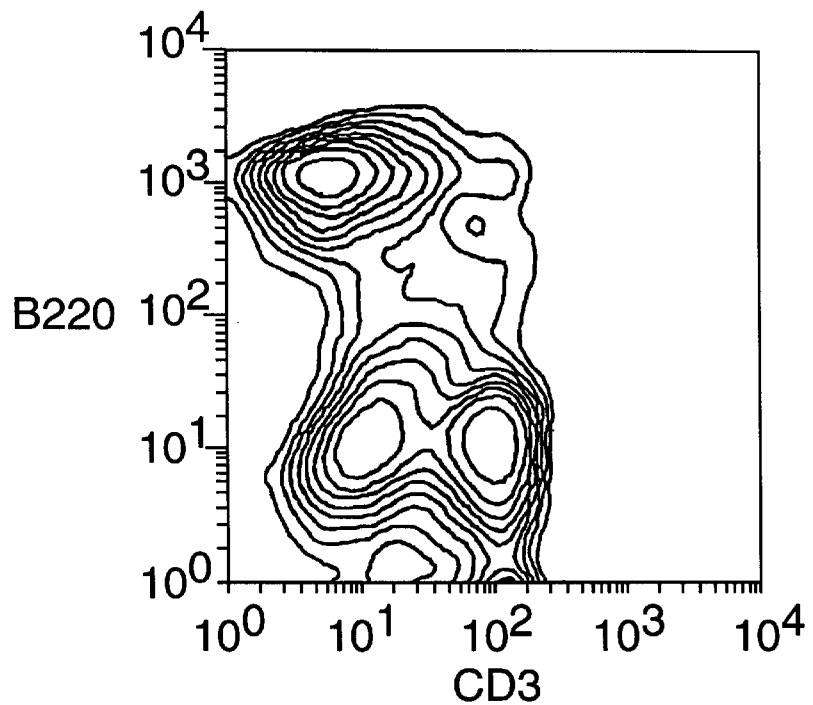
Figure 30D:
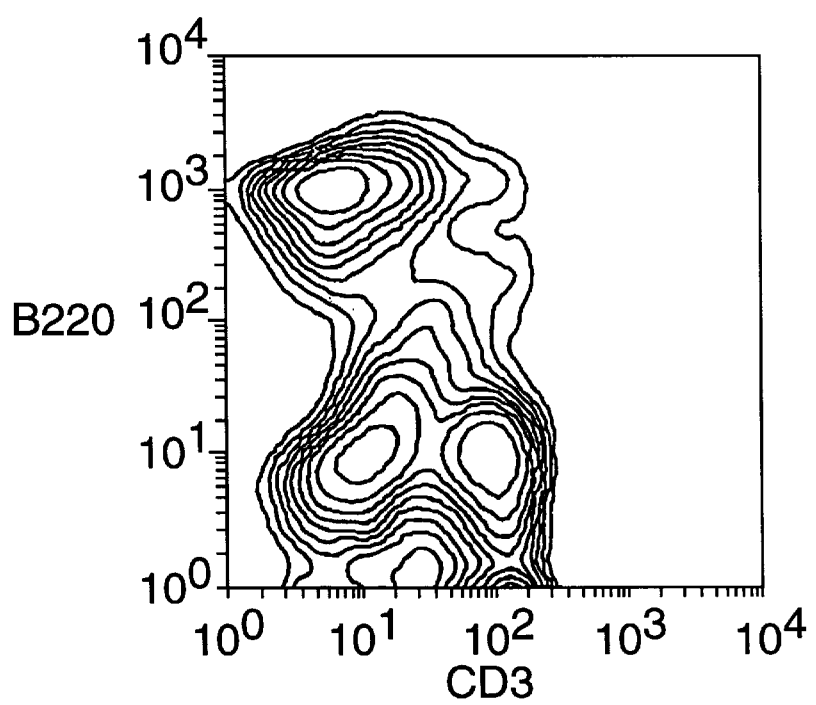

FIG. 29 is a graphical representation of the effect of phosphate buffered saline (PBS), a control antibody (J5/D) and a neutralizing anti-IL-10 antibody SXC.1 on the ability of BALB/c mice to generate in vivo antibody responses to phosphorylcholine (FIG. 29A) or to α1,3-dextran (FIG. 29B).

FIG. 30 shows an immunofluorescence analysis of surface B220 and CD3 expression of live splenic lymphoid cells obtained from SXC.1 anti-IL-10-treated and control mice. The mice were untreated (FIG. 30A) or injected from birth until week 8 with PBS (FIG. 30B), a control antibody (FIG. 30C), or an anti-IL-10 antibody (FIG. 30D).

Figure 31A:
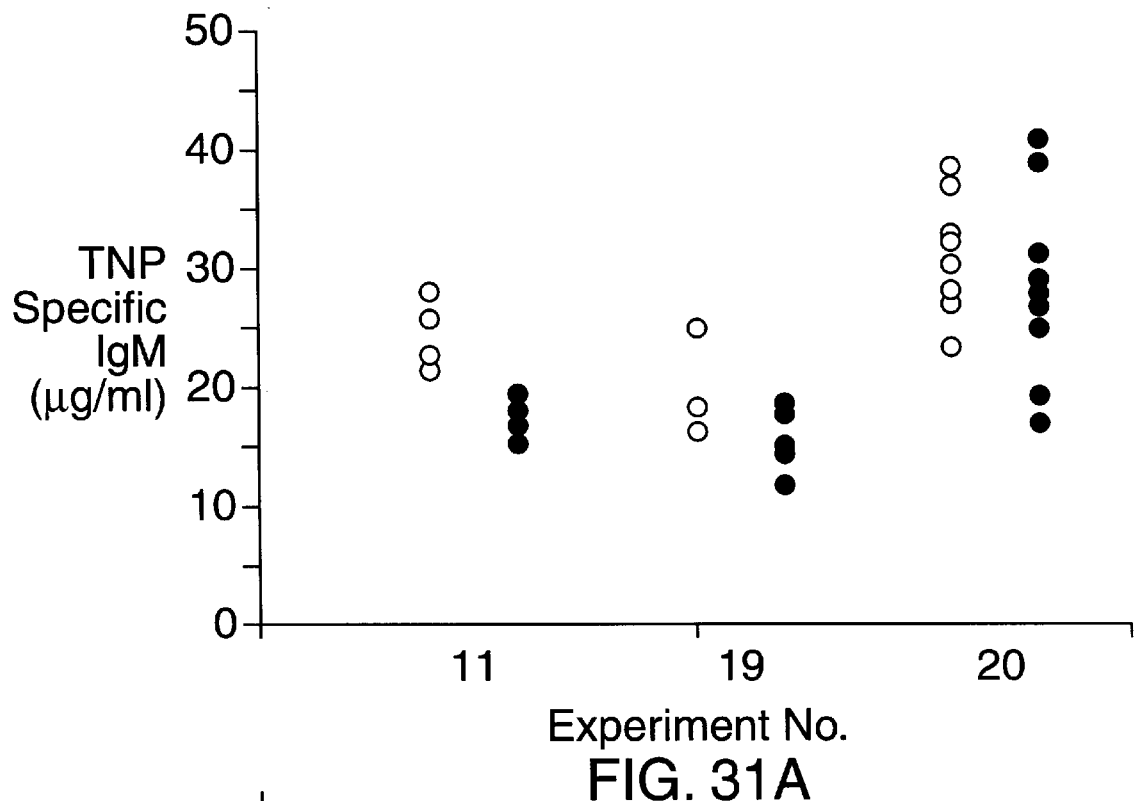
Figure 31B:
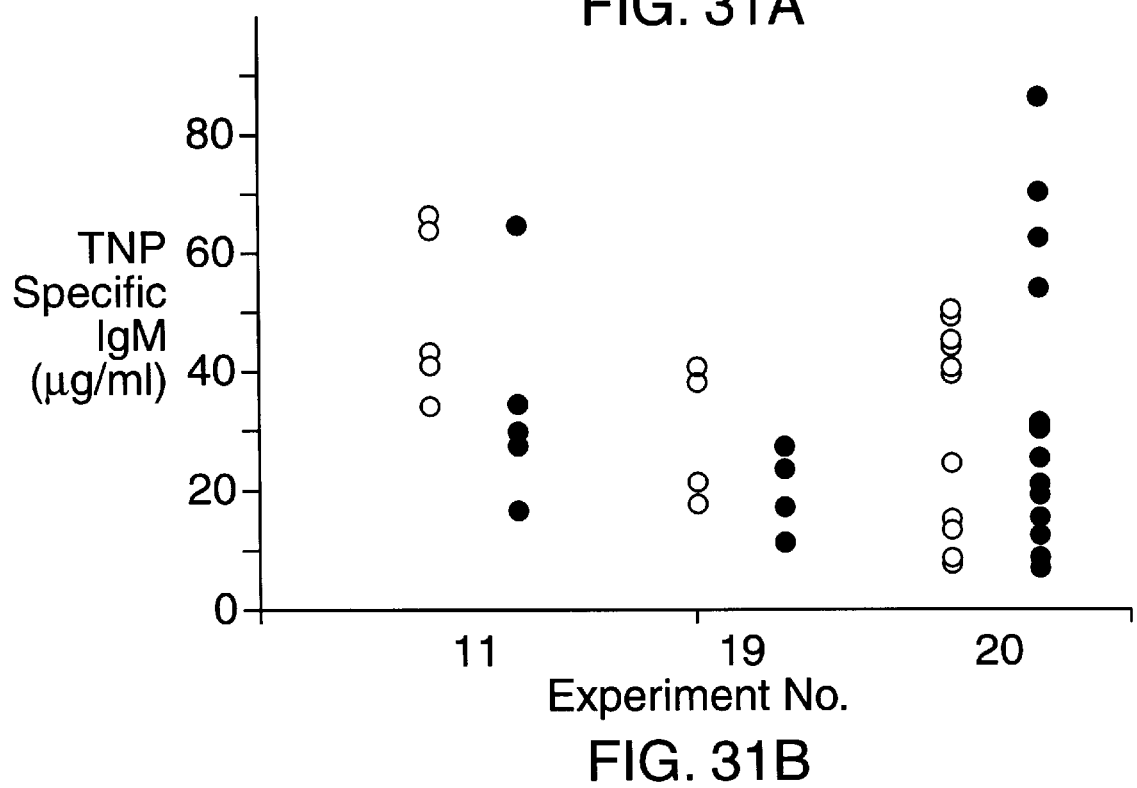

FIG. 31 shows the in vivo response of anti-IL-10-treated or control mice to TNP-KLH. Mice were injected from birth until 10 weeks of age with anti-IL-10 antibody (•) or with an isotype control antibody (○). At 8 weeks, the animals were challenged intraperitoneally with 10 μg of TNP-KLH, and serum levels of TNP-specific IgM (FIG. 31A) and IgG (FIG. 31B) were determined 7 and 14 days after immunization, respectively.

FIG. 32 shows an immunofluorescence analysis of the effect of anti-IL-10 antibodies on coexpression of surface B220 and IgM in peritoneal wash B cells. Results are shown for BALB/c mice treated with an isotype control antibody (J5/D; FIGS. 32A–C) and with an anti-IL-10 antibody (SXC.1; FIGS. 32D–F), with peritoneal wash cells collected 1, 2, and 3 days thereafter for analysis.

Figure 33:
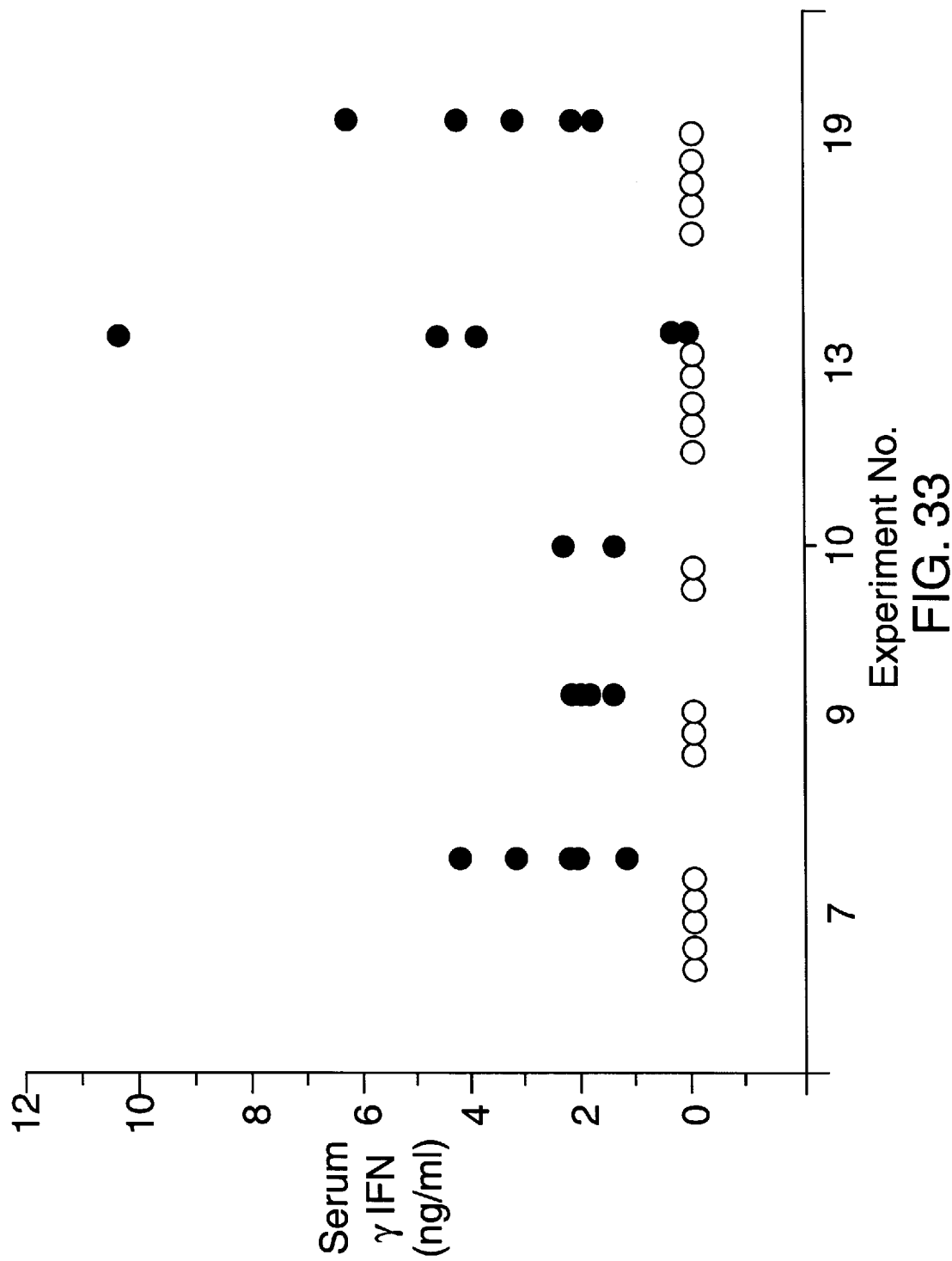

FIG. 33 shows the effect on serum IFNγ levels in BALB/c mice treated with an anti-IL-10 antibody (•) or with an isotype control antibody (○), following 8 weeks of treatment.

Figure 34A:
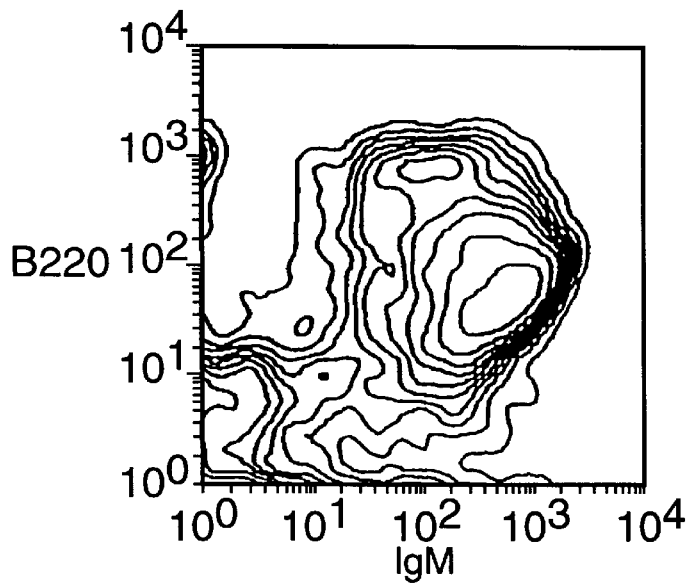
Figure 34B:
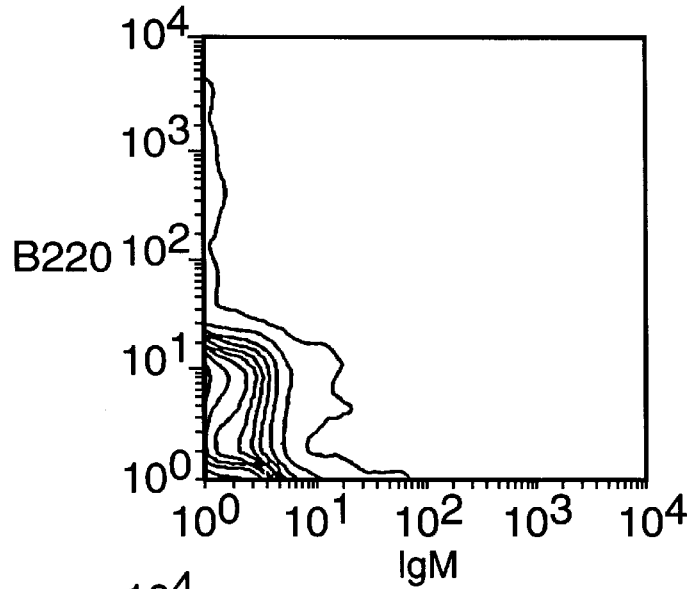
Figure 34C:
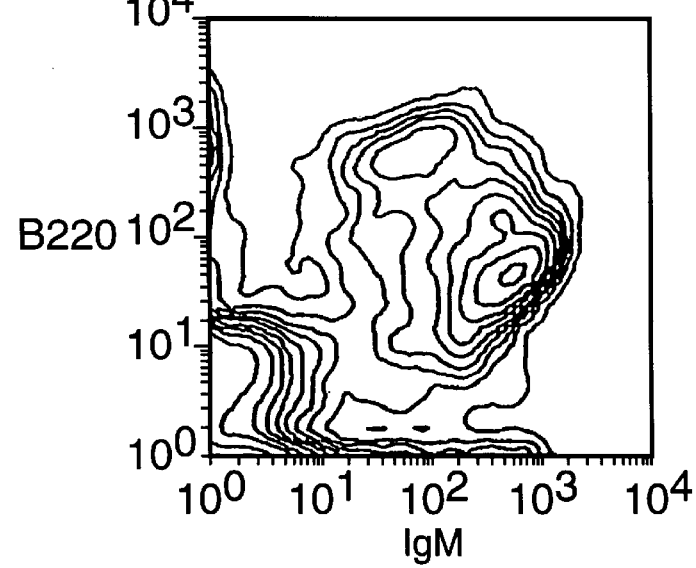

FIG. 34 shows an immunofluorescence analysis of the coexpression of B220 and IgM on peritoneal wash cells from BALB/c mice that were untreated (FIG. 34A) or treated from birth to 8 weeks of age with anti-IL-10 antibodies (FIG. 34B) or with anti-IL-10 antibodies plus anti-IFNγ antibodies (FIG. 34C).

Figure 35:
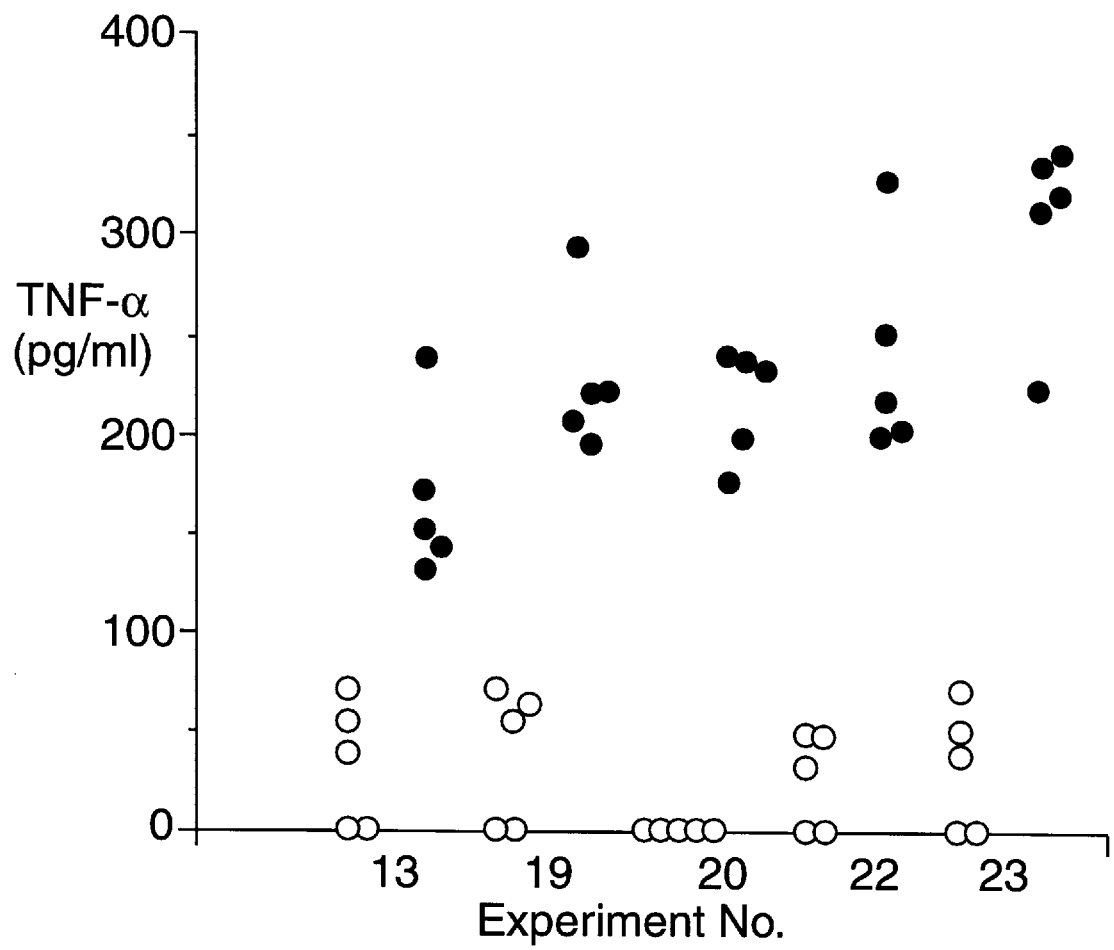

FIG. 35 shows serum TNFα levels in mice treated from birth until 8 weeks of age with an anti-IL-10 antibody (•) or with an isotype matched control antibody (○).

Figure 36:
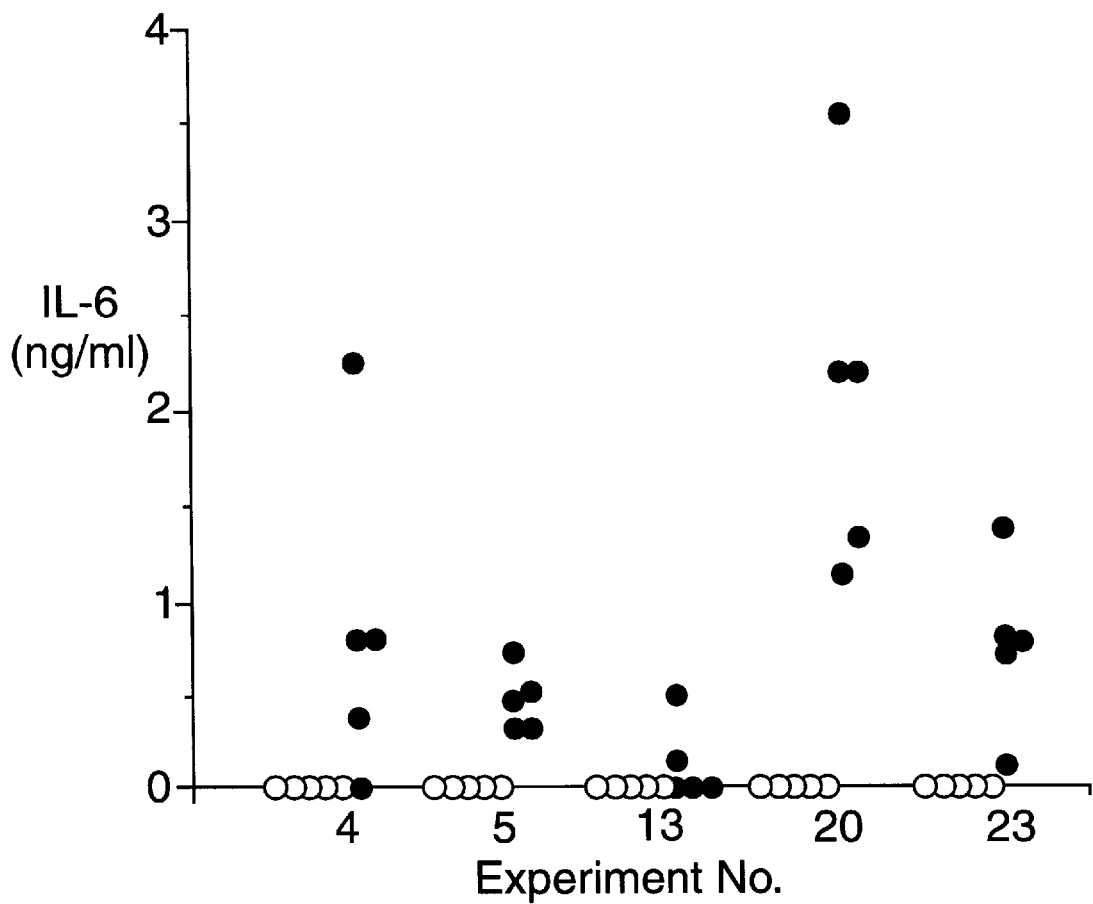
Figure 37A:
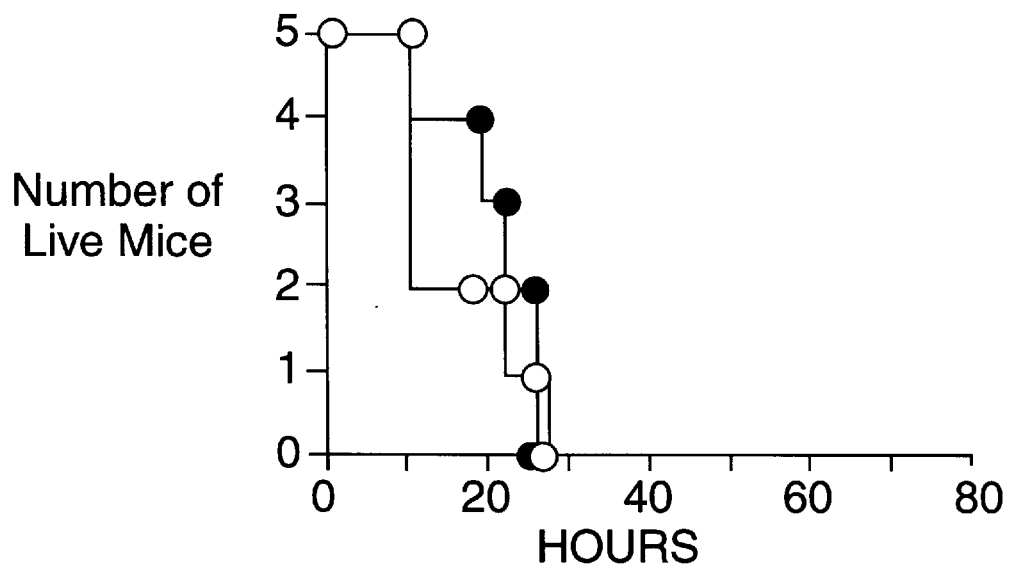
Figure 37B:
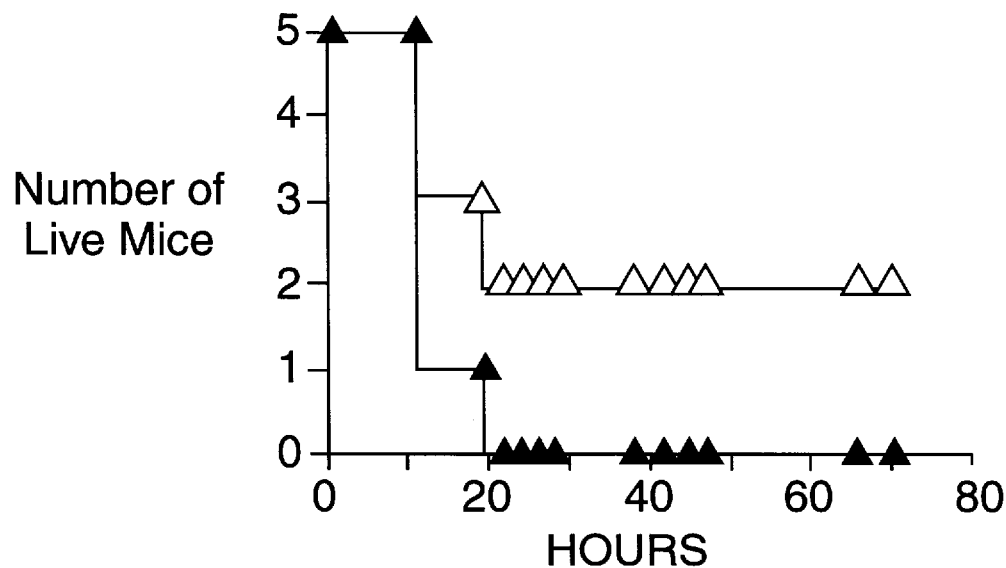
Figure 37C:
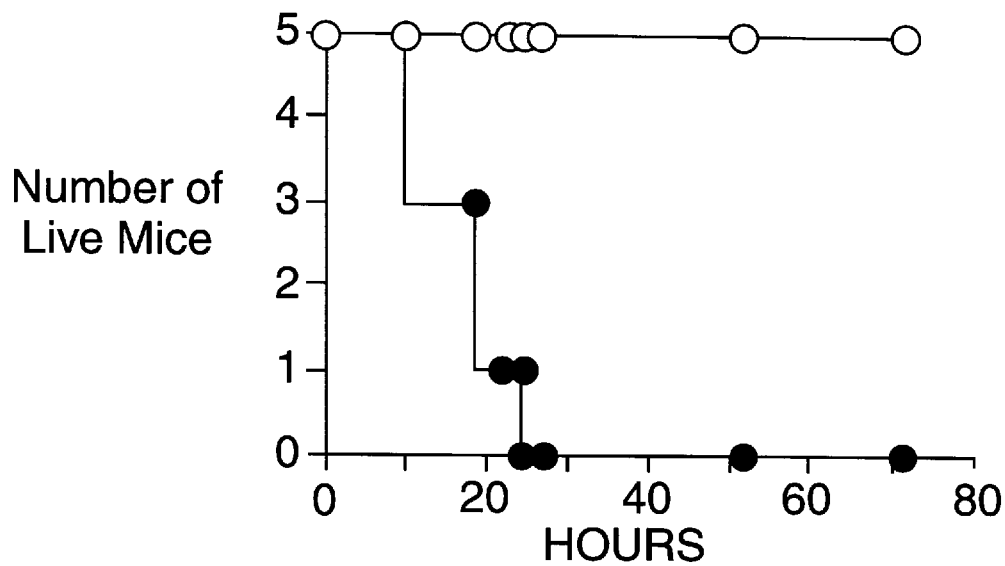
Figure 37D:
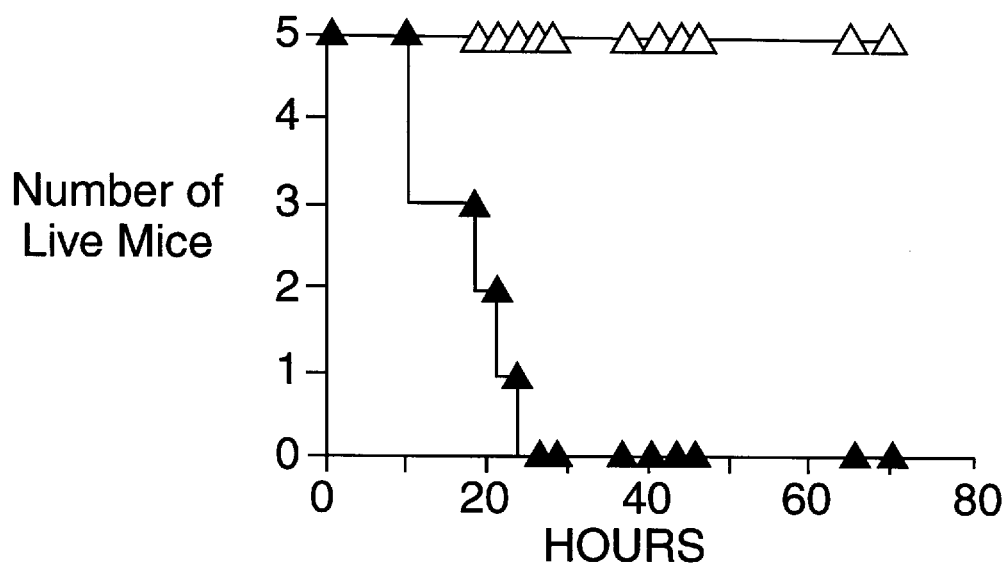
Figure 37E:
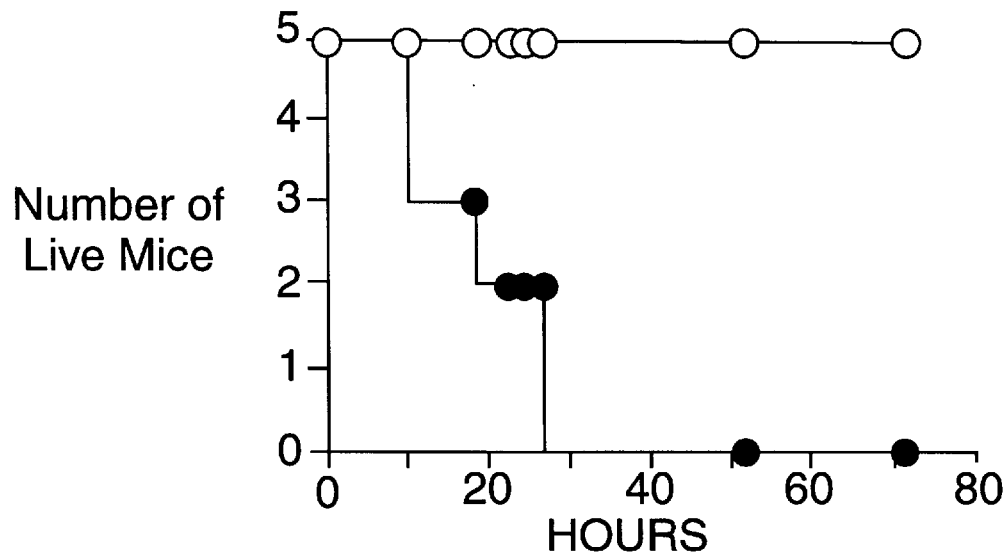
Figure 37F:
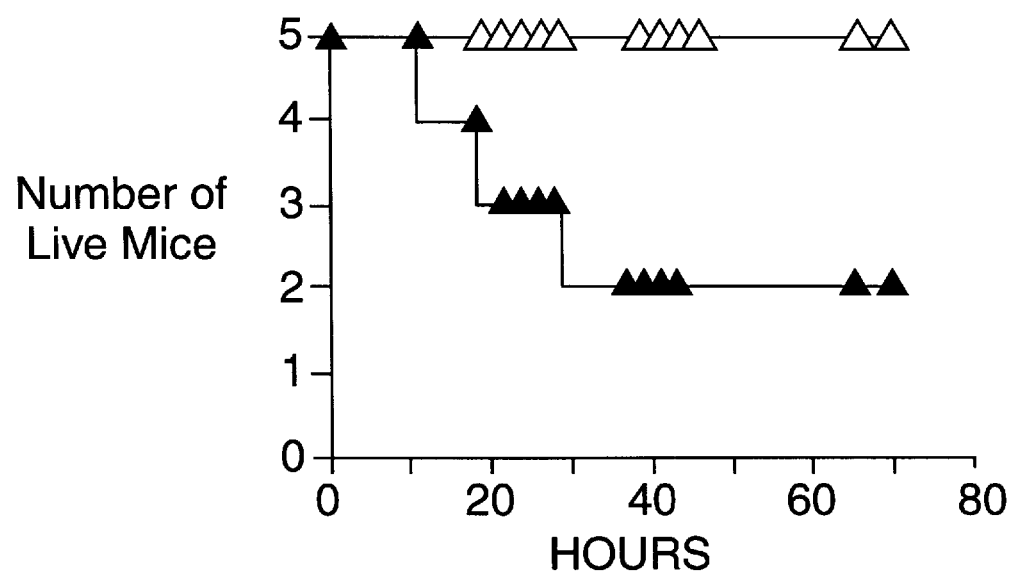

FIG. 36 shows serum IL-6 levels in mice treated from birth until 8 weeks of age with an anti-IL-10 antibody (•) or with an isotype matched control antibody (○).

FIG. 37 graphically illustrates survival over 4 days following LPS administration to groups of 5 mice. From birth to 8 weeks of age, the mice had been administered a rat IgM anti-IL-10 antibody (•), a rat $IgG_1$ anti-IL-10 antibody (▲), or a corresponding isotype control antibody (○) (Δ), after which LPS was administered. FIGS. 37A–F shows the results obtained following the administration of 500, 400, 100, 50, 50, and 1 μg of LPS, respectively.

Figures 38A, 38B:
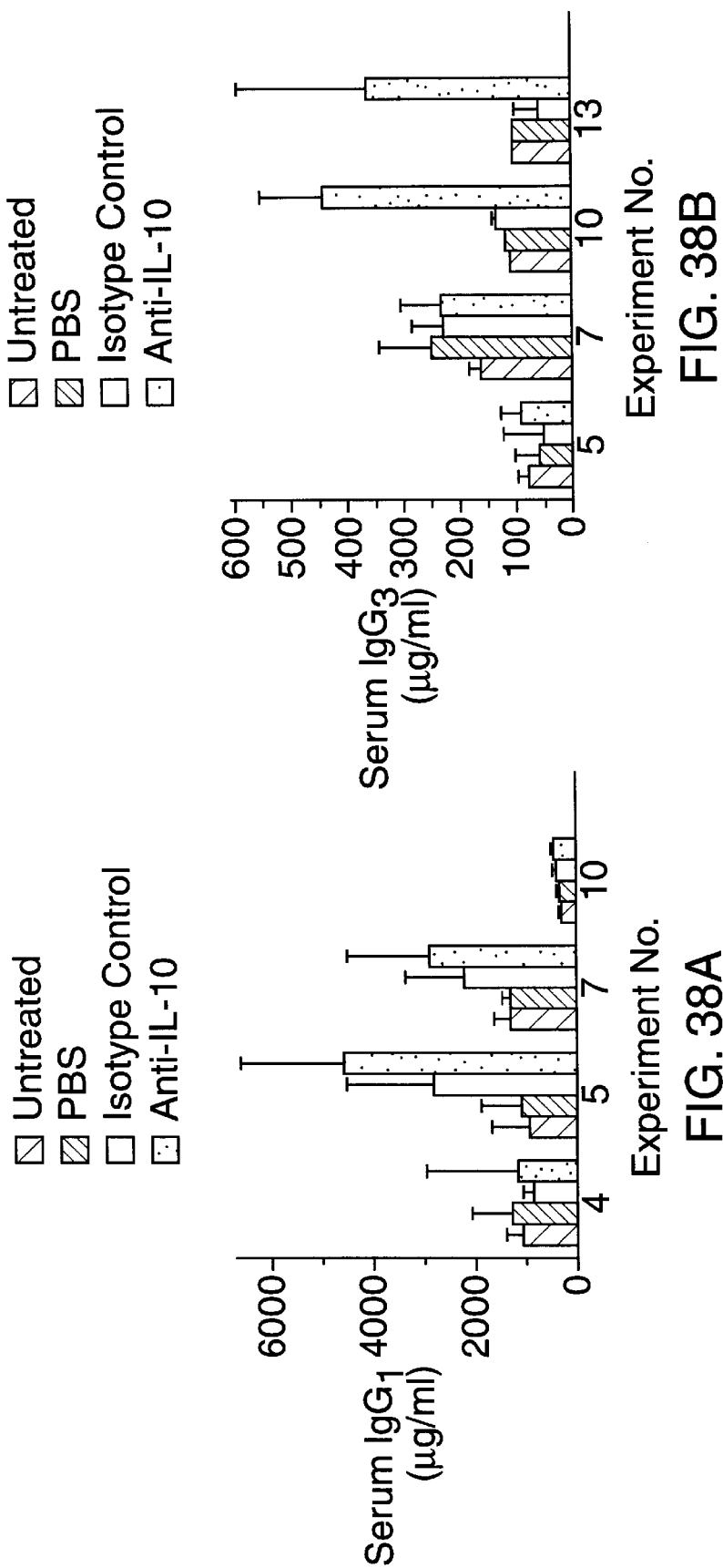
Figures 38C, 38D:
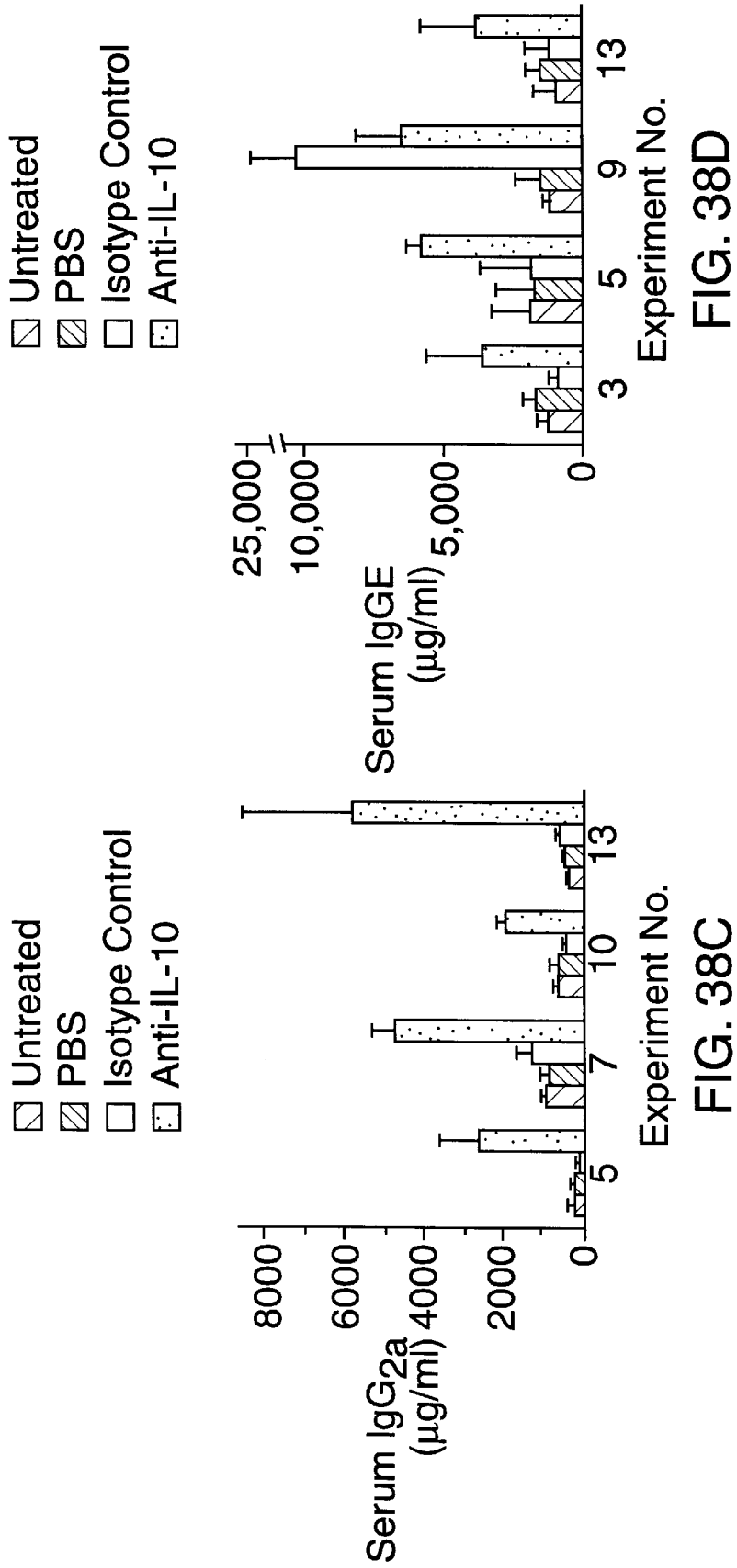

FIG. 38 is a graphical representation of serum levels of various immunoglobulin isotypes in mice treated from birth until 8 weeks of age as indicated.

Figure 39A:
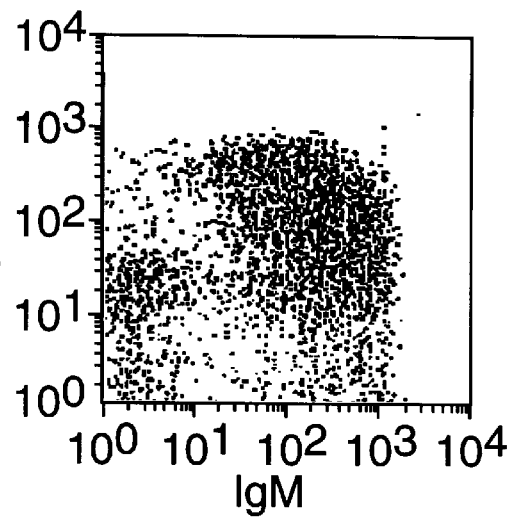
Figure 39B:
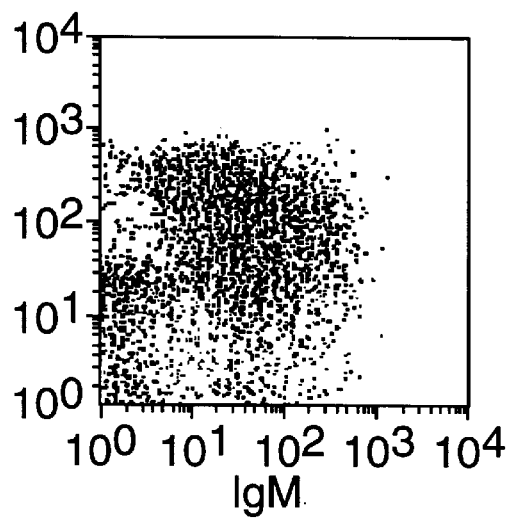
Figure 39C:
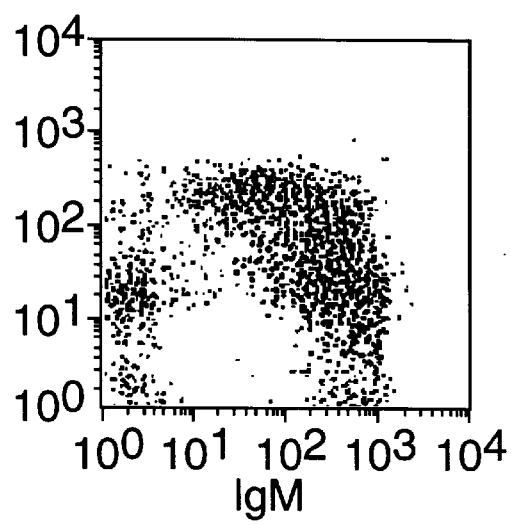
Figure 39D:
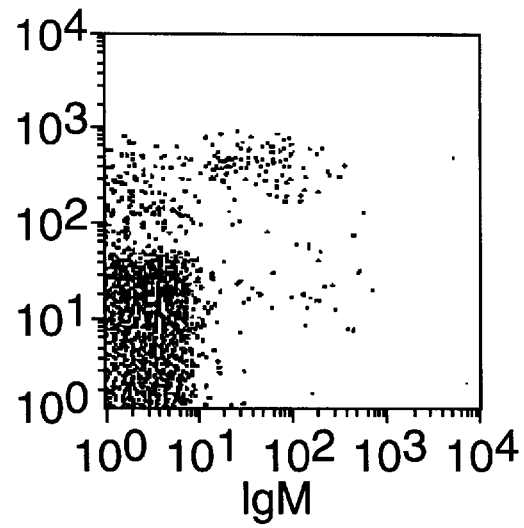
Figure 39E:
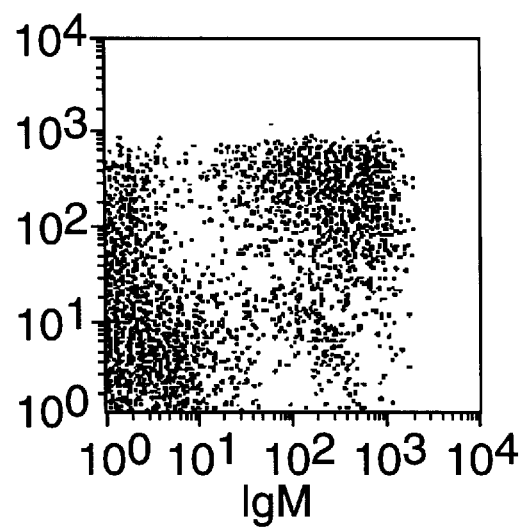
Figure 39F:
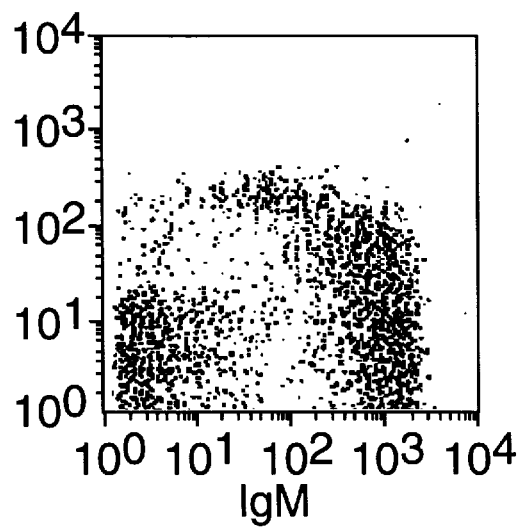

FIG. 39 shows an immunofluorescence analysis of surface B220 and IgM expression on peritoneal wash cells from mice following treatment from birth for 8, 12, and 16 weeks with an isotype control antibody (FIGS. 39A–C) or with an anti-IL-10 antibody (FIGS. 39D–F).

Figure 40A:
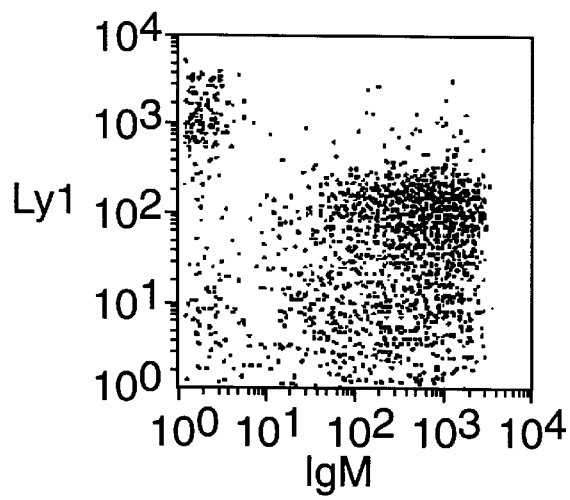
Figure 40B:
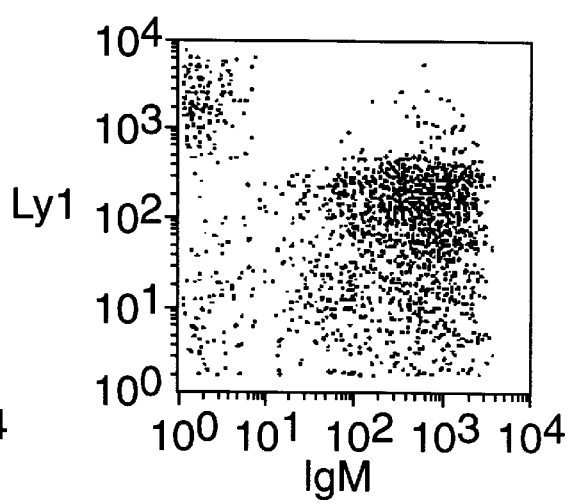
Figure 40C:
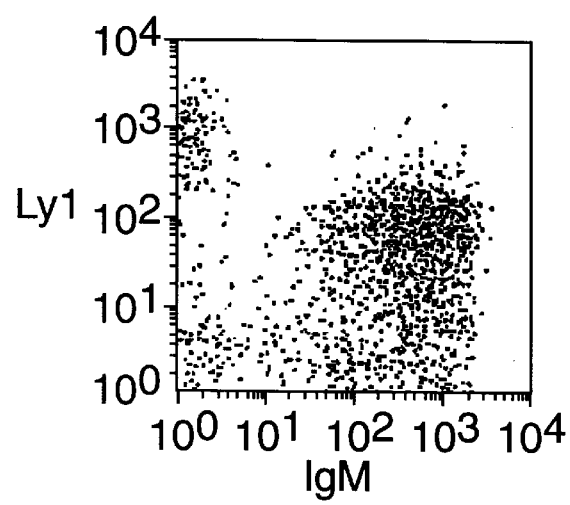
Figure 40D:
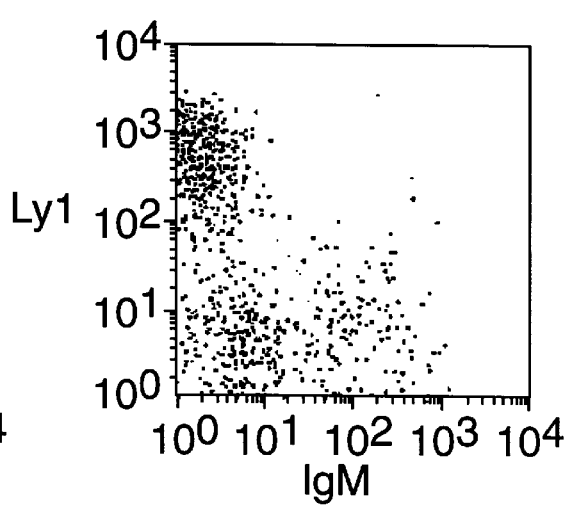

FIG. 40 shows an immunofluorescence analysis of surface Ly1 and IgM expression by live peritoneal wash lymphoid cells obtained from mice that were untreated (FIG. 40A) or treated with PBS (FIG. 40B), a control antibody (FIG. 40C), or an anti-IL-10 antibody (FIG. 40D).

Figure 41A:
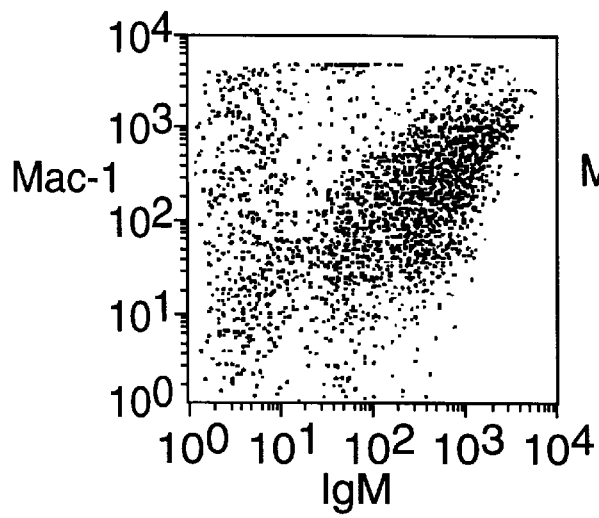
Figure 41B:
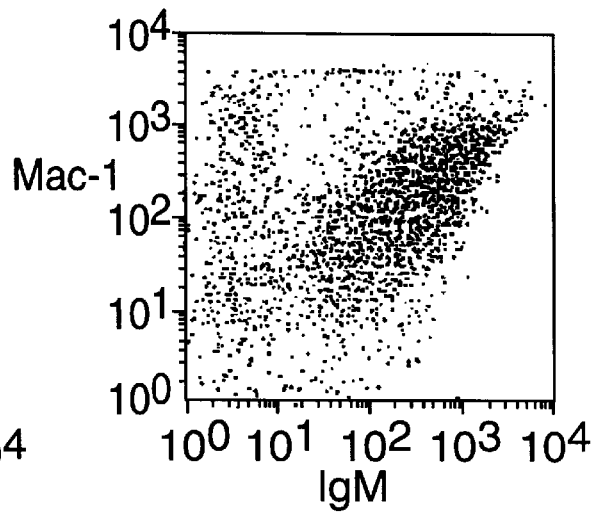
Figure 41C:
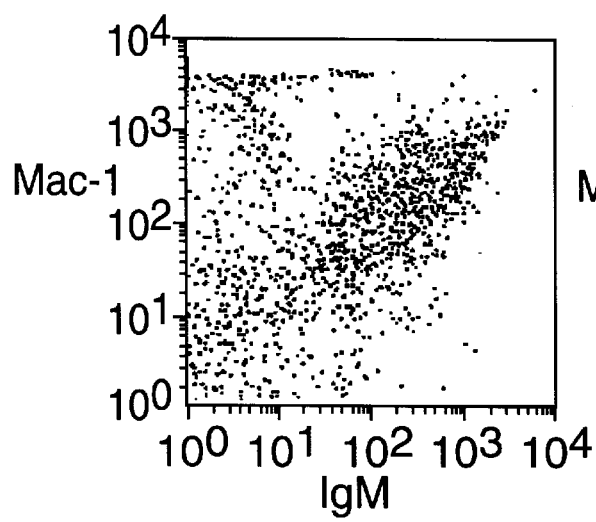
Figure 41D:
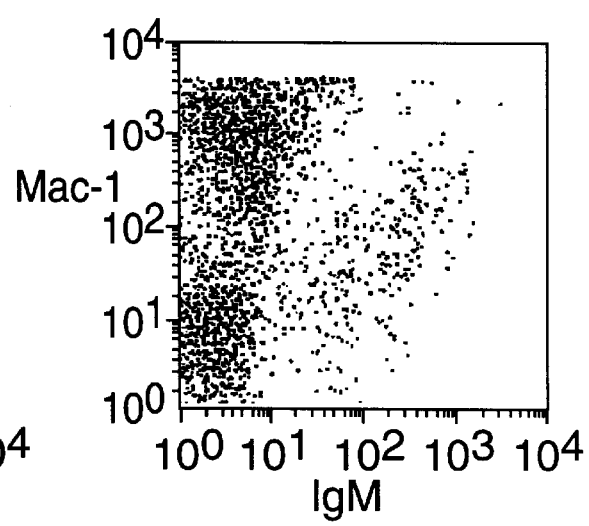

FIG. 41 shows an immunofluorescence analysis of surface Mac-1 and IgM expression by live peritoneal wash cells obtained from mice that were untreated (FIG. 41A) or treated with PBS (FIG. 41B), a control antibody (FIG. 41C), or an anti-IL-10 antibody (FIG. 41D).

FIG. 42 shows the in vivo IgM and IgG antibody response to TNP-Ficoll in mice that were injected from birth until 9 weeks of age with an anti-IL-10 antibody (○) or with an isotype control antibody (•) and challenged with TNP-Ficoll at 8 weeks.

Figure 43:
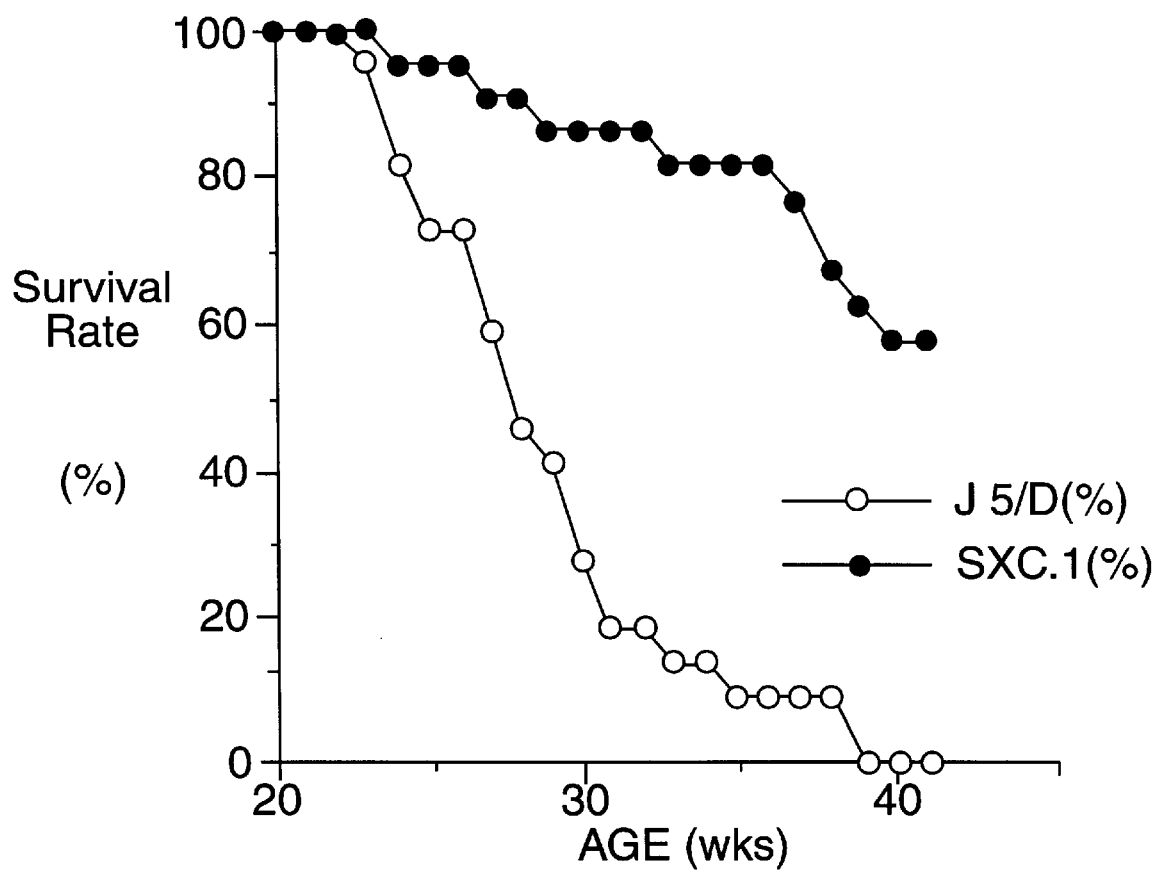

FIG. 43 is a graphical representation of the survival rate in lupus-prone NZB/W female mice which from birth had been administered either a rat IgM anti-mouse IL-10 antibody (○) or an isotype control antibody (•).

Figure 44:
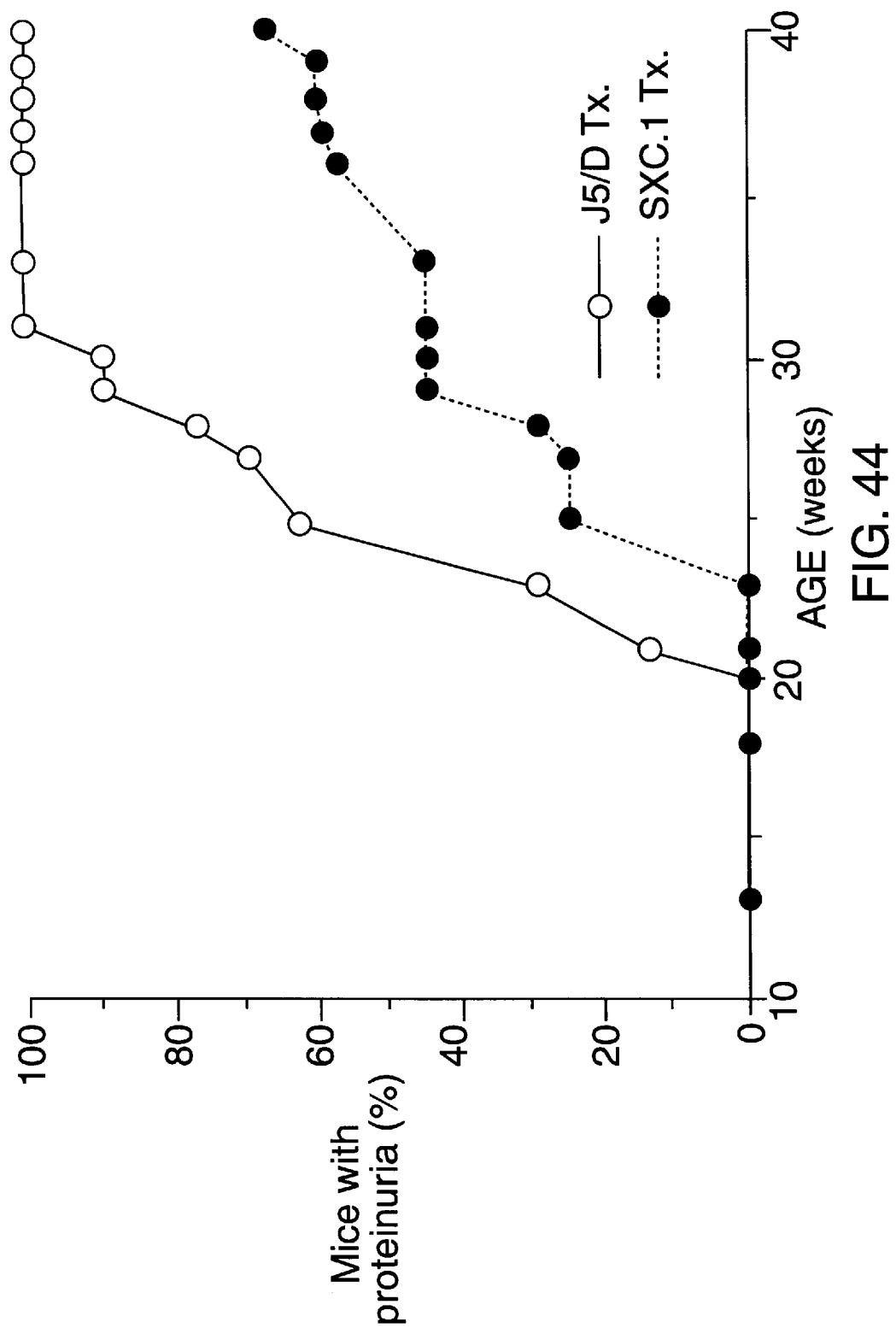

FIG. 44 shows the development of proteinuria in NZB/W female mice treated from birth with either an anti-IL-10 antibody (•) or with an isotype control antibody (○).

Figure 45:
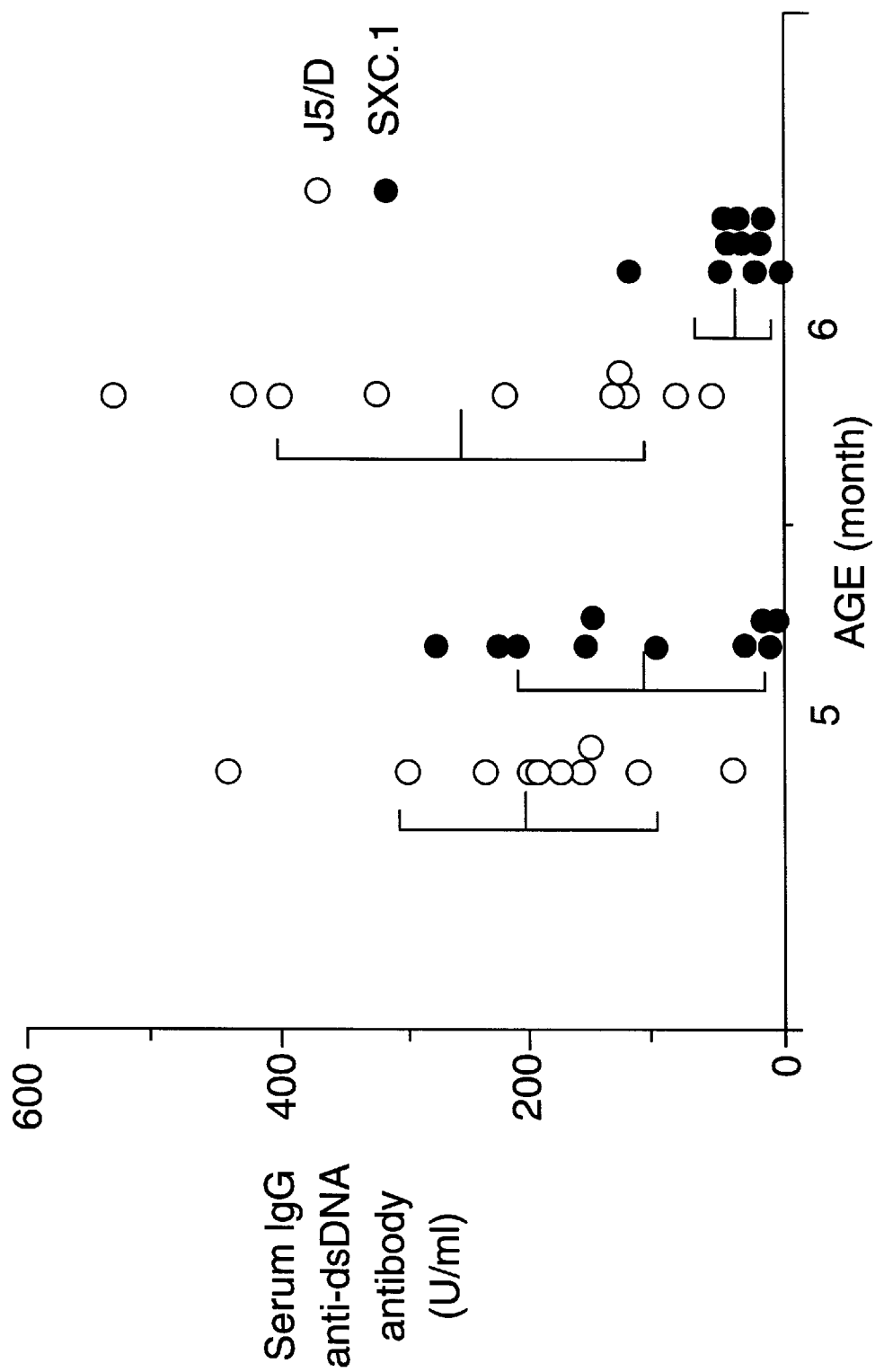

FIG. 45 shows autoantibody production in NZB/W female mice treated from birth with an anti-IL-10 antibody (•) or with an isotype control antibody (○).

Figure 46:
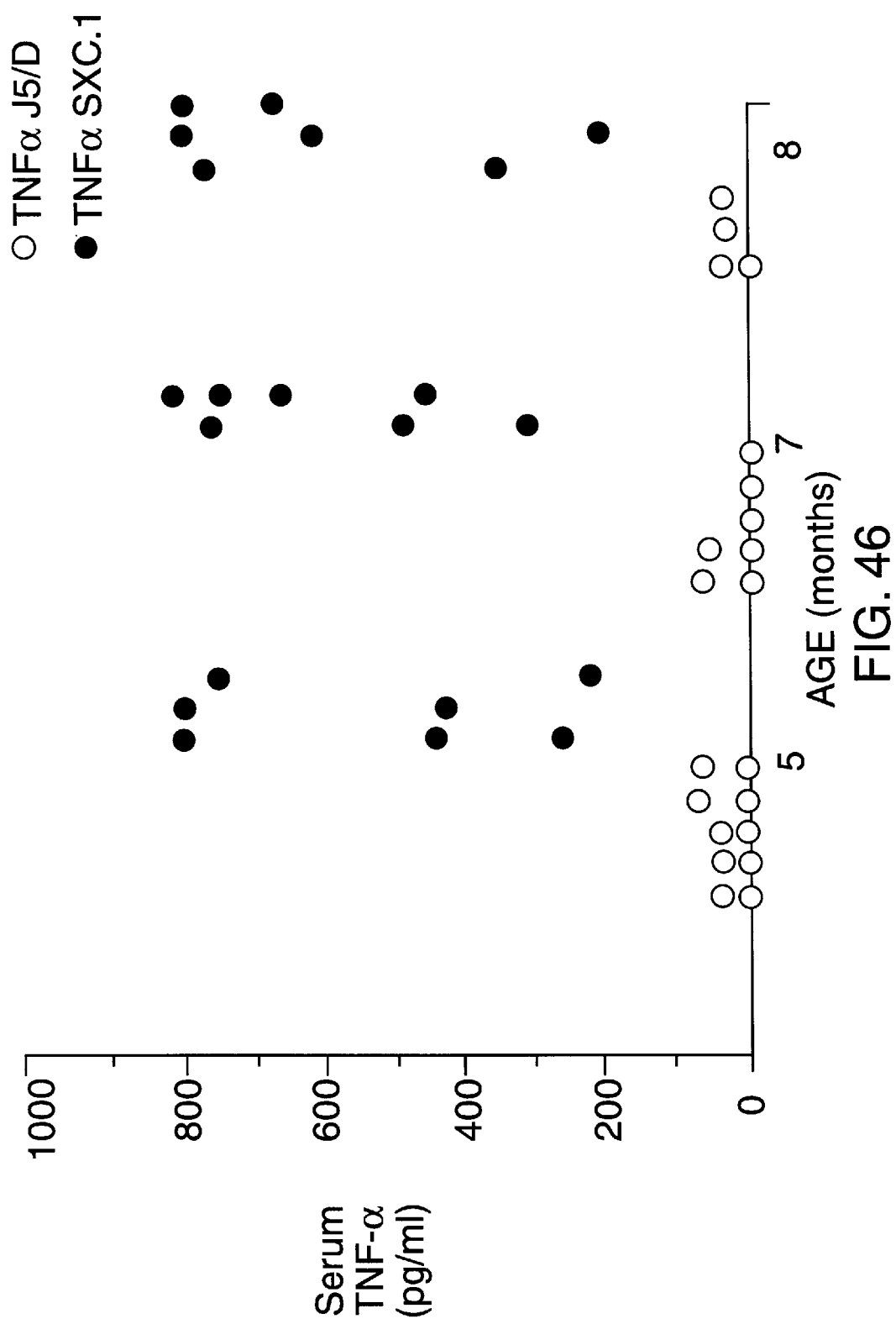

FIG. 46 shows serum TNFα levels in NZB/W female mice treated from birth with an anti-IL-10 antibody (•) or with an isotype control antibody (○).

FIG. 47 is a graphical representation of the effect of anti-TNFα antibodies on anti-IL-10 induced protection of NZB/W mice, showing results obtained from mice treated from birth with an anti-IL-10 antibody, either alone (■) or with an anti-TNFα antibody (▲), or with an isotype control antibody (□).

DETAILED DESCRIPTION OF THE INVENTION

The present invention is directed to methods of using IL-10, or analogs or antagonists thereof, to modulate immune function, particularly to prevent and/or reduce the deleterious effects of microbially induced shock or control B cell differentiation or development. The invention also includes pharmaceutical compositions comprising IL-10, or analogs or antagonists thereof, for carrying out these methods. IL-10 for use in the invention is preferably selected from the group of mature polypeptides encoded by the open reading frames defined by the cDNA inserts of pH5C, pH15C, and pBCRF1(SRα), which are deposited with the American Type Culture Collection (ATCC), Rockville, Md., under accession numbers 68191, 68192, and 68193, respectively.

IL-10 inhibits TNFα and IFNγ synthesis by monocytes or monocytes plus natural killer (NK) cells, but not by NK cells alone. IL-4 inhibits cytokine secretion from IL-2 activated NK cells directly. This suggests that IL-4 and IL-10 act on NK cells via distinct pathways, e.g., IL-10 action requires participation of monocytes. IL-10 inhibits cytokine secretion from IL-2 activated NK cells but not LAK activity, suggesting that IL-2-induced cytokine synthesis and lymphocyte-activated killer (LAK) activity are regulated by different mechanisms.

IL-10 is demonstrated to have an anti-inflammatory activity, apparently by a mechanism of its ability to inhibit production of pro-inflammatory cytokines by monocytes and/or activated macrophages or NK cells. This inhibition of cytokine production occurs at the transcriptional level.

IL-10 has also been demonstrated herein to modulate superantigen-induced responses, e.g., T cell mediated responses, in animals. Staphylococcal enterotoxin B (SEB) can induce a severe toxic shock response, and studies in mice demonstrate efficacy in vivo. Administration of IL-10 simultaneously with, or even after, exposure to superantigen is effective in preventing lethality from high SEB exposure.

The gram-negative bacterial lipopolysaccharide (LPS) induces a septic shock response in mammals. This endotoxin-induced shock response results from release of TNFα, IL-1, and/or IL-6 from stimulated macrophages/monocytes, as described above. However, adminstration of IL-10 suppresses induced expression of IL-1α, IL-1β, IL-6, IL-8, and GM-CSF. Data show herein that IL-10 is capable of protecting mice from endotoxin-induced shock, even if administered after LPS presentation. Conversely, anti-IL-10 antibodies can block the protective effect. Further studies indicate that anti-Il-10 treated mice also exhibit substantially elevated levels of circulating tumor necrosis factor alpha (TNFα) and circulating IL-6 and profound susceptibility to endotoxin-induced shock (e.g., LPS-induced).

Anti-IL-10 antibodies also have utility in treatment of other immunological conditions. Data is presented indicating that long term anti-IL-10 antibody administration to a young mouse can deplete the Ly-1 subclass of B cells. This implicates IL-10 as a regulator of Ly-1 B cell development, and provides a means to deplete Ly-1 B cells. This observation led to insight in treatment of autoimmune conditions.

The development of an autoimmune response requires a complex T cell interaction. The NZB/W strain of mice are lupus (systemic lupus erythematosus, SLE) prone and provide a model for testing therapeutic reagents for treatment of autoimmune conditions. Moreover, these mice exhibit an unusual proportion of Ly-1 B cells compared to other B cell types. in vivo mouse experiments are described using the NZB/W strain.

Anti-IL-10 treatment of these mice substantially delayed onset of the autoimmune response as monitored by overall survival, or by development of proteinenia, kidney nephritis, or autoantibody titers. This result indicates that anti-IL-10 treatment should be useful in treating other mammals, e.g., humans.

A wide range of single-cell and multicellular expression systems (i.e., host-expression vector combinations) can be used to produce the polypeptides for use in the methods of the present invention. Host cells types include, but are not limited to, bacterial, yeast, insect, mammalian, and the like. Many reviews are available which provide guidance for making choices and/or modifications of specific expression systems. See, e.g., de Boer and Shepard "Strategies for Optimizing Foreign Gene Expression in *Escherichia coli*," pgs. 205–247, in Kroon (ed.) Genes: Structure and Expression (John Wiley & Sons, New York, 1983), which reviews several *E. coli* expression systems; Kucherlapati et al., Critical Reviews in Biochemistry, Vol. 16, Issue 4, pgs. 349–379 (1984), and Banerji et al., Genetic Engineering, Vol. 5, pgs. 19–31 (1983), which review methods for transfecting and transforming mammalian cells; Reznikoff and Gold, eds., Maximizing Gene Expression (Butterworths, Boston, 1986) which reviews selected topics in gene expression in *E. coli*, yeast, and mammalian cells; and Thilly, Mammalian Cell Technology (Butterworths, Boston, 1986) which reviews mammalian expression systems.

Likewise, many reviews are available which describe techniques and conditions for linking and/or manipulating specific cDNAs and expression control sequences to create and/or modify expression vectors suitable for use with the present invention, e.g., Maniatis et al. (1982) *Molecular Cloning: A Laboratory Manual*, Cold Spring Harbor Press, Cold Spring Harbor, N.Y.; Sambrook et al. *Molecular Cloning: A Laboratory Manual* (2d ed.; vols 1–3), Cold Spring Harbor Press, Cold Spring Harbor, N.Y.; and Ausubel et al. (1987 and periodic supplements) *Current Protocols in Molecular Biology*, Wiley and Sons, New York.

An *E. coli* expression system is disclosed by Riggs in U.S. Pat. No. 4,431,739. A particularly useful prokaryotic promoter for high expression in *E. coli* is the tac promoter, disclosed by de Boer in U.S. Pat. No. 4,551,433. Secretion expression vectors are also available for *E. coli* hosts. Particularly useful are the pIN-III-ompA vectors, disclosed by Ghrayeb et al., in EMBO J., Vol. 3, pgs. 2437–2442 (1984), in which the cDNA to be transcribed is fused to the portion of the *E. coli* OmpA gene encoding the signal peptide of the ompA protein which, in turn, causes the mature protein to be secreted into the periplasmic space of the bacteria. U.S. Pat. Nos. 4,336,336 and 4,338,397 also disclose secretion expression vectors for prokaryotes.

Numerous stains of bacteria are suitable hosts for prokaryotic expression vectors including strains of *E. coli*, such as W3110 (ATCC No. 27325), JA221, C600, ED767, DH1, LE392, HB101, X1776 (ATCC No. 31244), X2282, RR1 (ATCC No. 31343) MRCI; strains of *Bacillus subtilus;* and other enterobacteriaceae such as *Salmonella typhimurium* or *Serratia marcescens,* and various species of Pseudomonas. General methods for deriving bacterial strains, such as *E. coli* K12 X1776, useful in the expression of eukaryotic proteins is disclosed by Curtis III in U.S. Pat. No. 4,190,495.

In addition to prokaryotic and eukaryotic microorganisms, expression systems comprising cells derived from multicellular organism may also be used to produce proteins of the invention. Of particular interest are mammalian expression systems because their posttranslational processing machinery is more likely to produce biologically active mammalian proteins. Several DNA tumor viruses have been used as vectors for mammalian hosts. Particularly important are the numerous vectors which comprise SV40 replication, transcription, and/or translation control sequences coupled to bacterial replication control sequences, e.g., the pcD vectors developed by Okayama and Berg, disclosed in Mol. Cell. Biol., Vol. 2, pgs. 161–170 (1982) and Mol. Cell. Biol., Vol. 3, pgs. 280–289 (1983), and improved by Takebe et al, Mol. Cell. Biol., Vol. 8, pgs. 466–472 (1988).

Other SV40-based mammalian expression vectors include those disclosed by Kaufman and Sharp, in Mol. Cell. Biol., Vol. 2, pgs. 1304–1319 (1982), and Clark et al., in U.S. Pat. No. 4,675,285. Monkey cells are usually the preferred hosts for the above vectors. Such vectors containing the SV40 ori sequences and an intact A gene can replicate autonomously in monkey cells (to give higher copy numbers and/or more stable copy numbers than nonautonomously replicating plasmids). Moreover, vectors containing the SV40 ori sequences without an intact A gene can replicate autonomously to high copy numbers (but not stably) in COS7 monkey cells, described by Gluzman, Cell, Vol. 23, pgs. 175–182 (1981) and available from the ATCC (accession No. CRL 1651). The above SV40-based vectors are also capable of transforming other mammalian cells, such as mouse L cells, by integration into the host cell DNA.

Multicellular organisms can also serve as hosts for the production of the polypeptides of the invention, e.g., insect larvae, Maeda et al, Nature, Vol. 315, pgs. 592–594 (1985) and Ann. Rev. Entomol., pgs. 351–372 (1989); and transgenic animals, Jaenisch, Science, Vol. 240, pgs. 1468–1474 (1988).

Agonists and antagonists

IL-10 agonists may be molecules which mimic IL-10 interaction with its receptors. Such may be analogs or fragments of IL-10, or antibodies against ligand binding site epitopes of the IL-10 receptors, or anti-idiotypic antibodies against particular antibodies which bind to receptor-interacting portions of IL-10.

Antagonists may take the form of proteins which compete for receptor binding, e.g., which lack the ability to activate the receptor while blocking IL-10 binding, or IL-10 binding molecules, e.g., antibodies.

Antibodies can be raised to the IL-10 cytokine, fragments, and analogs, both in their naturally occurring forms and in their recombinant forms. Additionally, antibodies can be raised to IL-10 in either its active forms or in its inactive forms, the difference being that antibodies to the active cytokine are more likely to recognize epitopes which are only present in the active conformation. Anti-idiotypic antibodies are also contemplated in these methods, and could be potential IL-10 agonists.

Antibodies, including binding fragments and single chain versions, against predetermined fragments of the desired antigens, e.g., cytokine, can be raised by immunization of animals with conjugates of the fragments with immunogenic proteins. Monoclonal antibodies are prepared from cells secreting the desired antibody. These antibodies can be screened for binding to normal or inactive analogs, or screened for agonistic or antagonistic activity. These monoclonal antibodies will usually bind with at least a $K_D$ of about 1 mM, more usually at least about 300 $\mu$M, typically at least about 10 $\mu$M, more typically at least about 30 $\mu$M, preferably at least about 10 $\mu$M, and more preferably at least about 3 $\mu$M or better. Although the foregoing addresses IL-10, similar antibodies will be raised against other analogs, its receptors, and antagonists.

The antibodies, including antigen binding fragments, of this invention can have significant diagnostic or therapeutic value. They can be potent antagonists that bind to the IL-10 receptors and inhibit ligand binding to the receptor or inhibit the ability of IL-10 to elicit a biological response. IL-10 or fragments may be joined to other materials, particularly polypeptides, as fused or covalently joined polypeptides to be used as immunogens.

The cytokine and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York, and Williams et al. (1967) *Methods in Immunology and Immunochemistry*, Vol. 1, Academic Press, New York, for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts, such as mice, rodents, primates, humans, etc. Description of techniques for preparing such monoclonal antibodies may be found in, e.g., Stites et al. (eds) *Basic and Clinical Immunology* (4th ed.), Lange Medical Publications, Los Altos, Calif., and references cited therein; Harlow and Lane (1988) *Antibodies: A Laboratory Manual*, CSH Press, Goding (1986) *Monoclonal Antibodies: Principles and Practice* (2d ed) Academic Press, New York; Coligan et al. (eds; 1991 and periodic supplements) *Current Protocols in Immunology*, Wiley and Sons, New York; and particularly in Kohler and Milstein (1975) in *Nature* 256: 495–497, which discusses one method of generating monoclonal antibodies.

Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro under selective conditions, unlike the myeloma parent cells. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or alternatively to selection of libraries of antibodies in phage or similar vectors. See, Huse et al. (1989) "Generation of a Large Combinatorial Library of the Immunoglobulin Repertoire in Phage Lambda," *Science* 246:1275–1281; and Ward et al. (1989) *Nature* 341:544–546. The polypeptides and antibodies of the present invention may be used with or without modification, including chimeric or humanized antibodies. Also, recombinant immunoglobulins may be produced, see Cabilly, U.S. Pat. No. 4,816,567.

Antibodies raised against the cytokine or its receptor will also be useful to raise anti-idiotypic antibodies which may exhibit agonist or antagonist properties. These will be useful in modulating various immunological responses as discussed herein.

Purification and Pharmaceutical Compositions

When polypeptides of the present invention are expressed in soluble form, e.g., as a secreted product of transformed yeast or mammalian cells, they can be purified according to standard procedures of the art, including steps of ammonium sulfate precipitation, ion exchange chromatography, gel filtration, electrophoresis, affinity chromatography, and/or the like, see, e.g., "Enzyme Purification and Related Techniques," Methods in Enzymology, 22:233–577 (1977), and Scopes, R., Protein Purification: Principles and Practice (Springer-Verlag, New York, 1982), provide guidance in such purifications. Likewise, when polypeptides of the invention are expressed in insoluble form, for example as aggregates, inclusion bodies, or the like, they can be purified by standard procedures in the art, including separating the inclusion bodies from disrupted host cells by centrifugation, solublizing the inclusion bodies with chaotropic and reducing agents, diluting the solubilized mixture, and lowering the concentration of chaotropic agent and reducing agent so that the polypeptide takes on a biologically active conformation. The latter procedures are disclosed in the following references: Winkler et al, Biochemistry, 25: 4041–4045 (1986); Winkler et al, Biotechnology, 3: 992–998 (1985); Koths et al, U.S. Pat. No. 4,569,790; and European patent applications 86306917.5 and 86306353.3.

As used herein "effective amount" means an amount sufficient to ameliorate or prevent a shock condition, as determined, for example, by recognized symptoms, such as chills, vasoconstriction, mental confusion, hypoperfusion, hyperpyrexia, and the like. The effective amount for a particular patient may vary depending on such factors as the state and type of the sepsis being treated, the overall health of the patient, method of administration, the severity of side-effects, and the like. Generally, an IL-10 reagent is administered as a pharmaceutical composition comprising an effective amount of the reagent and a pharmaceutical carrier. See, e.g., Kaplan and Pasce (1984) *Clinical Chemistry: Theory, Analysis, and Correlation*, Mosby and Co., St. Louis, Mo.; and Gilman et al. (1990) *Goodman and Gilmans: The Phamacological Basis of Therapeutics* (8th ed.), Pergamon Press. In certain applications, the IL-10 therapeutic reagent may be combined with another pharmaceutically active ingredient, including an antibiotic composition.

A pharmaceutical carrier can be any compatible, non-toxic substance suitable for delivering the compositions of the invention to a patient. Many compositions useful for parenteral administration of such drugs are known, e.g., Remington's Pharmaceutical Science, 15th Ed. (Mack Publishing Company, Easton, Pa. 1980). Alternatively, compositions of the invention may be introduced into a patient's body by an implantable or injectable drug delivery system. See, e.g., Urquhart et al., Ann. Rev. Pharmacol. Toxicol., Vol. 24, pgs. 199–236 (1984); Lewis, ed. Controlled Release of Pesticides and Pharmaceuticals (Plenum Press, New York, 1981); U.S. Pat. No. 3,773,919; U.S. Pat. No. 3,270,960.

When administered parenterally, the IL-10 is formulated in a unit dosage injectable form (solution, suspension, emulsion) in association with a pharmaceutical carrier. Examples of such carriers are normal saline, Ringer's solution, dextrose solution, and Hank's solution. Nonaqueous carriers such as fixed oils and ethyl oleate may also be used. A preferred carrier is 5% dextrose/saline. The carrier may contain minor amounts of additives such as substances that enhance isotonicity and chemical stability, e.g., buffers and preservatives. The IL-10 reagent is preferably formulated in purified form substantially free of aggregates and other proteins at a concentration in the range of about 5 to 20 mg/ml. Preferably, IL-10 is administered by continuous infusion so that an amount in the range of about 50–800 mg is delivered per day (i.e., about 1–16 mg/kg/day). The daily infusion rate may be varied based on monitoring of side effects and blood cell counts.

Similar considerations apply in determining an effective amount of an IL-10 agonist or antagonist, although certain antagonists might require broader dose ranges, e.g., in the higher ranges.

Biological Observations and Mechanisms

Although not bound by the following proposed mechanisms, the following discussion provides insight into the uses and applications of IL-10 analogs, agonists, and antagonists. A useful background to immune system function, development, and differentiation is provided, e.g., in Paul (ed) (1989) *Fundamental Immunology* (2d ed) Raven Press, New York. Chapters 26 on inflammation, 28 on delayed type hypersensitivity, and 31 on autoimmunity are particularly relevant to uses described herein.

The effects of IL-4 and IL-10 on cytokine synthesis and LAK activity induced by IL-2 in human PBMC and purified NK cells are described in detail below. While IL-4 and IL-10 both inhibit IL-2-induced IFN$\gamma$ and TNF$\alpha$ synthesis in PBMC, only IL-4 inhibits IL-2-induced IFN$\gamma$ synthesis by purified NK cells. Thus IL-4 and IL-10 inhibit NK cell cytokine synthesis by different mechanisms.

Results of experiments investigating TNF$\alpha$ production suggested a similar conclusion. However in this case, monocytes also produce this cytokine. IL-10 had no direct effect on IL-2-induced TNF$\alpha$ synthesis by NK cells, but was able to block TNF$\alpha$ production by monocytes. Stimulation by IL-2 of cultures containing both NK cells and CD14+ cells resulted in a large enhancement of TNF$\alpha$ production, and IL-10 completely blocked this enhancement. Since IL-2 did not activate CD14+ cells to produce additional TNF$\alpha$, the synergistic enhancement probably represents augmentation of NK cell TNF$\alpha$ synthesis. Thus, it appears that IL-10 inhibits both TNF$\alpha$ production by monocytes as well as their co-stimulatory effects on NK cell TNF$\alpha$ synthesis.

Although both IL-4 and hIL-10/vIL-10 suppress IFN$\gamma$ and TNF$\alpha$ synthesis by IL-2-stimulated PBMC, only IL-4 inhibits IL-2-induced LAK activity. These observations indicate that IL-2-induced cytokine production and cytotoxicity in PBMC are regulated via different pathways. These findings are of importance in the clinical use of IL-2 and LAK cells. Problems associated with IL-2 therapy have included cardiovascular effects and a capillary leak syndrome. The causes of these side effects are uncertain, but may involve release of cytokines such as TNF$\alpha$ induced by IL-2 in cancer patients. That IL-10 inhibits IL-2-induced cytokine synthesis but not LAK activity suggests that this cytokine may be useful in combination with IL-2 for treating such patients. In addition, in view of data suggesting that TNF$\alpha$ can induce expression of human immunodeficiency virus in infected T cells, the ability of IL-10 to inhibit synthesis of TNF$\alpha$ is of possible interest in this connection.

These studies also demonstrate that human IL-10 is produced in relatively large quantities by monocytes following activation. Kinetic studies showed that low levels of IL-10 could be detected 7 hrs after activation of the monocytes, and maximal IL-10 production occurred 24–48 hrs after activation. This was relatively late as compared to the production of IL-1$\alpha$, IL-1$\beta$, IL-6, IL-8, and TNF$\alpha$, which were secreted at high levels between 4–8 hrs after activation. It was also shown that human IL-10 has strong inhibitory effects on cytokine production by monocytes following activation with IFN$\gamma$, LPS, or combinations of IFN$\gamma$ and LPS. These inhibitory effects are specific for IL-10 since they could be completely neutralized by mAb 19F1 which inhibits both IL-10 and v-IL-10 activity. IL-10 added at concentrations of 100 U/ml reduced IL-1$\alpha$, TNF$\alpha$, GM-CSF, and G-CSF synthesis by more than 90% following optimal activation of the monocytes by combinations of IFN$\gamma$ (100 U/ml) and LPS (1 $\mu$g/ml). The inhibitory effects on IL-1$\beta$, IL-6, and IL-8 production were somewhat less pronounced, particularly when the monocytes were optimally activated by combinations of IFN$\gamma$ and LPS. The mechanism by which IL-10 inhibits cytokine production by monocytes is not clear, e.g., whether these effects of IL-10 are direct or indirectly mediated via other factors. Since IL-1 can induce IL-6 production in fibroblasts, thymocytes, and monocytes, it is, for example, possible that the partial inhibition of IL-6 production is the result of reduced IL-1 production.

Viral-IL-10, which has been shown to possess biological activities on human cells, similar to human IL-10, was less extensively tested. However, v-IL-10 inhibited TNF$\alpha$ and GM-CSF production by LPS activated monocytes to the same extent as did human IL-10. These inhibitory effects of v-IL-10 on TNF$\alpha$ and GM-CSF production were neutralized by mAb 19F1, illustrating the specificity of the v-IL-10 effects.

Inhibition of IL-1$\alpha$, IL1$\beta$, IL-6, IL-8, TNF$\alpha$, GM-CSF, and G-CSF secretion occurred at the transcriptional level. IL-10 strongly inhibited cytokine specific mRNA synthesis induced by LPS, as determined by northern and PCR analyses. PCR analyses were performed under conditions that allowed a comparison of the reaction products of individual samples in a semi-quantitative manner. This was validated by the fact that amplification of cDNA's with primers specific for $\beta$-actin resulted in equivalent amounts of reaction products between the samples and quantitatively comparable results were obtained when IL-10 mRNA expression was determined in the same samples by both northern and PCR analysis. In addition, cytokine mRNA expression levels correlated with the protein levels in the supernatants of these cultures. IL-10 failed to affect TGF$\beta$ mRNA expression in activated monocytes. However, it should be noted that TGF$\beta$ was constitutively expressed in nonactivated monocytes and that activation of the monocytes by LPS did not affect TGF$\beta$ mRNA levels. Assoian et al. (1987) *Proc. Nat'l Acad. Sci. USA* 84:6020–6024, have demonstrated that monocytes constitutively express TGF$\beta$ mRNA and that TGF$\beta$ secretion requires monocyte activation. However, whether IL-10 has an effect on the conversion of TGF$\beta$ from a latent to an active form is unclear.

The production of IL-10 was shown to be inhibited by IL-4 at the transcriptional level. Although the inhibitory effects of IL-4 on IL-10 production were considerable, IL-4 was not able to block the production of IL-10 completely. IL-4 inhibited the production of IL-10 only up to 70%, even when high IL-4 concentrations (400 U/ml), which were sufficient to completely inhibit the production of IL-1, IL-6 and TNFα, were used. It has already been demonstrated that IL-4 is able to inhibit the production of IL-1α, IL-1β, IL-6, IL-8, and TNFα by human monocytes. These findings were confirmed and extended by demonstrating that IL-4 also inhibited the production of IL-8, GM-CSF, and G-CSF by LPS activated human monocytes. This inhibition occurred at the transcriptional level. The data furthermore illustrate that IL-4 and IL-10 have similar effects on cytokine expression by human monocytes, which underlines the pleiotropic effects of cytokines and redundancy in the immune system.

Interestingly, IL-10 is an autoregulatory cytokine, since it strongly inhibited IL-10 mRNA synthesis in monocytes activated for 24 h. In addition, activation of monocytes by LPS in the presence of neutralizing anti-IL-10 mAbs resulted in an increased expression of IL-10 mRNA at 24 hrs, indicating that endogenously produced IL-10 also inhibited IL-10 mRNA synthesis. The fact that IL-10 is able to downregulate its own production by human monocytes makes this the first cytokine that is regulated by a negative feedback mechanism. Autoregulatory effects of endogenously produced IL-10 were also observed on the production of IL-1α, IL-1β, IL-6, IL-8, TNFα, GM-CSF, and G-CSF by LPS activated monocytes with LPS in the presence of anti-Il-10 antibodies. However, the inhibitory effects of endogenous IL-10 on the production of these cytokines were less pronounced than those of exogenous IL-10 added at the onset of the culture. This is related to the fact that IL-1α, IL-1β, IL-6, IL-8, TNFα, and G-CSF are already produced at high levels 4–8 hrs after activation, whereas maximal endogenous IL-10 production occurs much later at 24–48 hrs after activation. This notion is supported by the observation that the strongest inhibitory effects of endogenously produced IL-10 were found on GM-CSF secretion which was shown to be produced late following activation of the monocytes. Assuming that IL-10 mRNA synthesis reflects and precedes IL-10 protein secretion, and that IL-10 can only interact with its receptor on the cell surface, these results suggest that the inhibitory effects of endogenously produced IL-10 occur relatively late and may therefore be of particular importance in the later phases of an immune response.

IL-10 was first described in the mouse as a cytokine synthesis inhibitor factor (CSIF) produced by Th2 cells, which inhibited cytokine production (predominately IFNγ) by Th1 cells. This inhibitory effect of m-IL-10 on cytokine production by Th1 cells require the presence of macrophages, see, e.g. Fiorentino et al. (1991) *J. Immunol.* 146:3444–3451; Trowbridge et al. (1981) *J. Ept'l Med.* 154:1517–1524; Lambert et al. (1989) *Cell. Immunol.* 120:401–418; and Hirsch et al. (1981) *J. Ept'l Med.* 154:713–725. Herein Il-10 and v-Il-10 strongly inhibit antigen specific T cell proliferation when monocytes are used as APC.

In addition, reduction in the antigen specific proliferative T cell responses are largely due to reduced antigen presenting capacity of monocytes caused by strong downregulatory effects of IL-10 on class II MHC antigen expression on these cells. These data, together with the present finding that IL-10 is produced late by monocytes and has autoregulatory effects on IL-10 secretion by these cells, indicate that IL-10 has strong downregulatory effects on ongoing antigen specific T cell responses. Therefore IL-10 can play a major role in dampening antigen driven proliferative T cell responses. The notion that IL-10 produced by monocytes may also have strong autoregulatory feedback activity on T cell activation is supported by the observation that IL-10 produced by monocytes following activation by LPS is responsible for downregulation of class II MHC antigens on these cells, since class II MHC expression was not reduced and even strongly enhanced when LPS stimulations were carried out in the presence of the neutralizing anti-IL-10 mAb.

The proinflammatory cytokines, IL-1α, IL-1β, IL-6, IL-8, and TNFα, are involved in acute and chronic inflammatory processes, and many autoimmune diseases, including rheumatoid arthritis. These cytokines modulate the activation and function of cells of the immune system, but also those of endothelial cells, keratinocytes, and hepatocytes. The finding that IL-10 has strong downregulatory effects on the secretion of these cytokines suggests that IL-10 is a powerful inhibitor of inflammation. Based on its properties described thus far, which include inhibition of antigen specific T cell proliferation by reducing the APC capacity of monocytes through downregulation of class II MHC antigens on these cells and inhibitory effects on proinflammatory cytokine secretion by monocytes, it seems that IL-10 plays a major role as a suppressor of immune and inflammatory responses. This role is confirmed in further in vitro studies and in vivo models of both endotoxin and enterotoxin superantigen responses.

The present studies demonstrate that IL-10 has an inhibitory effect on LPS-induced cytokine production by macrophage cell lines and peritoneal macrophages. Thus, IL-10 not only has an important role in the regulation of T-cell responses, but also on inflammatory responses elicited during infection or injury.

The effect of IL-10 on the macrophage cell lines is more pronounced than that elicited by similar amounts of IL-4, which has previously been shown to inhibit cytokine production by both murine and human macrophages and monocytes. These results show a significant inhibition of LPS-induced TNFα protein production by IL-4, but a less marked inhibition of IL-6 synthesis, in these cell lines. However, inhibition of TNFα by IL-4 is not as great as that previously reported for human monocytes. This difference may be explained by the difference in species, the use of differentiated macrophage cell lines rather than monocytes, or because these studies used 10 μg/ml of LPS as opposed to the 100 ng/ml dose used in one of the human monocyte systems.

In contrast to IL-4, IL-10 significantly inhibited IL-6, TNFα, and IL-1 protein production at this high concentration of LPS. Stimulation of the macrophage cell lines with LPS and IFNγ induced a much higher level of TNFα and IL-6 and, in some cases, this was refractory to IL-4 action, suggesting that IL-4 and IFNγ may have opposite and counteracting effects on certain aspects of macrophage activation. Again this is in contrast to the studies on human monocytes, which were performed with lower amounts of LPS. Once more, the IL-10-mediated inhibition of IFNγ plus LPS-induced production of IL-6 and TNFα protein was more significant than that seen with IL-4.

Inhibition of LPS or IFNγ plus LPS-induced expression of RNA encoding IL-6 and TNFα was also observed using a semi-quantitative PCR amplification method for reverse transcribed RNA. In some cases, IL-4 inhibited expression to a similar extent as IL-10, suggesting that IL-10 also has an effect on secretion or stability of the translated proteins. However IL-10 achieves its effects, it would appear that its final inhibitory effect on cytokine production by macrophages is more potent than that seen with IL-4. The effects of IL-10 on monokine production suggest that this powerful inhibitor may have potential as an anti-inflammatory agent perhaps in a wide variety of clinical manifestations.

Since it had also been shown that peritoneal macrophages were inhibited by IL-10 from stimulating T cells, whether IL-10 inhibited cytokine secretion by this purified cell population was tested. FACS-purified peritoneal macrophages obtained from BALB/c or CBA/J mice, stimulated with LPS produced significant levels of IL-6 protein which was only slightly reduced in the presence of IL-10. Since preliminary PCR data suggested that purified macrophages produced IL-10, an antibody directed against IL-10 was included in some of the LPS stimulations. Addition of this antibody to LPS stimulations in both strains of mouse elevated the production of IL-6 protein to a much higher level (30–35 ng/ml per $7\times10^5$ cells/ml, in 20 h). This is consistent with cytokine production by macrophages being under tight autocrine control, or that more than one population of macrophages is contained in the Mac-1 $^{+,Bright}$ peritoneal macrophages, one of which has control over the other by its production of IL-10. Data obtained in parallel in the human monocyte system also shows that IL-10 inhibits LPS-induced cytokine production, including the production of IL-10 itself, by human monocytes purified by elutriation.

In accordance with previous reports contrasting effects of T-helper cell derived cytokines such as IL-4 and IL-10 with Th1 T-helper cell cytokines such as IFNγ, further evidence that these cytokines may have counteracting effects on each other is provided. IFNγ increased the level of IL-6 produced in response to LPS, to almost as high a level as that achieved by anti-IL-10, by ostensibly inhibiting the production of IL-10 by the same macrophages. These data suggest that production of cytokines such as IL-6 and TNFα is regulated by IL-10, which in turn is under the control of IFNγ produced by activated T-cells and NK cells. This action of IFNγ may explain the previous observations showing that incubation of peritoneal macrophages with IFNγ for 24 h improved their capacity to stimulate Th1 cells.

The mechanism of how IL-10 inhibits the macrophage from stimulating cells from synthezising cytokines is still unresolved. In view of the significant decrease in cytokine synthesis observed when macrophages are stimulated in the presence of IL-10, IL-10 may down-regulate a co-stimulatory activity needed for optimal cytokine secretion in response to macrophages and antigen. Using supernatants obtained from stimulated 1G18.LA macrophage cells, it was not possible to overcome the inhibitory effect of IL-10 on macrophage and antigen-dependent stimulation of Th1 cells. This is consistent with a mechanism where IL-10 does not mediate its effects on cytokine synthesis by down-regulation of a soluble co-stimulator.

It is possible, though unlikely, that IL-10 interferes with the action rather than the production of such a factor, or that such a co-stimulator is highly labile or absorbed, and thus not present in these supernatant preparations. Alternatively, IL-10 may inhibit the expression of a membrane-bound co-stimulator, which would also explain previous reports suggesting that stimulation of cells requires an APC/accessory cell which cannot be replaced by a soluble co-stimulator.

An alternative explanation for the mechanism of IL-10 inhibition of cytokine synthesis could be that IL-10 induces production of an inhibitory factor(s) by the macrophage, which then acts on the T-cell to inhibit cytokine secretion. Mixing of macrophage and B-cell APC in an antigen-specific system for stimulation of Th1 cells leads to an additive stimulation of the T-cell, as compared to stimulation with each individual APC. The presence of IL-10 inhibits cytokine synthesis by the cell to the level that the B cell APC achieves on its own. This suggests that the macrophage does not induce the production of an inhibitor which acts directly on the T-cell, or the B cell APC. Although unlikely, it is possible that such an inhibitor may either be specific for macrophage-T cell interactions, or that the B cell APC somehow overcomes or evades the effect of such an activity.

Data obtained in the human system suggests that IL-10 does not achieve its inhibition of T-helper cell proliferation via a soluble inhibitory or co-stimulatory factor produced by the monocyte. However, their effects can be explained by the down-regulation of MHC-Class II antigens by IL-10 on human monocytes, which as yet have not been observed in the mouse system.

In addition to regulation of effector function, IL-10 could also play a role in the initiation of an immune response towards antibody production or delayed type hypersensitivity (DTH), by activation of different subsets of CD4 T-helper cells producing different patterns of cytokines. That both B cells and macrophages produce IL-10, and also function as APC, while being sensitive to different cytokine modulators (IFNγ inhibits many B cell functions; IL-10 inhibits macrophage but not B cell APC function) lends support to this theory. In addition these studies show that IL-10 has a significant inhibitory effect on cytokine synthesis by macrophages, as well as causing a marked morphological change in peritoneal macrophages.

Taken together, these observations suggest an important role for IL-10, not only in the regulation of T cell responses but also as an important modulator of acute inflammatory responses elicited by infection or injury.

In Example 24, the ability IL-10 to inhibit superantigen-mediated toxicity in vivo was tested. IL-10 is capable of inhibiting cytokine production by T cells, in part by inhibiting the ability of macrophages to activate T cells. Superantigens have been defined as molecules that activate T cells by forming a "bridge" between the Vβ chain of the TCR and class II MHC molecules present on APCs. These results suggested that IL-10. could inhibit cytokine production by T cells activated by superantigens presented by macrophages. This effect has been observed in vitro. Superantigens can be endogenous, e.g., encoded by viruses, or exogenous, e.g., microbial enterotoxins. The most studied superantigens of the latter group include the staphylococcal enterotoxins. It is now known that the toxicity exhibited by these toxins depends on their ability to activate T cells in vivo. These observations suggest that agents that inhibit T cell activation will prevent the toxicity exhibited by superantigens. This is consistent with the observation that cyclosporin prevents SEB-mediated toxicity. According to this model, TNFα is the main mediator of toxicity. The results presented here indicate that IL-10 is able to prevent the toxicity of SEB, probably through its ability to inhibit TNF production by T cells.

These observations have interesting implications for the mechanism of IL-10 action in vivo. IL-10 has been shown to inhibit macrophage functions, e.g.,cytokine production, ability to activate T cells, and induces Ia antigen expression in B cells. But since the toxicity of SEB depends on the expression of Ia antigens by APC, the outcome of these experiments in vivo was uncertain. That IL10 prevents SEB-induced toxicity suggests that the main APC in vivo is the macrophage, not the B cell.

These results have important implications for the therapeutic use of IL-10. Besides food poisoning caused by staphylococcal enterotoxins, a number of diseases have been recently reported to be superantigen-induced, e.g., toxic shock syndrome, Kawasaki disease, diseases caused by streptococcal toxins, and autoimmune diseases like rheumatoid arthritis.

IL-10 is highly effective at protecting mice from lethal endotoxemia, a finding which suggests IL-10 can be useful in treatment of bacterial sepsis. While numerous other reagents, e.g., antibodies to TNFα or endotoxin, and the IL-1Ra, are currently in clinical trials for treatment of bacterial sepsis, most of these need to be given prior to sepsis induction in animal model experiments for optimal protection. One exception to this, the IL-1Ra, is effective when administered at the time of sepsis induction in animal model experiments, but must be administered in quantities large enough to block all endogenous IL-1 receptors. Pharmacological doses of IL-10 also produce an array of effects on macrophage/monocyte function that should contribute to protection from lethal endotoxemia, quite possibly at less than receptor saturating amounts.

While the foregoing discussions are directed to the effects of IL-10 administration in regulation and differentiation of various aspects of the immune system, further insight is achieved through blockage of the effects of the IL-10 cytokine using anti-IL-10 antibodies.

Data presented here indicates that continuous treatment of mice from birth to adulthood with anti-IL-10 antibodies drastically reduces total Ly-1 B cell number and function, without altering the number, phenotype, or immunocompetence of conventional B cells located in spleens of these same animals. Several observations support the proposed depletion of Ly-1 B cells in anti-IL-10-treated mice: (a) anti-IL-10-treated mice contain few or no B cells in their peritoneal cavities, a site of Ly-1 B cell enrichment in normal mice. (Peritoneal wash cells of 8-wk-old BALB/c mice in the DNAX animal facility contain fewer than 5% conventional B cells by phenotypic analysis); (b) anti-IL-10-treated mice contain 0–10% of normal serum IgM levels, which is consistent with previous reconstitution experiments identifying Ly-1 B cells as the predominant source of circulating IgM; and (c) anti-IL-10 treated mice generate little or no antibody in response to injection with phosphorylcholine and α1,3-dextran, antigens for which specific B cells reside in the Ly-1 B cell subset.

The data suggesting an unaltered conventional B cell compartment in anti-IL-10-treated mice are equally compelling, with unchanged numbers of splenic B cells displaying normal cell surface marker phenotypes, and responding normally to a thymus-dependent antigen and B cell mitogens. The selective depletion of Ly-1 B cells in anti-IL-10-treated mice was found to be transient, as Ly-1 B cells reappeared in the peritoneal cavities of these animals several weeks after anti-IL-1-treated was discontinued.

Several possible mechanisms were considered as explanation for the selective depletion of Ly-1 B cells in anti-IL-10-treated mice. The data presented indicate that this is at least partially the consequence of IFNγ elevation after anti-IL-10-treated treatment, since coadministration of neutralizing anti-IL-10 and anti-IFNγ antibodies substantially prevented the depletion of peritoneal B cells in these studies. The implication that IFNγ either directly or indirectly inhibits Ly-1 B cells development is reminiscent of previous observations that IFNγ causes slight suppression of IL-5 induced in vitro proliferation of the Ly-1$^+$ B lymphoma BCL1.

In extending these studies, IFNγ-mediated suppression of LPS-induced proliferation of peritoneal cells, but not spleen cells from normal BALB/c mice was observed. Whether the elevation of IFNγ in anti-IL-10-treated mice totally accounts for Ly-1 B cell depletion, and whether this reflects a direct action of IFNγ of Ly-1 B cells or some IFNγ mediated indirect effect, is not fully understood. Possibly, other changes in anti-IL-10-treated mice additionally contribute to the depletion of Ly-1 B cells. Anti-IL-10-treatment will probably lead to elevation of endogenous monokine levels.

Anti-IL-10-treated mice are ~50-fold more susceptible to death by LPS-induced shock, an event that is known to be mediated by monokines, and that 5 of 32 individual anti-IL-10 treated mice contain substantial levels of serum IL-6, a monokine that is generally not found in the circulation of normal animals and that could not be detected in the sera of any of 10 control mice from these experiments. However, IL-6 transgenic mice or animals having greatly elevated serum monokine levels upon in vivo administration of LPS appear to have normal serum IgM levels, suggesting unchanged numbers of Ly-1. B cells.

Earlier findings that Ly-1 B cells, but not conventional B cells generate constitutive and inducible IL-10 led to a suggestion that IL-10 acts as an autocrine growth factor. This now seems unlikely in light of the substantial numbers of peritoneal Ly-1 B cells recovered from mice treated with both anti-IL-10 and anti-IFNγ antibodies.

The Ly-1 B cell-depleted mouse created by continuous anti-IL-10 treatment bears considerable similarity to immunodeficient xid mice, a spontaneous mutant strain derived from CBA/CaH mice which lacks Ly-1 B cells, and is unresponsive to a subset of thymus-independent antigens. Despite these similarities, our preliminary investigations have revealed that xid mice produce IL-10 normally, and contain functional IL-10 receptors, thus distinguishing xid mice and anti-IL-10-treated mice mechanistically. Furthermore, one property that distinguished anti-IL-10-treated mice from xid mice is the in vitro responsiveness of spleen cells to anti-IgM stimulation, exhibited by the former but not the latter animals.

The physiological role of IL-10 was studied by injecting mice from birth to adulthood with monoclonal antibodies that specifically neutralize IL-10. Such treatment leads to numerous distinct changes in the immune status of these animals. The animals are characterized by increases in circulating TNFα IFN-γ, and in many cases, IL-6. These effects are consistent with the previously reported in vitro properties of IL-10, a potent suppressant of IFNγ and monokine production in cell culture experiments The increase in endogenous IFN-γ appears responsible for several of the other consequences resulting from anti-IL-10 treatment.

For example, it leads to the depletion of Ly-1 B cells, and, this in turn accounts for the reduction of circulating IgM and IgA antibodies, and specific antibody responses to phosphorylcholine and α1,3 dextran. The elevated IFN-γ levels are likely also responsible for the increases in circulating IgG$_{2a}$ that this isotype is positively regulated by IFN-γ. The remaining changes of increases in peritoneal T cells, granulocytes, and circulating IgG$_{2b}$ are not understood mechanistically, but these may be the consequence of secondary cytokine perturbations.

While generally healthy, anti-IL-10 treated mice were found to be highly susceptible to death resulting from endotoxin-induced shock. This lethal inflammatory reaction is a monokine mediated event which can be prevented by passive transfer of antibodies specific for either TNF-α, IL-1 IL-6, or endotoxin. It is therefore not surprising that anti-IL-10 treated mice, which exhibit endogenous monokine upregulation and which lack the B cell population most likely to produce anti-endotoxin antibodies (i.e. Ly-1 B cells), are more susceptible to this inflammatory reaction. These data suggest clinical role for IL-10 as an anti-inflammatory reagent. Consistent with this notion, experiments indicate that pharmacological doses of IL-10 protect mice from death due to endotoxin-induced shock.

While the outlined phenotype of anti-IL-10 treated mice is clearly consistent with the known in vitro properties of IL-10, it is nevertheless in contrast to that of preliminary reports about mice rendered IL-10 deficient by gene targeting. These mutants have undetectable levels of circulating IFN-γ, TNF-α and IL-6, normal numbers of Ly1 B cells in the peritoneal cavity, and, in a first approximation, normal serum Ig levels. The explanation for this discrepancy is not clear, although a similar discrepant situation exists between IL-2 knock-out mice and at least some reports of mice treated from birth until adulthood with anti-IL-2 receptor antibodies.

One explanation involves the well-recognized redundancy that exists within the cytokine system. It is possible that a developing mouse embryo will compensate the loss of a critical cytokine gene by amplifying expression of a gene encoding a cytokine of closely related function. For example, since IL-4 shares many properties with IL-10, this cytokine would be an excellent candidate to compensate the total loss of IL-10, and thus its expression may become upregulated in IL-10 knock-out mice. In contrast, neutralization of endogenous IL-10 via antibody treatment of mice from birth would represent a "leaky" elimination of the cytokine at best, and so remaining traces of endogenous IL-10 may be sufficient to avoid a profound immunodeficiency and a regulatory activation of a compensatory cytokine pathway.

An alternative explanation that antibody treated animals mount artifactual immune responses to the administered xenogeneic antibodies and/or resultant immune complexes cannot be totally eliminated. Nevertheless, this alternative seems unlikely since isotype control antibodies and antibodies to other cytokines that would also generate immune complexes in vivo do not produce the immune modulations ascribed to anti-IL-10 treated mice.

While the pattern of immune-modulation observed in anti-IL-10 treated mice does not correlate completely with any of the known human immunodeficiency diseases, certain similarities to both Wiskott-Aldrich patients and IgA deficiency syndrome patients exist. These human immunodeficiencies are characterized by a lack of circulating IgM or IgA respectively, reduced abilities to generate anti-bacterial antibody responses, and frequently an increase in circulating IgG1, the major complement fixing human antibody isotype that probably correlates with murine IgG2a. Whether such patients exhibit diminished IL-10 production or responsiveness, and if so, whether this in turn contributes to their immunodeficiency, awaits confirmation.

The potential role of IL-10 in IgA deficiency syndrome is particularly intriguing in light of a recent study clearly implicating IL-10 as an important co-factor required for naive human B cells to differentiate into IgA-secreting cells following their activation with cross-linked anti-CD40 antibodies and TGFβ. The inability of anti-IL-10 treated mice to generate specific antibody responses to two bacterial antigens further supports the proposition that IL-10 will be an effective adjuvant in anti-bacterial immunity.

In addition to providing information about the physiological role and clinical potential of IL-10, anti-IL-10 treated mice provide a novel opportunity to evaluate the contribution of Ly-1 B cells to the immune system. The secondary consequences resulting from Ly-1 B cell depletion in anti-IL-10 treated mice confirm many of the properties previously ascribed to this minor B cell sub-population. However these data additionally provide new insights regarding the contribution of Ly-1 B cells to the immune system.

In particular, it is reasonable to conclude that Ly-1 B cells are not needed for development of IgG1, IgG2a, IgG2b, IgG3, or IgE responses, since serum levels of these isotypes are not diminished in Ly-1 B cell depleted anti-IL-10 treated mice. Similarly, while Ly-1 B cells are essential for responsiveness to some thymus independent type II antigens, e.g., phosphorylcholine and α1,3 dextran, they are apparently not needed for others, e.g., TNP-Ficoll and anti-IgM. Indeed, the unchanged or slightly elevated levels of circulating IgG3, an isotype uniquely associated with B cell responsiveness to polysaccharide antigens, suggest that Ly-1 B cell deficient mice are probably capable of responding to most thymus independent type II antigens. This aspect of anti-IL-10 treated mice readily distinguishes them from the xid mouse, a spontaneously arising immunodeficient mouse strain which also lacks Ly-1 B cells, but which is unresponsive to all thymus independent type II antigens.

In addition to providing information about the contribution of Ly1 B cells to the immune system, anti-IL-10 treated mice allow us to evaluate the consequences of TNFα elevation in vivo. Our data clearly illustrates that in vivo antagonism of Il-10 leads to substantial elevation of serum TNFα levels. While the unfavorable consequences of TNFα elevation have been considered in detail above (e.g., septic shock, cerebral malaria, etc.), numerous favorable consequences of TNFα elevation should also be considered. These include the demonstration in animal models of direct anti-tumor effects, expansion of granulocyte-monocyte hemopoietic lineages, radioprotection and protection against some autoimmune and infectious diseases.

These considerations therefore implicate Il-10 antagonists as candidates for therapeutic intervention in treatment of these types of diseases. Indeed, we have confirmed this proposal to the extent of demonstrating that anti-Il-10 antibodies can substantially delay the development of autoimmunity in the lupus-prone NZB/W mouse.

In summary, the present invention relates to the use of Il-10 or Il-10 antagonists to regulate production of monokines which are major mediators of many disease states. Il-10 and its agonists will cause marked suppression of monokines such as TNFα and in this way provide protection against undesirable inflammatory reactions such as bacterial sepsis, toxic shock, rheumatoid arthritis, and psonasis. Similarly, Il-10 antagonists will enhance the level of monokines such as TNFα, which in turn may act as an anti-tumor agent, and in providing radioprotection and protection agains certain autoimmune and infectious diseases.

EXAMPLES

The following examples serve to illustrate the present invention. Selection of vectors and hosts as well as the concentration of reagents, temperatures, and the values of other variable parameters are to exemplify application of the present invention and are not to be considered as limitations thereof.

Some general assays were carried out as follows.
Assays for Interleukin-10 and Analogs IL-10 related proteins and peptides, referred to collectively as IL-10s, exhibit several biological activities which could form the basis of assays and units. In particular, IL-10s have property of inhibiting the synthesis of at least one cytokine in the group consisting of IFNγ, lymphotoxin, IL-2, IL-3, and GM-CSF in a population of T helper cells induced to synthesize one or more of these cytokines by exposure to syngeneic antigen presenting cells (APCs) and antigen. In this activity, the APCs are treated so that they are incapable of replication, but that their antigen processing machinery remains functional. This is conveniently accomplished by irradiating the APCs, e.g., with about 1500–3000 R (gamma or X-radiation) before mixing with the T cells.

The following protocol can be used to assay for mouse IL-10.

IL-10 (CSIF) Assay—Modified to Proliferation Assay Antigen Presenting Cells (APC)

1) Take BALB/c spleens (approx. $10^8$ cells/spleen into tube of cRPMI.
2) Make a single cell suspension using a strainer and barrel of 10 ml syringe (using sterile technique in hood), spin at 1200 rpm.
3) Resuspend pellet in 5 ml cold $NH_4Cl$ (0.83% in $H_2O$). Spin again at 1200 rpm.
4) Resuspend pellet in 5 ml cRPMI (no IL-2 for assay) and spin to wash.
5) Resuspend in 5 ml cRPMI and count.
6) Irradiate for 3000 rad. (currently 20 min).
7) Adjust cell concentration to $8 \times 10^6$/ml. (will add 50 µl per well in assay to give final of $4 \times 10^5$/well).

(Titrate IL-10 in either 100 µl final volume in microtiter plate, or 50 µl final volume if wish to add anti-IL-10 antibody).

Th1 Cells

1) Three days before assay thaw out an ampoule of HDK1 cells directly into $2 \times 25$ ml CRPMI containing IL-2.
2) Check cells day after and if necessary split 1 in 2 or 1 in 3.
3) On day of assay spin cells at 1200 rpm. immediately before plating and resuspend in 5 ml cRPMI and count (dilute 1 in 2 in trypan blue).
4) Readjust concentration to $2 \times 10^5$ per ml and add 50 µl per well (final $10^4$ cells per well). Before plating out add KLH to give concentration of 400 µg/ml. (This will give final concentration of 100 µg/ml).

Controls

50 µl Th1 cells no KLH.
50 µl Th1 cells+KLH.
50 µl Spleen APC.
plus and minus IL10 (probably highest concentration is fine).
brought up to a final volume of 200 µl Order of assay 1) Prepare APC.
2) Plate out IL-10.
3) Prepare Th1 cells and plate out.
4) Plate out APC.

After 48 hr. remove 100 µl sup. for IFNγ ELISA; then add $^3$H-thymidine (1 µCi per well) and harvest next morning.

Alternatively, cytokine inhibition may be assayed in primary or, preferably, secondary, mixed lymphocyte reactions (MLR), in which case syngeneic APCs need not be used. MLRs are well known in the art, see, e.g., Bradley, pgs. 162–166, in Mishell et al, eds. *Selected Methods in Cellular Immunology* (Freeman, San Francisco, 1980); and Battisto et al, Meth. in Enzymol., Vol. 150, pgs. 83–91 (1987). Briefly, two populations of allogenic lymphoid cells are mixed, one of the populations having been treated prior to mixing to prevent proliferation, e.g., by irradiation. Preferably, the cell populations are prepared at a concentration of about $2 \times 10^6$ cells/ml in supplemented medium, e.g., RPMI 1640 with 10% fetal calf serum. For both controls and test cultures, mix 0.5 ml of each population for the assay. For a secondary MLR, the cells remaining after 7 days in the primary MLR are restimulated by freshly prepared, irradiated stimulator cells. The sample suspected of containing IL-10 may be added to the test cultures at the time of mixing, and both controls and test cultures may be assayed for cytokine production from 1 to 3 days after mixing.

Obtaining T cell populations and/or APC populations for IL-10 assays employs techniques well known in the art which are fully described, e.g., in DiSabato et al., eds., Meth. in Enzymol., Vol. 108 (1984). APCs for the preferred IL-10 assay are peripheral blood monocytes or tissue macrophages. These are obtained using standard techniques, e.g., as described by Boyum, Meth. in Enzymol., Vol. 108, pgs. 88–102 (1984); Mage, Meth. in Enzymol., Vol. 108, pgs. 118–132 (1984); Litvin et al., Meth. in Enzymol., Vol. 108, pgs. 298–302 (1984); Stevenson, Meth. in Enzymol., Vol. 108, pgs. 242–249 (1989); and Romain et al, Meth. in Enzymol., Vol. 108, pgs. 148–153 (1984).

Preferably, helper T cells are used in the IL-10 assays, which are obtained by first separating lymphocytes from the peripheral blood, spleen, or lymph nodes, then selecting, e.g., by panning or flow cytometry, helper cells using a commercially available anti-CD4 antibody, e.g., OKT4 described in U.S. Pat. No. 4,381,295 and available from Ortho Pharmaceutical Corp. Mouse anti-CD4 is available from Becton-Dickson or Pharmingen. The requisite techniques are fully disclosed in Boyum, Scand. J. Clin. Lab. Invest., Vol. 21 (Suppl. 97), pg. 77 (1968); Meth. in Enzymol., Vol. 108 (cited above), and in Bram et al, Meth. in Enzymol., Vol. 121, pgs. 737–748 (1986). Generally, PBLs are obtained from fresh blood by Ficoll-Hypaque density gradient centrifugation.

A variety of antigens can be employed in the assay, e.g., Keyhole limpet hemocyanin (KLH), fowl γ-globulin, or the like. More preferably, in place of antigen, helper T cells are stimulated with anti-CD3 monoclonal antibody, e.g., OKT3 disclosed in U.S. Pat. No. 4,361,549, in the assay.

Cytokine concentrations in control and test samples are measured by standard biological and/or immunochemical assays. Construction of immunochemical assays for specific cytokines is well known in the art when the purified cytokine is available. See, e.g., Campbell, Monoclonal Antibody Technology (Elsevier, Amsterdam, 1984); Tijssen, Practice and Theory of Enzyme Immunoassays (Elsevier, Amsterdam, 1985); and U.S. Pat. No. 4,486,530, are exemplary of the extensive literature on the subject. ELISA kits for human IL-2, human IL-3, and human GM-CSF are commercially available from Genzyme Corp. (Boston, Mass.); and an ELISA kit for human IFNγ is commercially available from Endogen, Inc. (Boston, Mass.). Polyclonal antibodies specific for human lymphotoxin are available from Genzyme Corp. which can be used in a radioimmunoassay for human lymphotoxin, e.g., Chard, An Introduction to Radioimmunoassay and Related Techniques (Elsevier, Amsterdam, 1982).

Biological assays of the cytokines listed above can also be used to determine IL-10 activity. A biological assay for human lymphotoxin is disclosed in Aggarwal, Meth. in Enzymol., Vol. 116, pgs. 441–447 (1985), and Matthews et al, pgs. 221–225, in Clemens et al, eds., Lymphokines and Interferons: A Practical Approach (IRL Press, Washington, D.C., 1987). Human IL-2 and GM-CSF can be assayed with factor dependent cell lines CTLL-2 and KG-1, available from the ATCC under accession numbers TIB 214 and CCL 246, respectively. Human IL-3 can be assayed by its ability to stimulate the formation of a wide range of hematopoietic cell colonies in soft agar cultures, e.g., as described by Metcalf, The Hemopoietic Colony Stimulating Factors (Elsevier, Amsterdam, 1984). INF-γ can be quantified with anti-viral assays, e.g., Meager, pgs. 129–147, in Clemens et al, eds. (cited above). Mouse equivalents can likewise be assayed with appropriate cell lines.

Cytokine production can also be determined by mRNA analysis. Cytokine mRNAs can be measured by cytoplasmic dot hybridization as described by White et al., J. Biol. Chem., Vol. 257, pgs. 8569–8572 (1982) and Gillespie et al., U.S. Pat. No. 4,483,920. Other approaches include dot blotting using purified RNA, e.g., chapter 6, in Hames et al., eds., Nucleic Acid Hybridization A Practical Approach (IRL Press, Washington, D.C., 1985). Polymease chain reaction (PCR) techniques can also be used, see Innis et al. (ed) (1990) *PCR Protocols: A Guide to Methods and Applications,* Academic Press, Inc., New York, which incorpates herein by reference.

In some cases, samples to be tested for IL-10 activity will be pretreated to remove predetermined cytokines that might interfere with the assay. For example, IL-2 increases the production of IFNγ in some cells. Thus, depending on the helper T cells used in the assay, IL-2 may have to be removed from the sample being tested. Such removals are conveniently accomplished by passing the sample over a standard anti-cytokine affinity column.

For convenience, units of IL-10 activity are defined in terms of IL-10's ability to augment the IL-4-induced proliferation of MC/9 cells, which are described in U.S. Pat. No. 4,559,310 and available from the ATCC under accession number CRL 8306. One unit/ml is defined as the concentration of IL-10 which gives 50% of maximum stimulation of MC/9 proliferation above the level of IL-4 in the following assay. Duplicate or triplicate dilutions of IL-4 and IL-10 are prepared in 50 ul of medium per well in a standard microtiter plate. Medium consists of RPMI 1640, 10% fetal calf serum, 50 uM 2-mercaptoethanol, 2 mM glutamine, penicillin (100 U/L), and streptomycin (100 mg/L). Add IL-4, 25 µl/well of 1600 U/ml (400 U/ml final) diluted in medium and incubate overnight, e.g., 20–24 hours. $^3$H-thymidine (e.g., 50 mCi/ml in medium) is added at 0.5–1.0 mCi/well and the cells are again incubated overnight, after which cells are harvested and incorporated radioactivity measured.

For general descriptions of preparation of the cytokines IL-4 and IL-10, see U.S. Pat. No. 5,017,691, and U.S. Ser. No. 07/453,951.

Example 1
Expression of Human IL-10 in a Bacterial Host

A synthetic human IL-10 gene was assembled from a plurality of chemically synthesized double stranded DNA fragments to form an expression vector designated TAC-RBS-hIL-10. Cloning and expression were carried out in a standard bacterial system, for example *E. coli* K-12 strain JM101, JM103, or the like, described by Viera and Messing, in Gene, Vol. 19, pgs. 259–268 (1982). Restriction endonuclease digestions and ligase reactions were typically performed using standard protocols, e.g., Maniatis et al., *Molecular Cloning: A Laboratory Manual* (Cold Spring Harbor Laboratory, New York, 1982), Sambrook et al. *Molecular Cloning: A Laboratory Manual* (Cold Spring Harbor Laboratory, New York), and Ausubel et al. (1987 and periodic supplements) *Current Protocols in Molecular Biology,* Wiley and Sons, New York.

The alkaline method was used for small scale plasmid preparations. For large scale preparations a modification of the alkaline method was used in which an equal volume of isopropanol is used to precipitate nucleic acids from the cleared lysate. Precipitation with cold 2.5M ammonium acetate was used to remove RNA prior to cesium chloride equilibrium density centrifugation and detection with ethidium bromide.

For filter hybridizations Whatman 540 filter circles were used to lift colonies which were then lysed and fixed by successive treatments with 0.5M NaOH, 1.5M NaCl; 1M Tris-HCl pH 8.0, 1.5M NaCl (2 min each); and heating at 80° C. (30 min). Hybridizations were in 6×SSPE, 20% formamide, 0.1% sodium dodecylsulphate (SDS), 100 µg/ml *E. coli* tRNA, and 100 µg/ml Coomassie Brilliant Blue G-250 (Bio-Rad) at 42° C. for 6 hrs using $^{32}$P-labelled (kinased) synthetic DNAs. (20×SSPE was prepared by dissolving 174 g of NaCl, 27.6 g of NaH$_2$PO$_4$9H$_2$O, and 7.4 g of EDTA in 800 ml of H$_2$O. The pH was adjusted to 7.4 with NaOH. The volume was adjusted to 1 liter, and sterilized by autoclaving). Filters were washed twice (15 min, room temperature) with 1×SSPE, 0.1% SDS.

After autoradiography (Fuji RX film), positive colonies were located by aligning the regrown colonies with the blue-stained colonies on the filters. DNA was sequenced according to the dideoxy method, Sanger et al. Proc. Natl. Acad. Sci., Vol. 74, pg. 5463 (1977). Templates for the dideoxy reactions were either single stranded DNAs of relevant regions recloned into M13mp vectors, e.g., Messing et al. Nucleic Acids Res., Vol. 9, pg. 309 (1981), or double-stranded DNA prepared by the minialkaline method and denatured with 0.2M NaOH (5 min, room temperature) and precipitated from 0.2M NaOH, 1.43M ammonium acetate by the addition of 2 volumes of ethanol. DNA was synthesized by phosphoramidite chemistry using Applied Biosystems 380A synthesizers. Synthesis, deprotection, cleavage, and purification (7M urea PAGE, elution, DEAE-cellulose chromotography) were performed as described in the 380A synthesizer manual.

Complementary strands of synthetic DNAs to be cloned (400 ng each) were mixed and phosphorylated with polynucleotide kinase in a reaction volume of 50 ml. This DNA was ligated with 1 mg of vector DNA, digested with appropriate restriction enzymes, and ligations were performed in a volume of 50 ul at room temperature for 4 to 12 hours. Conditions for phosphorylation, restriction enzyme digestions, polymerase reactions, and ligation have been described (Maniatis et al., cited above). Colonies were scored for lacZ+ (when desired) by plating on L agar supplemented with ampicillin, isopropyl-1-thio-beta-D-galactoside (IPTG) (0.4 mM), and 5-bromo-4-chloro-3-indolyl-beta-D-galactopyranoside (X-gal) (40 µg/ml).

The TAC-RBS vector was constructed by filling-in with DNA polymerase the single BamHI site of the tacP-bearing plasmid pDR540 (Pharmacia). This was then ligated to unphosphorylated synthetic oligonucleotides (Pharmacia) which form a double-stranded fragment encoding a consensus ribosome binding site (RBS, GTAAGGAGGTTTAAC) (SEQ ID NO: 5). After ligation, the mixture was phosphorylated and religated with the SstI linker ATGAGCTCAT (SEQ ID NO: 6). This complex was then cleaved with SstI and EcoRI, and the 173 bp fragment isolated via polyacrylamide gel electrophoresis (PAGE) and cloned into EcoRI-SstI restricted pUC19 (Pharmacia) (as described below). The sequence of the RBS-ATG-polylinker regions of the final construction (called TAC-RBS) is disclosed in U.S. Pat. No. 5,017,691.

The synthetic IL-10 gene was assembled into a pUC19 plasmid in eight steps. At each step inserts free of deletions and/or inserts could be detected after cloning by maintaining the lacZ(a) gene of pUC19 in frame with the ATG start codon inserted in step 1. Clones containing deletion and/or insertion changes could be filtered out by scoring for blue colonies on L-ampicillin plates containing X-gal and IPTG. Alternatively, at each step, sequences of inserts can be readily confirmed using a universal sequencing primer on small scale plasmid DNA preparations.

In step 1 the TAC-RBS vector was digested with SstI, treated with T4 DNA polymerase (whose 3' exonuclease activity digests the 3' protruding strands of the SstI cuts to form blunt end fragments), and after deactivation of T4 DNA polymerase, treated with EcoRI to form a 173 base pair (bp) fragment. This fragment contains the TAC-RBS region and has a blunt end at the ATG start codon and an EcoRI cut at the opposite end. Finally, the 173 bp TAC-RBS fragment was isolated.

In step 2 the isolated TAC-RBS fragment of step 1 was mixed with EcoRI/KpnI digested plasmid pUC19 and synthetic fragment 1A/B which, as shown below, has a blunt end at its upstream terminus and a staggered end corresponding to an KpnI cut at its downstream terminus. This KpnI end is adjacent to and downstream of a BstEII site. The fragments were ligated to form the pUC19 of step 2.

In step 3 synthetic fragment 2A/B and 3A/B (shown below) were mixed with BstEII/SmaI digested pUC19 of step 2 (after amplification and purification) and ligated to form pUC19 of step 3. Note that the downstream terminus of fragment 3A/B contains extra bases which form the SmaI blunt end. These extra bases were cleaved in step 4. Also fragments 2A/B and 3A/B have complementary 9 residue single stranded ends which anneal upon mixture, leaving the upstream BstEII cut of 2A/B and the downstream blunt end of 3A/B to ligate to the pUC19.

In step 4 AflII/XbaI digested pUC19 of step 3 (after amplification and purification) was repurified, mixed with synthetic fragment 4A/B (shown below), and ligated to form pUC19 of step 4.

In step 5 XbaI/SalI digested pUC19 of step 4 (after amplification and purification) was mixed with synthetic fragment 5A/B (shown below) and ligated to form the pUC19 of step 5. Note that the SalI staggered end of fragment 5A/B is eliminated by digestion with HpaI in step 6.

In step 6 HpaI/PstI digested pUC19 of step 5 (after amplification and purification) was mixed with synthetic fragment 6A/B (shown below) and ligated to form the pUC19 of step 6.

In step 7 ClaI/SphI digested pUC19 of step 6 (after amplification and purification) was mixed with synthetic fragment 7A/B (shown below) and ligated to form the pUC19 of step 7.

In step 8 MluI/HindIII digested pUC19 of step 7 (after amplification and purification) was mixed with synthetic fragments 8A/B and 9A/B and ligated to form the final construction. The final construction was inserted into *E. coli* K-12 strain JM101, e.g., available from the ATCC under accession number 33876, by standard techniques. After culturing, protein was extracted from the JM101 cells and dilutions of the extracts were tested for biological activity. The referred to fragment sequences are presented in Table 1.

TABLE 1

Fragment 1A/B

AGCCCAGGCC AGGGCACCCA GTCTGAGAAC AGCTGCACCC ACTTC-
TCGGGTCCGG TCCCGTGGGT CAGACTCTTG TCGACGTGGG TGAAG-
CCAGGtAACC ggtac (SEQ ID NO: 7)
GGTCCaTTGG c (SEQ ID NO: 8)

Fragment 2A/B

GtAACCTGCC TAACATGCTT CGAGATCTCC GAGATGCCTT CAGCA-
GACGG ATTGTACGAA GCTCTAGAGG CTCTACGGAA GTCGT-
GAGTGAAGACTTTCTTT (SEQ ID NO: 9)
CTCACTTC (SEQ ID NO: 10)

Fragment 3A/B

CAAATGAAGG ATCAGCTGGA CAACTTGTTc TtAAG (SEQ ID NO: 11)
TGAAAGAAA GTTTACTTCC TAGTCGACCT GTTGAACAAg AaTTC (SEQ
ID NO: 12)

Fragment 4A/B

GAGTCCTTGC TGGAGGACTT TAAGGGTTAC CTGGGTTGCC AAGCC-
CTCAGGAACG ACCTCCTGAA ATTCCCAATG GACCCAACGG TTCGG-
TTGTCTGAGA TGATCCAGTT TTAt (SEQ ID NO: 13)
AACAGACTCT ACTAGGTCAA AATaGAtC (SEQ ID NO: 14)

Fragment 5A/B

CTaGAGGAGG TGATGCCCCA AGCTGAGAAC CAAGACCCAG ACATC-
GAtCTCCTCC ACTACGGGGT TCGACTCTTG GTTCTGGGTC TGTAG-
AAGGCGCATG TtAACg (SEQ ID NO: 15)
TTCCGCGTAC AaTTGcagct (SEQ ID NO: 16)

Fragment 6A/B

AACTCCCTGG GGGAGAACCT GAAGACCCTC AGGCTGAGGC TACGG-
TTGAGGGACC CCCTCTTGGA CTTCTGGGAG TCCGACTCCG ATGCC-
CGCTGTCATC GATctgca (SEQ ID NO: 17)
GCGACAGTAG CTAg (SEQ ID NO: 18)

Fragment 7A/B

CGATTTCTTC CCTGTCAAAA CAAGAGCAAG GCCGTGGAGC AGGTG-
TAAAGAAG GGACAGTTTT GTTCTCGTTC CGGCACCTCG TCCAC-
AAGAAcGCgT gcatg (SEQ ID NO: 19)
TTCTTgCGcA c (SEQ ID NO: 20)

Fragment 8A/B

CGCGTTTAAT AATAAGCTCC AAGACAAAGG CATCTACAAA GCCAT-
AAATTA TTATTCGAGG TTCTGTTTCC GTAGATGTTT CGGTA-

TABLE 1-continued

GAGTGAGTTT GAC (SEQ ID NO: 21)
CTCA (SEQ ID NO: 22)

Fragment 9A/B

ATCTTCATCA ACTACATAGA AGCCTACATG ACAAT-
CTAAACTG TAGAAGTAGT TGATGTATCT TCGGATGTAC TGTTA-
GAAGATACGA AACTGA (SEQ ID NO: 23)
CTTCTATGCT TTGACTtcga (SEQ ID NO: 24)

Lower case letters indicate that a base differs from that of the native sequence at the same site.

Example 2
Expression of vIL-10 in COS 7 Monkey Cells

A gene encoding the open reading frame for vIL-10 was amplified by polymerase chain reaction using primers that allowed later insertion of the amplified fragment into an Eco RI-digested pcD(SRa) vector, described in Takebe et al. (1988) *Mol. Cell. Biol.* 8:466–472. The coding strand of the inserted fragment is shown below (the open reading frame being given in capital letters).

| | | | | |
|---|---|---|---|---|
| aattcATGGA | GCGAAGGTTA | GTGGTCACTC | TGCAGTGCCT | GGTGCTGCTT |
| TACCTGGCAC | CTGAGTGTGG | AGGTACAGAC | CAATGTGACA | ATTTTCCCCA |
| GACCTAAGAG | ATGCCTTCAG | TCGTGTTAAA | ACCTTTTTCC | AGACAAAGGA |
| CGAGGTAGAT | AACCTTTTGC | TCAAGGAGTC | TCTGCTAGAG | GACTTTAAGG |
| ATGCCAGGCC | CTGTCAGAAA | TGATCCAATT | CTACCTGGAG | GAAGTCATGC |
| CACAGGCTGA | AACCAGGAC | CCTGAAGCCA | AAGACCATGT | CAATTCTTTG |
| GGTGAAAATC | TAAAGACCCT | ACGGCTCCGC | CTGCGCAGGT | GCCACAGGTT |
| CCTGCCGTGT | GAGAACAAGA | GTAAAGCTGT | GGAACAGATA | AAAAATGCCT |
| TTAACAAGCT | GCAGGAAAAA | GGAATTTACA | AAGCCATGAG | TGAATTTGAC |
| ATTTTTATTA | ACTACATAGA | AGCATACATG | ACAATTAAAG | CCAGGTGAg |

Clones carrying the insert in the proper orientation were identified by expression of vIL-10 and/or the electrophoretic pattern of restriction digests. One such vector carrying the vIL-10 gene was designated pBCRF1(SRa) and was deposited with the ATCC under accession number 68193. pBCRF1(SRa) was amplified in *E. coli* MC1061, isolated by standard techniques, and used to transfect COS 7 monkey cells as follows: One day prior to transfection, approximately $1.5 \times 10^6$ COS 7 monkey cells were seeded onto individual 100 mm plates in Dulbecco's modified Eagle medium (DME) containing 5% fetal calf serum (FCS) and 2 mM glutamine.

To perform the transfection, COS 7 cells were removed from the dishes by incubation with trypsin, washed twice in serum-free DME, and suspended to $10^7$ cells/ml in serum free DME. A 0.75 ml aliquot was mixed with 20 μg DNA and transferred to a sterile 0.4 cm electroporation cuvette. After 10 minutes, the cells were pulsed at 200 volts, 960 mF in a BioRad Gene Pulser unit. After another 10 minutes, the cells were removed from the cuvette and added to 20 ml of DME containing 5% FCS, 2 mM glutamine, penicillin, streptomycin, and gentamycin. The mixture was aliquoted to four 100 mm tissue culture dishes. After 12–24 hours at 37° C., 5% $CO_2$, the medium was replaced with similar medium containing only 1% FCS and the incubation continued for an additional 72 hours at 37° C., 5% $CO_2$, after which the medium was collected and assayed for its ability to inhibit IFNγ synthesis.

Ten-ml aliquots of freshly isolated peripheral blood leukocytes (PBLs) (about $2 \times 10^6$ cells/ml) were incubated at 37° C. with phytohemo-agglutinin (PHA) (100 ng/ml) in medium consisting of (i) 90% DME supplemented with 5% FCS and 2 mM glutamine, and (ii) 10% supernatant from COS 7 cells previously transfected with pBCRF1(SRa). After 24 hours the cells and supernatants were harvested to assay for the presence of either IFNγ mRNA or IFNγ protein, respectively. Controls were treated identically, except that the 10% supernatant was from COS 7 cultures previously transfected with a plasmid carrying an unrelated cDNA insert. The vIL-10-treated samples exhibited about a 50% inhibition of IFNγ synthesis relative to the controls.

Example 3
Expression of vIL-10 in *Escherichia coli*

A gene encoding the following mature vIL-10 may be expressed in *E. coli*.

| | | | | | | | | | | | | | | |
|---|---|---|---|---|---|---|---|---|---|---|---|---|---|---|
| Thr | Asp | Gln | Cys | Asp | Asn | Phe | Pro | Gln | Met | Leu | Arg | Asp | Leu | Arg |
| Asp | Ala | Phe | Ser | Arg | Val | Lys | Thr | Phe | Phe | Gln | Thr | Lys | Asp | Glu |
| Val | Asp | Asn | Leu | Leu | Leu | Lys | Glu | Ser | Leu | Leu | Glu | Asp | Phe | Lys |
| Gly | Tyr | Leu | Gly | Cys | Gln | Ala | Leu | Ser | Glu | Met | Ile | Gln | Phe | Tyr |
| Leu | Glu | Glu | Val | Met | Pro | Gln | Ala | Glu | Asn | Gln | Asp | Pro | Glu | Ala |
| Lys | Asp | His | Val | Asn | Ser | Leu | Gly | Glu | Asn | Leu | Lys | Thr | Leu | Arg |
| Leu | Arg | Leu | Arg | Arg | Cys | His | Arg | Phe | Leu | Pro | Cys | Glu | Asn | Lys |
| Ser | Lys | Ala | yal | Glu | Gln | Ile | Lys | Asn | Ala | Phe | Asn | Lys | Leu | Gln |
| Glu | Lys | Gly | Ile | Tyr | Lys | Ala | Met | Ser | Glu | Phe | Asp | Ile | Phe | Ile |
| Asn | Tyr | Ile | Glu | Ala | Tyr | Met | Thr | Ile | Lys | Ala | Arg. | (SEQ ID NO: 4) | | |

The cDNA insert of pBCRF1(SRa) was recloned into an M13 plasmid where it was altered twice by site-directed mutagenesis: first to form a Cla I site at the 5' end of the coding region for the mature vIL-10 polypeptide, and second to form a Bam HI site at the 3' end of the coding region for the mature vIL-10 polypeptide. The mutated sequence was then readily inserted into the TRPC11 expression vector described below.

The TRPC11 vector was constructed by ligating a synthetic consensus RBS fragment to ClaI linkers (ATGCAT) and by cloning the resulting fragments into ClaI restricted pMT11hc (which had been previously modified to contain the ClaI site). pMT11hc is a small (2.3 kilobase) high copy, $AMP^R$, $TET^S$ derivative of pBR322 that bears the pVX plasmid EcoRI-HindIII polylinker region. (pVX is described by Maniatis et al. (1982) *Molecular Cloning: A Laboratory Manual,* Cold Spring Harbor Press, Cold Spring Harbor. This was modified to contain the ClaI site by restricting pMT11hc with EcoRI and BamHI, filling in the 5' resulting sticky ends and ligating with ClaI linker (CATCGATG), thereby restoring the EcoRI and BamHI sites and replacing the SmaI site with a ClaI site. One transformant from the TRPC11 construction had a tandem RBS sequence flanked by ClaI sites. One of the ClaI sites and part of the second copy of the RBS sequence were removed by digesting this plasmid with PstI, treating with Bal31 nuclease, restricting with EcoRI and treating with T4 DNA polymerase in the presence of all four deoxynucleotide triphosphates. The resulting 30–40 bp fragments were recovered via PAGE and cloned into SmaI restricted pUC12.

Figure 1:
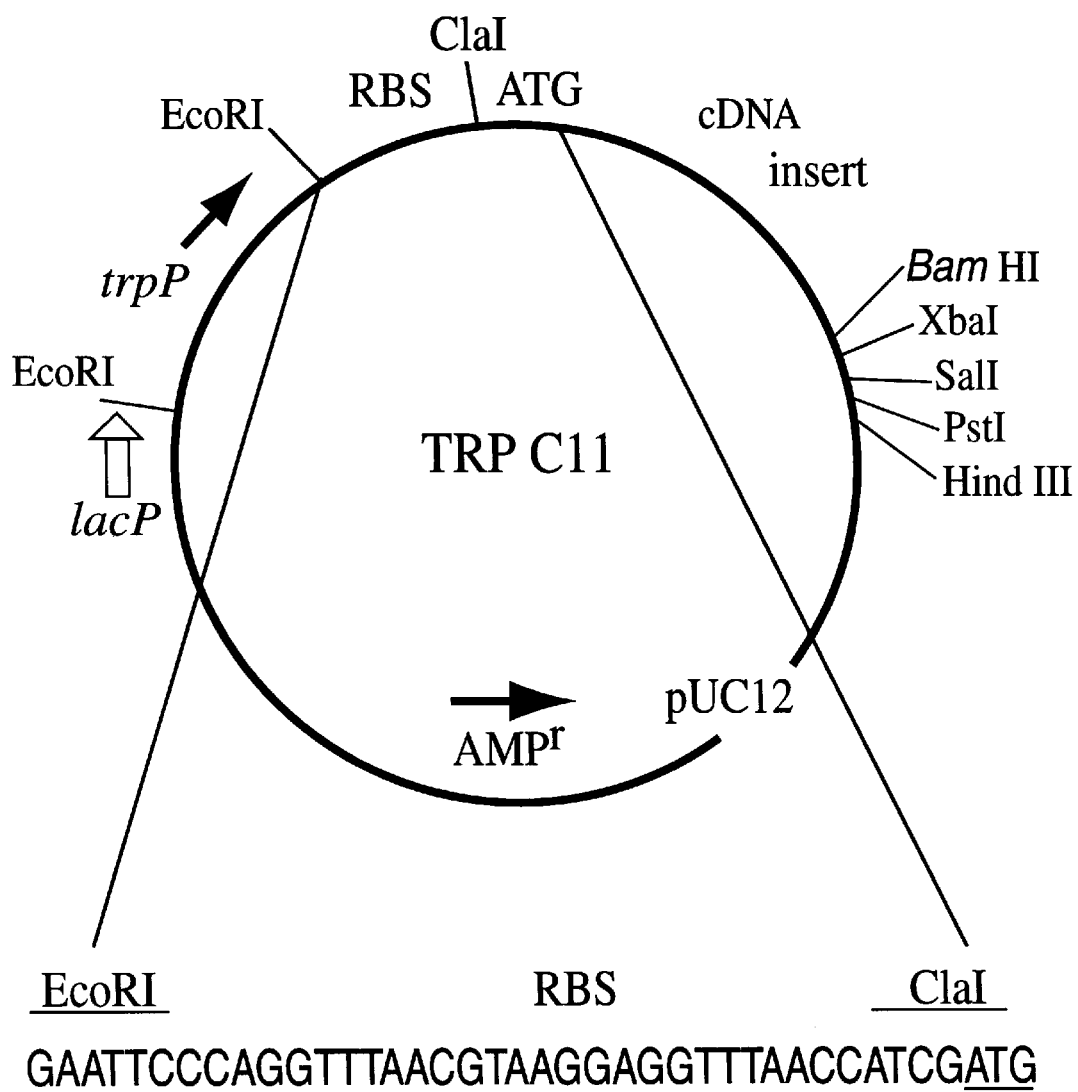
FIG. 1 is an illustration of plasmid TRPC11

A 248 bp *E. coli* trpP-bearing EcoRI fragment derived from pKC101 (described by Nichols et al. (1983) *Methods in Enzymology* 101:155–164, Academic Press, N.Y.) was then cloned into the EcoRI site to complete the TRPC11 construction. This is illustrated in FIG. 1. TRPC11 was employed as a vector for vIL-10 by first digesting it with ClaI and Bam HI, purifying it, and then mixing it in a standard ligation solution with the ClaI-Bam HI fragment of the M13 containing the nucleotide sequence coding for the mature BCRF1. The insert-containing TRPC11, referred to as TRPC11-BCRF1, was propagated in *E. coli* K12 strain JM101, e.g., available from the ATCC under accession number 33876.

Example 4
Differential Effects of Interleukin-4 and -10 on Interleukin-2-Induced Interferon-γ Synthesis and Lymphokine-Activated Killer Activity Culture of human peripheral blood mononuclear cells (PBMC) with interleukin-2 (IL-2) stimulates synthesis of cytokines and generation of lymphokine-activated killer (LAK) activity. Both interleukin-4 (IL-4) and interleukin-10 (IL-10; cytokine synthesis inhibitory factor, CSIF) inhibit IL-2-induced synthesis of IFNγ and TNFα by human PBMC. However, unlike IL-4, IL-10 inhibits neither IL-2-induced proliferation of PBMC and fresh natural-killer (NK) cells, nor IL-2-induced LAK activity.

Moreover, IL-4 inhibits IL-2-induced IFNγ synthesis by purified fresh NK cells, while in contrast, the inhibitory effect of IL-10 is mediated by CD14+ cells (monocytes/macrophages). IL-10 inhibits TNFα synthesis by monocytes or monocytes plus NK cells, but not by NK cells alone. Thus IL-4 and IL-10 act on NK cells via distinct pathways, and IL-2-induced cytokine synthesis and LAK activity are regulated via different mechanisms.

Interleukin-10 (cytokine synthesis inhibitory factor, CSIF) inhibits synthesis of cytokines, such as IFNγ, by mouse and human T-lymphocytes and monocytes/macrophages. The inhibitory effect on T cell cytokine synthesis is indirect, mediated by monocytes/macrophages in their capacity as antigen presenting cells. Both mouse and human IL-10 (mIL-10; hIL-10) are homologous to the Epstein-Barr virus open reading frame BCRF1 (viral IL-10; vIL-10), which also exhibits IL-10 activity on mouse and human cells.

It was observed earlier that vIL-10 inhibited IL-2-induced IFNγ synthesis by human PBMC. Because NK cells have been reported to be the principal source of IFNγ in IL-2-stimulated PBMC, the effects of hIL-10 and vIL-10 on IL-2-induced cytokine synthesis and LAK activity have been studied along with comparing these cytokines to IL-4, a known inhibitor of LAK activity. The data show that IL-4, hIL-10, and vIL-10 inhibit synthesis of IFNγ and TNFα by IL-2-stimulated PBMC, but only IL-4 inhibits IFNγ synthesis by purified NK cells. Furthermore, unlike IL-4, IL-10 does not inhibit IL-2-induced LAK activity. These results support a model that IL-4 and IL-10 act on NK cells by different mechanisms, and that IL-2-induced cytokine synthesis and LAK activity are regulated via distinct pathways.

Example 5
Effects of IL-4 and IL-10 on IL-2-induced Cytokine Synthesis and LAK Activity
Cytokines Human recombinant IL-2 (rIL-2) was kindly prepared using standard procedures by S. Zurawski (DNAX) or purchased (Cetus, Emeryville, Calif.). Human rIL-4 was from Schering-Plough Research. Human rIL-1β was purchased from Biosource International (Camarillo, Calif.). Recombinant hIL-10 and vIL-10 were used as COS7 transfection supernatants; supernatants from transfections with an irrelevant cDNA or no cDNA were used as controls. See, Viera et al. (1991) *Proc. Nat'l Acad Sci., USA* 88:1172–1176, and Hsu et al. (1990) *Science* 250:830–832, and above. IFNγ and TNFα (Endogen, Boston, Mass.) were measured by ELISA. Cytokine production in the absence of IL-2 was below the limits of sensitivity of the IFNγ and TNFα ELISA assays, which were 0.3 ng/ml and 12 pg/ml, respectively.
Cell lines Daudi (Burkitt lymphoma) cells were provided by Schering-Plough (Lyon, France). COLO (colon carcinoma) cells provided by Dr. Lewis Lanier were cultured in RPMI 1640 plus 5% fetal calf serum.
Antibodies Monoclonal antibodies against leukocyte cell surface antigens (CD3, CD4, CD5, CD14, CD16, CD19, CD56) were purchased from Becton-Dickinson (San Jose, Calif.). Antibodies for magnetic bead depletion experiments (CD3, CD4, CD5, CD14, CD19) were prepared from ascites fluids of SCID mice injected with the appropriate cell line. Anti-IL4 and anti-IL-10 neutralizing antibodies are described, e.g., in Chretien et al. (1989) *J. Immunol. Methods* 117:67–81; and Yssel et al., *J. Immuno. Methods.* 72:219–227.
PBMC preparation and culture Human PBMC were isolated from buffy coats from healthy donors by centrifugation over Ficoll-Hypaque and cultured at $10^6$/ml ub rIL-2 (200 unit/ml) with our without other cytokines in Yssel's medium with 1% human Ab+ serum. Cultures were carried out for five days in 24-(or 96)-well plates and supernatants were harvested. PBMC from different donors varied in their capacity to product IFN-γ and TNF-α when stimulated by IL-2.
Cell purifications PBMC were washed and incubated in tissue culture dishes for 40 min at 37° C. Adherent cells were collected by scraping with a rubber policeman. Non-adherent cells were removed, pelleted, and applied to a nylon wool column and incubated for 40 min at 37° C. After elution from the column, cells were pelleted and resuspended in 30% Percoll with 10% FCS/PBS and layered on 40% Percoll. Following centrifugation for 30 min at room temperature, the large granular lymphocytes at the interface were recovered and washed twice.

These cells were incubated with anti-CD56 antibody (Becton-Dickinson, San Jose, Calif.) for 30 min at 4° C., washed, and then stained with goat-anti-mouse-FITC (Jackson Immunoresearch, Avondale, Pa.) prior to FACS sorting. CD56+ cells comprised about 35–50% of the cells subjected to sorting. Sorted cells were greater than 99.5% CD56+ upon reanalysis. $9 \times 10^4$ purified NK cells were mixed with $3 \times 10^4$ adherent cells or T cells in a final volume of 100 ml and cultured with IL-2 with or without other cytokines.

Purified NK cells and monocytes from the same donor were obtained as follows: PBMC were incubated with sheep blood red cells overnight; resetting "E+" (CD2+) and non-rosetting "E−" cells were separated by centrifugation over a ficoll-hypaque gradient. E+ cells were subjected to the same purification procedure as described for PBMC (see above) to obtain purified NK cells. E− cells were incubated subsequently with anti-CD14 mAb (LeuM3) and FITC-labelled goat anti-mouse IgG antibody and CD14+ cells were sorted on a FACStar plus. Purity of these cells was greater than 98%. $10^5$ purified NK cells were mixed with $10^4$ pure monocytes in 100 ml and cultured alone or with IL-2 and other additions as described above.

Alternatively, NK cells and monocytes were enriched by magnetic bead selection, then sorted as follows: PBMC were first incubated with monoclonal anti-CD3, -CD4, -CD5, and anti-CD19 antibodies to stain T cells and B cells. After washing twice with PBS, goat anti-mouse IgG-coated magnetic beads (Dynabeads M-450, Dynal Inc., Great Neck, N.Y.) were added to remove the antibody-coated T cells and B cells by magnetic selection. The resulting enriched NK cells and monocytes were stained with anti-CD56-PE and anti-CD14-FITC, and CD56+ and CD14+ cells isolated on the cell sorter. Purity of the two sorted cell populations was greater than 98.5%.

Cytotoxicity assay

PBMC were incubated with 200 U/ml IL-2 at $10^6$ cells/ml for 3 days in Yssel's medium containing 1% human AB+ serum. The cultures were performed in 1-ml wells of a Linbro 24-well plate (Flow Laboratories, McLean, Va.). After the culture period, the cells were harvested, washed twice and used as effector cells in a $^{51}$Cr release assay. See Spits et al. (1988) *J. Immunol.* 141:29–36. One thousand $^{51}$Cr-labelled target cells (COLO or Daudi) were mixed with varied numbers of effector cells in Iscovels medium containing 0.25% BSA (Sigma Chemical Co., St. Louis, Mo.) in U-shaped 96-well plates. The plates were centrifuged for 5 min at. 50×g before incubation for 4 hours at 37° C. in a humidified 5% $CO_2$ atmosphere. The samples were harvested and counted in a gamma counter (LAB, Bromma, Sweden).

Figure 2A:
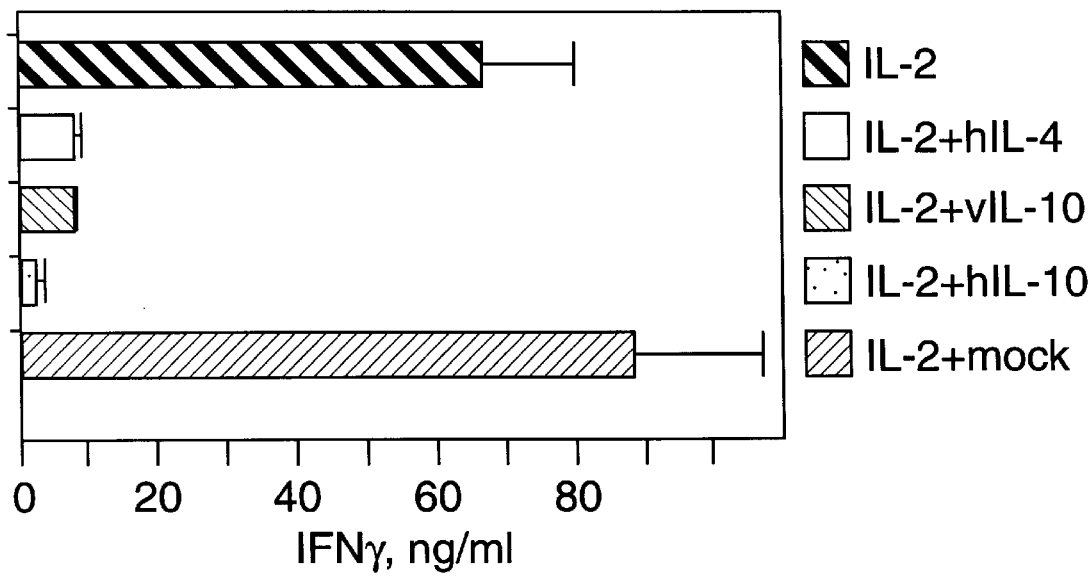
FIG. 2 is a graphical representation of the effects of IL-4, hIL-10, and vIL-10 on IFNγ (FIG. 2A) and TNFα (FIG. 2B) synthesis by IL-2-activated peripheral blood mononuclear (PBMC) cells.
Figure 2B:
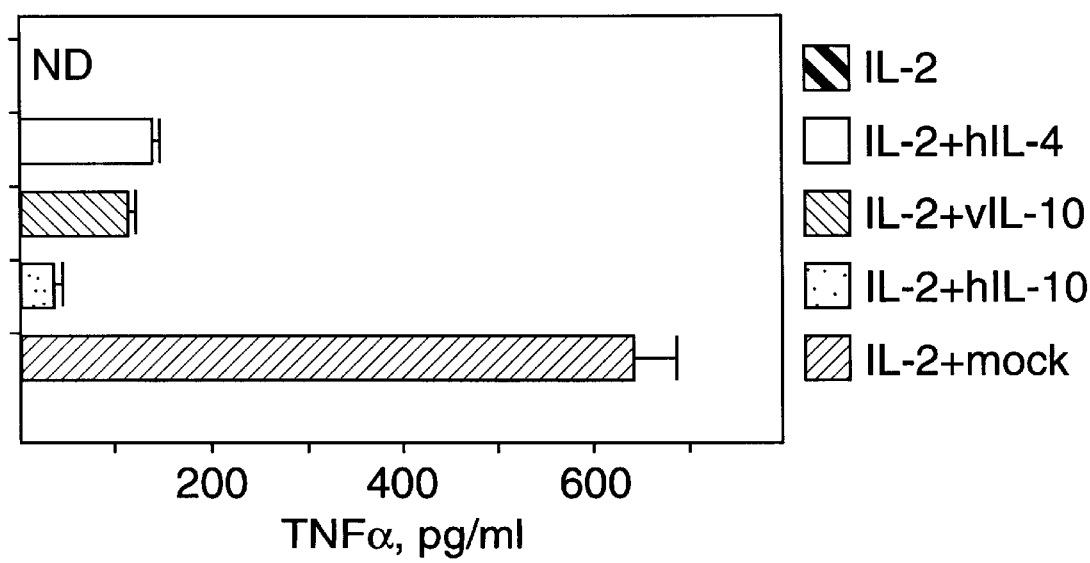
Figure 4:
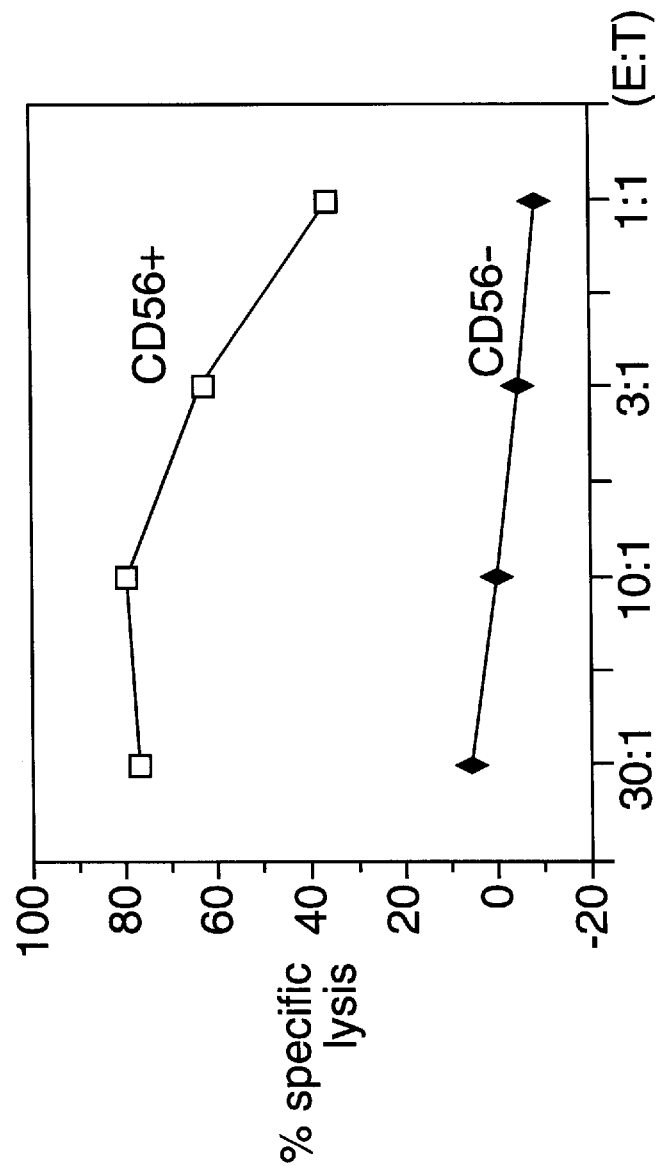
FIG. 4 is a graphical representation of the effects of IL-2 and IL-10 on LAK activity in CD56+ and CD56− PBMC.

Recombinant hIL-10, vIL-10, and hIL-4 were tested for their effects on synthesis of IFNγ and TNFα, and on LAK activity induced by IL-2 in peripheral blood mononuclear cells (PBMC). PBMC were cultured in 200 U/ml rIL-2 with either rIL-4 (200 U/ml) or COS7 supernatants containing hIL-10, vIL-10, or no cytokine (mock) for 5 days, after which cytokine synthesis was measured. IL-2-induced IFNγ and TNFα synthesis in cultures containing hIL-10, vIL-10, or IL-4 was substantially inhibited (FIG. 2).

The result obtained with IL-4 confirms observations that IL-4 inhibits IL-2-induced expression of IFNγ mRNA and protein. Inhibition of cytokine synthesis by both IL-4 and IL-10 is dose-dependent, and reversed by blocking anti-hIL-4 and anti-hIL-10 monoclonal antibodies, respectively, but not by isotype control immunoglobulins.

LAK activity was also assessed against the Burkitt lymphoma cell line Daudi and the colon carcinoma line COLO, which are killed efficiently by LAK cells, but not by fresh NK cells. IL-2-induced LAK activity against Daudi and COLO cells was inhibited only in cultures containing IL-4, and was unchanged or even slightly enhanced in the hIL-10 and vIL-10 cultures (FIG. 3A). IL-2-induced LAK activity is mediated primarily by CD56(Leu19)+ NK cells.

That LAK activity against COLO cells was not inhibited by IL-10 indicated that cytotoxicity mediated by activated NK cells was not affected by this cytokine. However, since activated CD3+ gd+ T cells can kill Daudi cells, it was possible that IL-10 stimulated IL-2-induced gd+ T cell cytotoxicity against Daudi while simultaneously blocking IL-2-induced NK activity against this target cell.

To determine the phenotype of anti-Daudi LAK cells induced in PBMC cultured with IL-2 and hIL-10, CD56+ and CD56-populations were sorted by FACS and tested for cytotoxicity against Daudi cells. FIG. 3B shows that, as with IL-2 alone, significant LAK activity was observed only in the CD56+ population. Thus, while both IL-4 and IL-10 inhibit IL-2-induced synthesis of IFNγ and TNFα, only IL-4 inhibits IL-2-induced cytotoxicity by activated NK cells present in PBMC.

Example 6

IL-10 Does Not Inhibit IFNγ Synthesis by or Proliferation of IL-2-stimulated Purified NK Cells Proliferation assay Cells were distributed at $10^5$ cells/well in 96-well round-bottom plates and incubated in the presence or absence of cytokines for four days in a final volume of 200 ul/well. Then 1 mCi of $^3$H-thymidine in 10 ul was added to each well. After six hr the cultures were harvested and incorporated radioactivity was assessed by scintillation counting. The majority of IL-2-induced IFNγ synthesis in PBMC is reportedly derived from NK cells rather than T cells. Therefore the effect of hIL-10, vIL-10, and IL-4 on IL-2-induced IFNγ synthesis was tested by FACS-purified NK cells (purity >99.5%).

IL-4 inhibited IL-2-induced IFNγ secretion by these cells; in contrast, neither hIL-10 nor vIL-10 suppressed IFNγ synthesis by purified fresh NK cells (FIG. 5). Furthermore, IL-4 significantly inhibited IL-2-induced proliferation by PBMC or purified NK cells, while IL-10 had no effect on IL-2-mediated proliferation (FIG. 6).

In contrast to IL-4, IL-10 does not affect the NK cell directly, but inhibits the ability of the monocyte to provide a co-stimulatory signal. This conclusion is supported most clearly by the effects of IL-10 on IL-2-induced IFNγ production. As noted above, accessory cell preparations did not produce IFNγ. Although IL-2-stimulated NK cells produced significant levels of IFNγ without accessory cells (FIGS. 5 and 7), addition of both plastic-adherent cells and purified CD14+ cells to purified NK cells resulted in a large enhancement of IFNγ synthesis. The absence of a direct effect of IL-10 on the NK cell suggests that IL-10 inhibits IL-2-induced IFNγ production by acting on the monocyte. Similarly, inhibition of T cell cytokine synthesis by IL-10 is mediated by monocyte/macrophage accessory cells.

Example 7

Monocytes Mediate Inhibition by IL-10 of IL-2-stimulated IFNγ and TNFα Synthesis by NK Cells That IFNγ synthesis was inhibited by IL-10 in cultures of PMBC but not pure NK cells suggested that this effect of IL-10 was mediated by accessory cells. To investigate the nature of these accessory cells, NK cells were purified by sorting CD56+ cells from the low-density cell fraction obtained by percoll gradient centrifugation, or from T cell-, B cell-, and monocyte-depleted PBMC, and were mixed with plastic-adherent cells or with the high-density cell population (98% T cells) from the percoll gradient. Addition of adherent cells to the NK cells strongly enhanced IL-2-induced IFNγ production by NK cells; this stimulatory effect of adherent cells was blocked by IL-10 (FIG. 7). The adherent cell population itself did not produce detectable levels of IFNγ in response to IL-2. In contrast, the T cell containing fraction had no effect on IL-2-induced IFNγ production by NK cells and did not mediate inhibition of IFNγ production by IL-10 (FIG. 7).

Plastic-adherent cells are enriched for monocytes, but can contain other cell populations. To confirm that monocytes both enhanced IL-2-induced IFNγ production and mediated its inhibition by IL-10, NK cells and CD14+ monocytes were purified by sorting and were cultured in the presence of IL-2 and IL-10. FIG. 7 shows that addition of purified monocytes to NK cells enhanced IL-2-induced IFNγ production, and that IL-10 inhibited this enhancement.

Qualitatively similar results were observed for TNFα synthesis. FIG. 8 shows that, as expected, NK cells produced detectable TNFα in response to IL-2. CD14+ cells produce TNFα independently of IL-2. IL-10 inhibits TNFα production by monocytes in both the presence (FIG. 8) and absence of IL-2. In contrast, TNFα synthesis by NK cells was not inhibited by IL-10. Stimulation of NK and CD14+ cells together resulted in a level of TNFα production substantially higher than that observed for either cell alone, and this augmentation was blocked by IL-10.

Monocytes and their products have been shown to substantially augment IL-2-induced IFNγ production by resting NK cells. Several monokines, such as IL-1 and TNFα, have been implicated as co-stimulators of IFNγ synthesis by human and mouse NK cells under various conditions. That IL-10 inhibits synthesis of monokines such as IL-1, IL-6, and TNFα by LPS- or IFNγ-stimulated monocytes/macrophages suggests that the effects of IL-10 reported here were due to IL-10's inhibiting production of co-stimulatory molecules by accessory cells. Supernatants of adherent cells (containing mostly monocytes) were observed to enhance IFNγ production by IL-2-stimulated, purified NK cells, while supernatants of adherent cells cultured in the presence of IL-10 lack this capacity, even when depleted of IL-10.

Whether this supernatant activity accounts for the entire co-stimulatory effect of accessory cells is not clear. It has been observed that IL-1α and IL-1β, but not IL-6 or TNFα, co-stimulate IL-2-induced IFNγ production by NK cells; however, addition of up to 1000 U/ml IL-1 does not reverse the inhibitory effect of IL-10 on IL-2-induced IFNγ synthesis by unfractionated PBMC. Therefore, the possibility exists that one or more additional activities function in this system, or that IL-10 induces synthesis of a secondary factor which inhibits cytokine synthesis by NK cells.

Example 8
IL-10 Inhibits Cytokine Synthesis by Human Monocytes: An Autoregulatory Role of IL-10 Produced by Monocytes Human monocytes activated by LPS are able to produce high levels of Interleukin 10 in a dose dependent fashion. IL-10 was detectable 7 hrs after activation of the monocytes and maximal levels of IL-10 production were observed after 24–48 hrs. These kinetics indicated that the production of IL-10 by human monocytes was relatively late as compared to the production of IL-1α, IL-1β, IL-6, IIL-8, TNFα, and G-CSF, which were all secreted at high levels 4–8 hrs after activation. The production of IL-10 by LPS activated monocytes was, similar to that of IL-1α, IL-1β, IL-6, IL-8, TNFα, GM-CSF, and G-CSF, inhibited by IL-4. Furthermore IL-10, added to monocytes, activated by IFNγ, LPS or combinations of LPS and IFNγ at the onset of the cultures, strongly inhibited the production of IL-1α, IL-1β, IL-6, IL-8, TNFα, GM-CSF, and G-CSF at the transcriptional level.

Viral-IL-10, which has similar biological activities on human cells, also inhibited the production of TNFα and GM-CSF by monocytes following LPS activation. Activation of monocytes by LPS in the presence of neutralizing anti-IL-10 mAbs resulted in the production of higher amounts of cytokines relative to LPS treatment alone, indicating that endogenously produced IL-10 inhibited the production of IL-1α, IL-1β, IL-6, IL-8, TNFα, GM-CSF, and G-CSF. In addition, IL-10 had autoregulatory effects since it strongly inhibited IL-10 mRNA synthesis in LPS activated monocytes.

Furthermore, endogenously produced IL-10 was found to be responsible for the reduction in class II MHC expression following activation of monocytes with LPS. Taken together these results indicate that IL-10 has important regulatory effects on immunological and inflammatory responses because of its capacity to downregulate class II MHC expression and to inhibit the production of proinflammatory cytokines by monocytes.

Murine-interleukin 10 (IL-10) was recently identified and its gene cloned based on its Cytokine Synthesis Inhibitory (CSIF) activity. In murine systems, IL-10 was produced by the $CD4^+$ Th2 subset and inhibits the cytokine production, particularly IFNγ, by Th1 clones. The inhibition of cytokine production by IL-10 was observed only when macrophages, but not B cells, were used as antigen presenting cells (APC). In addition to its CSIF activity, IL-10 was shown to be pleiotropic and to act on different cell types, including thymocytes, cytotoxic T cells, mast cells, B cells, and macrophages.

Human IL-10 also exhibits CSIF activity. The production of IFNγ and GM-CSF by PBMC activated by PHA or anti-CD3 mAbs was strongly inhibited by IL-10 and this inhibition occurred at the transcriptional level. Both human and murine IL-10 have extensive sequence homology to a previously uncharacterized open reading frame in the Epstein Barr virus genome, BCRF-1. Expression of this open reading frame yielded an active protein, designated viral-IL-10 (v-IL-10), which shared most properties with human and murine IL-10, including CSIF activity on mouse and human T cells.

Human IL-10 and v-IL-10 are able to inhibit antigen specific proliferative T cell responses by reducing the antigen presenting capacity of human monocytes via downregulation of class II MHC molecules. Human monocytes are able to produce high levels of IL-10 following activation with LPS and that this production is relatively late as compared to that of other monokines. In addition, it is reported here that IL-10 strongly inhibits the production of the proinflammatory cytokines, e.g., IL-1α, IL-1β, IL-6, IL-8, and TNFα and the haematopoietic growth factors, GM-CSF and G-CSF, by monocytes activated by LPS, IFNγ, or LPS and IFNγ. Endogenously produced IL-10 has not only autoregulatory effects on IL-1α, IL-1β, IL-6, IL-8, TNFα, GM-CSF, and G-CSF production by monocytes, but also downregulates its own production and class II MHC expression on monocytes in an autoregulatory fashion.

These results indicate that IL-10 has important regulatory effects on immunological and inflammatory responses.

Example 9
IL-10 is Produced by Human Monocytes
Isolation and culture of human monocytes Human peripheral blood monocytes were isolated from 500 ml blood of normal donors. Mononuclear cells were isolated by density centrifugation in a blood component separator, followed by fractionation into lymphocytes and monocytes by centrifugal elutriation. The monocyte preparation was >95% pure, as judged by nonspecific esterase staining and contained more than 98% viable cells. Monocytes were cultured in Yssel's medium containing human serum albumin (HSA) supplemented with 1% pooled, heat inactivated human AB+ serum. This culture medium was endotoxin free as determined by the Limulus amebocyte lysate assay (<0.2 ng/ml of endotoxin). The monocytes were cultured at a concentration of $4 \times 10^6$ cells/ml in teflon bags (Jansen MNL, St Niklaas, Belgium), which prevented adhesion of these cells.

After culture for the times indicated, monocytes were collected and analyzed for cell surface expression by indirect immunofluorescence or analyzed for lymphokine gene expression by Northern and PCR analysis. In addition, monocyte culture supernatants were collected for determination of IL-1α, IL-1β, IL-6, IL-8, IL-10, TNFα, GM-CSF, and G-CSF production following activation of these cells. The viability of the cells after culture always exceeded 95% as determined by trypan blue exclusion.

Reagents

Recombinant human IL-10 and v-IL-10 were expressed in E. coli as glutathione-S-transferase fusion proteins, purified, and digested with thrombin to remove the N-terminal fusion part, resulting in active human and viral IL-10. Purified human r-IL-4 and r-IFNγ were provided by Schering-Plough Research (Bloomfield, N.J.). LPS (E. coli 0127:B8) was obtained from Difco laboratories (Detroit, Mich.). The neutralizing anti-IL-10 mAb 19F1 was raised against v-IL-10 and efficiently neutralized both human and viral-IL-10.

Lymphokine determinations

The production of IL-1α and TNFα by monocytes was measured by lymphokine specific ELISA's obtained from Endogen (Boston, Mass.). The lower detection limit of these ELISA's were 50 pg/ml and 10 pg/ml respectively. Production of IL-1β was determined by lymphokine specific ELISA obtained from Cistron (Pine Brook, N.J.). The sensitivity of this ELISA was 20 pg/ml. IL-6 levels were determined by lymphokine specific ELISA purchased from Genzyme (Boston, Mass.). The sensitivity of this assay was 0.313 ng/ml. IL-8 and G-CSF specific ELISA's were obtained from R&D Systems (Minneapolis, Minn.) and used to quantitate IL-8 and G-CSF production. The sensitivity of these ELISA's was 4.7 pg/ml and 7.2 pg/ml respectively. GM-CSF production was determined by lymphokine specific ELISA. The sensitivity of this ELISA was 50 pg/ml. IL-10 production was determined by a specific ELISA in which an anti-IL-10 mAb (JES 9D7) was used as a coating antibody and another anti-IL-10 mAb (JES3-12G8) as a tracer antibody. The sensitivity of this ELISA was 50 pg/ml.

IL-10 is produced by activated human T cell clones, activated peripheral blood T and B cells, EBV transformed B cell lines, and monocytes. Highly purified human monocytes, isolated by centrifugal elutriation, produced IL-10 following activation by LPS. In addition, it is shown that these human monocytes were able to produce high levels of IL-6, TNFα and GM-CSF (FIG. 9). Kinetics of cytokine production by LPS activated monocytes indicated that IL-10 production by LPS activated monocytes was relatively late. It was first detected in supernatants harvested at 7.5 hrs, but maximal production was observed 20–48 hrs after activation.

In contrast, TNFα and IL-6 were produced rapidly upon activation and reached maximal levels of production at 3.5 and 7.5 hrs following activation respectively (FIG. 9). However, GM-CSF production was also first detected 7.5 hrs after activation of monocytes by LPS, but in this case maximal production levels were reached at 20 hrs. Dose response studies indicated that activation of monocytes by LPS at 10 ng/ml already resulted in significant levels of IL-10 production, whereas the maximal IL-10 synthesis was observed at LPS concentrations of 1 μg/ml. (FIG. 10).

Example 10
IL-10 Inhibits Cytokine Production by Human Monocytes

IL-10 has been shown to inhibit IFNγ and GM-CSF production by activated PBMC. To determine the effects of IL-10 on the production of cytokines by monocytes, highly purified monocytes were activated for 24 hrs by LPS in the absence or presence of IL-10. In addition, monocytes were activated with LPS for 24 hrs in the presence of IL-4 (100 U/ml) or neutralizing anti-IL-10 mAb 19F1, which was raised against v-IL-10 but efficiently neutralized both human IL-10 and v-IL-10. Cytokine production was determined in the supernatants of these cultures, harvested 24 hrs after activation, by cytokine specific ELISA's. As shown in shown in Table 2, monocytes which were incubated in medium alone at 37° C. did not produce IL-1α, IL-1β, IL-6, IL-10, TNFα, GM-CSF and G-CSF. Under these conditions, only significant levels of IL-8 were synthesized.

Activation of monocytes with LPS (1 μg/ml) resulted in production of high levels of IL-1α, IL-1β, IL-6, IL-8, IL-10, TNFα, GM-CSF, and G-CSF. IL-10 inhibited the production of IL-1α, IL-1β, IL-6, IL-8, TNFα, GM-CSF, and G-CSF to various extents (Table 2). The strongest inhibitory effects of IL-10 were observed on the production of IL-1α, TNFα, GM-CSF, and G-CSF, which were blocked by 80–100%. The inhibition of IL-1β and IL-6 production was less pronounced, whereas the synthesis of IL-8 was only slightly affected by IL-10.

TABLE 2

Effects of Exogenous IL-10, Endogenqus IL-10, and IL-4 on Cytokine Production by Human Monocytes

|  | IL-1α | IL-1β | IL-6 | IL-8 | IL-10 ng/ml | TNFα | GM-CSF | G-CSF |
| --- | --- | --- | --- | --- | --- | --- | --- | --- |
| Medium 37° C. | 0 | 0 | 0 | 150 | 0 | 0 | 0 | 0 |
| LPS | 1.2 | 44.8 | 261.7 | 479 | 30.6 | 21.2 | 0.6 | 90 |
| LPS + IL-4 | 0 | 9.7 | 135.7 | 418 | 11.9 | 5.1 | 0 | 17.5 |

TABLE 2-continued

Effects of Exogenous IL-10, Endogenqus IL-10, and IL-4
on Cytokine Production by Human Monocytes

|  | IL-1α | IL-1β | IL-6 | IL-8 | IL-10 ng/ml | TNFα | GM-CSF | G-CSF |
|---|---|---|---|---|---|---|---|---|
| LPS + IL-10 | 0 | 13.6 | 78 | 434 | ND | 2.6 | 0 | 21.1 |
| LPS + αIL-10 | 2.7 | 50.6 | 323 | 672 | ND | 47.6 | 5.5 | 110 |

Human monocytes isolated by centrifugal elutriation were cultured in teflon bags at a concentration of 4 × 10$^6$ cells/ml and activated by 1 μg/ml LPS in the absence and presence of 100 U/ml IL-10, 100 U/ml IL-4 or 10 μg/ml of an anti-IL-10 mAb 19F1 for 24 hours, and production of cytokines was determined in the supernatants by cytokine specific ELISA's.
ND: not done.

Example 11
IL-10 Also Inhibits Cytokine Production of Monocytes Activated by IFNγ

IL-10 also inhibited cytokine production by monocytes activated by IFNγ, or combinations of IFN-γ and LPS. FIG. 11 shows that IFNγ at optimal concentrations of 100 U/ml generally was a less potent inducer of cytokine secretion than was LPS at optimal concentrations of 1 μg/ml. Furthermore, it is demonstrated that the effects of combinations of IFNγ and LPS on cytokine production by monocytes generally were additive. The strongest inhibitory effects of IL-10 were observed on IL-1α, TNFα, and GM-CSF production. TNFα and GM-CSF secretion was suppressed by more than 90%, even following activation of the monocytes by optimal LPS and IFNγ concentrations. Although considerable inhibitory effects on IL-1β and IL-6 secretion were observed at optimal stimulation conditions, their inhibition was more pronounced when the monocytes were stimulated by suboptimal concentrations of LPS, either in the absence or presence of optimal concentrations of IFNγ.

Example 12
Viral-IL-10 Inhibits Cytokine Production by Monocytes

Viral IL-10 and human IL-10 have similar effects on human cells. FIG. 12 shows that both IL-10 and v-IL-10 inhibited TNFα and GM-CSF production by monocytes in a similar fashion. IL-10 and v-IL-10, added at concentrations of 100 U/ml, had significant inhibitory effects on TNFα and GM-CSF production by monocytes following activation by LPS (1 μg/ml).

These inhibitory effects of IL-10 and v-IL-10 on TNFα and GM-CSF secretion were reversed when incubations were carried out in the presence of mAb 19F1 (FIG. 12), demonstrating the specificity of the inhibitory effects of v-IL-10. In fact, activation of monocytes by LPS in the presence of IL-10 or v-IL-10 and the neutralizing anti-IL-10 mAb resulted even in enhanced production of TNFα and GM-CSF, indicating that endogenously produced IL-10 suppressed the production of these cytokines.

The inhibitory effects of endogenously produced IL-10 on cytokine production by monocytes were further evaluated by quantifying cytokine levels produced by LPS activated monocytes in the presence of neutralizing anti-IL-10 mAb. In Table 2 it is shown that LPS plus anti-IL-10 treatment of monocytes resulted in higher levels of cytokine production as compared to activation by LPS alone, indicating that endogenously produced IL-10 in addition to its inhibitory effects on TNFα and GM-CSF production blocked the production of IL-1α, IL-1β, IL-6, IL8, and G-CSF.

The most significant inhibitory effects were found on the production of IL-1α, GM-CSF, and TNFα, whereas the inhibitory effects on IL-1β IL-6, IL-8, and G-CSF expression were considerable, but less pronounced. Taken together these results indicate that both exogenous IL-10 and endogenously produced IL-10 inhibit the production of IL-1α, IL-1β, IL-6, IL-8, TNFα, GM-CSF, and G-CSF by LPS activated monocytes.

Example 13
IL-4 Inhibits IL-10 production by Activated Monocytes

IL-4 inhibits production of IL-1β, IL-6, and TNFα by LPS activated monocytes. To determine whether IL-4 also inhibited IL-10 production, monocytes were activated by LPS for 24 hrs and IL-10 secretion was measured. Table 2 shows IL-4 strongly inhibited IL-10 production by LPS-activated monocytes. Furthermore, IL-4, in addition to its inhibitory effects on IL-1β, IL-6, and TNFα secretion, efficiently blocks the production of GM-CSF and G-CSF. However, as observed for IL-10, the production of IL-8 was only slightly affected by IL-4. Collectively these data indicate that IL-4 and IL-10 have comparable inhibitory effects on cytokine production by activated monocytes.

Example 14
Inhibition of Monokine Production Occurs at the Transcriptional Level Probes The following probes were used for Northern analysis: 600 bp Sma I fragment (nt 1299–1899) of pCD-hTGFβ, see Yokota et al. (1987) in *Lymphokines* vol. 13, Goeddel and Webb (eds.) Academic Press, New York; 1200 bp Pst I fragment of pAL (β-actin), see Vieira et al. (1991) *Proc. Natl. Acad. Sci. USA* 88:1172–1176; 567 bp BamHI-Xba I fragment (nt 1–567) of pCD-hIL-6, see Yokota et al. (1987); 268 bp Hind III fragment (nt 29–297) of SP64–3–10c (IL-8), see Schmid et al. (1987) *J. Immunol.* 139:250–256; 760 bp Bgl II-Hind III fragment (nt 159–919) of pCD-SRa-hIL-10, see Vierea et al. (1991).

The following oligonucleotides were used for Southern analysis of PCR products: IL-1α: 5'-CATGGGTGCTTATAAGTCATC-3' (nt 500–521) (SEQ ID NO: 26), see March et al. (1985) *Nature* 315:641–647; IL-1γ:

5'-CGATCACTGAACTGCACGCTCCGGG-3'

(nt 444–469) (SEQ ID NO: 27), see March et al. (1985) *Nature*; IL-6:

5'-GAGGTATACCTAGAGTACCTC-3'

(nt 510–531) (SEQ ID NO: 28), see Hirano et al. (1986) *Nature* 324:73–76; IL-8:

5'-TAAAGACATACTCCAAACCTT-3'

(nt 200–221) (SEQ ID NO: 29), see Schmid et al. (1987) *J. Immunol.*; IL-10:

5'-CAGGTGAAGAATGCCTTTAATAAGCTCCAAGAGAAAGGCATCTACAAAGCCATGAGTG—AGTTTGACATC-3'

(nt 429–498) (SEQ ID NO: 30), Vierea et al. (1991) *Proc. Nat'l Acad. Sci. USA*; TNFα:

5-GGCGTGGAGCTGAGAGATAAC-3'

(nt 500–521) (SEQ ID NO: 31), see Pennica et al. (1984) *Nature* 312:724–729; GM-CSF:

5'-CCGGCGTCTCCTGAACCT-3'

(nt 150–168) (SEQ ID NO: 32), see Lee et al. (1985) *Proc. Nat'l Acad. Sci. USA* 82:4360–4364; actin:

5'-CTGAACCCTAAGGCCAACCGTG-3'

(nt 250–272) (SEQ ID NO: 33), see Alonso et al. (1986) *J. Mol. Evol.* 23:11–22; and G-CSF:

5'-GCCCTGG—AAGGGATCTCCCCC-3'

(nt 400–421) (SEQ ID NO: 34), see Nagata et al. (1986) *Nature* 319:415–418.

Nucleotide sequences are also available from GENBANK, c/o Intelligenetics, Inc., Menlo Park, Calif., and the BCCG data base, and University of Wisconsin Biotechnology Center, Madison, Wis. Synthetic nucleotide biosynthesis is described in Gait (1984) *Oligonucleotide Synthesis: A Practical Approach* IRL Press, Oxford.

mRNA isolation and northern analysis

Total RNA was isolated from 20×10$^6$ monocytes by a guanidinium thiocyanate-CsCl procedure. For northern analysis, 10 μg total RNA per sample was separated according to size on 1% agarose gels containing 6.6% formaldehyde, transferred to Nytran nylon membranes (Schleicher & Schuell, Keene, N.H.) and hybridized with probes, labelled to high specific activity (>10$^8$ cpm/mg). Filters were hybridized, washed under stringent conditions, and developed.

PCR analysis

One microgram of total RNA was reverse transcribed using oligo (dT)$_{12-18}$ as primer (Boehringer Mannheim, Indianapolis, Ind.) and AMV reverse transcriptase (Boehringer Mannheim) in a 20 ul reaction. Two microliters of reverse transcript (equivalent to 100 ng of total RNA) was used directly for each amplification reaction. Conditions for PCR were as follows: in a 50 ul reaction, 25 nmol of each primer, 125 uM each of dGTP, dATP, dCTP, and dTTP (Pharmacia, Uppsala, Sweden), 50 mM KCl, 10 mM Tris-HCl, pH 8.3, 1.5 mM MgCl$_2$, 1 mg/ml gelatin, 100 μg/ml non-acetylated BSA and 1 unit Vent DNA polymerase (New England Biolabs, Beverly, Mass.).

Primers used were as follows: IL-1α sense primer

5'-CATCGCCAATGACTCAGAGGAAG-3'

(nt 302–325) (SEQ ID NO: 35); IL-1α anti-sense primer

5'-TGCCAAGCACACCCAGTAGTCTTGCTT-3'

(nt 770–743) (SEQ ID NO: 36); IL-1β sense primer

5'-CCAGCTACGAATCTCGGACCACC-3'

(nt 230–253) (SEQ ID NO: 37); IL-1β anti-sense primer

5'-TTAGGAAGACACAAATTGCATGGTGAAGT—CAGT-3'

(nt 896–863) (SEQ ID NO: 38); IL-6 sense primer

5'-ATGAACTCCTTCTCCACAAGC-3'

(nt 1–21); (SEQ ID NO: 39) IL-6 anti-sense primer

5'-CTACATTTGCCGAAGAGCCCTCAGGCTGGACTG-3'

(nt 810–777) (SEQ ID NO: 40); IL-8 sense primer

5'-ATGACTTCCAAGCTGGCCGTG-3'

(nt 1–21) (SEQ ID NO: 41); IL-8 anti-sense primer

5'-TTATGAATTCTCAGCCC—TCTTCAAAAACTTCTC-3'

(nt 302–269) (SEQ ID NO: 42); IL-10 sense primer

5'-ATGCCCCAAG—CTGAGAACCAAGACCCA-3'

(nt 323–349) (SEQ ID NO: 43); IL-10 anti-sense primer

5'-TCTCAAGGGGCTGGGTCAGCTATCCCA-3'

(nt 674–648) (SEQ ID NO: 44); TNFα sense primer

5'-AGAGGGAAGAGTTCCCCAGGGAC-3'

(nt 310–333) (SEQ ID NO: 45); TNFα anti-sense primer

5'-TGAGTCGGTCACCCTT—CTCCAG-3'

(nt 782–760) (SEQ ID NO: 46); GM-CSF sense primer

5'-GCATCTCTGCACCCGCCC—GCTCGCC-3'

(nt 76–100) (SEQ ID NO: 47); GM-CSF anti-sense primer

5'-CCTGCTTGTACAGCTCCAGGCGGGT-3'

(nt 276–250) (SEQ ID NO: 48); G-CSF sense primer

5'-GAGTGTGCCACCTACAAGCTGTGCC-3'

(nt 233–258) (SEQ ID NO: 49); G-CSF anti-sense primer

5'-CCTGGGTGGGCTGCAGGGCAGGGGC-3'

(nt 533–508) (SEQ ID NO: 50); β-actin sense primer

5'-GTGGGGCGCCCCAGGCACCA-3'

(nt 1–20) (SEQ ID NO: 51); β-actin anti-sense primer

5'-GTCCTTAA—TGTCACGCACGATTTC-3'

(nt 548–530) (SEQ ID NO: 52).

Reactions were incubated in a Perkin-Elmer/Cetus DNA Thermal cycler for 20 cycles (denaturation 30 s 94° C., annealing 30 s 55° C., extension 60 s 72° C.) . Reactions were extracted with CHCl$_3$ and 40 ul per sample was loaded on 1% agarose gels in TAE buffer. Products were visualized by ethidium bromide staining. Subsequently, gels were denatured in 0.5M NaOH, 1.5M NaCl, neutralized in 10M ammonium acetate, and transferred to Nytran nylon membranes. Membranes were pre-hybridized in 6×SSC, 1% SDS, 10×Denhardt's solution (0.2% Ficoll, 0.2% polyvinylpyrrolidone, 0.2% BSA, pentax fraction V), and 200 μg/ml *E. coli* tRNA (Boehringer, Mannheim, FRG) for 4 hrs at 55° C. Oligonucleotide probes (200 ng), specific for a sequence internal to the primers used in the amplification, were labelled at the 5' end by T4 polynucleotide kinase (New England Biolabs) and $\gamma$-$^{32}$P-ATP (Amersham, Arlington Heigths, Ill.).

Probes were separated from non-incorporated nucleotides by passage over a Nick column (Pharmacia, Uppsala, Sweden) and added to the hybridization mix. Following hybridization for 12 hrs at 55° C., filters were washed in 0.1×SSC (1×SSC: 150 mM NaCl, 15 mM Na-citrate pH=7.0), and 1% SDS at room temperature and exposed to Kodak XAR-5 films for 1–2 hrs.

To determine at which level IL-10 inhibited the production of cytokines by monocytes, comparative PCR analyses were performed on RNA isolated from monocytes, activated by LPS in the absence or presence of IL-10, IL-4, or the neutralizing anti-IL-10 mAb for 24 hrs. The cytokine measurements of this experiment are shown in Table 2. mRNA isolated from these samples was reverse transcribed into cDNA and subsequently amplified with cytokine specific primers. A relatively small number of cycles was used for amplification to ensure that the amount of amplified DNA was proportional to the cycle number and correlated with the amount of specific mRNA in the original sample. FIG. 13 shows that under these conditions equivalent amounts of β-actin specific cDNA were amplified.

Monocytes incubated at 4° C. in medium alone for 24 hrs expressed very low levels of IL-8 mRNA. Incubation of these cells at 37° C. resulted in an increased expression of IL-8 mRNA, but did not induce expression of IL-1α, IL-1β, IL-6, IL-10, TNFα, GM-CSF or G-CSF mRNA. LPS activation resulted in a strong expression of IL-1α, IL-1β, IL-6, IL-8, and G-CSF mRNA, whereas TNFα and GM-CSF mRNA were moderately induced. Furthermore, FIG. 13 shows that IL-1α, IL-6, TNFα, GM-CSF, and G-CSF expression were strongly inhibited by IL-10 and IL-4 at the mRNA level. whereas IL-1β and IL-8 expression were only sligthly affected by IL-10.

Activation of monocytes by LPS in the presence of the anti-IL-10 mAb resulted in a moderate enhancement in expression of IL-1α, IL-1β, IL-6, IL-8, and G-CSF mRNA and a strong increase in TNFα and GM-CSF mRNA synthesis. The levels of expression of cytokine specific mRNA and their modulation by exogenous and endogenous IL-10 or IL-4 correlated well with secretion of the corresponding proteins as shown in Table 2 indicating that IL-10 and IL-4 inhibited cytokine expression by LPS activated monocytes at the transcriptional level.

Example 15
IL-10 Regulates IL-10 mRNA but not TGFβ mRNA Expression in Activated Monocytes Having demonstrated that human monocytes produced IL-10 relatively late following activation by LPS, it was determined whether IL-10 could affect endogenous IL-10 mRNA synthesis. Human monocytes were activated by LPS in the presence or absence of IL-10 for 7 hrs and mRNA expression was analyzed by northern blotting. FIG. 14 shows that IL-10 mRNA was detected 7 hrs after activation by LPS and that IL-10 had no or only minimal inhibitory effects on IL-10 mRNA expression at this time point. In contrast, the expression of IL-6 and IL-8 mRNA was strongly inhibited by IL-10. However, in another series of experiments where monocytes were activated for 24 hrs by LPS, IL-10 strongly reduced the expression of IL-10 mRNA as shown by northern analysis in FIG. 15. Furthermore, FIG. 15 shows that activation of monocytes with LPS in the presence of a neutralizing anti-v-IL-10 mAb resulted in an upregulation of IL-10 mRNA expression at 24 hrs.

These results were confirmed by PCR analysis with IL-10 specific primers since the RNA used in this latter experiment was also used for the PCR analyses shown in FIG. 13. It is shown in FIG. 15B that the quantitative differences observed in IL-10 mRNA expression by Northern analysis correlated with those observed by comparative PCR analysis. In addition, more sensitive PCR analysis allowed detection of low levels of IL-10 mRNA that were induced 24 hrs after culture of monocytes in medium alone at 37° C. These results indicate that IL-10 has autoregulatory effects on IL-10 mRNA synthesis and, if mRNA levels accurately reflect IL-10 protein production, probably on IL-10 production by human monocytes as well. However, downregulation of IL-10 production occured rather late in the activation process. TGFβ mRNA, which was expressed constitutively in freshly isolated non activated monocytes, was not enhanced by LPS activation for 7 or 24 hrs. In addition, the levels of TGFβ mRNA were not affected when activations were carried out in the presence of IL-4, IL-10, or neutralizing anti-IL-10 mAbs.

Example 16
IL-10 Has Autoregulatory Effects on Class II MHC Expression by Monocytes
Immunofluorescence analysis Cells ($10^5$) were incubated in V bottom microtiter plates (Flow Laboratories, McLean, Va.) with 10 ul of purified mAb (1 mg/ml) for 30 min at 40° C. After two washes with PBS containing 0.02 mM sodium azide and 1% BSA (Sigma, St Louis, Mo.), the cells were incubated with $\frac{1}{40}$ dilution of FITC labelled F(ab')2 fragments of goat anti-mouse antibody (TAGO, Inc. Burlingame, Calif.) for 30 min at 4° C. After three additional washes, the labelled cell samples were analyzed by flow microfluometry on a FAC-Scan (Becton Dickinson, Sunnyvale, Calif.). The anti MHC class II mAbs PdV5.2 (HLA-DR/DP/DQ), Q5/13 HLA-DR/DP, and L243 (HLA-DR) were described previously, see Koning et al. (1984) *Hum. Immunol.* 9:221–230; Quaranta et al. (1980) *J. Immunol.* 125:1421–1425; and Lampson et al. (1980) *J. Immunol.* 125:293–299.

IL-10 downregulates the expression of class II MHC molecules on the cell surface of human monocytes. IL-10 was shown to downregulate constitutive IL-4- or IFNγ-induced MHC class II expression. Since monocytes produce high levels of IL-10 following activation by LPS, whether endogenous IL-10 could inhibit class II MHC expression by LPS activated monocytes was investigated. Monocytes were activated by various concentrations of LPS in the presence or absence of neutralizing anti-IL-10 mAb. FIG. 16 shows that activation of monocytes with LPS reduced the constitutive HLA-DR/DP expression on these cells in a dose dependent manner. However, in the presence of the neutralizing anti-IL-10 mAb 19F1 strong induction of HLA-DR/DP expression was observed. Identical results were obtained with several HLA-DR or HLA-DR/DP specific mAb. These results indicate that endogenously produced IL-10, in an autoregulatory fashion, is responsible for the downregulation of class II MHC expression on human monocytes following LPS activation.

Example 17
IL-10 Inhibits Cytokine Production By Activated Macrophages

IL-10 inhibits the ability of macrophage but not B cell antigen presenting cells (APC) to stimulate cytokine synthesis by Th1 T cell clones. The direct effects of IL-10 on both macrophage cell lines and normal peritoneal macrophages were studied. LPS- (or LPS and IFNγ) induced production of IL-1, IL-6, and TNFα proteins was significantly inhibited by IL-10 in two macrophage cell lines. Furthermore, IL-10 appears a more potent inhibitor of monokine synthesis than IL-4 when added at similar concentrations. LPS or LPS and IFNγ-induced expression of IL-1α, IL-6, or TNFα mRNA was also inhibited by IL-10, as shown by semi-quantitative PCR or northern blot analysis. Inhibition of LPS-induced IL-6 secretion by IL-10 was less marked in FACS-purified peritoneal macrophages than in the macrophage cell lines.

However, IL-6 production by peritoneal macrophages was enhanced by addition of anti-IL-10 antibodies, implying the presence in these cultures of endogenous IL-10, which results in an intrinsic reduction of monokine synthesis following LPS activation. Moreover, LPS-stimulated peritoneal macrophages were shown to directly produce IL-10 detectable by ELISA. IFNγ was found to enhance IL-6 production by LPS-stimulated peritoneal macrophages, and this likely results from its suppression of IL-10 production by this same population of cells. In addition to its effects on monokine synthesis, IL-10 also induces a significant change in morphology in IFNγ-stimulated peritoneal macrophages. The potent action of IL-10 on the macrophage, particularly at the level of monokine production, indicates an important role for this cytokine not only in the regulation of T-cell responses but also in acute inflammatory responses.

IL-10 was first described as a cytokine produced by Th2 T helper cell clones which inhibits macrophage APC-dependent cytokine synthesis by Th1 T helper cells, and exhibits pleiotropic effects on various other cells and is produced by other cells. Th1 cells secrete IL-2 and IFNγ and preferentially induce macrophage activation and delayed type hypersensitivity (DTH), while Th2 cells produce IL-4 and IL-5 and provide help for B cell responses.

Once activated, each type of Th cell may be able to regulate the proliferation and/or function of the other. Such cross-regulation is mediated by various cytokines, and offers an explanation for the observation that some antibody and DTH responses can be mutually exclusive. IL-10 acts on the macrophage but not the B cell to inhibit cytokine synthesis by Th1 clones, and IL-10 exerts a direct effect on macrophages.

Macrophage products, such as IL-1, IL-6, and TNFα have been implicated in many inflammatory and immunological responses elicited during infection or tissue injury. TNFα and IL-1 are endogenous pyrogens which, additionally cause a number of metabolic changes in a variety of cell types. Moreover, IL-1 and IL-6 are the principal inducers of the synthesis of hepatic acute-phase proteins. The following Examples show that IL-10 inhibits the production of cytokines such as IL-1, TNFα, and IL-6 by LPS-activated macrophages. Thus, IL-10 plays an important part in inflammatory responses by regulating macrophage function in addition to its role in T-cell activation.

Example 18
IL-10 Inhibits APC Function of Different Macrophage Lines
Cytokines Purified recombinant mIL-1α was obtained as a generous gift from P. Lomedico, Hoffman-La Roche, Nutley, N.J. Recombinant mIL-2 and mIFNγ were obtained from Schering Research, Bloomfield, N.J. Recombinant purified mouse IL-6, kindly provided my M. Pearce, DNAX, was expressed in Cos 7 cells, and immunoaffinity purifed. Mouse TNFα was obtained from Genzyme Corporation (Boston, Mass.). Recombinant mouse IL-10 (CSIF), obtained by transfecting COS7 cells with the F115 cDNA clone as described above and control supernatants from mock transfected cells, were used at 2% final concentration unless otherwise indicated. Alternatively, recombinant mouse IL-10, kindly provided by Warren Dang was expressed in E. coli and affinity purified using the SXC2 anti-IL-10 antibody.

Antibodies

Neutralizing monoclonal antibodies (mAbs) against IFNγ (XMG1.2), and IL-10 (SXC1) were used, see Cherwinski et al. (1987) J. Expt'l Med. 166:1229–1244; and Mosmann et al. (1990) J. Immunol. 145:2938–2945. J5, an isotype matched control for SXC-1, was kindly provided by Robert Coffman (DNAX). Monoclonal antibodies to IL-6 (20F3 and 32C11), see Starnes et al. (1990) J. Immunol. 145:4185–4191, and to TNFα (MP6.XT3.11 and XT22.11) were purified and generously provided by John Abrams (DNAX). Antibodies used for FACS-sorting included rat anti-mouse B220 (RA3-6B2), see Coffman et al. (1981) Nature 289:681–683, anti-mouse Mac-1 (M1/70), see Springer et al. (1978) Eur. J. Immunol. 8:539–542. The rat anti-mouse monoclonal antibody to Fc-gR was 2.4G2, see Unkeless (1979) J. Expt'l Med. 150:580–596.

Media

Assay medium (cRPMI) consisted of RPMI 1640 (J. R. Scientific Inc., Woodland, Calif.) with 10% heat-inactivated fetal calf serum (FCS) (J. R. Scientific Inc.), 0.05 mM 2-ME (Sigma Chemical Co., St. Louis, Mo.), and 10 mM Hepes buffer (Gibco Laboratories, Grand Island, N.Y.). For T cell growth, recombinant mIL-2 (330 U/ml) was added to CRPMI.

Antigens

Keyhole limpet hemocyanin (KLH) obtained from Pacific Bio-Marine Laboratories, Inc. (Venice, Calif.) or Calbiochem Labs (La Jolla, Calif.) was used at a final concentration of 100–500 μg/ml, and ovalbumin from Sigma was used at a final concentration of 1 mg/ml.

Cell Lines

The Th1 clone, HDK1, (specific for I-A$^d$/KLH), see Cherwinski et al. (1987) J. Expt'l Med., and the T-cell hybridoma DO11.10, (specific for I-A$^d$/ovalbumin), see Kappler et al. (1981) J. Expt'l Med. 153:1198–1214, were used for the cytokine synthesis (CSIF) inhibition assay. The Th2 clone, D10.G4.1 (D10), AKR/J anti-conalbumin, obtained from C. Janeway (Yale University, New Haven, Conn.), see Kaye et al. (1983) J. Expt't Med. 153: 836–856, was used for an IL-1 assay, see Suda et al. (1989) J. Immunol. Methods 120:173–178. All clones were maintained by periodic stimulation with antigen (Ag) and irradiated APC, followed by growth in IL2-containing medium, see Cherwinski et al. (1987) J. Expt'l Med.

The cloned IG.18. LA macrophage cell line (H-2$^d$) was derived from the thymic stromal cell cultures and maintained in 20% L-cell supernatant. The PU5.1 macrophage cell line (H-2d), see Ralph et al. (1977) J. Immunol. 119:950–954, was maintained in cRPMI with 10% FCS. For use as APC, the 1G.18. LA and PU5.1 cell lines were activated for 20–24 hr with IFNγ (0.5–2 ng/ml). The WEHI.164.13 cell-line, which is responsive to TNFα and TNFβ, see Espevik et al. (1986) J. Immunol. Methods 65:55–63, was maintained in cRPMI/5% FCS.

Immunometric Assays for Cytokines

Cytokine levels (IL-6, IFNγ and CSIF/IL-10) were measured, in a two-site sandwich ELISA format.

Bioassays

A colorimetric MTT proliferation assay was used for the TNFα (WEHI 164.13 cells), IL-2 (HT-2 cells), and IL-1 (D10 cells) ($10^4$ cells/well for all assays) bioassays. Activity is either expressed as Units/ml relative to a known standard or pg or ng/ml. In each case, a unit per ml represents the amount of a particular cytokine which produces 50% of the maximal response of that bioassay.

Induction and Measurement of Th1 Cytokine Synthesis $1-5 \times 10^4$ Th1, HDK.1 cells, or DO-11.10 T-cell hybridoma cells were combined with varying numbers of live APC in the presence or absence of antigen in 96-well flat-bottomed microtiter trays in a total volume of 200 ul/well. Levels of cytokines were measured in 20 or 48 hr supernatants Stimulation of Macrophage Cell Lines Macrophage cell lines 1G.18.LA and PU 5.1 were harvested by gentle scraping, washed, and resuspended in cRPMI/5% FCS at $10^6$ cells/ml in 9.5 cm tissue culture dishes (Becton Dickinson, N.J.), at 37° C. in 5% $CO_2$/95% air, for 6 hr for RNA expression, or 24 hr for cytokine detection in the supernatants. Stimulation with LPS was at 10 μg/ml, or in some cases LPS and IFNγ at 100 units/ml, in the presence or absence of IL-10 (200 units/ml) or IL-4 (200 units/ml). Supernatants were collected, centrifuged (800×g), and stored at −80° C., and then used to assay levels of IL-1, IL-6, or TNFα.

In addition, the macrophage cell lines were stimulated with IFNγ, for 24 hr as above, and in some cases further stimulated for 24 hr in the presence of the Th1 clone, HDK.1 and its specific antigen KLH. In this case the supernatants were further concentrated using an AMICON filter with a membrane of 10,000 MW cut-off, and depleted of IL-2 and IFNγ, using immunoaffinity columns. These supernatants and the flow throughs from the concentration step were then tested for their ability to co-stimulate antigen-specific and APC-dependent Th1 cytokine synthesis. In addition, for use as APC, the macrophage cell lines 1G18.LA and PU5.1 were first activated for 20–24 h with IFNγ (0.5–2 ng/ml).

IL-10 will inhibit the ability of APC to stimulate IFNγ production by Th1 cells when normal peritoneal or splenic macrophages or the macrophage cell line 1G18.LA were used as APC. IL-10 is also effective on the PU5.1 macrophage line which has a different origin from the 1G18.LA (FIG. 17), although the stimulation achieved using the PU5.1 cell line as APC for Th1 cells was not as great as that observed with the 1G18.LA macrophage cell line. FIG. 17B shows that the 1G18.LA cell line can also mediate antigen-specific induction of IL-2 production by both the Th1 clone, and the ovalbumin-specific T cell hybridoma DO11.10. Both stimulations were significantly inhibited by IL-10.

Example 19

IL-10 Induces A Morphological Change In IFNγ-Stimulated Peritoneal Macrophages

Purification and Stimulation of Peritoneal Macrophages

Peritoneal cells were obtained by injection and withdrawal of 7 ml of cold cRPMI/10% FCS, and macrophages were sorted on the basis of Mac-1and B220 (macrophages are Mac-1$^{+\ bright}$; B220$^-$). The cells were stimulated with 10 μg/ml LPS in the presence or absence of IL-10, anti-IL-10 monoclonal antibodies, or IFNγ. Supernatants were collected after incubation for 20 hrs, at $8 \times 10^5$ cells/ml, in a humidified atmosphere of 5% $CO_2$ at 37° C. The supernatants were assayed for TNFα and IL-6 using an enzyme-linked immunoassay.

FACS-purified peritoneal macrophages, were incubated with IFNγ in the presence or absence of IL-10 for various periods of time. Supernatants were then removed, the cells air-dried, fixed and stained with Wright's-Giemsa. As shown in FIG. 18, IL-10 induces rounding up of the cells, and de-adherence, which may be of significance with regards to the inhibition of macrophage APC function.

Example 20

IL-10 Down-Regulates Production of Biologically Active or Secreted Cytokines by Activated Macrophage Cell Lines Earlier findings suggest that IL-10 has a direct effect on the ability of macrophages to function as APC and activate Th1 cytokine synthesis. The direct effect of IL-10 on monokine production by these macrophage cell lines was tested. Supernatants collected from macrophage cell lines stimulated with IFNγ, LPS, or IFNγ plus LPS, in the presence or absence of IL-10, were tested for their levels of cytokine(s). Where possible IL-4 was used as a control, since this factor has been shown to inhibit cytokine production by activated macrophages. Stimulation of the macrophage cell lines with IFNγ alone did not induce detectable levels of the monokines, IL-1, IL-6, or TNFα in the supernatants.

In contrast, LPS, or LPS plus IFNγ induced significant levels of these cytokines (FIG. 19). The D10.G4.1 assay used to detect IL-1, performed in the absence of Conconavalin A (ConA), does not detect other cytokines expressed by macrophages. The 1G.18.LA and PU5.1 macrophage cell lines were both significantly inhibited in their ability to produce IL-1 bioactivity after induction with LPS (FIG. 19). IL-10 also has a very significant inhibitory effect on LPS, or IFNγ plus LPS induced production of TNFα in the supernatants of both macrophage cell lines, as demonstrated in the WEHI.164.13. bioassay (all the activity in these macrophage supernatants was shown to be attributable to TNFα using a specific blocking antibody).

Similarly, IL-10 inhibits the production of IL-6 protein by the macrophage cell lines, stimulated by IFNγ plus LPS and/or LPS induced as measured in an enzyme-linked immunoassay for IL-6. In all experiments tested IL-10 had a much more significant inhibitory effect than IL-4 on LPS or IFNγ plus LPS-induced monokine production (at the protein level).

Example 21

IL-10 Down-Regulates Cytokine mRNA Expression by Activated Macrophages

RNA Extraction and analysis of RNA

Total cellular RNA was extracted from the macrophage cell lines using a guanidinium-isothiocyanate procedure. The concentration of RNA was was measured by absorption at 260 nm. RNA blot analysis was as described in Moore et al. (1990) *Science* 248:1230–1234, or PCR of reverse-transcribed RNA, see O'Garra et al. (1990) *Intn'l Immunol* 2:821–832. A specific amount of each cDNA sample (dilutions of one twentieth of cDNA) was amplified with 2.5 units of Thermalase (Thermus aquaticus DNA polymerase) (IBI) and a Cetus/Perkin-Elmer thermocycler under the following conditions: 94° C. melting, 30 s; 55° C. annealing, 30 s; and 72° C. extension, 1 min., using specific primers for HPRT (house-keeping enzyme), TNFα, and IL-6 as shown: HPRT sense: 5'-GTA ATG ATC AGT CAA CGG GGG AC-3' (nt 422–444) (SEQ ID NO: 53); HPRT anti-sense: 5'-CCA GCA AGC TTG CAA CCT TAA CCA-3' (nt 598–575) (SEQ ID NO: 54); HPRT probe: 5'-GCT TTC CCT GGT TAA GCA GTA CAG CCC C-3' (nt 543–570) (SEQ ID NO: 55) ; TNFα sense: 5'-GCG ACG TGG AAC TGG CAG AAG-3' (nt 4499–4519) (SEQ ID NO: 56); TNFα anti-sense: 5'-GGT ACA ACC CAT CGG CTG GCA-3' (nt 5865–5845) (SEQ ID NO: 57); TNFα probe: 5'-CAG TTC TAT GGC CCA GAC CCT C-3' (nt 5801–5821) (SEQ ID NO: 58); IL-6 sense: 5'-CCA GTT GCC TTC TTG GGA CTG-3' (nt 1520–1540) (SEQ ID NO: 59); IL-6 anti-sense; 5'-GGT AGC TAT GGT ACT CCA-3' (nt 6093–6075) (SEQ ID NO: 60); IL-6 probe: 5'-GTG ACA ACC ACG GCC TTC CCT ACT-3' (nt 1547–1570) (SEQ ID NO: 61).

All primers spanned intervening sequences in the gene. Sensitivity and specificity were further increased by probing dot-blots of the amplified products with radiolabelled ($^{32}$-P, γ-ATP) oligonucleotides internal to the amplified product. Radioactive blots were quantitated using the Ambis Image Scanner, and visualised by exposing to x-ray film. In each case, a standard curve of P388D1 RNA was included to ensure reproducibility of the assay, and arbitrary units relative to pg of input RNA in a final dot blot were obtained from it. In addition, an internal standard of the housekeeping enzyme HPRT was used to ensure that exactly the same amount of RNA was used and that all samples were reverse transcribed and amplified by PCR at the same efficiency.

PCR method for analysing reverse-transcribed RNA from both cell lines. By including a standard curve for each cytokine, it was possible to obtain arbitrary units relative to the pg of total standard RNA represented in each dot and thus present the data numerically. Table 3 shows that IL-10 and IL-4 inhibit LPS- and IFNγ plus LPS-induced expression of TNFα in the 1G18.LA macrophage cell line.

This is best illustrated with values obtained from the linear part of the standard curve, and the Table 3 legend explains the method used to derive the numerical data.

Analysis of RNA expression by the PU5.1 macrophage cell line in response to LPS and IFNγ plus LPS, using the same method, showed that expression of IL-6 and TNFα were also inhibited by IL-10 (Table 4).

TABLE 3

Inhibition of LPS-Induced TNFα Expression in the IG18.LA Macrophage Cell Line by IL-10 and IL-4

| Stimulus | cDNA Dilution Factor | 0 | | | IL-4 | | | IL-10 | | |
|---|---|---|---|---|---|---|---|---|---|---|
| | | cpm | *pgRNA | | cpm | *cpm | *pgRNA | cpm | *cpm | *pgRNA |
| LPS + IFNγ | 1:9 | 1260 | 300 | | 1987 | 2682 | Plateau | 1232 | 1034 | 200 |
| | 1:27 | 984 | 160 | | 601 | 769 | 110 | 713 | 589 | 90 |
| | 1:81 | 722 | 110 | | 358 | 332 | 57 | 411 | 312 | 50 |
| LPS | 1:9 | 1114 | 210 | | 1620 | 1587 | 330 | 1387 | 1068 | 200 |
| | 1:27 | 896 | 120 | | 517 | 403 | 60 | 460 | 271 | 45 |
| | 1:81 | 472 | 72 | | 480 | 403 | 60 | 310 | 220 | 33 |

The 1G18.LA macrophage cell line was stimulated as in FIG. 19. Supernatants were removed after 6 h and guanidinium isothiocyanate solution was added for harvest of the cells for RNA preparation. One microgram of total RNA from the 1G18.LA macrophage cell line was reverse transcribed in a total of 20 μl. Dilutions were made of the cDNA (shown in the figure) and 1 μl of each dilution was amplified by PCR using specific primers for HPRT. (internal standard) or TNFα. Ten microliters of the amplified cDNA product was dot-blotted and further probed with each respective radioactively labeled probe (internal to the primers). The signal shown was measured with the use of an Ambis Image Scanner. For each dilution, the raw cpm for TNFα were standardized (*cpm) according to a correction factor (*) obtained from the HPRT cpm relative to the "0" sample (i.e., no IL-10 or IL-4). Arbitrary units, relative to a titration of the positive control, and corrected for their HPRT content (*pg RNA/dot) could then be assigned using a standard curve (not shown).

TABLE 4

IL-10 Inhibits LPS-Induced Expression of RNA Encoding IL-6 and TNFα in the PU5.1 Macrophage Cell Line

| | Stimulus | | | | | | | |
|---|---|---|---|---|---|---|---|---|
| | LPS + IFNγ | | | | LPS | | | |
| Cytokine | +0 | | +IL-10 | | +0 | | +IL-10 | |
| RNA Tested | cpm | *Pg RNA | cpm | *Pg RNA | cpm | *Pg RNA | cpm | *Pg RNA |
| TNFα | 1031 | 370 | 587 | 80 | 1864 | 730 | 469 | 23 |
| IL-6 | 589 | 1000 | 207 | 700 | 108 | 90 | 27 | 44 |

Samples of PU5.1 were treated essentially as described in Table 3 and analyzed for HPRT, TNFα and IL-6 levels. The raw cpm shown above were first corrected according to the levels of HPRT per sample as described in Table 3. By using the standard curves of known amounts of positive controls for TNFα or IL-6, an arbitrary unit *pg RNA per dot blot, was assigned to it as described in Table 3. Values for both TNFα were obtained from a 1 in 27, and IL-6 from a 1 in 9 dilution of 1 μl of cDNA (1 μg of RNA was reverse transcribed in a total volume of 20 μl.)

RNA was extracted from the macrophage cell lines, 1G18.LA and PU5.1, 6 hr after stimulation with LPS or LPS and IFNγ, in the presence or absence of IL-10 or IL-4. RNA blot analysis of 10 μg total RNA revealed that IL-10 down-regulated expression of TNFα RNA, induced by LPS or IFNγ plus LPS, in both cell lines, albeit to a lesser extent in the latter case. This was confirmed using a semi-quantitative Example 22

IL-10 Down-Regulates Production of IL-6 Protein by LPS-Activated Peritoneal Macrophages Peritoneal macrophages (sorted on the basis of Mac-1 and B220) (macrophages are Mac-1$^{+\ (bright)}$; B220$^-$) already shown to be inhibited by IL-10 for APC function to Th1 cells, were further tested for their production of TNFα and IL-6 in response to LPS. TNFα was not detectable in the supernatants of LPS-stimulated FACS sorted macrophages (cell density, 7×10$^5$ cells/ml). In contrast, significant levels of IL-6 were detectable in supernatants obtained from peritoneal macrophages from BALB/c or CBA/J mice, stimulated with LPS as above (FIG. 21).

IL-6 levels were reduced if cells were stimulated by LPS in the presence of IL-10, but surprisingly, the level of inhibition was less marked (FIG. 21) than that observed with the macrophage cell lines (FIG. 19). However, the level of IL-6 production induced by LPS could be increased by the inclusion of a monoclonal antibody directed against IL-10, in the LPS-stimulation (FIG. 21). That macrophages produced IL-10 in response to LPS was confirmed in a specific ELISA for IL-10 (CBA/J or BALB/c peritoneal macrophages stimulated with LPS as above, produced 2 units/ml or 4.5 units/ml of IL-10, respectively).

FIG. 21 also shows that purified BALB/c peritoneal macrophages produce higher levels of IL-6 when stimulated with LPS in the presence of IFNγ as opposed to when stimulated with LPS alone. This can be explained by the results of a further experiment on IL-10 production by peritoneal macrophages from BALE/c mice. In this case, macrophages stimulated with LPS produced 12 units/ml IL-10, and this was reduced to less than 3 units/ml if the cells were stimulated with LPS in the presence of IFNγ.

Example 23
Test for a Soluble Co-stimulator Mechanism for IL-10 Inhibition of Macrophage APC Function IL-10 will only inhibit Th1 cytokine synthesis in the presence of live antigen presenting cells (APC) (macrophages). One possible mechanism of IL-10 action is suppression of production of a soluble co-factor needed for optimal cytokine release from Th1 cells. Supernatants were obtained from macrophages stimulated with IFNγ, in the presence or absence of Th1 cells and specific antigen. Such supernatants (FIG. 22A), or the flow throughs generated during their concentration were unable to reverse the IL-10-mediated inhibition of macrophage APC function for Th1 cells. These data provide no evidence that IL-10 down-regulates a soluble co-stimulator required for Th1 cytokine synthesis. Similar experiments provide no evidence that IL-10 induces macrophages to produce a soluble inhibitory factor which acts directly on the T cell, although such an inhibitor may be labile or membrane bound.

To test this, a cell mixing experiment was performed as follows. Splenic B cells and macrophages were FACS sorted (on the basis of B220 and Mac-1). Graded doses of macrophages, in the presence or absence of B cells, and also in the presence or absence of IL-10, were used as APC for antigen-specific stimulation of HDK.1 cells. Macrophage but not B cell stimulation of Th1 cytokine synthesis was inhibited by IL-10 (FIG. 22B). Mixing of graded doses of macrophages with a constant number of B cells, gave an additive stimulation of Th1 cytokine synthesis (FIG. 22B). However, addition of IL-10 to this mixture of APC brought the level of Th1 cytokine synthesis only down to the level achieved with B cell APC alone, an observation that argues against the presence of a short-range or labile inhibitor which acts directly on the Th1 cell, or the B cell APC.

Example 24
IL-10 Protects Mice Against Superantigen-induced Lethal Shock

The role of IL10 in protection against the lethal shock induced by Staphylococcal entorotoxin B (SEB) in a mouse model was investigated. Pretreatment of mice with IL-10 prevented death of mice later injected with SEB and D-galactosamine (the latter was necessary to overcome the natural resistance of mice to SEB). This effect indicates that IL-10 is capable of inhibiting T cell activation in vivo, probably through its ability to inhibit the ability of macrophages to activate T cells.

Superantigens are T cell mitogens that activate T cells in a T cell receptor (TCR) VB-specific manner by binding TcR VB chains and the B chain of class II MHC molecules. Superantigens include endogenous molecules produced by murine mammary tumor viruses and exogenous superantigens which include enterotoxins like those produced by Staphylococcus aureus. The toxic effect of superantigens depends on the presence of antigen presenting cells (APC). In recent years it has been recognized that the toxic effect of these toxins are due to their T cell mitogenic activity a conclusion that has been demonstrated in vivo.

IL-10 is a cytokine which exhibits pleiotropic activities on a variety of cell lineages. These include: growth cofactor for murine T cells and mast cells, Ia induction in B cells, and the ability to inhibit T cell activation. The latter effect has been demonstrated to be indirect, by inhibiting the ability of macrophages to act as APC. This effect seems to be part of a general inhibitory effect of IL-10 on macrophage function, including their ability to produce cytokines like IL-1, TNFα, and IL-6.

The present study used staphylococcal enterotoxin B (SEB) induced shock in mice as an in vivo model of T cell mediated lethal shock. In this model, mice are rendered sensitive to the toxic effects of SEB by pretreatment with D-Galactosamine. This treatment lowers the natural resistance that mice have towards enterotoxins, probably by affecting the liver clearance mechanisms. Subsequent administraton of small doses of SEB results in death within 2 days. In this model, toxicity is shown to be due to massive T cell activation in which T cell produced TNFα production has been shown to play a critical role. Treatment of the mice with IL-10 inhibits SEB-mediated toxicity, probably through its ability to inhibit macrophage-dependent T cell activation.

Example 25
IL-10 Prevents SEB-mediated Toxicity in vivo
Mice

Four to five week old male, BALB/c H-2$^d$ mice were purchased from Simonson Laboratories, Gilroy, Calif.
Reagents The materials used were: murine interleukin-10 (mIL-10) was prepared by standard procedures by Satish Menon of DNAX Research Institute (Palo Alto, Calif.). D(+)-Galactosamine (G-0500) was purchased from Sigma, St. Louis, Mo. The Staphylococcal Enterotoxin B (SEB) used in the initial experiment was also purchased from Sigma. SEB used in subsequent experiments was from Toxin Technology, Madison, Wis. kindly provided by P. Hugo (National Jewish Center for Immunology, Denver, Colo.). All materials were diluted in balanced salt solution.
Treatment Four to five week old male mice were injected (i.p.) with various concentrations of mIL-10. Three to four hours later the same mice were injected (i.p.) with D-Galactosamine. One hour after the second injection, the mice were injected with SEB at several different concentrations. The mice were inspected at 24, 36, and 48 hours, post injection. The initial experiments established that IL-10 would alter the toxicity of SEB in an in vivo mouse model. Preliminary experiments were designed at determining the minimum dose of SEB required to observe high mortality in this model. This dose varied depending on the origin (supplier) and lot of SEB. Once this dose was determined for a given lot of SEB, pretreatment with IL-10 (10 μg/mouse) was tested. FIG. 23 demonstrates that pretreatment with IL-10 resulted in survival of all mice injected with 10 μg SEB/mouse. Although pretreatment with IL-10 did not prevent eventual death of the animals injected with 20 μg SEB/mouse, it prolonged their survival.

Example 26
Interleukin 10 Protects Mice From Lethal Endotoxemia

IL-10 decreases production of IL-1, IL-6 and TNFα in vitro, and neutralization of IL-10 in mice leads to elevation of the same monokines. The present study tests whether this monokine-suppressing property of IL-10 confers the capacity to protect mice from LPS-induced shock, a monokine mediated inflammatory reaction. A single injection of 0.5–1 μg of recombinant murine IL-10 reproducibly protected BALB/c mice from a lethal intraperitoneal injection of endotoxin. This result was obtained whether the IL-10 was administered either concurrently with, or 30 minutes after the injection of endotoxin. The protective effect of IL-10 was reversed by prior injection of neutralizing anti-IL-10 antibodies, and correlated with a substantial decrease in endotoxin-induced TNFα release. These data implicate IL-10 as a candidate for treatment of bacterial sepsis, and more generally as an effective anti-inflammatory reagent.

Severe bacterial infections can result in profound physiological changes including hypotension, fever, tissue necrosis, widespread organ dysfunction, and ultimately death. In the case of gram-negative bacteria, this toxicity is due to endotoxin, a lipopolysaccharide (LPS) component of the bacterial cell wall. Indeed, injection of appropriate doses of LPS into rabbits, mice, and other animals produces changes which are typical of the septic shock syndrome, thus yielding a simple animal model of this inflammatory reaction. Endotoxin-induced toxicity appears to be due to the release of TNFα, IL-1, and/or IL-6 from endotoxin-stimulated macrophages/monocytes, since animals can be protected from bacterial and endotoxin-induced shock by neutralization of these monokines, using either monoclonal antibodies or a physiological IL-1 antagonist termed IL-1Ra.

Interleukin 10 (IL-10) has numerous in vitro properties including suppression of IFNγ production by helper T cells and NK cells; growth co-stimulation of thymocytes, mast cells, and B cells; and suppression of monokine production. With respect to the latter property, IL-10 profoundly suppresses the induced production of TNFα, IL-1α, IL-1β, IL-6, IL-8, and GM-CSF by human monocytes and mouse peritoneal macrophages. In contrast, IL-10 has no effect on constitutive expression of TGFβ by monocytes and actually upregulates monocyte production of the IL-1Ra. These in vitro data are supported by in vivo experiments showing that neutralization of IL-10 using specific monoclonal antibodies leads to elevated levels of circulating TNFα and IL-6 in mice. Whether the ability of IL-10 to suppress production of TNFα, IL-1, and IL-6, combined with its ability to increase IL-1Ra, would render this cytokine capable of protecting mice against endotoxin-induced shock was tested.

Example 27
Effect of IL-10 on Lethal Endotoxemia in Mice
Mice
8 week old BALB/c female mice were obtained from Simonsen Laboratories (Gilroy, Calif.).
Reagents
Lipopolysaccharide (LPS) from *Escherichia coli* serotype 0111:B4 was purchased from Sigma Chemical Co. Recombinant murine IL-10 was expressed in *E. coli* and purified to high specific activity by affinity-purification and ion-exchange chromatography. This material contained minimal endotoxin, and remained stable at 4° C. for at least 4 months. The specific activity of murine IL-10 was evaluated in both the cytokine synthesis inhibition assay, see Fiorentino et al.(1989) *J. Expt'l. Med.* 170:2081–2095, and the MC/9 mast cell co-stimulation assay, see Thompson-Snipes et al. (1991) *J Exp Med.* 173:507–510. Neutralizing antibody experiments utilized the 2A5, a rat IgG$_1$ anti-mouse IL-10 monoclonal antibody, or an isotype control antibody designated GL113.
TNFα assay
Serum levels of TNFα were evaluated using a cytokine specific ELISA.

Groups of 20 BALB/c mice were injected intraperitoneally with either a lethal dose of LPS alone, or the same amount of LPS together with varying amounts of recombinant murine IL-10. In several experiments of this type, mice were totally protected from death resulting from LPS-induced shock when either 0.5 μg, 1.0 μg, or 10 μg of IL-10 was administered to the animal concurrently with the LPS (FIG. 24). In some of these experiments, partial protection was also observed in mice receiving 0.1 μg or 0.05 μg of IL-10 at the time of LPS administration (FIG. 24).

Example 28
Neutralization of Protection by Anti-IL-10 Antibodies

IL-10 mediated protection from lethal endotoxemia could be blocked by prior administration of neutralizing anti-IL-10 antibodies, but not by an isotype control antibody (FIG. 25), confirming the specificity of this effect.

Example 29
Delayed Administration of IL-10 Remains Effective in Protection

A kinetics study revealed that IL-10 mediated protection from lethal endotoxemia was achieved even if the IL-10 was administered 30 minutes after the LPS injection (FIG. 26). However, further delays in IL-10 administration substantially reduced protection, and no protection was observed when IL-10 was administered 5 hours after the LPS injection (FIG. 26).

Example 30
Effect on TNFα of IL-10

Lethal endotoxemia is an undesirable monokine-mediated inflammatory reaction. IL-10 has been shown to suppress monokine production by activated macrophages and monocytes in vitro, suggesting that the above IL-10-mediated protection reflected a suppression of monokine production in the endotoxin-induced response. Indeed, sera collected 1, 2 and 3 hours following LPS±IL-10 injection indicated a profound reduction in circulating TNFα levels in animals protected by IL-10. Since anti-TNF antibodies similarly protect mice from lethal endotoxemia, it is likely that IL-10-induced suppression of TNFα at least contributes to the protection this cytokine provides against lethal endotoxemia.

Other effects of IL-10 on macrophage/monocyte function may also contribute to its ability to protect against lethal endotoxemia. In vitro studies have indicated IL-10 not only suppresses IL-1 and IL-6, but up-regulates IL-1Ra, consequences which will also protect against lethal endotoxemia, as suggested by reports using neutralizing anti-cytokine antibodies, or direct IL-1Ra administration.

Example 31
Continuous Anti-Interleukin-10 Antibody Administration Depleted Mice of Ly-1 B Cells But Not Conventional B Cells Ly-1 B cells have the distinctive property of continuous self-replenishment and, can be further distinguished from conventional B cells on the basis of greatly elevated constitutive and inducible production of the recently described cytokine interleukin 10 (IL-10). Whether IL-10 acts as either an autocrine or paracrine growth factor for Ly-1 B cells was tested by treating mice continuously from birth to 8 weeks of age with a monoclonal rat IgM antibody that specifically neutralizes mouse IL-10. Mice treated in this way lacked peritoneal-resident Ly-1 B cells, contained greatly reduced serum immunoglobulin M levels, and were unable to generate significant in vivo antibody responses to intraperitoneal injections of α1,3-dextran or phosphorylcholine, antigens for which specific B cells reside in the Ly-1 B cell subset.

In contrast, conventional splenic B cells of anti-IL-10 treated mice were normal with respect to total numbers, phenotype, and in vitro responsiveness to B cell mitogens and the thymus-dependent antigen trinitrophenyl-keyhole limpet hemocyanin (TNP-KLH). The mechanism of Ly-1 B cell depletion appeared to be related to elevation of endogenous interferon-γ (IFNγ) levels in anti-IL-10-treated mice, since coadministration of neutralizing anti-IFNγ antibodies substantially restored the number of peritoneal-resident Ly-1 B cells in these mice. These results implicate IL-10 as a regulator of Ly-1 B cell development, and identify a procedure to specifically deplete Ly-1 B cells, thereby allowing further evaluation of the role of these cells in the immune system.

Ly-1 B cells comprise ~2% of the total B cells of an adult mouse and exhibit several intriguing properties that distinguished them from conventional B cells: (a) although barely detectable in most primary and secondary lymphoid tissues, they are greatly enriched in the peritoneal and pleural cavities, as are their progeny in gut-associated lymphoid tissue; (b) they develop and predominate in early ontogeny, and are then self-replenishing for the life of the animal; (c) they produce a restricted repertoire of low-affinity antibodies that are highly cross-reactive with self-determinants, and do not appear to mature by somatic mutation; and (d) they generate most of the IgM antibody found in serum, and produce the entire antibody response elicited by several bacterial determinants, such as phosphorylcholine and α1,3-dextran.

Although their precise roles in immune system function is unclear, the various models that have been advanced, based on the specificities of antibodies produced by Ly-1 B cells, include roles in anti-bacterial immunity; in clearance of host cellular debris such as senescent erythrocytes; and in modulation of the antibody repertoire during development. Our recent finding that Ly-1 B cells are potent producers of IL-10, an immunosuppressive cytokine that down regulates production of several monokines and T cell-derived cytokines, raises the possibility of a broader immunoregulatory role of Ly-1 B cells. Many of these distinguishing features are difficult to evaluate in humans, but a population of Ly-1-bearing human B lymphocytes with related properties has been identified.

Example 32

Continuous IL-10 Neutralization Depletes Mice of Ly-1 B Cells

Mice

Mid-term pregnant BALB/c mice and C3H/HeJ mice were obtained from Simonsen Laboratory (Gilroy, Calif.).

Anti-IL-10 Treatment

5–10 age-matched BALB/c mice were injected intraperitoneally three times per week from birth until 8 weeks of age with the neutralizing rat IgM anti-mouse IL-10 antibody designated SXC.1 (0.2 mg/injection for week one, 0.5 mg/injection for week two, 1.0 mg/injection for weeks three to eight), equivalent amounts of an isotype control designated J5/D, or equivalent volumes (100 or 200 μl) of phosphate buffered saline (PBS).

Untreated age-matched BALB/c mice were included in all experiments for comparison. The SXC.1 and J5/D antibodies were obtained from serum-free hybridoma supernatants, and purified by two sequential 35% ammonium sulfate precipitation steps. In some experiments, mice received similar amounts of a separate rat IgG1 anti-mouse IL-10 antibody designated 2A5 or its isotype, control GL113. These latter antibodies were administered intraperitoneally at 0.5 mg/injection for week one, 1 mg/injection for week two, 2 mg/injection for weeks three to eight.

Immunofluorescence

Washed cells were stained with combinations of the following reagents; fluoresceinated anti-mouse IgM antibody (DS-1; Pharmingen, San Diego, Calif.); biotinylated rat anti-mouse IgD antibody (11–26c) produced by J. Kearney); fluoresceinated anti-mouse CD3 antibody (145–2C11, Boehringer Mannheim Corp., Indianapolis, Ind.); Caltag Labs., South San Francisco, Calif.). Biotinylated reagents were used in conjunction with phycoerythrin-conjugated streptavidin (Becton Dickinson & Co., Mountain View, Calif.). Cells were analyzed using a FACScan, and dead cells were excluded on the basis of forward angle and side scatter. Results show the fluorescence intensities of 5,000 live cells counted from each experimental group.

Antibody ELISAs

Serum samples collected after 8 weeks of treatment were assayed for the presence of mouse IgM using a sandwich ELISA where rat anti-mouse IgM (R8–103, Pharmingen) was coated at 5 μg/ml on PVC microtiter plates, dilutions of serum samples, or a mixture of several purified myeloma mouse IgM proteins as standard were added, and immune complexes were subsequently detected using biotinylated rat anti-mouse IgM (R19–15, Pharmingen) and avidin-conjugated horseradish peroxidase (CalBiochem Corp., La Jolla, Calif.), plus 1 mg/ml substrate (2, 2'-azinobis[3-ethylbenzthiazolin sulforic acid; Sigma Chemical Corp.).

Specific antibody responses against phosphorylcholine and α1,3-dextran were determined after challenging anti-IL-10 or control mice intraperitoneally with 0.5 ml saline, 50 μg α1,3-dextran derived from Leuconostoc mesenteroides provided by Dr. Slodki (U.S. Department of Agriculture Agricultural Research Service), or $2 \times 10^8$ heat-killed Streptococcus pneumoniae as a source of phosphorylcholine. Sera were collected from all mice 7 days later, and analyzed for specific antibody to α1,3-dextran or phosphorylcholine using ELISAs. Specific antibody responses against TNP-KLH were determined after challenging mice intraperitoneally with 10 μg TNP-KLH, and collecting sera 7 days later for IgM analysis, and 10 and 14 days later for IgG analysis. TNP-specific antibodies were quantitated using an ELISA. In all cases, anti-IL-10 treatment was continued between antigen challenge and sera collection.

IFNγ ELISA

Serum samples collected from anti-IL-10-treated or control mice were assayed for murine IFNγ using a cytokine-specific ELISA.

Male and female BALB/c mice were injected three times per week from birth to 8 weeks of age with graded doses of a neutralizing rat IgM anti-mouse IL-10 mAb designated SXC.1, and subsequently analyzed for Ly-1 B cell number and function. Control groups of age-matched BALB/c mice receiving no treatment or equivalent injections of either PBS or an irrelevant rat IgM isotype control (designated J5/D) were included for comparison. Antibodies were administered either intraperitoneally or subcutaneously without significant alteration of the outcome. The antibody injection regimen used yielded an average serum rat IgM level at 8 weeks of 50 mg/ml as measured by a rat IgM-specific ELISA in the case of both SXC.1 and J5/D antibodies.

After the 8 weeks of treatment, the anti-IL-10-treated mice were indistinguishable from the three control groups of mice in terms of the following criteria: total body weight, gross histological examination of liver spleen, thymus, lymph nodes, intestines and lungs; hematocrits; total number of white blood cells in spleen, thymus, lymph nodes, and peritoneum; and proportions of B cells, T cells, and non-B/-T cells in spleen, lymph nodes, and thymus. In contrast, immunofluorescent phenotyping of cells obtained in the pooled peritoneal washes collected from the 5–10 mice comprising each of the four experimental groups described revealed a striking depletion of IgM+ and IgD+cells in the anti-IL-10 (SXC.1)-treated mice, but not in any of the control animals (FIG. 27).

Identical data were obtained in 24 independent experiments including two using C3H/HeJ mice, and several using a separate rat IgG1 anti-IL-10 neutralizing antibody. Anti-IL-10-treated animals were also depleted of B220-bearing peritoneal cells, as evaluated by immunofluorescence, and of LPS-responsive peritoneal cells, as evaluated by the ability of these cells to incorporate [$^3$H]-thymidine after 3 days of co-culture with 50 µg/ml LPS. These findings suggest that anti-IL-10-treated BALB/c mice contained no B cells in their peritoneal cavities, in contrast to the 1–5×10$^6$ B cells that can normally be recovered from this site. It is significant that by three-color immunofluorescence the peritoneal cavities of 8 wk-old BALB/c mice in our animal facility contain very few (<5%) conventional B cells. The results shown in FIG. 27 therefore represent a depletion of Ly-1 B cells, predominantly.

Despite this striking depletion of peritoneal B cells, the total cellularity of the peritoneal cavities of anti-IL-10-treated mice did not differ significantly from those of the control groups. Further immunofluorescence analysis, together with differential hemopoietic cell counts, showed that the loss of B cells was compensated by an increase in peritoneal CD4+ T cells and granulocytes in the anti-IL-10 treated animals.

Two other observations indicated that depletion of Ly-1 B cells in anti-IL-10-treated mice occurred throughout the immune system and was not restricted to the peritoneal cavity. First, anti-IL-10-treated mice exhibited a striking 90–100% reduction in serum IgM levels compared with the three control groups, as monitored by a mouse IgM-specific ELISA (FIG. 28). Second, anti-IL-10-treated mice were profoundly deficient in their abilities to generate in vivo antibody responses to α1,3-dextran or phosphorylcholine (FIG. 29), two thymus-dependent antigens for which functionally responsive B cells reside entirely within the Ly-1 B cell subset.

Example 33
Anti-IL-10-treated Mice Contain Phenotypically and Functionally Normal Conventional B Cells In view of the striking effect of anti-IL-10 treatment of Ly-1 B cells, it was important to carefully evaluate the status of conventional B cells in these animals. As stated above, the total number of white blood cells in spleens of anti-IL-10-treated or control animals did not differ significantly in 24 independent experiments. FIG. 30 shows that the proportions of B220+ B cells, CD3+ T cells, and non-B/T cells (B220$^-$CD3$^-$) did not differ in any of the four experimental groups of mice. Equivalent data were obtained when Ig$^+$ B cells or CD4$^+$ T cells were compared. These data indicate that the total number of phenotype of splenic B cells in anti-IL-10-treated mice are the same as that of each of the control groups.

The immunocompetence of conventional B cells in anti-IL-10-treated mice was tested in two ways. First, anti-IL-10-treated mice developed normal IgM and IgG antibodies in response to injection with the thymus-dependent antigen TNP-KLH (FIG. 31). Secondary responses to TNP-KLH were also normal in anti-IL-10-treated mice. Second, splenic B cells from anti-IL-10-treated mice developed normal in vitro proliferative responses to 50 µg/ml LPS or anti-IgM antibody (Table 5). The background proliferative responses of spleen cells for anti-IL-10-treated mice were frequently three to five-fold higher than that of controls (Table 5). Collectively, these data suggest that conventional B cells in anti-IL-10-treated mice are quantitatively and functionally indistinguishable from those in control mice.

TABLE 5

In Vitro Proliferative Response of Spleen Cells from Anti-IL-10-treated and Control Mice to LPS, Anti-IgM, and Anti-CD3 Stimulation

| | [$^3$H] thymidine | | | |
|---|---|---|---|---|
| Animal group* | +0 | +LPS | +Anti-IgM | +Anti-CD3 |
| | | cpm | | |
| Untreated | 224 | 22,570 | 3,346 | 90,093 |
| PBS | 320 | 42,298 | 3,821 | 115,692 |
| J5/D | 547 | 46,748 | 2,897 | 135,172 |
| SXC.1 | 2,779 | 61,609 | 7,218 | 96,389 |

To produce the data of Table 5, animals were treated from birth to 8 wk of age as described in FIG. 27. Pooled spleen cells at 2×10$^6$/ml obtained from three mice in each group were cultured for 3 d in medium alone, or medium supplemented with LPS (50 µg/ml), goat anti-mouse IgM antibodies (50 µg/ml), or hamster anti-mouse CD3 antibodies (5 mg/ml). For anti-CD3 stimulation, the antibody was coated onto the microtiter plate before addition of spleen cells. Proliferation was evaluated via incorporation of [$^3$H] thymidine, after a 16 h pulse with 1 mCi/well [$^3$H]thymidine (NET 027; New England Nuclear, Boston, Mass.).

Example 34
Mechanism of Ly-1 B Cell Depletion
Proliferation Assays

Pooled spleen cells at 2×10$^6$ cells/ml obtained from three mice in each group were cultured for 3 days in medium alone, or medium supplemented with LPS (50 µg/ml), goat anti-mouse-IgM antibodies (0611–0201; Cappel Laboratories, Cochranville, Pa.) (50 µg/ml) or hamster anti-mouse CD3 anti-bodies (from D. J. Bluestone, University of Chicago, Chicago, Ill.) (5 µg/ml). For anti-CD3 stimulation, the antibody was coated onto the microtiter plate before addition of spleen cells. Proliferation was evaluated via incorporation of [$^3$H]thymidine, after a 16-h pulse with 1 mCi/well [$^3$H]thymidine (NET 027; New England Nuclear, Boston, Mass.).

Several possible mechanisms were considered as explanations for the depletion of Ly-1 B cells in anti-IL-10-treated mice. This effect did not appear to involve selective cytotoxicity of Ly-1 B cells by the anti-IL-10-treated antibodies, as injection of the same antibodies into adult mice had no effect on subsequent recoveries of total peritoneal wash cells, or total peritoneal B cells (FIG. 32) 1, 2, or 3 days later. As an alternative explanation, we considered the possibility that Ly-1 B cell depletion reflected a secondary consequence of some other endogenous cytokine perturbation. Indeed, anti-IL-10-treated mice were generally found to have elevated serum IFNγ levels (FIG. 33), an observation that was consistent with the previously reported ability of IL-10 to suppress IFNγ production by Th1 and NK cells in vitro.

To test the possibility that this anti-IL-10-induced elevation of IFNγ was either directly or indirectly responsible for depletion of Ly-1 B cells, mice were injected from birth to adulthood with a combination of anti-IL-10 and anti-IFNγ-neutralizing antibodies, or anti-IL-10 and an appropriate isotype control antibody. The results showed that of anti-IFNγ antibodies (FIG. 34), but not its isotype control, substantially reduced the ability of anti-IL-10 treatment to deplete mice of peritoneal Ly-1 B cells. It is important to note that continued administration of anti-IFNγ antibodies alone, or the combination of anti-IL-10 plus anti-IFNγ antibodies, did not alter the recovery of total peritoneal wash cells from mice treated with just anti-IL-10 or its isotype control. These data support the concept that Ly-1 B cell depletion is at least in part a consequence of IFNγ elevation in anti-IL-10 treated mice.

Example 35
Modified Immunological Status of Anti-IL-10 Treated Mice

It was shown above that continuous treatment of mice from birth to adulthood with neutralizing anti-IL-10 antibodies leads to specific depletion of Ly1 B cells, while conventional B cells remain normal in terms of number, phenotype, and function. Extending the characterization of these animals, this data show that anti-IL-10 treated mice can be distinguished from untreated or isotype control treated mice by several other criteria. Anti-IL-10 treated mice contained substantially elevated levels of circulating TNFα, and in many cases circulating IL-6, and were profoundly susceptible to death by LPS-induced shock, a monokine mediated inflammatory reaction.

Analysis of serum immunoglobulin levels in anti-IL-10 treated mice revealed a decrease in serum IgA levels to accompany the previously reported reduction in serum IgM, plus a striking increase in IgG2a and IgG2b levels. Further investigation of the Ly1 B cell depletion of anti-IL-10 treated mice revealed that this effect was transient as evidenced by the return of Ly1 B cells in normal numbers 8 weeks after anti-IL-10 treatment was discontinued. The Ly1 B cell depletion that occurred during anti-IL-10 treatment was found to be compensated by an increase in peritoneal T cells and granulocytes.

Finally, while anti-IL-10 treated mice were unable to produce antibodies to phosphorylcholine and α1,3 dextran, they developed normal antibody responses following intraperitoneal injections of TNP-Ficoll. This result suggests the existence of sub-categories within the family of thymus independent type II polysaccharide antigens. These data are discussed within the context of their implications for the roles of IL-10 and Ly1 B cells in the immune system.

The immune system is regulated by a family of soluble glycoproteins termed cytokines which are produced by a variety of hemopoietic and non-hemopoietic cells. Extensive in vitro characterization of these immunoregulators over the last five years has lead to the concept of extensive functional pleiotropy and redundancy within the cytokine system. Immunologists are now faced with the challenge of evaluating whether this concept accurately reflects the physiological roles of cytokines in vivo. The physiological role of a recently discovered cytokine IL-10 has been the subject of investigation.

An extensive list of in vitro properties has characterized IL-10 as a potent immunosuppressant capable of down-regulating production of several monokines and cytokines, and of inhibiting antigen presentation by some, but not all, antigen presenting cells. An equally long list of stimulatory properties portray the same cytokine as a growth co-stimulator of thymocytes, peripheral T cells, B cells, and mast cells; an amplifier of cytotoxic T cell development and function; and an inducer of B cell viability and differentiation.

To evaluate the physiological role of IL-10 in vivo, mice were injected two to three times per week from birth to adulthood with neutralizing anti-IL-10 monoclonal antibodies. Early analysis revealed that this treatment leads to a striking depletion of a minor subset of B lymphocytes, termed Ly-1 or B-1 B cells, thus implicating IL-10 as a regulator of Ly-1/B-1 B cell development.

Ly-1 B cells are a subpopulation of B lymphocytes which are highly prevalent in fetal and neonatal lymphoid tissues of man and mouse, but which are found in small numbers only in the adult immune system. While barely detectable in adult primary and secondary lymphoid tissues, Ly-1 B cells are greatly enriched in the peritoneal and pleural cavities of an adult mouse, and are found in low numbers in the circulation of adult man. Their extensive characterization in the murine system has revealed numerous intriguing properties, including a restricted repertoire of low affinity antibodies which do not readily undergo somatic mutation and which are highly cross-reactive with autoantigens and bacterial cell wall components.

Furthermore, murine reconstitution experiments have indicated that, in contrast to conventional B cells, Ly-1 B cells are capable of self-replenishment for the entire life of the host, and that they generate most serum IgM and the entire antibody response to several bacterial determinants such as phosphorylcholine and α1,3 dextran. Previous characterization of Ly-1 B cells has shown that they can be further distinguished from conventional B cells on the basis of greatly elevated and inducible production of IL-10, raising the possibility of a broader immunoregulatory role for these cells. Despite these intriguing properties, the precise role of Ly-1 B cells in the immune system remains obscure.

Mice that have been treated continuously from birth to adulthood with neutralizing anti-IL-10 antibodies become depleted of Ly-1 B cells as evidenced by their lack of peritoneal B cells and the fact that they have drastically reduced serum IgM levels and in vivo antibody responses to α1,3 dextran and phosphorylcholine. The depletion of Ly-1 B cells was found to be a secondary consequence of endogenous IFNγ elevation, and could be prevented by co-administration of anti-IFNγ antibodies. The consequences of specifically depleting both Ly-1 B cells and endogenous IL-10 on the subsequent immune status of these mice are reported here.

Example 36
Effect of anti-IL-10 treatment of mice on endogenous cytokine levels

Mice

Midterm pregnant BALB/c mice were obtained from Simonsen Laboratory (Gilroy, Calif.).

Anti-IL-10 treatment 5 to 10 age-matched BALB/c mice were injected intraperitoneally with either of two anti-IL-10 antibodies from birth until 8 weeks of age according to the following protocols. In some experiments, mice were injected three times a week with SXC.1 rat IgM anti-mouse IL-10 antibody, see Mosmann et al. (1990) *J. Immunol.* 145:2938–2945, (0.2 mg/injection forweek 1, 0.5 mg/injection for week 2, 1.0 mg/injection for weeks 3 to 8), equivalent amounts of an isotype control designated J5/D, or equivalent volumes (100 or 200 ul) of phosphate buffer saline (PBS). In other experiments, mice were injected twice a week with 2A5, a rat IgG1 anti-mouse IL-10 antibody (0.2 mg/injection for week 1, 0.5 mg/injection for week 2, 1 mg/injection for weeks 3 to 8), equivalent amounts of an isotype control designated GL113, or equivalent volumes (100 or 200 ul) of phosphate buffered saline (PBS). Untreated age-matched BALB/c mice were included in all experiments for comparison. All antibodies were obtained from serum-free hybridoma supernatants and purified by ammonium sulfate precipitation. Following this treatment regimen, pooled spleens, thymuses, lymph nodes or peritoneal wash cells were collected from each of the four groups of mice and analyzed by flow cytometry and functional assays.

Cytokine ELISAs

Serum samples collected from anti-IL-10 treated or control mice were assayed for murine TNFα or murine IL-6 using cytokine specific ELISAs.

Continuous anti-IL-10 treatment of mice from birth until adulthood leads to the presence of substantial quantities of IFNγ in sera collected at 8 weeks, in contrast to untreated or isotype control treated mice, both of which lack detectable IFNγ in their sera. To further explore endogenous cytokine perturbations resulting from anti-IL-10 treatment, sera collected after 8 weeks of treatment were evaluated for the presence of TNFα and IL-6, using cytokine specific ELISAs. Sera from anti-IL-10 treated mice contained greatly elevated TNFα levels (FIG. 35), and frequently contained elevated IL-6 levels (FIG. 36) Elevation of TNFα and IL-6 in anti-IL-10 treated mice is consistent with the reported ability of IL-10 to suppress monokine production in vitro.

Example 37
Effect of anti-IL-10 Treatment on Mouse Serum Ig Levels
Endotoxin-induced shock Mice were injected intraperitoneally with doses of endotoxin (lipopolysaccharides from *Escherichia coli* serotype 0111:B4, Sigma Chemical Co.) ranging from 1 μg to 500 μg. Survival was monitored over the following 1–6 day period.

The effect of anti-IL-10 treatment on endogenous monokine levels was further analyzed by evaluating the susceptibility of these animals to LPS-induced shock, a monokine-mediated inflammatory reaction. Earlier presented data have shown that neutralizing monoclonal antibodies to TNFα, IL-1, or IL-6, and a physiological IL-1 antagonist termed IL-1Ra, effectively protect mice from LPS-induced shock. Those experiments indicate that mice injected with either SXC.1 (rat IgM) or 2A5 (rat IgG1) anti-IL-10 antibodies from birth until 8 weeks were profoundly susceptible to death by LPS induced shock (FIG. 37).

While the LPS $LD_{100}$ for 8 week old BALB/c mice in the DNAX animal facillty was found to be >380 μg/mouse i.p., as little as 1 μg of endotoxin killed most anti-IL-10 treated mice (FIG. 37). The precise mechanism for this enhanced susceptibility has not yet been determined, but these data are consistent with a generalized upregulation of inflammatory monokines in anti-IL-10 treated mice.

Antibody ELISAs

Serum samples collected after 8 weeks of treatment were assayed for the presence of mouse immunoglobulins of all isotypes using isotype specific sandwich ELISAS. The plate binding antibodies employed for this purpose were as follows: rat anti-mouse IgG1 (3096, generously provided by R. Coffman, DNAX); rat anti-mouse IgG2a (R8–103; Pharmingen, San Diego, Calif.); rat anti-mouse IgG2b (R9–91, Pharmingen); rat anti-mouse IgG3 (R2–38, Pharmingen); rat anti-mouse IgA (R5–140, Pharmingen); rat anti-mouse IgE (EM95, generously provided by R. Coffman). Plate coating antibodies were used at 1–5 μg/ml.

The sandwich antibodies used in these ELISAs were biotinylated rat anti-mouse IgG1 (3098B, generously provided by R. Coffman); biotinylated rat anti-mouse IgG2a (R19–15, Pharmingen); biotinylated rat anti-mouse IgG2b (R12–3, Pharmingen); biotinylated rat anti-mouse IgG3 (R40–82, Pharmingen); biotinylated rat anti-mouse IgA (2740B, generously provided by R. Coffman); biotinylated rat anti-mouse IgE (R35–118, Pharmingen). These sandwich antibodies were used at 1–3 μg/ml, in conjunction with streptavidin-conjugated horseradish peroxidase (Cal Biochem, La Jolla, Calif.) plus 1 mg/ml substrate [2,2-azinobis (3-ethylbenzthiasolin sulfuric acid); Sigma]. ELISAs were quantitated using purified mouse myeloma immunoglobulins as standards.

Continuous anti-IL-10 treatment of mice from birth until adulthood leads to a marked depletion of serum IgM levels compared to the normal serum IgM levels observed in isotype control treated mice. Measurement of the other immunoglobulin isotypes in sera collected after 8 weeks of treatment is shown in FIG. 38. The levels of each immunoglobulin isotype in the three control groups of mice (i.e. untreated, PBS treated, or treated with an isotype control antibody) did not vary significantly from the previously documented ranges of serum Ig levels in normal mice. However, numerous changes were observed in serum Ig levels in anti-IL-10 treated mice. These mice showed a marked reduction in serum IgA levels to accompany the previously reported reduction of serum IgM, and a striking increase in IgG2α and IgG2β (FIG. 38). The remaining isotypes (IgG1, IgG3, IgE) were either unchanged, or were increased two- to four-fold in some experiments.

Example 38
Ly-1 B Cell Depletion in Anti-IL-10 Treated Mice is Transient
Immunofluorescence Washed cells were stained with combinations of the following reagents: fluoresceinated anti-mouse IgM antibody (DS-1, Pharmingen, San Diego, Calif.); biotinylated rat anti-mouse IgD antibody (11–26c, produced by J. Kearney, U. Birmingham, Ala.); fluoresceinated anti-mouse CD3 antibody (145-2C11, Boehringer-Mannheim, Indianapolis, Ind.); biotinylated anti-mouse B220 antibody (RA3-6B2; Caltag, S. F.); and a biotinylated rat anti-mouse granulocyte/eosinophil antibody (8C5; produced by R. Coffman, DNAX). Biotinylated reagents were used together with phycoerythirin-conjugated streptavidin (Becton-Dickinson, Mountain View, Calif.). Cells were analyzed using a FACScan and dead cells were excluded on the basis of forward angle and side scatter. Results show the fluorescence intensities of 5000 live cells counted from each experimental group.

Anti-IL-10 treated mice were evaluated after anti-IL-10 treatment was discontinued to determine if depletion of Ly-1 B cells in these animals was irreversible. Several groups of mice were injected with anti-IL-10 antibodies from birth until 8 weeks, after which time treatment was discontinued. Each group was then analyzed for the presence of peritoneal Ly1 B cells either immediately or at different time-points during the 8 weeks following the termination of treatment. Importantly, no significant differences were observed in yields of total peritoneal wash cells collected at the different time points.

In several experiments of this nature the mice remained devoid of peritoneal Ly1 B cells for the initial 3 weeks following termination of anti-IL-10 treatment. After that time interval, Ly1 B cells began to reappear in the peritoneal cavity, with a normal complement of Ly1 B cells observed 8 weeks following termination of anti-IL-10 treatment (FIG. 39). Reconstitution of the peritoneal B cell compartment was characterized by an initial appearance of B220$^{bright}$IgM$^{dull}$ B cells approximately 4 weeks after anti-IL-10 treatment was discontinued, followed some weeks later by the appearance of B220$^{dull}$IgM$^{bright}$ B cells (FIG. 39).

Example 39
Increased Numbers of Peritoneal T Cells and Granulocytes in Anti-IL-10 Treated Mice
Differential hemopoietic cell counts Cell suspensions from spleens or peritoneal washes were used to prepare cytospins for cell morphology analysis. Samples were stained with Wright's-Giemsa (Sigma, St. Louis) and analyzed by microscopy for lymphocytes, macrophages, granulocytes, eosinophils and mast cells.

While mice treated continuously from birth until 8 weeks of age became depleted of peritoneal B cells, the total number of peritoneal wash cells that could be obtained from such mice did not vary significantly from that of control mice. Differential hemopoietic cell counts performed on peritoneal wash cells collected from anti-IL-10 treated mice indicated that this reflected an increase in peritoneal granulocytes/eosinophils and apparently-non-B cell lymphocytes (Table 5). Surface marker phenotyping of peritoneal wash cells from anti-IL-10 treated mice revealed increases in Ly1-bright Ig-negative cells (FIG. 40), CD3-positive Ig-negative cells, Mac1-bright Ig-negative cells (FIG. 41), and 8C5-bright Ig-negative cells. These analyses indicate an increase in Ly1-positive, CD3-positive T lymphocytes and confirm (Table 6) an increase in granulocytes which express the Mac1 and 8C5 surface markers.

TABLE 6

Proportions of Hemopoietic Sub-populations in Anti-IL-10 Treated or Control Mice

| | Lympho-cytes | Macro-phages | Neutro-phils | Eosino-phils | Mast Cells |
|---|---|---|---|---|---|
| Peritoneum* | | | | | |
| Untreated | 74 | 22 | 1.8 | 1.7 | 0.5 |
| PBS treated | 66 | 29 | 1.4 | 3.3 | 0.3 |
| Isotype control treated | 64 | 31 | 1.2 | 4.5 | 0.3 |
| Anti-IL-10 treated | 44 | 22 | 18.0 | 16.0 | 0 |
| Spleen* | | | | | |
| Untreated | 94 | 2.7 | 2.3 | 0.5 | 0 |
| PBS treated | 92 | 3.6 | 3.6 | 1.4 | 0 |
| Isotype control treated | 96 | 1.2 | 1.8 | 0.6 | 0 |
| Anti-IL-10 treated | 92 | 2.4 | 5.0 | 0.9 | 0 |

*All groups had approximately the same number of peritoneal and splenic cells/mouse; numbers represent percentage of total cells counted.

Example 40
Anti-IL-10 Treated Mice Respond to the Thymus-independent Antigen TNP-Ficoll
Specific antibody responses Specific antibody responses against TNP-Ficoll were determined after challenging mice intraperitoneally with 10 µg TNP-Ficoll (Provided by Dr. James Mond, USUHS) and collecting sera 5 or 10 days later. Anti-IL-10 or control antibody injections were continued between antigen challenge and sera collection. TNP-specific antibodies were quantitated using an ELISA.

Anti-IL-10 treated mice are deficient in their ability to elicit in vivo antibody responses to two thymus-independent type II antigens, phosphorylcholine and α1,3 dextran. FIG. 42 indicates anti-IL-10 treated mice develop normal in vivo antibody responses to a third thymus-independent type II antigen TNP-Ficoll. This responsiveness is consistent with our previous observations that splenic B cells from anti-IL-10 treated mice develop a normal proliferative response following stimulation with anti-IgM antibodies, the presumed polyclonal analogue of thymus independent type II antigens.

Example 41
Continuous Administration of Anti-IL-10 Antibodies Delays Onset of Autoimmunity in NZB/W Mice Continuous administration of anti-IL-10 antibodies to BALB/c mice modifies endogenous levels of auto-antibodies, plex TNFα, and IFNγ, three immune-mediators known to effect the development of autoimmunity in 'lupus-prone' NZB/W mice. To explore the consequences of IL-10 neutralization in NZB/W mice, animals were injected 2–3 times per week from birth until 8–10 months with anti-IL-10 antibodies or with isotype control antibodies. Anti-IL-10 treatment substantially delayed onset of autoimmunity in NZB/W mice as monitored either by overall survival, or by development of proteiuuria, kidney nephritis, or autoantibodies.

Survival at 9 months was increased from 10% to 80% in treated mice relative to controls. This protection against autoimmunity appeared to be due to an anti-IL-10 induced upregulation of endogenous TNFα, since protected NZB/W mice rapidly developed autoimmunity when neutralizing anti-TNFα antibodies were introduced at 30 weeks into the long-term anti-IL-10 treated mice. These data indicate that IL-10 antagonists will be beneficial in the treatment of human systemic lupus erythematosus.

The (NZB×NZW) F1 hybrid mouse develops a severe autoimmune disease that closely resembles systemic lupus erythematosus in humans. NZB/W mice spontaneously develop a fatal immune-complex mediated glomerulonephritis around 6–9 months in female animals, and 12–18 months in male animals. Previous attempts to define the underlying cause of autoimmunity in NZB/W mice have focused on the potential role of MHC genes. Indeed, interferon γ (IFNγ), a cytokine which upregulates expression of MHC class II antigens in a wide variety of cell types, accelerates the development of autoimmunity in NZB/W mice.

Several recent studies have suggested that the TNFα gene, which is located within the MHC complex, may be involved in the pathogenesis of lupus nephritis in NZB/W mice. These studies reveal that NZB/W mice produce exceptionally low levels of TNFα, and that this correlates with a restriction fragment length polymorphism in the TNFα gene j, and a polymorphism in simple dinucleotide tandem repeats in the 5' regulatory region of the TNFα gene. A causative role for these observations is implied by the fact that replacement therapy with recombinant TNFα significantly delays development of nephritis in NZB/W mice.

IL-10 is a cytokine produced by subsets of activated T cells, B cells, and macrophages, which mediates a variety of both immunostimulatory and immunosuppressive properties in mouse and human in vitro assays. In a recent effort to evaluate the physiological role of IL-10, BALB/c mice were treated continuously from birth until 8 weeks of age with neutralizing anti-IL-10 antibodies. Consistent with the known in vitro properties of IL-10, anti-IL-10 treated mice are characterized by elevated levels of endogenous IFNγ and TNFα. The elevated IFNγ in turn leads to the depletion of a numerically small subset of B lymphocytes, termed Ly1 or CD5 or B-1 B cells, a population from which most murine auto-antibodies are derived.

These studies in normal mice suggested that neutralization of IL-10 may produce some desirable consequences in NZB/W mice, i.e., elevation of endogenous TNFα and reduction of autoantibody production, and some undesirable consequences, i.e., elevation of endogenous IFNγ. The overall effects of continuous anti-IL-10 treatment on development of autoimmunity in NZB/W female mice are studied here. The data that neutralization of IL-10 significantly delays onset of autoimmunity in these mice due to an upregulation of endogenous TNFα.

Mice

NZB/W F1 mice were bred in the animal colony at DNAX Research Institute using NZB females purchased from the Jackson Laboratory (Bar Harbor, Me.) and NZW males purchased from Simonsen Laboratories (Gilroy, Calif.). Only female F1 mice were utilized due to their more rapid onset of autoimmunity.

Anti-IL-10 Treatment

Groups of 17–23 B/W F1 female mice were treated with a rat IgM mAb or IgG mAb against IL-10, designated SXC.1 or JES 2A5. Aged matched 21–23 B/W F1 female mice per group were treated with isotype-matched control mAbs, designated J5/D (IgM) or GL113 (IgG). Anti-IL-10 mAbs and isotype control mAbs were harvested as ascites from nude (nu/nu) mice, purified by two sequential ammonium sulfate precipitations, dialyzed against phosphate buffered saline (PBS), and quantified by protein electrophoresis and measurement of optical density. Treatment consisted of 3 parts: (a) from birth to 1st week, 0.2 mg of mAb per mouse was injected intraperitoneally (i.p.) 4 times in IgM or twice in IgG, (b) 2nd week 0.5 mg of mAb per mouse was injected i.p. 3 times with IgM or twice with IgG, and (c) from 3rd week to adulthood 1 mg of mAb per mouse was injected i.p. with 3 times with IgM or twice with IgG per week. Preliminary studies, indicated that this regimen could maintain the concentration of rat IgM in mice sera around 50 μg/ml.

Assessment of Renal Disease

Proteinuria was measured colorimetrically using Albustix dip sticks (Miles Laboratories, Inc., Elkhart, Ind.), and graded according to the following code: trace=10 mg/dl; 1+=30 mg/dl; 2+=100 mg/dl; 3+=300 mg/dl 4+=1,000 mg/dl. Histological severity of glomerulonephritis was graded on a 0 to 2+scale based on the intensity and extent of histopathologic changes 0=kidneys without glomerular lesions; 1+=mild lesions, e.g., increased mesangial matrix, mesangial/glomerular cellularity, crescent formation, or presence of inflammatory exudates and capsular adhesions; no noticeable tubular casts; 2+=severe lesions, e.g., glomerular architecture obliterated in more than 70% of gromeruli with extensive tubular cast formation.

Autoantibody ELISA

Serum antibodies specific for double- or single-stranded DNA (ds- or ss-DNA) were quantitated by ELISA. Briefly, 5 mg/ml ds- or ssDNA was used to cut ELISA plates (Flow Laboratories, McLean, Va.) in an overnight incubation at 4° C. Antigen-coated plates were subsequently blocked for 1 h with PBS containing 0.05% Tween 20, 0.02% $NaN_3$ and then incubated for 1 h at room temperature with test or standard sera diluted 1:100. Plates were then washed with PBS-0.05% Tween 20, and incubated for 1 h with 1 μg/ml horseradish peroxidase (HRP) conjugated anti-mouse IgG or IgM (Zymed laboratories, Inc. S. San Francisco, Calif.).

Absorbance was measured using a Vmax microplate reader (Molecular Devices, Menlo Park, Calif.) 30-min after the addition of 1 mg/ml 2, 2'-Azino-bis (3 ethylbenthiazoline-6-sulfonic acid); ABTS (Sigma Chemicals, St. Louis, Mo.). Anti-DNA titers were expressed as units, using a reference standard of pooled serum from 4-month-old MRL/MpJ-lpr/lpr mice provided by Dr. Shelby Umland of Schering-Plough Corp. A 1:100 dilution of this standard serum was arbitrarily assumed to be 100 units/ml.

Serum concentration of Ig and TNFα

For Ig ELISA, plates coated with 1 μg/ml goat anti-mouse IgG (Kirkegaard & Perry Laboratories, Inc., Gaithersburg, Md.) were incubated with 1:1000 or 1:5000 diluted test sera, then with HRP-conjugated goat anti-IgG or anti-IgM (Zymed Laboratories, Inc.). and color developed. IgG and IgM concentrations, were determined from a standard curve made by incubating with known concentrations of our stocks, which were the mixture of myeloma proteins.

For TNFα ELISA, plates coated with 5 μg/ml rat anti-mouse TNFα mAb (MP6-XT3.11) were incubated with 1:10 diluted test sera, then with HRP-conjugated rat-anti mouse TNFα mAb (MP6-XT22), and color developed.

Applicants have deposited separate cultures of *E. coli* MC1061 carrying pH5C, pH15C, and pBCRF1(SRa) with the American Type Culture Collection, Rockville, Md., U.S.A. (ATCC), under accession numbers 68191, 68192, and 68193, respectively. These deposits were made under conditions as provided under ATCC's agreement for Culture Deposit for Patent Purposes, which assures that the deposit will be made available to the US Commissioner of Patents and Trademarks pursuant to 35 USC 122 and 37 CFR 1.14, and will be made available to the public upon issue of a U.S. patent, which requires that the deposit be maintained. Availability of the deposited strain is not to be construed as a license to practice the invention in contravention of the rights granted under the authority of any government in accordance with its patent laws.

We claim:

1. A method for reducing an inflammatory response characterized by substantially elevated levels of IL-1α, IL-1β, IL-6, IL-8 and TNFα in a mammal comprising administering to a mammal afflicted with such an inflammatory response, or at risk of developing such an inflammatory response, an amount of IL-10 effective to substantially lower the levels of such cytokines.

2. The method of claim 1 in which the mammal is at risk of developing said inflammatory response.

3. The method of claim 1 in which the IL-10 is mouse, human or viral IL-10.

4. The method of claim 1 in which the mammal is a human.

5. The method of claim 3 in which the IL-10 is a recombinant mature protein produced from an amino acid sequence defined by SEQ ID NO: 1, SEQ ID NO: 2, SEQ ID NO: 3 or SEQ ID NO: 4.

6. The method of claim 1 in which the inflammatory response is caused by a bacterial infection.

7. The method of claim 6 in which the inflammatory response is caused by endotoxin produced by a gram negative bacterium.

8. The method of claim 7 in which the bacterial infection produces symptoms of septic shock.

9. The method of claim 6 in which the bacterial infection is caused by a gram positive bacterium.

10. The method of claim 9 in which the bacterial infection produces symptoms of toxic shock.

11. The method of claim 10 in which said infection results in a T cell dependent response.

12. The method of claim 1 in which IL-10 is administered prior to onset of the inflammatory response.

13. The method of claim 1 in which IL-10 is administered after onset of the inflammatory response.

14. A method for reducing an inflammatory response characterized by substantially elevated levels of IL-1α, IL-1β, IL-6, IL-8 and TNFα in a human comprising administering to a human afflicted with such an inflammatory response, or at risk of developing such an inflammatory response, an amount of IL-10 effective to substantially lower the levels of such cytokines.

15. The method of claim 14 in which the human is at risk of developing said inflammatory response.

16. The method of claim 14 in which IL-10 is administered prior to onset of the inflammatory response.

17. The method of claim 14 in which IL-10 is administered after onset of the inflammatory response.

18. The method of claim 15 in which IL-10 is administered prior to onset of the inflammatory response.

\* \* \* \* \*

SEQUENCE LISTING ( 1 ) GENERAL INFORMATION:

( i i i ) NUMBER OF SEQUENCES: 61

( 2 ) INFORMATION FOR SEQ ID NO:1:

( i ) SEQUENCE CHARACTERISTICS:
        ( A ) LENGTH: 178 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:1:

| Met | His | Ser | Ser | Ala | Leu | Leu | Cys | Cys | Leu | Val | Leu | Leu | Thr | Gly | Val |
|---|---|---|---|---|---|---|---|---|---|---|---|---|---|---|---|
| 1 | | | | 5 | | | | | 10 | | | | | 15 | |

| Arg | Ala | Ser | Pro | Gly | Gln | Gly | Thr | Gln | Ser | Glu | Asn | Ser | Cys | Thr | His |
|---|---|---|---|---|---|---|---|---|---|---|---|---|---|---|---|
| | | | 20 | | | | | 25 | | | | | 30 | | |

| Phe | Pro | Gly | Asn | Leu | Pro | Asn | Met | Leu | Arg | Asp | Leu | Arg | Asp | Ala | Phe |
|---|---|---|---|---|---|---|---|---|---|---|---|---|---|---|---|
| | | 35 | | | | | 40 | | | | 45 | | | | |

| Ser | Arg | Val | Lys | Thr | Phe | Phe | Gln | Met | Lys | Asp | Gln | Leu | Asp | Asn | Leu |
|---|---|---|---|---|---|---|---|---|---|---|---|---|---|---|---|
| | 50 | | | | | 55 | | | | | 60 | | | | |

| Leu | Leu | Lys | Glu | Ser | Leu | Leu | Glu | Asp | Phe | Lys | Gly | Tyr | Leu | Gly | Cys |
|---|---|---|---|---|---|---|---|---|---|---|---|---|---|---|---|
| 65 | | | | | 70 | | | | | 75 | | | | | 80 |

| Gln | Ala | Leu | Ser | Glu | Met | Ile | Gln | Phe | Tyr | Leu | Glu | Glu | Val | Met | Pro |
|---|---|---|---|---|---|---|---|---|---|---|---|---|---|---|---|
| | | | | 85 | | | | | 90 | | | | | 95 | |

| Gln | Ala | Glu | Asn | Gln | Asp | Pro | Asp | Ile | Lys | Ala | His | Val | Asn | Ser | Leu |
|---|---|---|---|---|---|---|---|---|---|---|---|---|---|---|---|
| | | | 100 | | | | | 105 | | | | | 110 | | |

| Gly | Glu | Asn | Leu | Lys | Thr | Leu | Arg | Leu | Arg | Leu | Arg | Arg | Cys | His | Arg |
|---|---|---|---|---|---|---|---|---|---|---|---|---|---|---|---|
| | | | 115 | | | | | 120 | | | | | 125 | | |

| Phe | Leu | Pro | Cys | Glu | Asn | Lys | Ser | Lys | Ala | Val | Glu | Gln | Val | Lys | Asn |
|---|---|---|---|---|---|---|---|---|---|---|---|---|---|---|---|
| | 130 | | | | | 135 | | | | | 140 | | | | |

| Ala | Phe | Asn | Lys | Leu | Gln | Glu | Lys | Gly | Ile | Tyr | Lys | Ala | Met | Ser | Glu |
|---|---|---|---|---|---|---|---|---|---|---|---|---|---|---|---|
| 145 | | | | | 150 | | | | | 155 | | | | | 160 |

| Phe | Asp | Ile | Phe | Ile | Asn | Tyr | Ile | Glu | Ala | Tyr | Met | Thr | Met | Lys | Ile |
|---|---|---|---|---|---|---|---|---|---|---|---|---|---|---|---|
| | | | | 165 | | | | | 170 | | | | | 175 | |

| Arg | Asn |
|---|---|

(2) INFORMATION FOR SEQ ID NO:2:

(i) SEQUENCE CHARACTERISTICS:
(A) LENGTH: 170 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:2:

| Met | Glu | Arg | Arg | Leu | Val | Val | Thr | Leu | Gln | Cys | Leu | Val | Leu | Leu | Tyr |
|---|---|---|---|---|---|---|---|---|---|---|---|---|---|---|---|
| 1 | | | | 5 | | | | | 10 | | | | | 15 | |

| Leu | Ala | Pro | Glu | Cys | Gly | Gly | Thr | Asp | Gln | Cys | Asp | Asn | Phe | Pro | Gln |
|---|---|---|---|---|---|---|---|---|---|---|---|---|---|---|---|
| | | | 20 | | | | | 25 | | | | | 30 | | |

| Met | Leu | Arg | Asp | Leu | Arg | Asp | Ala | Phe | Ser | Arg | Val | Lys | Thr | Phe | Phe |
|---|---|---|---|---|---|---|---|---|---|---|---|---|---|---|---|
| | | 35 | | | | | 40 | | | | | 45 | | | |

| Gln | Thr | Lys | Asp | Glu | Val | Asp | Asn | Leu | Leu | Leu | Lys | Glu | Ser | Leu | Leu |
|---|---|---|---|---|---|---|---|---|---|---|---|---|---|---|---|
| | 50 | | | | | 55 | | | | | 60 | | | | |

| Glu | Asp | Phe | Lys | Gly | Tyr | Leu | Gly | Cys | Gln | Ala | Leu | Ser | Glu | Met | Ile |
|---|---|---|---|---|---|---|---|---|---|---|---|---|---|---|---|
| 65 | | | | | 70 | | | | | 75 | | | | | 80 |

| Gln | Phe | Tyr | Leu | Glu | Glu | Val | Met | Pro | Gln | Ala | Glu | Asn | Gln | Asp | Pro |
|---|---|---|---|---|---|---|---|---|---|---|---|---|---|---|---|
| | | | | 85 | | | | | 90 | | | | | 95 | |

| Glu | Ala | Lys | Asp | His | Val | Asn | Ser | Leu | Gly | Glu | Asn | Leu | Lys | Thr | Leu |
|---|---|---|---|---|---|---|---|---|---|---|---|---|---|---|---|
| | | | 100 | | | | | 105 | | | | | 110 | | |

| Arg | Leu | Arg | Leu | Arg | Arg | Cys | His | Arg | Phe | Leu | Pro | Cys | Glu | Asn | Lys |
|---|---|---|---|---|---|---|---|---|---|---|---|---|---|---|---|
| | | | 115 | | | | | 120 | | | | | 125 | | |

Ser Lys Ala Val Glu Gln Ile Lys Asn Ala Phe Asn Lys Leu Gln Glu
    130                 135                 140

Lys Gly Ile Tyr Lys Ala Met Ser Glu Phe Asp Ile Phe Ile Asn Tyr
145                 150                 155                 160

Ile Glu Ala Tyr Met Thr Ile Lys Ala Arg
                165                 170

( 2 ) INFORMATION FOR SEQ ID NO:3:

( i ) SEQUENCE CHARACTERISTICS:
        ( A ) LENGTH: 160 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
                20                  25                  30

Val Lys Thr Phe Phe Gln Met Lys Asp Gln Leu Asp Asn Leu Leu Leu
            35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

( 2 ) INFORMATION FOR SEQ ID NO:4:

( i ) SEQUENCE CHARACTERISTICS:
        ( A ) LENGTH: 147 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Val Asp
                20                  25                  30

Asn Leu Leu Leu Lys Glu Ser Leu Leu Glu Asp Phe Lys Gly Tyr Leu
            35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ala Lys Asp His Val Asn
65                  70                  75                  80

```
        Ser  Leu  Gly  Glu  Asn  Leu  Lys  Thr  Leu  Arg  Leu  Arg  Leu  Arg  Arg  Cys
                            85                      90                      95

His  Arg  Phe  Leu  Pro  Cys  Glu  Asn  Lys  Ser  Lys  Ala  Val  Glu  Gln  Ile
                           100                     105                     110

Lys  Asn  Ala  Phe  Asn  Lys  Leu  Gln  Glu  Lys  Gly  Ile  Tyr  Lys  Ala  Met
                           115                     120                     125

Ser  Glu  Phe  Asp  Ile  Phe  Ile  Asn  Tyr  Ile  Glu  Ala  Tyr  Met  Thr  Ile
                           130                     135                     140

Lys  Ala  Arg
        145
```

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:5:

GTAAGGAGGT TTAAC                                                             15

( 2 ) INFORMATION FOR SEQ ID NO:6:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:6:

ATGAGCTCAT                                                                  10

( 2 ) INFORMATION FOR SEQ ID NO:7:

( i ) SEQUENCE CHARACTERISTICS:
        ( A ) LENGTH: 60 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:7:

AGCCCAGGCC AGGGCACCCA GTCTGAGAAC AGCTGCACCC ACTTCCCAGG TAACCGGTAC    60

( 2 ) INFORMATION FOR SEQ ID NO:8:

( i ) SEQUENCE CHARACTERISTICS:
        ( A ) LENGTH: 56 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:8:

CGGTTACCTG GGAAGTGGGT GCAGCTGTTC TCAGACTGGG TGCCCTGGCC TGGGCT    56

( 2 ) INFORMATION FOR SEQ ID NO:9:

( i ) SEQUENCE CHARACTERISTICS:
        ( A ) LENGTH: 62 base pairs ( B ) TYPE: nucleic acid
     ( C ) STRANDEDNESS: double
     ( D ) TOPOLOGY: linear ( i i ) MOLECULE TYPE: DNA (oligonucleotide)

( x i ) SEQUENCE DESCRIPTION: SEQ ID NO:9:

```
GTAACCTGCC  TAACATGCTT  CGAGATCTCC  GAGATGCCTT  CAGCAGAGTG  AAGACTTTCT      60

TT                                                                          62
```

( 2 ) INFORMATION FOR SEQ ID NO:10:

( i ) SEQUENCE CHARACTERISTICS:
     ( A ) LENGTH: 48 base pairs
     ( B ) TYPE: nucleic acid
     ( C ) STRANDEDNESS: double
     ( D ) TOPOLOGY: linear ( i i ) MOLECULE TYPE: DNA (oligonucleotide)

( x i ) SEQUENCE DESCRIPTION: SEQ ID NO:10:

```
CTTCACTCTG  CTGAAGGCAT  CTCGGAGATC  TCGAAGCATG  TTAGGCAG                    48
```

( 2 ) INFORMATION FOR SEQ ID NO:11:

( i ) SEQUENCE CHARACTERISTICS:
     ( A ) LENGTH: 35 base pairs
     ( B ) TYPE: nucleic acid
     ( C ) STRANDEDNESS: double
     ( D ) TOPOLOGY: linear ( i i ) MOLECULE TYPE: DNA (oligonucleotide)

( x i ) SEQUENCE DESCRIPTION: SEQ ID NO:11:

```
CAAATGAAGG  ATCAGCTGGA  CAACTTGTTC  TTAAG                                   35
```

( 2 ) INFORMATION FOR SEQ ID NO:12:

( i ) SEQUENCE CHARACTERISTICS:
     ( A ) LENGTH: 44 base pairs
     ( B ) TYPE: nucleic acid
     ( C ) STRANDEDNESS: double
     ( D ) TOPOLOGY: linear ( i i ) MOLECULE TYPE: DNA (oligonucleotide)

( x i ) SEQUENCE DESCRIPTION: SEQ ID NO:12:

```
CTTAAGAACA  AGTTGTCCAG  CTGATCCTTC  ATTTGAAAGA  AAGT                        44
```

( 2 ) INFORMATION FOR SEQ ID NO:13:

( i ) SEQUENCE CHARACTERISTICS:
     ( A ) LENGTH: 69 base pairs
     ( B ) TYPE: nucleic acid
     ( C ) STRANDEDNESS: double
     ( D ) TOPOLOGY: linear ( i i ) MOLECULE TYPE: DNA (oligonucleotide)

( x i ) SEQUENCE DESCRIPTION: SEQ ID NO:13:

```
GAGTCCTTGC  TGGAGGACTT  TAAGGGTTAC  CTGGGTTGCC  AAGCCTTGTC  TGAGATGATC      60

CAGTTTTAT                                                                   69
```

( 2 ) INFORMATION FOR SEQ ID NO:14:

( i ) SEQUENCE CHARACTERISTICS:
     ( A ) LENGTH: 73 base pairs
     ( B ) TYPE: nucleic acid ( C ) STRANDEDNESS: double
( D ) TOPOLOGY: linear ( i i ) MOLECULE TYPE: DNA (oligonucleotide)

( x i ) SEQUENCE DESCRIPTION: SEQ ID NO:14:

CTAGATAAAA CTGGATCATC TCAGACAAGG CTTGGCAACC CAGGTAACCC TTAAAGTCCT 60

CCAGCAAGGA CTC 73

( 2 ) INFORMATION FOR SEQ ID NO:15:

( i ) SEQUENCE CHARACTERISTICS:
( A ) LENGTH: 61 base pairs
( B ) TYPE: nucleic acid
( C ) STRANDEDNESS: double
( D ) TOPOLOGY: linear ( i i ) MOLECULE TYPE: DNA (oligonucleotide)

( x i ) SEQUENCE DESCRIPTION: SEQ ID NO:15:

CTAGAGGAGG TGATGCCCCA AGCTGAGAAC CAAGACCCAG ACATCAAGGC GCATGTTAAC 60

G 61

( 2 ) INFORMATION FOR SEQ ID NO:16:

( i ) SEQUENCE CHARACTERISTICS:
( A ) LENGTH: 65 base pairs
( B ) TYPE: nucleic acid
( C ) STRANDEDNESS: double
( D ) TOPOLOGY: linear ( i i ) MOLECULE TYPE: DNA (oligonucleotide)

( x i ) SEQUENCE DESCRIPTION: SEQ ID NO:16:

GTTAACATGC GCCTTGATGT CTGGGTCTTG GTTCTCAGCT TGGGGCATCA CCTCCTCTAG 60

TCGAC 65

( 2 ) INFORMATION FOR SEQ ID NO:17:

( i ) SEQUENCE CHARACTERISTICS:
( A ) LENGTH: 63 base pairs
( B ) TYPE: nucleic acid
( C ) STRANDEDNESS: double
( D ) TOPOLOGY: linear ( i i ) MOLECULE TYPE: DNA (oligonucleotide)

( x i ) SEQUENCE DESCRIPTION: SEQ ID NO:17:

AACTCCCTGG GGGAGAACCT GAAGACCCTC AGGCTGAGGC TACGGCGCTG TCATCGATCT 60

GCA 63

( 2 ) INFORMATION FOR SEQ ID NO:18:

( i ) SEQUENCE CHARACTERISTICS:
( A ) LENGTH: 59 base pairs
( B ) TYPE: nucleic acid
( C ) STRANDEDNESS: double
( D ) TOPOLOGY: linear ( i i ) MOLECULE TYPE: DNA (oligonucleotide)

( x i ) SEQUENCE DESCRIPTION: SEQ ID NO:18:

GATCGATGAC AGCGCCGTAG CCTCAGCCTG AGGGTCTTCA GGTTCTCCCC CAGGGAGTT 59

( 2 ) INFORMATION FOR SEQ ID NO:19:

( i ) SEQUENCE CHARACTERISTICS:
    ( A ) LENGTH: 60 base pairs
    ( B ) TYPE: nucleic acid
    ( C ) STRANDEDNESS: double
    ( D ) TOPOLOGY: linear ( i i ) MOLECULE TYPE: DNA (oligonucleotide)

( x i ) SEQUENCE DESCRIPTION: SEQ ID NO:19:

CGATTTCTTC CCTGTCAAAA CAAGAGCAAG GCCGTGGAGC AGGTGAAGAA CGCGTGCATG    60

( 2 ) INFORMATION FOR SEQ ID NO:20:

( i ) SEQUENCE CHARACTERISTICS:
        ( A ) LENGTH: 54 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:20:

CACGCGTTCT TCACCTGCTC CACGGCCTTG CTCTTGTTTT GACAGGGAAG AAAT    54

( 2 ) INFORMATION FOR SEQ ID NO:21:

( i ) SEQUENCE CHARACTERISTICS:
        ( A ) LENGTH: 58 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:21:

CGCGTTTAAT AATAAGCTCC AAGACAAAGG CATCTACAAA GCCATGAGTG AGTTTGAC    58

( 2 ) INFORMATION FOR SEQ ID NO:22:

( i ) SEQUENCE CHARACTERISTICS:
        ( A ) LENGTH: 45 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:22:

ACTCATGGCT TTGTAGATGC CTTTGTCTTG GAGCTTATTA TTAAA    45

( 2 ) INFORMATION FOR SEQ ID NO:23:

( i ) SEQUENCE CHARACTERISTICS:
        ( A ) LENGTH: 51 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:23:

ATCTTCATCA ACTACATAGA AGCCTACATG ACAATGAAGA TACGAAACTG A    51

( 2 ) INFORMATION FOR SEQ ID NO:24:

( i ) SEQUENCE CHARACTERISTICS:
        ( A ) LENGTH: 64 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:24:

| | | | | | | |
|---|---|---|---|---|---|---|
| AGCTTCAGTT | TCGTATCTTC | ATTGTCATGT | AGGCTTCTAT | GTAGTTGATG | AAGATGTCAA | 60 |
| ACTC | | | | | | 64 |

( 2 ) INFORMATION FOR SEQ ID NO:25:

( i ) SEQUENCE CHARACTERISTICS:
        ( A ) LENGTH: 498 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:25:

| | | | | | | |
|---|---|---|---|---|---|---|
| AATTCATGGA | GCGAAGGTTA | GTGGTCACTC | TGCAGTGCCT | GGTGCTGCTT | TACCTGGCAC | 60 |
| CTGAGTGTGG | AGGTACAGAC | CAATGTGACA | ATTTTCCCCA | GACCTAAGAG | ATGCCTTCAG | 120 |
| TCGTGTTAAA | ACCTTTTTCC | AGACAAAGGA | CGAGGTAGAT | AACCTTTTGC | TCAAGGAGTC | 180 |
| TCTGCTAGAG | GACTTTAAGG | ATGCCAGGCC | CTGTCAGAAA | TGATCCAATT | CTACCTGGAG | 240 |
| GAAGTCATGC | CACAGGCTGA | AACCAGGACC | CTGAAGCCAA | AGACCATGTC | AATTCTTTGG | 300 |
| GTGAAAATCT | AAAGACCCTA | CGGCTCCGCC | TGCGCAGGTG | CCACAGGTTC | CTGCCGTGTG | 360 |
| AGAACAAGAG | TAAAGCTGTG | GAACAGATAA | AAAATGCCTT | TAACAAGCTG | CAGGAAAAAG | 420 |
| GAATTTACAA | AGCCATGAGT | GAATTTGACA | TTTTTATTAA | CTACATAGAA | GCATACATGA | 480 |
| CAATTAAAGC | CAGGTGAG | | | | | 498 |

( 2 ) INFORMATION FOR SEQ ID NO:26:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:26:

| | | |
|---|---|---|
| CATGGGTGCT | TATAAGTCAT | C | 21 |

( 2 ) INFORMATION FOR SEQ ID NO:27:

( i ) SEQUENCE CHARACTERISTICS:
        ( A ) LENGTH: 25 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:27:

| | | | |
|---|---|---|---|
| CGATCACTGA | ACTGCACGCT | CCGGG | 25 |

( 2 ) INFORMATION FOR SEQ ID NO:28:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:28:

GAGGTATACC TAGAGTACCT C 21

( 2 ) INFORMATION FOR SEQ ID NO:29:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:29:

TAAAGACATA CTCCAAACCT T 21

( 2 ) INFORMATION FOR SEQ ID NO:30:

( i ) SEQUENCE CHARACTERISTICS:
        ( A ) LENGTH: 69 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:30:

CAGGTGAAGA ATGCCTTTAA TAAGCTCCAA GAGAAAGGCA TCTACAAAGC CATGAGTGAG 60

TTTGACATC 69

( 2 ) INFORMATION FOR SEQ ID NO:31:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:31:

GGCGTGGAGC TGAGAGATAA C 21

( 2 ) INFORMATION FOR SEQ ID NO:32:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:32:

CCGGCGTCTC CTGAACCT 18

( 2 ) INFORMATION FOR SEQ ID NO:33:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:33:

CTGAACCCTA AGGCCAACCG TG                                          22

(2) INFORMATION FOR SEQ ID NO:34:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (oligonucleotide)

(xi) SEQUENCE DESCRIPTION: SEQ ID NO:34:

GCCCTGGAAG GGATCTCCCC C                                           21

(2) INFORMATION FOR SEQ ID NO:35:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (oligonucleotide)

(xi) SEQUENCE DESCRIPTION: SEQ ID NO:35:

CATCGCCAAT GACTCAGAGG AAG                                         23

(2) INFORMATION FOR SEQ ID NO:36:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: DNA (oligonucleotide)

(xi) SEQUENCE DESCRIPTION: SEQ ID NO:36:

TGCCAAGCAC ACCCAGTAGT CTTGCTT                                     27

(2) INFORMATION FOR SEQ ID NO:37:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (oligonucleotide)

(xi) SEQUENCE DESCRIPTION: SEQ ID NO:37:

CAGCTACGAA TCTCGGACCA CC                                          22

(2) INFORMATION FOR SEQ ID NO:38:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: DNA (oligonucleotide)

(xi) SEQUENCE DESCRIPTION: SEQ ID NO:38:

TTAGGAAGAC ACAAATTGCA TGGTGAAGTC AGT                              33

(2) INFORMATION FOR SEQ ID NO:39:

(i) SEQUENCE CHARACTERISTICS:
   (A) LENGTH: 21 base pairs
   (B) TYPE: nucleic acid
   (C) STRANDEDNESS: double
   (D) TOPOLOGY: linear (ii) MOLECULE TYPE: DNA (oligonucleotide)

(xi) SEQUENCE DESCRIPTION: SEQ ID NO:39:

ATGAACTCCT TCTCCACAAG C                                    21

(2) INFORMATION FOR SEQ ID NO:40:

(i) SEQUENCE CHARACTERISTICS:
      (A) LENGTH: 33 base pairs
      (B) TYPE: nucleic acid
      (C) STRANDEDNESS: double
      (D) TOPOLOGY: linear (ii) MOLECULE TYPE: DNA (oligonucleotide)

(xi) SEQUENCE DESCRIPTION: SEQ ID NO:40:

CTACATTTGC CGAAGAGCCC TCAGGCTGGA CTG                        33

(2) INFORMATION FOR SEQ ID NO:41:

(i) SEQUENCE CHARACTERISTICS:
      (A) LENGTH: 21 base pairs
      (B) TYPE: nucleic acid
      (C) STRANDEDNESS: double
      (D) TOPOLOGY: linear (ii) MOLECULE TYPE: DNA (oligonucleotide)

(xi) SEQUENCE DESCRIPTION: SEQ ID NO:41:

ATGACTTCCA AGCTGGCCGT G                                    21

(2) INFORMATION FOR SEQ ID NO:42:

(i) SEQUENCE CHARACTERISTICS:
      (A) LENGTH: 33 base pairs
      (B) TYPE: nucleic acid
      (C) STRANDEDNESS: double
      (D) TOPOLOGY: linear (ii) MOLECULE TYPE: DNA (oligonucleotide)

(xi) SEQUENCE DESCRIPTION: SEQ ID NO:42:

TTATGAATTC TCAGCCCTCT TCAAAAACTT CTC                        33

(2) INFORMATION FOR SEQ ID NO:43:

(i) SEQUENCE CHARACTERISTICS:
      (A) LENGTH: 27 base pairs
      (B) TYPE: nucleic acid
      (C) STRANDEDNESS: double
      (D) TOPOLOGY: linear (ii) MOLECULE TYPE: DNA (oligonucleotide)

(xi) SEQUENCE DESCRIPTION: SEQ ID NO:43:

ATGCCCCAAG CTGAGAACCA AGACCCA                               27

(2) INFORMATION FOR SEQ ID NO:44:

(i) SEQUENCE CHARACTERISTICS:
      (A) LENGTH: 27 base pairs
      (B) TYPE: nucleic acid
      (C) STRANDEDNESS: double
      (D) TOPOLOGY: linear (i i) MOLECULE TYPE: DNA (oligonucleotide)

(x i) SEQUENCE DESCRIPTION: SEQ ID NO:44:

TCTCAAGGGG CTGGGTCAGC TATCCCA                              27

(2) INFORMATION FOR SEQ ID NO:45:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (i i) MOLECULE TYPE: DNA (oligonucleotide)

(x i) SEQUENCE DESCRIPTION: SEQ ID NO:45:

AGAGGGAAGA GTTCCCCAGG GAC                                  23

(2) INFORMATION FOR SEQ ID NO:46:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (i i) MOLECULE TYPE: DNA (oligonucleotide)

(x i) SEQUENCE DESCRIPTION: SEQ ID NO:46:

TGAGTCGGTC ACCCTTCTCC AG                                   22

(2) INFORMATION FOR SEQ ID NO:47:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (i i) MOLECULE TYPE: DNA (oligonucleotide)

(x i) SEQUENCE DESCRIPTION: SEQ ID NO:47:

GCATCTCTGC ACCCGCCCGC TCGCC                                25

(2) INFORMATION FOR SEQ ID NO:48:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (i i) MOLECULE TYPE: DNA (oligonucleotide)

(x i) SEQUENCE DESCRIPTION: SEQ ID NO:48:

CCTGCTTGTA CAGCTCCAGG CGGGT                                25

(2) INFORMATION FOR SEQ ID NO:49:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (i i) MOLECULE TYPE: DNA (oligonucleotide)

(x i) SEQUENCE DESCRIPTION: SEQ ID NO:49:

GAGTGTGCCA CCTACAAGCT GTGCC                                                                            25

( 2 ) INFORMATION FOR SEQ ID NO:50:

( i ) SEQUENCE CHARACTERISTICS:
          ( A ) LENGTH: 25 base pairs
          ( B ) TYPE: nucleic acid
          ( C ) STRANDEDNESS: double
          ( D ) TOPOLOGY: linear ( i i ) MOLECULE TYPE: DNA (oligonucleotide)

( x i ) SEQUENCE DESCRIPTION: SEQ ID NO:50:

CCTGGGTGGG CTGCAGGGCA GGGGC                                                                            25

( 2 ) INFORMATION FOR SEQ ID NO:51:

( i ) SEQUENCE CHARACTERISTICS:
          ( A ) LENGTH: 20 base pairs
          ( B ) TYPE: nucleic acid
          ( C ) STRANDEDNESS: double
          ( D ) TOPOLOGY: linear ( i i ) MOLECULE TYPE: DNA (oligonucleotide)

( x i ) SEQUENCE DESCRIPTION: SEQ ID NO:51:

GTGGGGCGCC CCAGGCACCA                                                                                  20

( 2 ) INFORMATION FOR SEQ ID NO:52:

( i ) SEQUENCE CHARACTERISTICS:
          ( A ) LENGTH: 24 base pairs
          ( B ) TYPE: nucleic acid
          ( C ) STRANDEDNESS: double
          ( D ) TOPOLOGY: linear ( i i ) MOLECULE TYPE: DNA (oligonucleotide)

( x i ) SEQUENCE DESCRIPTION: SEQ ID NO:52:

GTCCTTAATG TCACGCACGA TTTC                                                                             24

( 2 ) INFORMATION FOR SEQ ID NO:53:

( i ) SEQUENCE CHARACTERISTICS:
          ( A ) LENGTH: 23 base pairs
          ( B ) TYPE: nucleic acid
          ( C ) STRANDEDNESS: double
          ( D ) TOPOLOGY: linear ( i i ) MOLECULE TYPE: DNA (oligonucleotide)

( x i ) SEQUENCE DESCRIPTION: SEQ ID NO:53:

GTAATGATCA GTCAACGGGG GAC                                                                              23

( 2 ) INFORMATION FOR SEQ ID NO:54:

( i ) SEQUENCE CHARACTERISTICS:
          ( A ) LENGTH: 24 base pairs
          ( B ) TYPE: nucleic acid
          ( C ) STRANDEDNESS: double
          ( D ) TOPOLOGY: linear ( i i ) MOLECULE TYPE: DNA (oligonucleotide)

( x i ) SEQUENCE DESCRIPTION: SEQ ID NO:54:

CCAGCAAGCT TGCAACCTTA ACCA                                                                             24

( 2 ) INFORMATION FOR SEQ ID NO:55:

( i ) SEQUENCE CHARACTERISTICS:
  ( A ) LENGTH: 28 base pairs
  ( B ) TYPE: nucleic acid
  ( C ) STRANDEDNESS: double
  ( D ) TOPOLOGY: linear ( i i ) MOLECULE TYPE: DNA (oligonucleotide)

( x i ) SEQUENCE DESCRIPTION: SEQ ID NO:55:

GCTTTCCCTG GTTAAGCAGT ACAGCCCC 28

( 2 ) INFORMATION FOR SEQ ID NO:56:

( i ) SEQUENCE CHARACTERISTICS:
    ( A ) LENGTH: 21 base pairs
    ( B ) TYPE: nucleic acid
    ( C ) STRANDEDNESS: double
    ( D ) TOPOLOGY: linear ( i i ) MOLECULE TYPE: DNA (oligonucleotide)

( x i ) SEQUENCE DESCRIPTION: SEQ ID NO:56:

GCGACGTGGA ACTGGCAGAA G 21

( 2 ) INFORMATION FOR SEQ ID NO:57:

( i ) SEQUENCE CHARACTERISTICS:
    ( A ) LENGTH: 21 base pairs
    ( B ) TYPE: nucleic acid
    ( C ) STRANDEDNESS: double
    ( D ) TOPOLOGY: linear ( i i ) MOLECULE TYPE: DNA (oligonucleotide)

( x i ) SEQUENCE DESCRIPTION: SEQ ID NO:57:

GGTACAACCC ATCGGCTGGC A 21

( 2 ) INFORMATION FOR SEQ ID NO:58:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: DNA (oligonucleotide)

( x i ) SEQUENCE DESCRIPTION: SEQ ID NO:58:

CAGTTCTATG GCCCAGACCC TC 22

( 2 ) INFORMATION FOR SEQ ID NO:59:

( i ) SEQUENCE CHARACTERISTICS:
    ( A ) LENGTH: 21 base pairs
    ( B ) TYPE: nucleic acid
    ( C ) STRANDEDNESS: double
    ( D ) TOPOLOGY: linear ( i i ) MOLECULE TYPE: DNA (oligonucleotide)

( x i ) SEQUENCE DESCRIPTION: SEQ ID NO:59:

CCAGTTGCCT TCTTGGGACT G 21

( 2 ) INFORMATION FOR SEQ ID NO:60:

( i ) SEQUENCE CHARACTERISTICS:
    ( A ) LENGTH: 18 base pairs
    ( B ) TYPE: nucleic acid
    ( C ) STRANDEDNESS: double
    ( D ) TOPOLOGY: linear (i i) MOLECULE TYPE: DNA (oligonucleotide)

(x i) SEQUENCE DESCRIPTION: SEQ ID NO:60:

GGTAGCTATG GTACTCCA                                                                18

(2) INFORMATION FOR SEQ ID NO:61:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (i i) MOLECULE TYPE: DNA (oligonucleotide)

(x i) SEQUENCE DESCRIPTION: SEQ ID NO:61:

GTGACAACCA CGGCCTTCCC TACT                                                         24